(12) United States Patent
Brown et al.

(10) Patent No.: US 7,629,358 B2
(45) Date of Patent: Dec. 8, 2009

(54) COMPOUNDS USEFUL FOR THE TREATMENT OF DISEASES

(75) Inventors: Alan Daniel Brown, Sandwich (GB); Charlotte Alice Louise Lane, Sandwich (GB); Paul Alan Glossop, Sandwich (GB); David Anthony Price, Sandwich (GB); Russell Andrew Lewthwaite, Sandwich (GB); Mark Edward Bunnage, Sandwich (GB); Kim James, Sandwich (GB); Graham Lunn, Sandwich (GB)

(73) Assignee: Pfizer Inc, New York, NY (US)

( * ) Notice: Subject to any disclaimer, the term of this patent is extended or adjusted under 35 U.S.C. 154(b) by 189 days.

(21) Appl. No.: 11/083,265

(22) Filed: Mar. 16, 2005

(65) Prior Publication Data
US 2005/0234097 A1    Oct. 20, 2005

Related U.S. Application Data

(60) Provisional application No. 60/591,790, filed on Jul. 27, 2004, provisional application No. 60/642,875, filed on Jan. 10, 2005.

(30) Foreign Application Priority Data

Mar. 17, 2004 (EP) .................................. 04290725
Nov. 12, 2004 (GB) .................................. 0425064.3

(51) Int. Cl.
*A61K 31/47* (2006.01)
*A61K 31/165* (2006.01)
*C07D 217/00* (2006.01)
*C07C 237/00* (2006.01)

(52) U.S. Cl. ................ 514/310; 514/620; 546/150; 564/165

(58) Field of Classification Search ................ 514/310, 514/620; 546/150; 564/165
See application file for complete search history.

(56) References Cited

U.S. PATENT DOCUMENTS 5,561,142 A   10/1996  Fisher et al. ............... 514/312
6,106,864 A   8/2000   Dolan et al. ................ 424/488
6,538,035 B2* 3/2003   Gillberg et al. ............. 514/650

FOREIGN PATENT DOCUMENTS

| EP | 0236624 | 8/1993 |
| EP | 0654534 | 3/2000 |
| EP | 0939134 | 9/2002 |
| WO | WO 9111172 | 8/1991 |
| WO | WO 9402518 | 2/1994 |
| WO | WO 9855148 | 12/1998 |
| WO | WO 0035298 | 6/2000 |

OTHER PUBLICATIONS

Ainsworth et al. CAS Accession No. 1981:15372.*
Barnes, P. J. Chest, 111:2, pp. 17S-26S (1997).
Bryan, S.A. et al., Expert Opinion on Investigational Drugs, 9:1, pp. 25-42 (2000).
Tetrahedron Letters, 35(50), p. 9375 (1994).
Haleblian, J. Pharm Sci, 64(8), pp. 1269-1288 (1975).
Liang and Chen, Expert Opinion in Therapeutic Patents, 11(6), pp. 981-986 (2001).
Finnin and Morgan, J. Pharm Sci, 88(10), pp. 955-958 (1999).

* cited by examiner

*Primary Examiner*—Rebecca L Anderson
*Assistant Examiner*—Joseph R Kosack
(74) *Attorney, Agent, or Firm*—Gregg C. Benson; Robert T. Ronau

(57) ABSTRACT

The invention relates to compounds of formula (1)

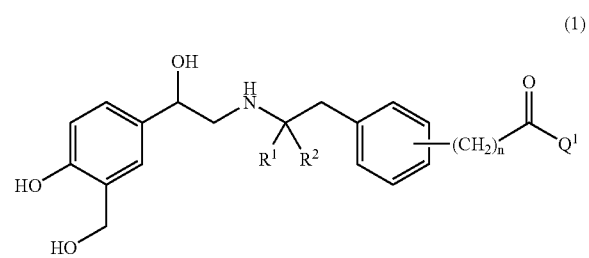

and to processes for the preparation of, intermediates used in the preparation of, compositions containing and the uses of, such derivatives. The compounds according to the present invention are useful in numerous diseases, disorders and conditions, in particular inflammatory, allergic and respiratory diseases, disorders and conditions.

11 Claims, No Drawings

COMPOUNDS USEFUL FOR THE TREATMENT OF DISEASES

This invention relates to β2 agonists of general formula:

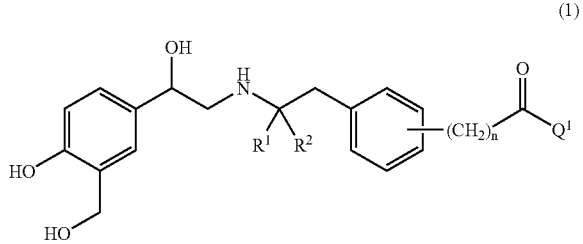

in which $R^1$, $R^2$, n and $Q^1$ have the meanings indicated below, and to processes for the preparation of, intermediates used in the preparation of, compositions containing and the uses of, such derivatives.

Adrenoceptors are members of the large G-protein coupled receptor super-family. The adrenoceptor subfamily is itself divided into the α and β subfamilies with the β sub-family being composed of at least 3 receptor sub-types: β1, β2 and β3. These receptors exhibit differential expression patterns in tissues of various systems and organs of mammals. β2 adrenergic (β2) receptors are mainly expressed in smooth muscle cells (e.g. vascular, bronchial, uterine or intestinal smooth muscles), whereas β3 adrenergic receptors are mainly expressed in fat tissues (therefore β3 agonists could potentially be useful in the treatment of obesity and diabetes) and β1 adrenergic receptors are mainly expressed in cardiac tissues (therefore β1 agonists are mainly used as cardiac stimulants).

The pathophysiology and treatments of airway diseases have been extensively reviewed in the literature (for reference see Barnes, P. J. Chest, 1997, 111:2, pp 17S-26S and Bryan, S. A. et al, Expert Opinion on investigational drugs, 2000, 9:1, pp 25-42) and therefore only a brief summary will be included here to provide some background information.

Glucocorticosteroids, anti-leukotrienes, theophylline, cromones, anti-cholinergics and β2 agonists constitute drug classes that are currently used to treat allergic and non-allergic airways diseases such as asthma and chronic obstructive airways disease (COPD). Treatment guidelines for these diseases include both short and long acting inhaled β2 agonists. Short acting, rapid onset β2 agonists are used for "rescue" bronchodilation, whereas, long-acting forms provide sustained relief and are used as maintenance therapy.

Bronchodilation is mediated via agonism of the β2 adrenoceptor expressed on airway smooth muscle cells, which results in relaxation and hence bronchodilation. Thus, as functional antagonists, β2 agonists can prevent and reverse the effects of all bronchoconstrictor substances, including leukotriene D4 (LTD4), acetylcholine, bradykinin, prostaglandins, histamine and endothelins. Because β2 receptors are so widely distributed in the airway, $β_2$ agonists may also affect other types of cells that play a role in asthma. For example, it has been reported that β2 agonists may stabilize mast cells. The inhibition of the release of bronchoconstrictor substances may be how β2 agonists block the bronchoconstriction induced by allergens, exercise and cold air. Furthermore, β2 agonists inhibit cholinergic neurotransmission in the human airway, which can result in reduced cholinergic-reflex bronchoconstriction.

In addition to the airways, it has also been established that β2 adrenoceptors are also expressed in other organs and tissues and thus β2 agonists, such as those described in the present invention, may have application in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

However, numerous β2 agonists are limited in their use due to their low selectivity or adverse side-effects driven by high systemic exposure and mainly mediated through action at β2 adrenoreceptors expressed outside the airways (muscle tremor, tachycardia, palpitations, restlessness). Therefore there is a need for improved agents in this class.

Accordingly, there is still a need for novel β2 agonists that would have an appropriate pharmacological profile, for example in terms of potency, selectivity, duration of action and/or pharmacodynamic properties. In this context, the present invention relates to novel β2 agonists. EP 0654534 B1 and EP0939134 B1 disclose a process for the preparation of compounds of formula (XI):

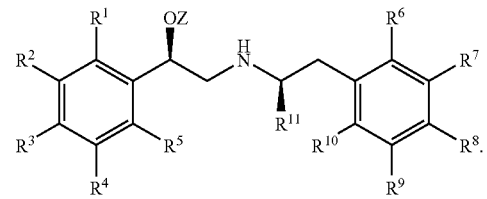

These compounds are disclosed as anti-obesity and anti-diabetic agents having specific β3 activity.

U.S. Pat. No. 5,561,142 discloses selective β3 agonists of formula

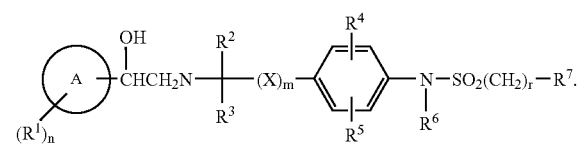

EP0236624 discloses compounds of formula

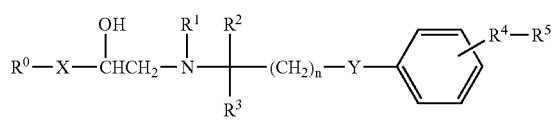

having anti-obesity and/or anti-hyperglycaemic activity coupled with good selectivity from cardiac side-effects.

The invention relates to compounds of general formula (1):

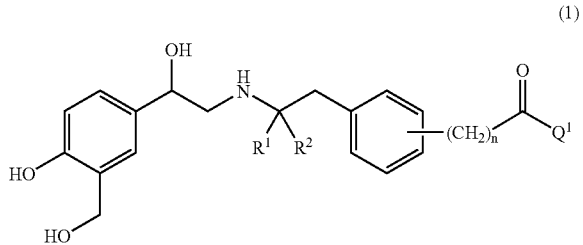

(1)

wherein the $(CH_2)_n$—C(=O)$Q^1$ group is in meta or para position, $R^1$ and $R^2$ are independently selected from H and $C_1$-$C_4$ alkyl, n is 0, 1 or 2, and, $Q^1$ is a group selected from:

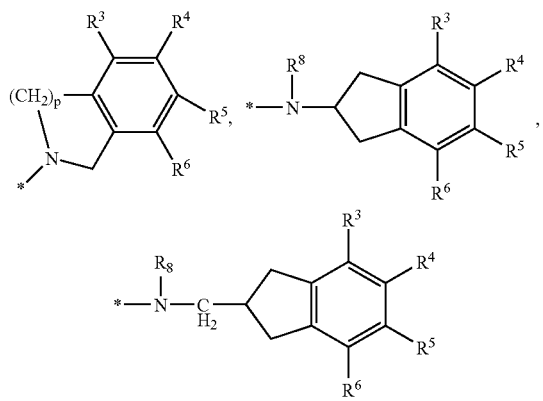

*—NH—$C_1$-$C_4$alkyl, and a group *—N($R^8$)-$Q^2$-A, wherein $Q^2$ is a single bond or a $C_1$-$C_4$ alkylene, $R^8$ is H or $C_1$-$C_4$ alkyl, p is 1 or 2, and A is a $C_3$-$C_{10}$ cycloalkyl, 2 carbon atoms or more of said cycloalkyl being optionally bridged by one or more carbon atoms, preferably by 1, 2, 3 or 4 carbon atoms, O-phenyl-pyrazolyl, 5 to 10 membered heterocyclic group, optionally aromatic, comprising one, two, three or four heteroatoms selected from O, S or N, optionally substituted with $C_1$-$C_4$ alkyl or O—$C_1$-$C_4$ alkyl, or a group of formula

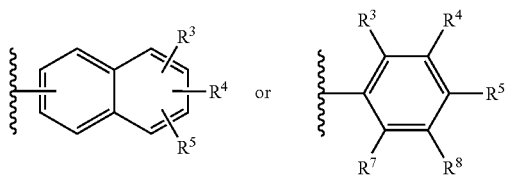

$R^3$, $R^4$, $R^5$, $R^6$ and $R^7$ are the same or different and are selected from H, $C_1$-$C_4$ alkyl, $OR^9$, $SR^9$, $SOR^9$, $SO_2R^9$, halo, CN, $CF_3$, $OCF_3$, phenyl, O-phenyl, S-phenyl, $SO_2$-morpholinyl, O—$(CH_2)_3$-pyrrolidinyl, $COOR^9$, $SO_2NR^9R^{10}$, $CONR^9R^{10}$, $NR^9R^{10}$ and $NHCOR^{10}$;

$R^9$ and $R^{10}$ are the same or different and are selected from H or $C_1$-$C_4$ alkyl and the * represents the attachment point to the carbonyl group;

or, if appropriate, their pharmaceutically acceptable salts and/or isomers, tautomers, solvates or isotopic variations thereof, with the proviso that when n is 0, then $Q^1$ is not —$NHCH_3$, and, when n is 1 or 2, then:

1) $Q^1$ is *—NH-$C_1$-$C_4$alkyl, or *—N($R^8$)-$Q^2$-A where A is $C_3$-$C_{10}$ cycloalkyl, 2 carbon atoms or more of said cycloalkyl being optionally bridged by one or more carbon atoms, O-phenyl-pyrazolyl, 5 to 10 membered heterocyclic group, optionally aromatic, comprising one, two, three or four heteroatoms selected from O, S or N optionally substituted with $C_1$-$C_4$ alkyl or O—$C_1$-$C_4$ alkyl, said heterocyclic group being other than pyridyl, a group of formula

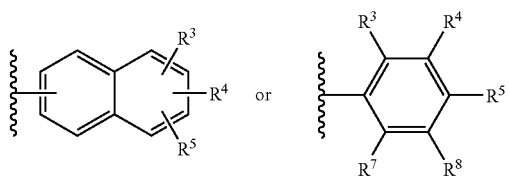

wherein one of $R^3$ to $R^7$ is CN, $SOR^9$, $SO_2R^9$, phenyl, O-phenyl, S-phenyl, $SO_2$-morpholinyl or O—$(CH_2)_3$-pyrrolidinyl and/or, 2) when one of $R^1$ and $R^2$ is H, the other is not $CH_3$.

It has now been found that the compounds of formula (1) are agonists of the β2 receptors, that are particularly useful for the treatment of β2-mediated diseases and/or conditions, and show good potency, in particular when administered via the inhalation route.

In the present invention, the term "potent" means that the compounds of formula (1) show an agonist potency for the β2 receptor, which is less than 10 nM as measured by the cell-based assay described herein.

Preferably, the compounds of the invention are selective agonists of the β2 receptor. Preferably, the compounds of the invention show an agonist potency for the β2 receptor, which is at least about 100-fold higher as for the β3 receptor and at least about 500-fold higher as for the β1 receptor.

In the here above general formula (1), $C_1$-$C_4$ alkyl and $C_1$-$C_4$ alkylene denote a straight-chain or branched group containing 1, 2, 3 or 4 carbon atoms. This also applies if they carry substituents or occur as substituents of other radicals, for example in O—$(C_1$-$C_4)$alkyl radicals, S—$(C_1$-$C_4)$alkyl radicals etc . . . . Examples of suitable $(C_1$-$C_4)$alkyl radicals are methyl, ethyl, n-propyl, iso-propyl, n-butyl, iso-butyl, sec-butyl, tert-butyl . . . . Examples of suitable O—$(C_1$-$C_4)$ alkyl radicals are methoxy, ethoxy, n-propyloxy, iso-propyloxy, n-butyloxy, iso-butyloxy, sec-butyloxy and tert-butyloxy . . . .

The $C_3$-$C_{10}$ cycloalkyl wherein 2 carbon atoms or more are optionally bridged by one or more carbon atoms include cyclopropyl, cyclobutyl, cyclopentyl, cyclohexyl, cycloheptyl, adamantyl, bicyclo[3.1.1]heptane, bicyclo[2.2.1]heptane, bicyclo[2.2.2]octane. Preferred cycloalkyl groups are cyclohexyl and adamantyl.

Examples of 5 to 10 membered heterocyclic group, optionally aromatic, comprising one, two, three or four heteroatoms independently selected from O, S or N are morpholinyl, pyrrolidinyl, piperidyl, piperazinyl, thienyl, isothiazolyl, oxazolyl, pyridyl, pyrimidyl oxazolyl, isoxazolyl, thiazolyl, furanyl, imidazolyl, pyrazolyl, pyrrolyl, pyridazinyl, pyrazinyl, triazolyl, tetrazolyl, oxadiazolyl, triazinyl, indolyl, quinolyl, isoquinolyl, benzofuranyl, quinazolyl, quinoxalyl, phthalazinyl, benzothiazolyl, benzoxazolyl, benzisothiazolyl, benzisoxazolyl, benzimidazolyl, indazolyl and benzotriazolyl.

Preferred heterocyclic groups are pyrrolidinyl, pyridyl, pyrimidyl, quinolyl, isoquinolyl, benzoimidazolyl and benzofuranyl.

Preferably said heterocyclic group contains 1 or 2 heteroatoms selected from O, S or N. More preferably said heterocyclic group contains one or two nitrogen atoms.

Finally, halo denotes a halogen atom selected from the group consisting of fluoro, chloro, bromo and iodo in particular fluoro or chloro.

In the following, the free bond on the phenyl group such as in the structure below,

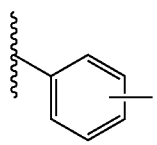

means that the phenyl can be substituted in the meta or para position.

The compounds of the formula (1)

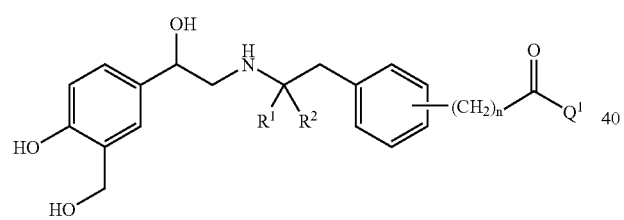

(1)

can be prepared using conventional procedures such as by the following illustrative methods in which $Q^1$, $Q^2$, A and n are as previously defined for the compounds of the formula (1) unless otherwise stated.

The amide derivatives of the formula (1) may be prepared by coupling an acid of formula (2):

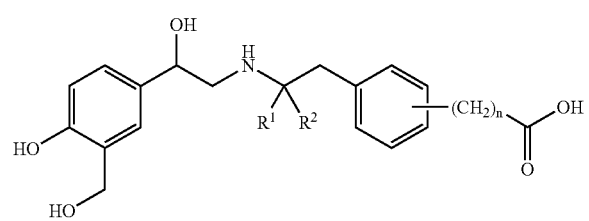

(2)

with an amine of formula $NH_2$—$C_1$-$C_4$alkyl, —$NH(R^8)$-$Q^2$-A,

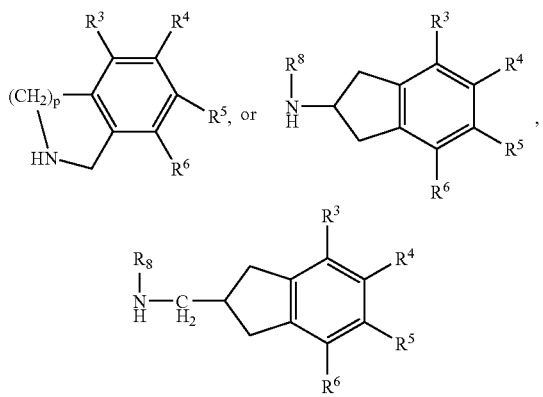

wherein $R^8$, $Q^2$, A, p and $R^3$ to $R^6$ are as previously defined for compounds of formula (1). The coupling is generally carried out in an excess of said amine as an acid receptor, with a conventional coupling agent (e.g. 1-(3-dimethylaminopropyl)-3-ethylcarbodiimide hydrochloride or N,N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or diisopropylethylamine). The reaction may be undertaken in a suitable solvent such as pyridine, dimethylformamide, tetrahydrofuran, dimethylsulfoxide, dichloromethane or ethyl acetate, and at temperature comprised between 10° C. and 40° C. (room temperature) for a period of 1-24 hours.

Said amine is either commercially available or may be prepared by conventional methods well known to the one skilled in the art (e.g. reduction, oxidation, alkylation, protection, deprotection etc . . . ) from commercially available material.

The acid of formula (2) may be prepared from the corresponding ester of formula (4):

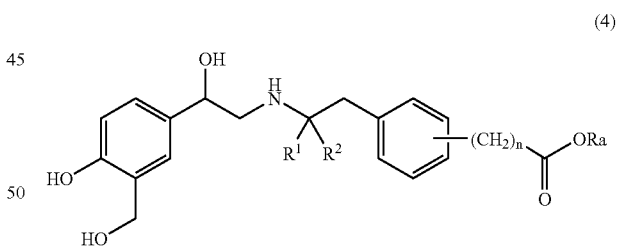

(4)

wherein Ra is a suitable acid protecting group, preferably a ($C_1$-$C_4$)alkyl group, which includes, but is not limited to, methyl and ethyl, according to any method well-known to the one skilled in the art to prepare an acid from an ester, without modifying the rest of the molecule. For example, the ester may be hydrolysed by treatment with aqueous acid or base (e.g. hydrogen chloride, potassium hydroxide, sodium hydroxide or lithium hydroxide), optionally in the presence of a solvent or mixture of solvents (e.g. water, 1,4-dioxan, tetrahydrofuran/water), at a temperature comprised between 20° C. and 100° C., for a period of 1 to 40 hours.

The ester of formula (4) may be prepared by reaction of an amine of formula (5):

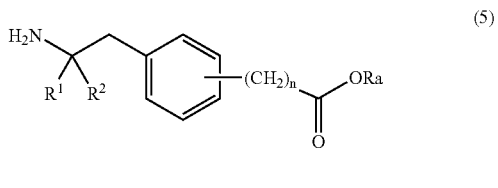

(5)

wherein Ra and n are as previously defined, with a bromide of formula (6):

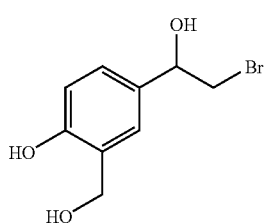

(6)

In a typical procedure, the amine of formula (5) is reacted with a bromide of formula (6) optionally in the presence of a solvent or mixture of solvents (e.g. dimethyl sulphoxide, toluene, N,N-dimethylformamide, acetonitrile), optionally in the presence of a suitable base (e.g. triethylamine, diisopropylethylamine, potassium carbonate) at a temperature comprised between 80° C. and 120° C., for 12 to 48 hours.

The bromide of formula (6) may be prepared from the ester of formula (7):

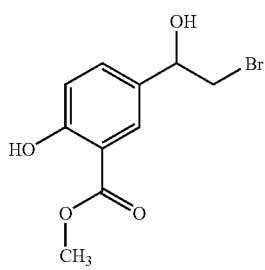

(7)

according to any method well-known to the one skilled in the art to prepare an alcohol from an ester, without modifying the rest of the molecule.

In a typical procedure, the ester of formula (7) is reduced with borane dimethylsulfide complex in tetrahydrofuran at a reflux for a period of 2 hours.

The alcohol of formula (7) may be prepared as either the (R) or (S) enantiomer according to methods well described in the literature (Tetrahedron Letters 1994, 35(50), 9375).

The amine of formula (5) may be prepared as either the (R) or (S) enantiomer from the corresponding protected amine of formula (8):

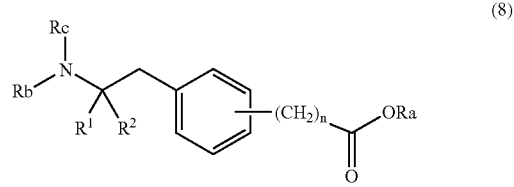

(8)

wherein Ra and n are as previously defined and Rb and Rc represent any suitable substituents so that HNRbRc is a chiral amine (for example, Rb may be hydrogen and Rc may be α-methylbenzyl), provided that the bonds between N and Rb and N and Rc can be easily cleaved to give the free amine of formula (5) using standard methodology for cleaving nitrogen protecting groups, such as those found in the text book T. W. GREENE, Protective Groups in Organic Synthesis, A. Wiley-Interscience Publication, 1981.

The amine of formula (8) may be prepared as a single diastereomer by reaction of an amine of formula HNRbRc with a ketone of formula (9):

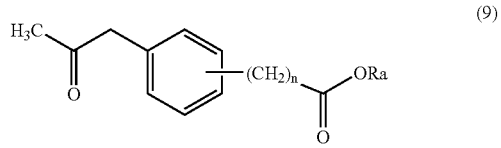

(9)

wherein Ra, Rb, Rc and n are as previously defined.

In a typical procedure, the reaction of the ketone of formula (9) with the amine of formula HNRbRc leads to a chiral intermediate which is in turn reduced by a suitable reducing agent (e.g. sodium cyanoborohydride of formula $NaCNBH_3$ or sodium triacetoxyborohydride of formula $Na(OAc)_3BH$) optionally in the presence of a drying agent (e.g. molecular sieves, magnesium sulfate) and optionally in the presence of an acid catalyst (e.g. acetic acid) to give the amine of formula (8) as a mixture of diastereomers. The reaction is generally done in a solvent such as tetrahydrofuran or dichloromethane at a temperature comprised between 20° C. and 80° C. for 3 to 72 hours. The resulting product is then converted to the hydrochloride salt and selectively crystallised from a suitable solvent or mixture of solvents (e.g. isopropanol, ethanol, methanol, diisopropyl ether or diisopropyl ether/methanol) to give (8) as a single diastereomer.

The ketone of formula (9) where n=1 may be prepared by palladium mediated coupling of an aryl halide of formula (10):

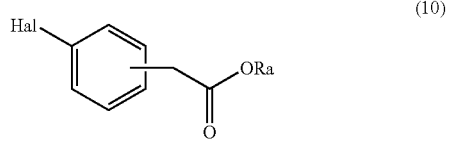

(10)

wherein Ra is as previously defined and Hal represents an halogen atom, which includes, but is not limited to bromo and iodo, with an enolate or enolate equivalent.

In a typical procedure, the aryl halide of formula (10) is reacted with a tin enolate generated in-situ by treatment of isopropenyl acetate with tri-n-butyltin methoxide of formula Bu$_3$SnOMe in the presence of a suitable palladium catalyst (palladium acetate/tri-ortho-tolylphosphine of formula Pd(OAc)$_2$/P(o-Tol)$_3$) in a non-polar solvent (e.g. toluene, benzene, hexane). Preferably, the reaction is carried out at a temperature comprised between 80° C. and 110° C. for 6 to 16 hours.

The aryl halide of formula (10) may be obtained by esterification of the corresponding acid of formula (11):

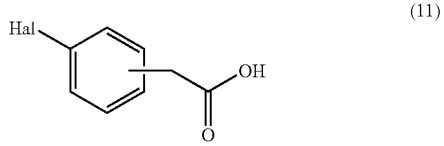

(11)

wherein Hal is as previously defined, according to any method well-known to the one skilled in the art to prepare an ester from an acid, without modifying the rest of the molecule.

In a typical procedure, the acid of formula (11) is reacted with an alcoholic solvent of formula RaOH, wherein Ra is as previously defined, in the presence of an acid such as hydrogen chloride at a temperature between 10° C. and 40° C. (room temperature) for 8 to 16 hours.

The acid of formula (11) is a commercial product.

The amine of formula (5), where $R^1$ and $R^2$ are both the same C$_1$-C$_4$ alkyl, may be prepared according to the following scheme:

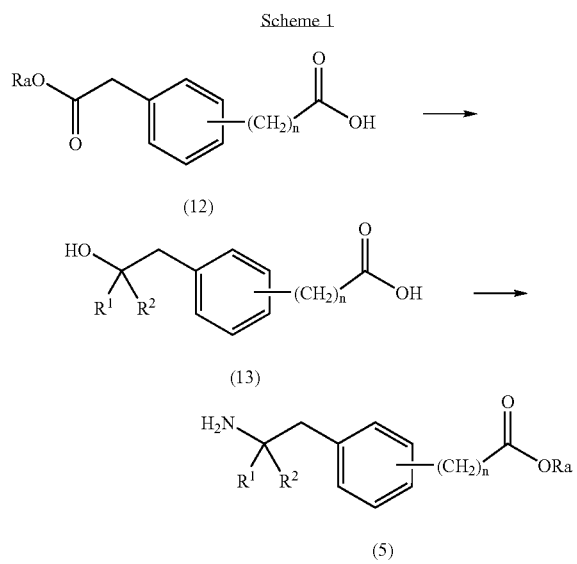

Scheme 1 wherein $R^1$, $R^2$ and Ra are as previously defined.

In a typical procedure, the ester of formula (12) is reacted with an "activated" alkyl (organometallic alkyl such as R$^2$MgBr, R$^2$MgCl or R$^2$Li) to give the corresponding tertiary alcohol of formula (13) using the method described above.

Said tertiary alcohol of formula (13) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks. The resulting amino acid is then esterified using the method described herein to give the amine of formula (5).

Alternatively, the amine of formula (5), where $R^1$ are $R^2$ both the same C$_1$-C$_4$ alkyl and n=0, may be prepared according to the following scheme:

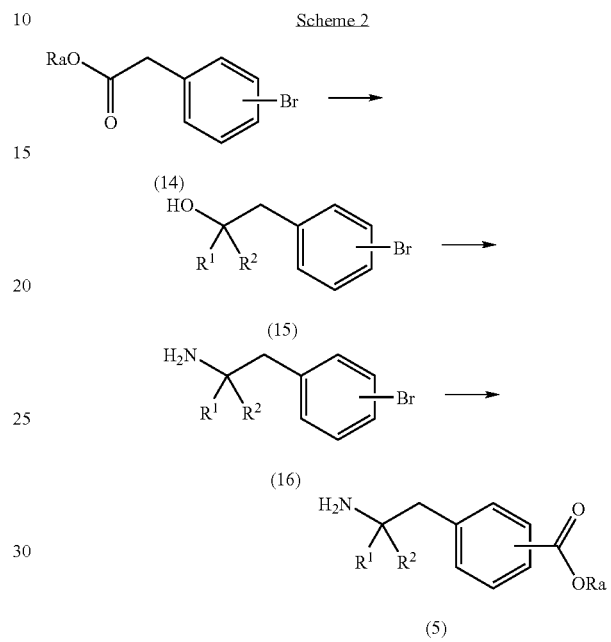

Scheme 2 wherein $R^1$, $R^2$ and Ra are as previously defined.

In a typical procedure, the ester of formula (14) is reacted with an "activated" alkyl (organometallic alkyl such as R$^2$MgBr, R$^2$MgCl or R$^2$Li) to give the corresponding tertiary alcohol of formula (15) using the method described above.

Said tertiary alcohol of formula (15) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks to give the bromo amine (16).

The resulting bromo amine (16) is treated with a suitable palladium catalyst (e.g. [1,1'-bis(diphenylphosphino)ferrocene]dichloropalladium(II)) under an atmosphere of carbon monoxide using RaOH as solvent (e.g. MeOH, EtOH) at elevated temperature (100° C.) and pressure (100 psi) to give the ester of formula (5).

The ketone of formula (9) where n=2 may be prepared by reduction of an alkene of formula (17):

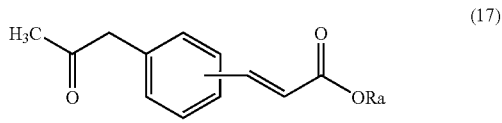

(17)

In a typical procedure, a solution of the olefin of formula (17) in a suitable solvent (e.g. methanol, ethanol, ethyl acetate) is treated with a palladium catalyst (e.g. 10% palladium on charcoal) and stirred under an atmosphere of hydrogen, optionally at elevated pressure (e.g. 60 psi), at temperature between room temperature and 60° C. for 8-24 hours.

The alkene of formula (17) may be prepared by a palladium mediated coupling of an activated olefin with an aryl halide of formula (18):

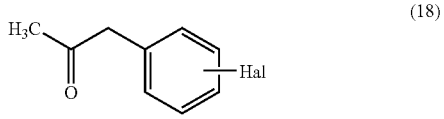

(18)

In a typical procedure, the aryl halide (18) is coupled with a vinyl ester (e.g. methyl acrylate) in the presence of a suitable palladium catalyst (e.g. tetrakis(triphenylphosphine)palladium(0) of formula Pd(PPh$_3$)$_4$, palladium acetate/tri-orthotolylphosphine of formula Pd(OAc)$_2$/P(o-tol)$_3$ or (diphenylphosphino)ferrocenyl palladium chloride of formula dppfPdCl$_2$) in a sutiable solvent (e.g. acetonitrile, N,N-dimethylformamide, toluene), optionally in the presence of a base such as triethylamine at a temperature between 40° C. and 110° C. for 8 to 24 hours.

The ketone of formula (18) is a commercial product.

The amine of formula (5), where R$^1$ and R$^2$ are both H and n is 1, may be prepared according to the following scheme:

Scheme 3

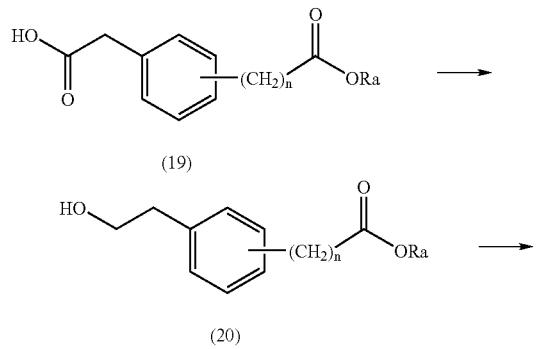

-continued

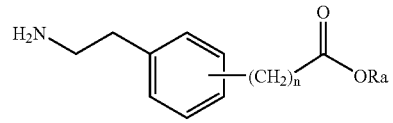

wherein R$^1$, R$^2$ and Ra are as previously defined.

In a typical procedure, the acid of formula (19) is preferentially reduced to the corresponding alcohol (20) in the presence of the ester. This may be performed by formation of the acyl imidazole or mixed anhydride and subsequent reduction with sodium borohydride or another suitable reducing agent.

Said primary alcohol of formula (20) is then converted into a leaving group such as mesylate, tosylate, bromide or iodide and displaced with appropriate amine nucleophile. The preferred nucleophile is azide ion which can then be reduced to the primary amine via hydrogenation or triphenylphosphine. Alternative nucleophiles could include ammonia or alkylamines such as benzylamine or allylamine and subsequent cleavage of the alkyl group to furnish the amine.

For some of the steps of the here above described process of preparation of the compounds of formula (1), it may be necessary to protect potential reactive functions that are not wished to react, and to cleave said protecting groups in consequence. In such a case, any compatible protecting radical can be used. In particular methods of protection and deprotection such as those described by T. W. GREENE (*Protective Groups in Organic Synthesis*, A. Wiley-Interscience Publication, 1981) or by P. J. Kocienski (*Protecting groups*, Georg Thieme Verlag, 1994), can be used.

Alternatively, compounds of general formula (1) can also be prepared according to the following scheme:

Where in R$^1$, R$^2$, Ra, Rb, Rc, n and Q$_1$ are as previously defined.

Scheme 4

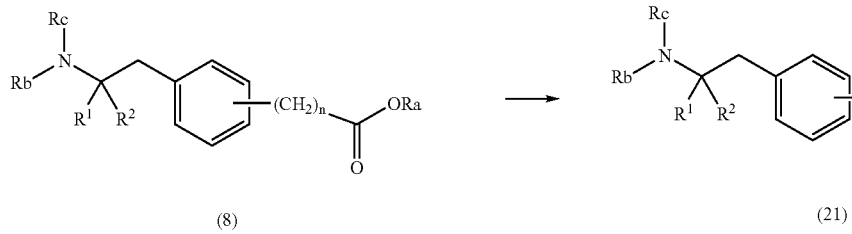

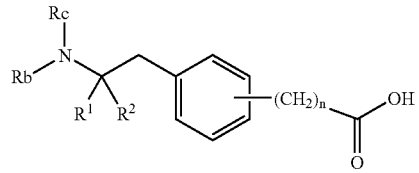

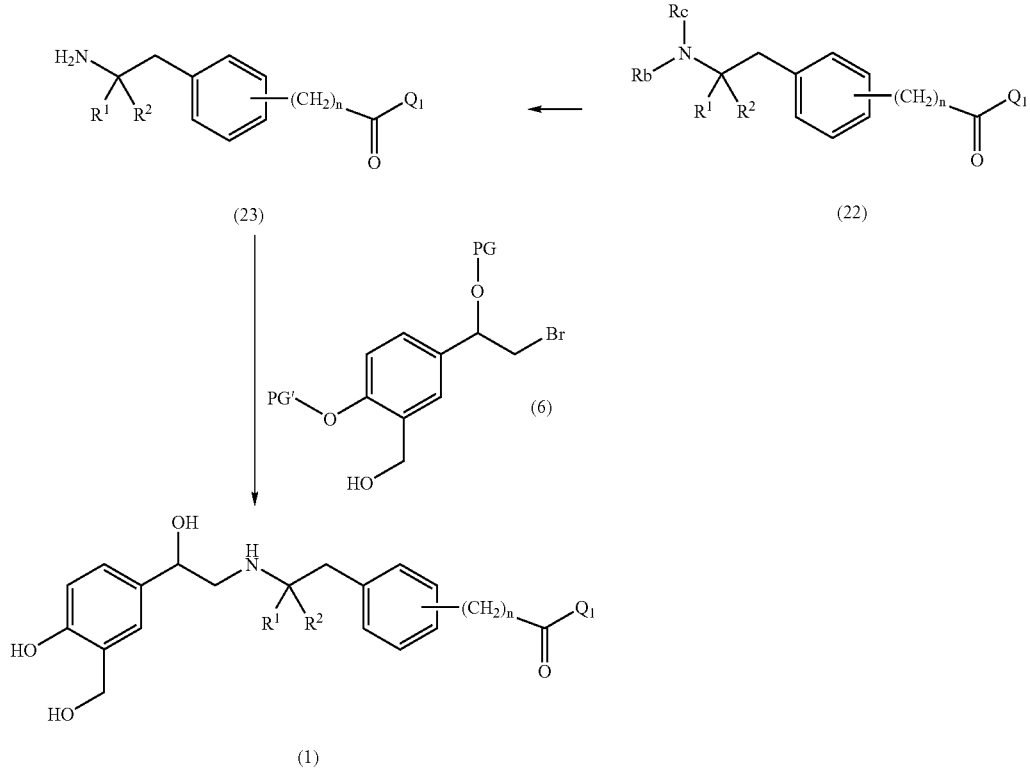

PG is a suitable bulky hydroxyl-protecting group and is preferably TBDMS.

PG' is a suitable hydroxyl-protecting group such as benzyl.

In a typical procedure, the acid of formula (21) is obtained by hydrolysis of the ester of formula (8). This is achieved by treatment with aqueous acid or base (e.g. hydrogen chloride, potassium hydroxide, sodium hydroxide or lithium hydroxide), optionally in the presence of a solvent or mixture of solvents (e.g. water, 1,4-dioxan, tetrahydrofuran/water), at a temperature comprised between 20° C. and 100° C., for a period of 1 to 40 hours.

Amide of formula (22) is prepared by coupling of acid (21) with a suitable amine of formula (3), (3') or (3"). The coupling is generally carried out in an excess of said amine as an acid receptor, with a conventional coupling agent (e.g. 2-chloro-1,3-dimethylimidazolidinum hexafluorophosphate, 1-(3-dimethylaminopropyl)-3-ethylcarbodiimide hydrochloride or N,N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or N,N-diisopropylethylamine). The reaction may be undertaken in a suitable solvent such as pyridine, N,N-dimethylformamide, tetrahydrofuran, dimethylsulfoxide, dichloromethane or ethyl acetate, and at temperature comprised between 10° C. and 40° C. (room temperature) for a period of 1-24 hours.

Said amine (3), (3') or (3") is either commercially available or may be prepared by conventional methods well known to the one skilled in the art (e.g. reduction, oxidation, alkylation, protection, deprotection etc) from commercially available material.

The amine of formula (23) can be prepared using standard methodology for cleaving nitrogen protecting groups, such as those found in the text book T. W. GREENE, Protective Groups in Organic Synthesis, A. Wiley-Interscience Publication, 1981.

When Rb or Rc=α-methylbenzyl, a typical deprotection procedure involves treatment of a solution of the protected amine of formula (22), in a suitable solvent (e.g. methanol, ethanol, ethyl acetate), with a suitable hydrogen donor such as ammonium formate or formic acid in the presence of a suitable palladium catalyst (e.g. 20% palladium hydroxide on charcoal), at a temperature between 25° C. and elevated temperature, for 1-4 hours.

Compounds of formula (1) can be obtained by reaction of said amine (23) with a bromide of formula (6). In a typical procedure amine (23) and bromide (6) can be heated together, optionally in the presence of a suitable solvent (e.g. toluene or xylene) and a suitable tertiary amine base (e.g. N-methylmorpholine, triethylamine or N,N-diisopropylethylamine) at elevated temperature, for 18-48 hours.

For some of the steps of the here above described process of preparation of the compounds of formula (1), it may be necessary to protect potential reactive hydroxyl functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of formula (1) as well as intermediate for the preparation thereof can be purified according to various well-known methods, such as for example crystallization or chromatography.

Compounds of formula (I) wherein,
$R^1$ and $R^2$ are independently selected from H and $C_1$-$C_4$ alkyl,
n is 0, 1 or 2 and,
$Q^1$ is a group selected from:

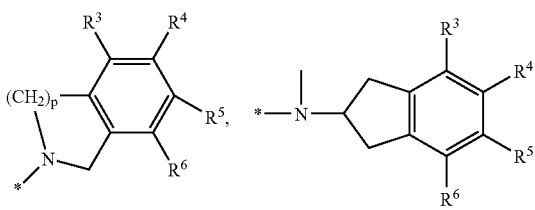

*-NH-$C_1$-$C_4$alkyl, and a group *'N($R^8$)-$Q^2$-A, wherein
$Q^2$ is a single bond or a $C_1$-$C_4$ alkylene,
$R^8$ is H or $C_1$-$C_4$ alkyl,
p is 1 or 2, and
A is a $C_3$-$C_{10}$ cycloalkyl, 2 carbon atoms or more of said cycloalkyl being optionally bridged by one or more carbon atoms, pyridyl, or a group of formula

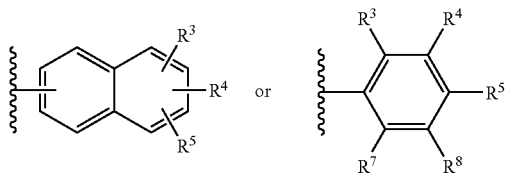

$R^3$, $R^4$ $R^5$, $R^6$ and $R^7$ are the same or different and are selected from H, $C_1$-$C_4$ alkyl, $OR^9$, $SR^9$, $SOR^9$, $SO_2R^9$, halo, CN, $CF_3$, $OCF_3$, $COOR^9$, $SO_2NR^9R^{10}$, $CONR^9R^{10}$, $NR^9R^{10}$, $NHCOR^{10}$;
$R^9$ and $R^{10}$ are the same or different and are selected from H or $C_1$-$C_4$ alkyl and the * represent the attachment point to the carbonyl group;

or, if appropriate, their pharmaceutically acceptable salts and/or isomers, tautomers, solvates or isotopic variations thereof, with the proviso that when n is 0, then $Q^1$ is not —NHCH$_3$, and, when n is 1 or 2, then:
1) $Q^1$ is *—NH—$C_1$-$C_4$alkyl, or *—N($R^8$)-$Q^2$-A where A is $C_3$-$C_{10}$ cycloalkyl, 2 carbon atoms or more of said cycloalkyl being optionally bridged by one or more carbon atoms, and/or,
2) when one of $R^1$ and $R^2$ is H, the other is not CH$_3$ are preferred A preferred *—NH-$C_1$-$C_4$alkyl is NH-isopropyl.

Preferred compounds of formula 1 are those wherein $Q^1$ is *—N($R^8$)-$Q^2$-A where A is $C_3$-$C_{10}$ cycloalkyl, 2 carbon atoms or more of said cycloalkyl being optionally bridged by one or more carbon atoms, preferably cyclohexyl, or adamantyl.

More preferably, n is 1, $Q_2$ is CH$_2$ or a bond and A is $C_3$-$C_{10}$ cycloalkyl, 2 carbon atoms or more of said cycloalkyl being optionally bridged by one or more carbon atoms, preferably cyclohexyl, or adamantyl.

Other preferred compounds of formula (I) are those wherein n is 0.

Preferably n is 0 and $Q^1$ is a group of formula

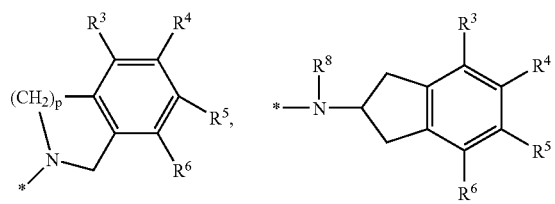

or *—N($R^8$)-$Q^2$-A, wherein $Q^2$ is a single bond or a $C_1$-$C_4$ alkylene, $R^8$ is H and A is naphthyl or

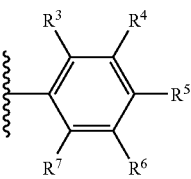

wherein $R^3$, $R^4$, $R^5$, $R^6$ and $R^7$ are the same or different and are selected from H, $C_1$-$C_4$ alkyl, $OR^9$, $SR^9$, $SOR^9$, $SO_2R^9$, halo, $CF_3$, $OCF_3$, $COOR^9$, $SO_2NR^9R^{10}$, $CONR^9R^{10}$, $NR^9R^{10}$, $NHCOR^{10}$, wherein at least 2 of $R^3$ to $R^7$ are equal to H;

wherein $R^9$ and $R^{10}$ are the same or different and are selected from H or $C_1$-$C_4$ alkyl and the * represent the attachment point to the carbonyl group.

Preferably $Q^1$ is

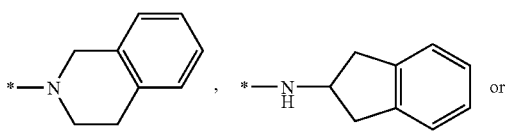

a group *—N($R^8$)-$Q^2$-A, wherein $Q^2$ is a single bond or a $C_1$-$C_4$ alkylene, $R^8$ is H or $C_1$-$C_4$ alkyl, and A is a cyclopropyl, cyclobutyl, cyclopentyl, cyclohexyl, cycloheptyl, adamantyl, naphthyl or a group of formula

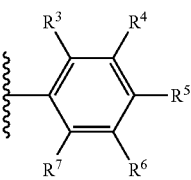

wherein $R^3$, $R^4$, $R^5$, $R^6$ and $R^7$ are as defined above.

Preferably, A is a group of formula

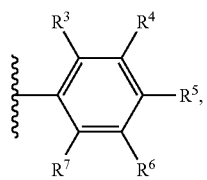

wherein $R^3$, $R^4$, $R^5$, $R^6$ and $R^7$ are selected from H, $C_1$-$C_4$ alkyl, $OR^9$, $SR^9$, Cl, F, $CF_3$, $OCF_3$, $COOR^9$, $SO_2NR^9R^{10}$, and at least 2 of $R^3$ to $R^7$ represent H, wherein $R^9$ and $R^{10}$ are the same or different and are selected from H or $C_1$-$C_4$ alkyl.

Preferably, $R^3$, $R^4$, $R^5$, $R^6$ and $R^7$ are the same or different and are selected from H, $CH_3$, OH, $OCH_3$, $SCH_3$, $OCH_2CH_3$, Cl, F, $CF_3$, $OCF_3$, COOH, $SO_2NH_2$, and at least 2 of $R^3$ to $R^7$ represent H.

Preferably, $R^3$, $R^4$, $R^5$, $R^6$ and $R^7$ are the same or different and are selected from H, $CH_3$, OH, $OCH_3$, $OCH_2CH_3$, Cl, F, $CF_3$, $OCF_3$, COOH, $SO_2NH_2$, and at least 3 of $R^3$ to $R^7$ are represent H.

Preferably, $R^8$ is H, methyl or ethyl, more preferably H.

Preferably, $Q^2$ is selected from a bond, —$CH_2$—, —$(CH_2)_2$—, —$(CH_2)_3$—, —$C(CH_3)_2$—$CH_2$—, —$CH_2$—$C(CH_3)_2$—, and —$CH(CH_3)$—.

Preferably n is 0 or 1.

In the above groups of compounds, the following substituents are preferred:

$R^1$ and $R^2$ are both $CH_3$ or, $R^1$ is H and $R^2$ is $CH_3$ or $CH_2$—$CH_3$ or, $R^1$ and $R^2$ are both H.

The compounds of formula (I) as described in the Examples section herein are particularly preferred.

According to one aspect of the present invention, the compounds of formula (1) wherein the $(CH_2)_n$—$C(=O)Q^1$ group is in position meta are generally preferred.

The compounds of formula (1) may also be optionally transformed into pharmaceutically acceptable salts. In particular, these pharmaceutically acceptable salts of the compounds of the formula (1) include the acid addition and the base salts (including disalts) thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Stahl and Wermuth, Handbook of Pharmaceutical Salts: Properties, Selection, and Use, Wiley-VCH, Weinheim, Germany (2002).

Pharmaceutically acceptable salts of compounds of formula (1) may be prepared by one or more of three methods:

(i) by reacting the compound of formula (1) with the desired acid or base;

(ii) by removing an acid- or base-labile protecting group from a suitable precursor of the compound of formula (1) or by ring-opening a suitable cyclic precursor, for example, a lactone or lactam, using the desired acid or base; or (iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labeled compounds of formula (1).

As indicated, so-called 'pro-drugs' of the compounds of formula (1) are also within the scope of the invention. Thus certain derivatives of compounds of formula (1) which may have little or no pharmacological activity themselves can, when administered into or onto the body, be converted into compounds of formula (1) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (1) with certain moieties known to those skilled in the art as 'pro-moieties' as described, for example, in "Design of Prodrugs" by H. Bundgaard (Elsevier, 1985).

Some examples of prodrugs in accordance with the invention include:

(i) where the compound of formula (1) contains a carboxylic acid functionality (—COOH), an ester thereof, for example, a compound wherein the hydrogen of the carboxylic acid functionality of the compound of formula (1) is replaced by ($C_1$-$C_8$)alkyl;

(ii) where the compound of formula (1) contains an alcohol functionality (—OH), an ether thereof, for example, a compound wherein the hydrogen of the alcohol functionality of the compound of formula (1) is replaced by ($C_1$-$C_6$)alkanoyloxymethyl; and (iii) where the compound of formula (1) contains a primary or secondary amino functionality (—$NH_2$ or —NHR where R≠H), an amide thereof, for example, a compound wherein, as the case may be, one or both hydrogens of the amino functionality of the compound of formula (1) is/are replaced by ($C_1$-$C_{10}$)alkanoyl.

Further examples of replacement groups in accordance with the foregoing examples and examples of other prodrug types may be found in the aforementioned references.

Moreover, certain compounds of formula (1) may themselves act as prodrugs of other compounds of formula (1).

Also included within the scope of the invention are metabolites of compounds of formula (1), that is, compounds formed in vivo upon administration of the drug. Some examples of metabolites in accordance with the invention include (i) where the compound of formula (1) contains a methyl group, an hydroxymethyl derivative thereof (—$CH_3$→—$CH_2OH$):

(ii) where the compound of formula (1) contains an alkoxy group, an hydroxy derivative thereof (—OR→—OH);

(iii) where the compound of formula (1) contains a tertiary amino group, a secondary amino derivative thereof (—$NR^1R^2$→—$NHR^1$ or —$NHR^2$);

(iv) where the compound of formula (1) contains a secondary amino group, a primary derivative thereof (—$NHR^1$→—$NH_2$);

(v) where the compound of formula (1) contains a phenyl moiety, a phenol derivative thereof (-Ph→-PhOH); and (I).(vi) where the compound of formula (1) contains an amide group, a carboxylic acid derivative thereof (—$CONH_2$→COOH).

Compounds of formula (1) containing one or more asymmetric carbon atoms can exist as two or more stereoisomers. Where a compound of formula (1) contains an alkenyl or alkenylene group, geometric cis/trans (or Z/E) isomers are possible. Where the compound contains, for example, a keto or structural isomers are interconvertible via a low oxime group or an aromatic moiety, energy barrier, tautomeric isomerism ('tautomerism') can occur. This can take the form of proton tautomerism in compounds of formula (1) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (1), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (1) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, New York, 1994).

According to one aspect of the present invention, the (R,R)-stereoisomer of the formula below wherein $R^1$ is hydrogen and $R^2$ is $C_1$-$C_4$ alkyl, preferably methyl, and n and $Q^1$ are as defined above, is generally preferred: is generally preferred:

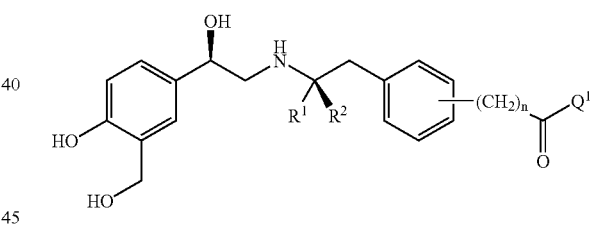

wherein n and $Q^1$ are as defined above for compounds of formula (1).

The present invention includes all pharmaceutically acceptable isotopically-labelled compounds of formula (1) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (1), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (1) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

The compounds of formula (1), their pharmaceutically acceptable salts and/or derived forms, are valuable pharmaceutically active compounds, which are suitable for the therapy and prophylaxis of numerous disorders in which the β2 receptor is involved or in which agonism of this receptor may induce benefit, in particular the allergic and non-allergic airways diseases but also in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

The compounds of formula (1) and their pharmaceutically acceptable salts and derived forms as mentioned above can be administered according to the invention to animals, preferably to mammals, and in particular to humans, as pharmaceuticals for therapy and/or prophylaxis. They can be administered per se, in mixtures with one another or in the form of pharmaceutical preparations which as active constituent contain an efficacious dose of at least one compounds of formula (1), its pharmaceutically acceptable salts and/or derived forms, in addition to customary pharmaceutically innocuous excipients and/or additives.

The compounds of formula (1), their pharmaceutically acceptable salts and/or derived forms may be freeze-dried, spray-dried, or evaporatively dried to provide a solid plug, powder, or film of crystalline or amorphous material. Microwave or radio frequency drying may be used for this purpose.

The compounds of formula (1), their pharmaceutically acceptable salts and/or derived forms may be administered alone or in combination with other drugs and will generally be administered as a formulation in association with one or more pharmaceutically acceptable excipients. The term "excipient" is used herein to describe any ingredient other than the compound of the invention. The choice of excipient will to a large extent depend on the particular mode of administration.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate nd polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (1), a film-forming polymer, a binder, a solvent, a humectant, a plasticiser, a stabiliser or emulsifier, a viscosity-modifying agent and a solvent. Some components of the formulation may perform more than one function.

The compound of formula (1) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (1) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology Online, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (1) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semisolid, or thixotropic liquid for administration as an implanted depot providing modified release of the active compound. Examples of such formulations include drug-coated stents and PGLApoly(dl-lactic-coglycolic) acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (1), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (1). The overall daily dose will typically be in the range 0.001 mg to 40 mg which may be administered in a single dose or, more usually, as divided doses throughout the day.

The compounds of formula (1) are particularly suitable for an administration by inhalation.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (1) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

Where used herein, the term "treatment" includes curative, palliative and prophylactic treatment.

According to another embodiment of the present invention, the compounds of the formula (1), or pharmaceutically acceptable salts, derived forms or compositions thereof, can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough. The second and more additional therapeutic agents may also be a compound of formula (1), or a pharmaceutically acceptable salt, derived forms or compositions thereof, or one or more β2 agonists known in the art. More typically, the second and more therapeutic agents will be selected from a different class of therapeutic agents.

As used herein, the terms "co-administration", "co-administered" and "in combination with", referring to the compounds of formula (1) and one or more other therapeutic agents, is intended to mean, and does refer to and include the following:

simultaneous administration of such combination of compound(s) of formula (1) and therapeutic agent(s) to a patient in need of treatment, when such components are formulated together into a single dosage form which releases said components at substantially the same time to said patient, substantially simultaneous administration of such combination of compound(s) of formula (1) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (1) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (1) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (1), or pharmaceutically acceptable salts, derived forms or compositions thereof, include, but are by no means limited to:

(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Histamine receptor antagonists including H1 and H3 antagonists,
(d) $\alpha_1$- and $\alpha_2$-adrenoceptor agonist vasoconstrictor sympathomimetic agents for decongestant use,
(e) muscarinic M3 receptor antagonists or anticholinergic agents,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids, such as DAGR (dissociated agonists of the corticoid receptor)
(k) Monoclonal antibodies active against endogenous inflammatory entities,
(l) Anti-tumor necrosis factor (anti-TNF-$\alpha$) agents,
(m) Adhesion molecule inhibitors including VLA-4 antagonists,
(n) Kinin-$B_1$- and $B_2$-receptor antagonists,
(o) Immunosuppressive agents,
(p) Inhibitors of matrix metalloproteases (MMPs),
(q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NF$\kappa\beta$ pathway, e.g. IKK inhibitors,
(w) modulators of cytokine signalling pathways such as p38 MAP kinase, syk kinase or JAK kinase inhibitor,
(x) Agents that can be classed as mucolytics or anti-tussive,
(y) Antibiotics,
(z) HDAC inhibitors, and,
(aa) PI3 kinase inhibitors.

According to the present invention, combination of the compounds of formula (1) with
H3 antagonists,
Muscarinic M3 receptor antagonists,
PDE4 inhibitors,
glucocorticosteroids,
Adenosine A2a receptor agonists,
Modulators of cytokine signalling pathyways such as p38 MAP kinase or syk kinase, or,
Leukotriene antagonists (LTRAs) including antagonists of $LTB_4$, $LTC_4$, $LTD_4$, and $LTE_4$, are preferred.

According to the present invention, combination of the compounds of formula (1) with
glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate, or
muscarinic M3 receptor antagonists or anticholinergic agents including in particular ipratropium salts, namely bromide, tiotropium salts, namely bromide, oxitropium salts, namely bromide, perenzepine, and telenzepine, are further preferred.

It is to be appreciated that all references herein to treatment include curative, palliative and prophylactic treatment. The description, which follows, concerns the therapeutic applications to which the compounds of formula (1) may be put.

The compounds of formula (1) have the ability to interact with the P2 receptor and thereby have a wide range of therapeutic applications, as described further below, because of the essential role which the $\beta 2$ receptor plays in the physiology of all mammals.

Therefore, a further aspect of the present invention relates to the compounds of formula (1), or pharmaceutically acceptable salts, derived forms or compositions thereof, for use in the treatment of diseases, disorders, and conditions in which the $\beta 2$ receptor is involved. More specifically, the present invention also concerns the compounds of formula (1), or pharmaceutically acceptable salts, derived forms or compositions thereof, for use in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A still further aspect of the present invention also relates to the use of the compounds of formula (1), or pharmaceutically acceptable salts, derived forms or compositions thereof, for the manufacture of a drug having a β2 agonist activity. In particular, the present inventions concerns the use of the compounds of formula (1), or pharmaceutically acceptable salts, derived forms or compositions thereof, for the manufacture of a drug for the treatment of $\beta_2$-mediated diseases and/or conditions, in particular the diseases and/or conditions listed above.

As a consequence, the present invention provides a particularly interesting method to treat a mammal, including a human being, with an effective amount of a compound of formula (1), or a pharmaceutically acceptable salt, derived form or composition thereof. More precisely, the present invention provides a particularly interesting method for the treatment of a β2-mediated diseases and/or conditions in a mammal, including a human being, in particular the diseases and/or conditions listed above, comprising admidministering said mammal with an effective amount of a compound of formula (1), its pharmaceutically acceptable salts and/or derived forms.

The following examples illustrate the preparation of the compounds of the formula (1):

EXAMPLE 1

N-cycloheptyl-2-{3-[(2R)-2-({(2R)-2-hydroxy-2-[4-hydroxy-3-(hydroxymethyl)phenyl]ethyl}amino)propyl]phenyl}acetamide

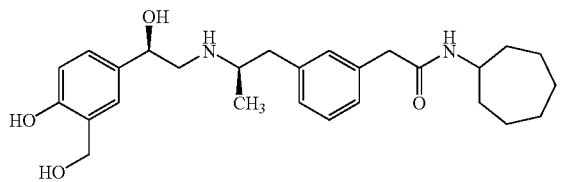

Ammonium fluoride (98 mg, 2.64 mmol) was added in one portion to a stirred solution of 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-cycloheptylacetamide (Preparation 1) (150 mg, 0.26 mmol) in methanol (3 ml) and water (1.5 ml) at room temperature. The reaction was heated at 40° C. for 18 hours and then allowed to cool to room temperature. The solvent was removed in vacuo and the residue dissolved in ethyl acetate (30 ml) and water (20 ml), the organic layer was separated, washed with brine (10 ml), dried (magnesium sulfate) and the solvent removed in vacuo to yield a clear oil. This was purified by flash column chromatography on silica gel eluting with dichloromethane:methanol: ammonia (90:10:1 by volume) to furnish the title compound as a white foam (87 mg).

$^1$H NMR (400 MHz, CD$_3$OD): δ=7.25-7.00 (6H, m), 6.85 (1H, d), 4.58 (3H, m), 3.80 (1H, m), 3.40 (2H, s), 2.95 (2H, m), 2.75 (2H, m), 2.58 (1H, m), 1.83 (2H, m), 1.70-1.40 (10H, m), 1.05 (3H, d) ppm. LRMS (electrospray): m/z [M+Na]$^+$ 477, [M−H]$^−$ 453.

EXAMPLE 2

N-(cyclohexylmethyl)-2-{3-[(2R)-2-({(2R)-2-hydroxy-2-[4-hydroxy-3-(hydroxymethyl)phenyl]ethyl}amino)propyl]phenyl}-N-methylacetamide

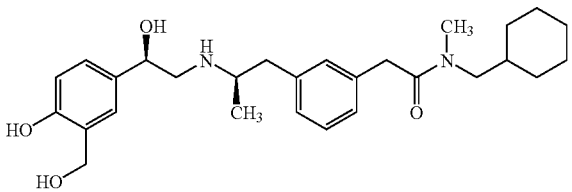

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(cyclohexylmethyl)-N-methylacetamide (Preparation 2) using the method for example 1 to give the title compound as a white foam.

$^1$H NMR (400 MHz, CD$_3$OD): δ=7.21 (2H, m), 7.00 (4H, m), 6.68 (1H, d), 4.61 (3H, m), 3.71 (2H, s), 3.31 (2H, m), 3.20 (2H, m), 2.91 (5H, m), 2.71 (2H, m), 2.60 (1H, m), 1.70 (5H, m), 1.22 (4H, m), 1.04 (3H, d), 0.95 (2H, m) ppm. LRMS (electrospray): m/z [M+H]$^+$ 469, [M+Na]$^+$ 491.

EXAMPLE 3

N-[(1S)-1-cyclohexylethyl]-2-{3-[(2R)-2-({(2R)-2-hydroxy-2-[4-hydroxy-3-(hydroxymethyl)phenyl]ethyl}amino)propyl]phenyl}acetamide

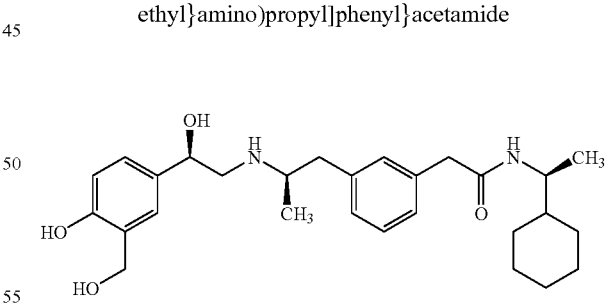

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-[(1S)-1-cyclohexylethyl]acetamide (Preparation 3) using the method for example 1 to give the title compound as a white foam.

$^1$H NMR (400 MHz, CD$_3$OD): δ=7.20 (4H, m), 7.01 (2H, dd), 6.71 (1H, d), 4.60 (3H, m), 3.62 (1H, m), 3.48 (1H, d), 3.41 (1H, d), 2.85 (2H, m), 2.63 (2H, m), 2.58 (1H, dd), 1.60 (5H, m), 1.40-1.02 (10H, m), 0.93 (2H, m) ppm. LRMS (electrospray): m/z [M+H]$^+$ 469, [M+Na]$^+$ 491.

EXAMPLE 4

2-{3-[(2R)-2-({(2R)-2-hydroxy-2-[4-hydroxy-3-(hydroxymethyl)phenyl]ethyl}amino)propyl]phenyl}-N-isopropylacetamide

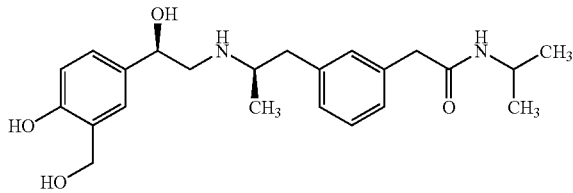

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-isopropylacetamide (Preparation 4) using the method for example 1 to give the title compound as a white foam.

$^1$H NMR (400 MHz, CD$_3$OD): δ=7.22 (1H, d), 7.18-7.16 (1H, d), 7.12-7.10 (1H, d), 7.07 (1H, s), 7.04-6.99 (2H, t), 6.71-6.69 (1H, d), 4.63-4.60 (3H, m), 3.97-3.90 (1H, m), 3.41 (2H, s), 2.98-2.93 (1H, q), 2.91-2.86 (1H, dd), 2.74-2.70 (2H, dd), 2.60-2.55 (1H, dd), 1.13-1.11 (6H, d), 1.08-1.07 (3H, d) ppm. LRMS (electrospray): m/z [M+H]$^+$ 401, [M−H]$^-$ 399.

EXAMPLE 5

N-cyclopentyl-2-{3-[(2R)-2-({(2R)-2-hydroxy-2-[4-hydroxy-3-(hydroxymethyl)phenyl]ethyl}amino)propyl]phenyl}acetamide

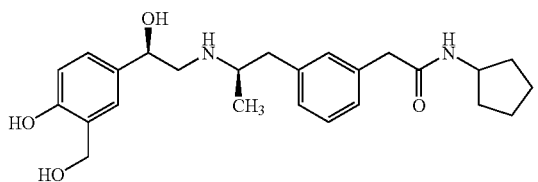

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-cyclopentylacetamide (Preparation 5) using the method for example 3 to give the title compound as a white foam.

$^1$H NMR (400 MHz, CD$_3$OD): δ=7.22 (1H, d), 7.18-7.16 (1H, d), 7.11-7.09 (1H, d), 7.06 (1H, s), 7.04-6.98 (2H, t), 6.71-6.69 (1H, d), 4.63-4.60 (3H, m), 4.10-4.04 (1H, m), 3.42 (2H, s), 2.98-2.93 (1H, q), 2.90-2.85 (1H, dd), 2.74-2.69 (2H, dd), 2.60-2.55 (1H, dd), 1.94-1.86 (2H, m), 1.73-1.65 (2H, m), 1.62-1.54 (2H, m), 1.47-1.39 (2H, m), 1.08-1.07 (3H, d), ppm. LRMS (electrospray): m/z [M+H]$^+$ 427, [M−H]$^-$ 425. CHN analysis: found C, 68.48%; H, 8.20%; N, 6.35%. C$_{25}$H$_{34}$N$_2$O$_4$+0.66H$_2$O requires C, 68.49%; H, 8.12%; N, 6.39%.

EXAMPLE 6

N-(cyclobutylmethyl)-2-{3-[(2R)-2-({(2R)-2-hydroxy-2-[4-hydroxy-3-(hydroxymethyl)phenyl]ethyl}amino)propyl]phenyl}acetamide

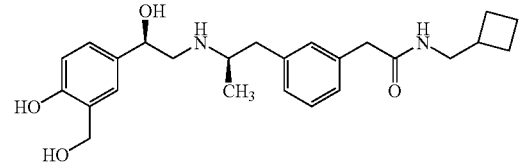

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(cyclobutylmethyl)acetamide (Preparation 6) using the method for example 1 to give the title compound as a white foam.

$^1$H NMR (400 MHz, CD$_3$OD): δ=7.22 (1H, d), 7.18-7.16 (1H, d), 7.12-7.10 (1H, d), 7.07 (1H, s), 7.04-6.99 (2H, t), 6.71-6.69 (1H, d), 4.62-4.59 (3H, m), 3.44 (2H, s), 3.18-3.17 (2H, d), 2.97-2.92 (1H, q), 2.90-2.85 (1H, dd), 2.73-2.69 (2H, dd), 2.60-2.55 (1H, dd), 2.50-2.43 (1H, m), 2.04-1.97 (2H, m), 1.92-1.78 (2H, m), 1.72-1.63 (2H, m), 1.08-1.06 (3H, d), ppm. LRMS (electrospray): m/z [M+H]$^+$ 427, [M−H]$^-$ 425. CHN analysis: found C, 68.24%; H, 8.09%; N, 6.39%. C$_{25}$H$_{34}$N$_2$O$_4$+0.75H$_2$O requires C, 68.23%; H, 8.13%; N, 6.37%.

EXAMPLE 7

N-(cyclopentylmethyl)-2-{3-[(2R)-2-({(2R)-2-hydroxy-2-[4-hydroxy-3-(hydroxymethyl)phenyl]ethyl}amino)propyl]phenyl}acetamide

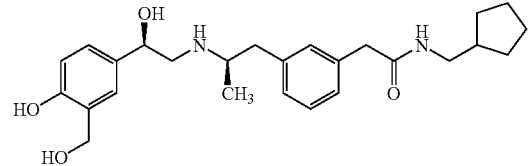

Prepared from 2-{3-[(2R)-2-({(2R)-2-{([tert-butyl(dimethyl)silyl]oxy}-2-[4-hydroxy-3-(hydroxymethyl )phenyl]ethyl}amino)propyl]phenyl}-N-(cyclopentylmethyl)acetamide (Preparation 7) using the method for example 1 to give the title compound as a white foam.

$^1$H NMR (400 MHz, CD$_3$OD): δ=7.22 (1H, d), 7.19-7.17 (1H, d), 7.12-7.11 (1H, d), 7.08 (1H, s), 7.04-7.00 (2H, t), 6.71-6.69 (1H, d), 4.63-4.60 (3H, m), 3.44 (2H, s), 3.10-3.08 (2H, d), 2.98-2.94 (1H, q), 2.90-2.85 (1H, dd), 2.74-2.70 (2H, dd), 2.60-2.55 (1H, dd), 2.07-2.00 (1H, m), 1.73-1.66 (2H, m), 1.62-1.46 (4H, m), 1.22-1.12 (2H, m), 1.08-1.07 (3H, d), ppm. LRMS (electrospray): m/z [M+H]$^+$ 441, [M−H]$^-$ 439. CHN analysis: found C, 69.12%; H, 8.19%; N, 6.26%. C$_{26}$H$_{36}$N$_2$O$_4$+0.62H$_2$O requires C, 69.13%; H, 8.31%; N, 6.20%.

EXAMPLE 8

N-cyclohexyl-2-{3-[(2R)-2-({(2R)-2-hydroxy-2-[4-hydroxy-3-(hydroxymethyl)phenyl]ethyl}amino)propyl]phenyl}acetamide

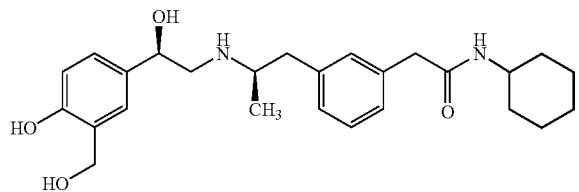

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-cyclohexylacetamide (Preparation 8) using the method for example 1 to give the title compound as a white foam.

$^1$H NMR (400 MHz, CD$_3$OD): δ=7.22 (1H, d), 7.19-7.17 (1H, d), 7.12-7.10 (1H, d), 7.07 (1H, s), 7.04-6.99 (2H, t), 6.71-6.69 (1H, d), 4.64-4.60 (3H, m), 3.64-3.56 (1H, m), 3.42 (2H, s), 3.00-2.94 (1H, q), 2.91-2.86 (1H, dd), 2.76-2.72 (2H, dd), 2.61-2.56 (1H, dd), 1.86-1.80 (2H, m), 1.75-1.70 (2H, m), 1.65-1.59 (1H, m), 1.38-1.28 (2H, m), 1.25-1.15 (3H, m), 1.09-1.07 (3H, d), ppm. LRMS (electrospray): m/z [M+H]$^+$ 441, [M–H]$^-$ 439. CHN analysis: found C, 68.49%; H, 8.27%; N, 6.14%. C$_{26}$H$_{36}$N$_2$O$_4$+0.85H$_2$O requires C, 68.50%; H, 8.34%; N, 6.14%.

EXAMPLE 9

N-cyclobutyl-2-{3-[(2R)-2-({(2R)-2-hydroxy-2-[4-hydroxy-3-(hydroxymethyl)phenyl]ethyl}amino)propyl]phenyl}acetamide

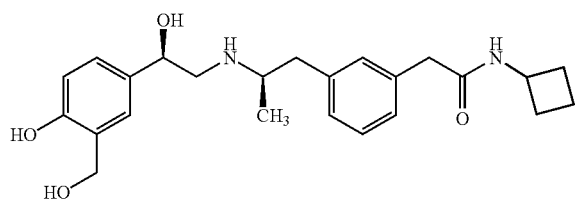

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-cyclobutylacetamide (Preparation 9) using the method for example 1 to give the title compound as a white foam.

$^1$H NMR (400 MHz, CD$_3$OD): δ=7.21 (1H, d), 7.18-7.16 (1H, d), 7.11-7.09 (1H, d), 7.06 (1H, s), 7.03-6.98 (2H, t), 6.70-6.68 (1H, d), 4.62-4.59 (3H, m), 4.29-4.21 (1H, m), 3.40 (2H, s), 2.88-2.43 (1H, q), 2.90-2.85 (1H, dd), 2.73-2.68 (2H, m), 2.61-2.56 (1H, dd), 2.29-2.21 (2H, m), 1.98-1.89 (2H, m), 1.76-1.66 (2H, m), 1.08-1.07 (3H, d), ppm. LRMS (electrospray): m/z [M+H]$^+$ 413, [M–H]$^-$ 411. CHN analysis: found C, 67.18%; H, 7.75%; N, 6.51%. C$_{24}$H$_{32}$N$_2$O$_4$+0.93H$_2$O requires C, 67.15%; H, 7.95%; N, 6.53%.

EXAMPLE 10

N-(cyclohexylmethyl)-2-{3-[(2R)-2-({(2R)-2-hydroxy-2-[4-hydroxy-3-(hydroxymethyl)phenyl]ethyl}amino)propyl]phenyl}acetamide

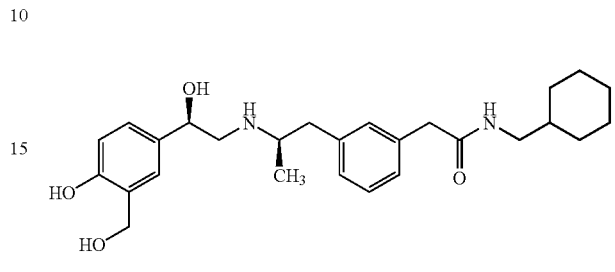

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(cyclohexylmethyl)acetamide (Preparation 10) using the method for example 1 to give the title compound as a yellow foam.

$^1$H NMR (400 MHz, CD$_3$OD): δ=7.21-7.20 (1H, m), 7.18-7.16 (1H, d), 7.11-7.09 (1H, d), 7.06 (1H, s), 7.02-6.98 (2H, t), 6.70-6.68 (1H, d), 4.61-4.58 (3H, m), 3.44 (2H, s), 2.99-2.98 (2H, d), 2.94-2.83 (2H, m), 2.71-2.67 (2H, q), 2.58-2.53 (1H, dd), 1.70-1.60 (5H, m), 1.49-1.40 (1H, m), 1.26-1.12 (3H, m), 1.06-1.05 (3H, d), 0.93-0.83 (2H, m) ppm. LRMS (electrospray): m/z [M+H]$_+$ 455, [M+Na]$^+$ 477, [M–H]$^-$ 453. CHN analysis: found C, 70.07%; H, 8.50%; N, 6.17%. C$_{27}$H$_{38}$N$_2$O$_4$+0.45H$_2$O requires C, 70.09%; H, 8.47%; N, 6.05%.

EXAMPLE 11

N-(cyclopropylmethyl)-2-{3-[(2R)-2-({(2R)-2-hydroxy-2-[4-hydroxy-3-(hydroxymethyl)phenyl]ethyl}amino)propyl]phenyl}acetamide

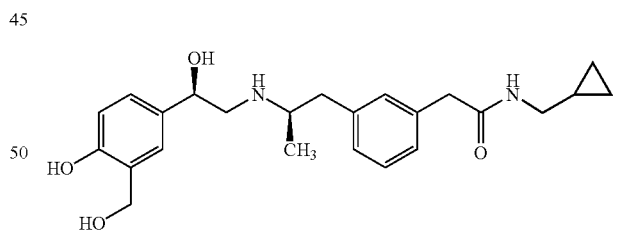

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(cyclopropylmethyl)acetamide (Preparation 11) using the method for example 1 to give the title compound as a white foam.

$^1$H NMR (400 MHz, CD$_3$OD): δ=7.21-7.16 (2H, m), 7.12-7.10 (1H, d), 7.07 (1H, s), 7.02-6.98 (2H, m), 6.70-6.68 (1H, d), 4.61-4.58 (3H, m), 3.45 (2H, s), 3.03-3.01 (2H, d), 2.95-2.83 (2H, m), 2.71-2.67 (2H, m), 2.59-2.54 (1H, m), 1.07-1.06 (3H, d), 0.97-0.90 (1H, m), 0.48-0.43 (2H, q), 0.19-0.15 (2H, q) ppm. LRMS (electrospray): m/z [M+H]$^+$ 413, [M+Na]$^+$ 435, [M–H]$^-$ 411. CHN analysis: found C, 67.85%;

H, 7.82%; N, 6.48%. $C_{24}H_{32}N_2O_4+0.70H_2O$ requires C, 67.80%; H, 7.92%; N, 6.59%.

EXAMPLE 12

N-(cycloheptylmethyl)-2-{3-[(2R)-2-({(2R)-2-hydroxy-2-[4-hydroxy-3-(hydroxymethyl)phenyl]ethyl}amino)propyl]phenyl}acetamide

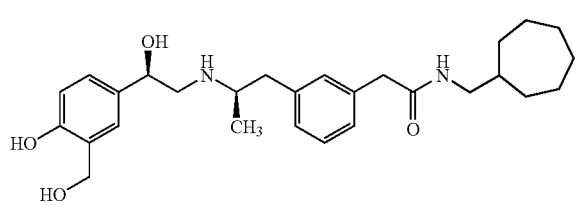

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(cycloheptylmethyl)acetamide (Preparation 12) using the method for example 1 to give the title compound as a white foam.

$^1$H NMR (400 MHz, CD$_3$OD): δ=7.24-6.95 (6H, m), 6.72-6.69 (1H, d), 4.62 (2H, s), 4.62-4.59 (1H, m), 3.26 (2H, s), 3.00-2.97 (2H, d), 2.98-2.54 (m, 5H), 1.70-1.02 (m, 13H), 1.05 (3H, d) ppm. LRMS (electrospray): m/z [M+H]$^+$ 469.

EXAMPLE 13

N-1-adamantyl-2-{3-[(2R)-2-({(2R)-2-hydroxy-2-[4-hydroxy-3-(hydroxymethyl)phenyl]ethyl}amino)propyl]phenyl}acetamide

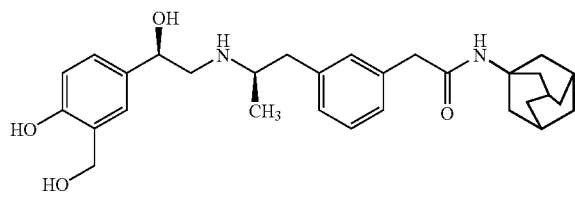

Prepared from N-1-adamantyl-2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}acetamide (Preparation 13) using the method for example 1 to give the title compound as a white foam. $^1$H NMR (400 MHz, CD$_3$OD): δ=7.22-6.96 (6H, m), 6.68-6.65 (1H, d), 4.63-4.59 (3H, m), 3.38 (2H, s), 2.98-2.92 (1H, q), 2.88-2.54 (4H, m), 2.02 (3H, s), 2.00 (6H, s), 1.68 (6H, s), 1.05-1.03 (3H, d) ppm. LRMS (electrospray): m/z [M−H]$^-$ 491.

EXAMPLE 14

N-(1-adamantylmethyl)-2-{3-[(2R)-2-({(2R)-2-hydroxy-2-[4-hydroxy-3-(hydroxymethyl)phenyl]ethyl}amino)propyl]phenyl}acetamide

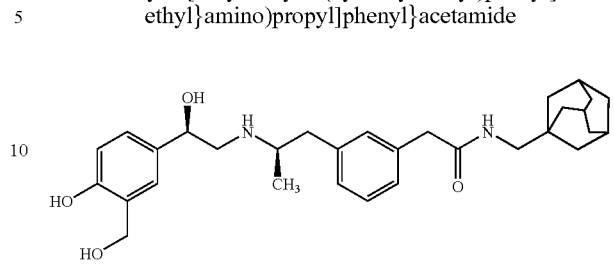

Prepared from N-(1-adamantylmethyl )-2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}acetamide (Preparation 14) using the method for example 1 to give the title compound as a white foam. $^1$H NMR (400 MHz, CD$_3$OD): δ=7.22-7.12 (5H, m), 7.06-7.00 (1H, t), 6.72-6.70 (1H, d), 4.62-4.59 (1H, m), 4.61 (2H, s), 3.46 (2H, s), 2.98-2.92 (1H, q), 2.91-2.54 (6H, m), 2.90 (3H, s), 1.68-1.56 (6H, m), 1.42 (6H, s), 1.06-1.04 (3H, d) ppm. LRMS (electrospray): m/z [M+H]$^+$ 507, [M+Na]$^+$ 529.

EXAMPLE 15

N-2-adamantyl-2-{3-[(2R)-2-({(2R)-2-hydroxy-2-[4-hydroxy-3-(hydroxymethyl)phenyl]ethyl}amino)propyl]phenyl}acetamide

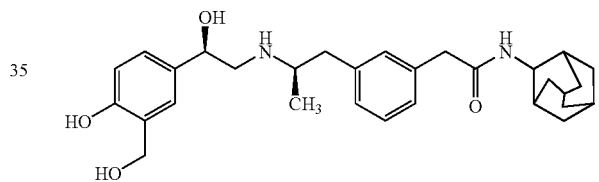

Prepared from N-2-adamantyl-2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}acetamide (Preparation 15) using the method for example 1 to give the title compound as a white foam. $^1$H NMR (400 MHz, CD$_3$OD): δ=7.24-7.10 (5H, m), 7.05-6.98 (1H, t), 6.70-6.68 (2H, d), 4.61 (2H, s), 4.62-4.58 (1H, m), 3.94 (1H, s), 3.54 (2H, s), 2.96-2.52 (5H, m), 1.96-1.75 (12H, m), 1.62-1.56 (2H, d), 1.05-1.03 (3H, d) ppm. LRMS (electrospray): m/z [M−H]$^-$ 491.

EXAMPLE 16

N-(2-cyclohexylethyl)-2-{3-[(2R)-2-({(2R)-2-hydroxy-2-[4-hydroxy-3-(hydroxymethyl)phenyl]ethyl}amino)propyl]phenyl}-N-methylacetamide

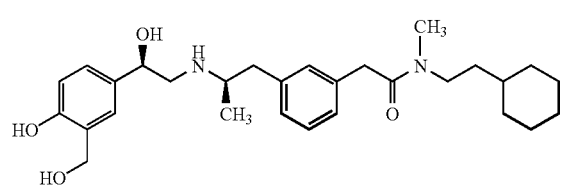

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(2-cyclohexylethyl)-N-methylacetamide (Preparation 16) using the method for example 1 to give the title compound as a white foam.

$^1$H NMR (400 MHz, CD$_3$OD): δ=7.23-7.00 (6H, m), 6.71-6.68 (1H, d), 4.61 (2H, s), 4.61-4.57 (1H, m), 3.71-3.68 (2H, m), 4.61-4.57 (1H, m), 3.71-3.68 (2H, m), 3.43-3.26 (2H, m), 2.97-2.52 (8H, m), 1.78-0.82 (13H, m), 1.08-1.06 (3H, d) ppm. LRMS (electrospray): m/z [M+Na]$^+$ 505, [M−H]$^−$ 491.

EXAMPLE 17

N-cycloheptyl-2-{3-[(2R)-2-({(2R)-2-hydroxy-2-[4-hydroxy-3-(hydroxymethyl)phenyl]ethyl}amino)propyl]phenyl}-N-methylacetamide

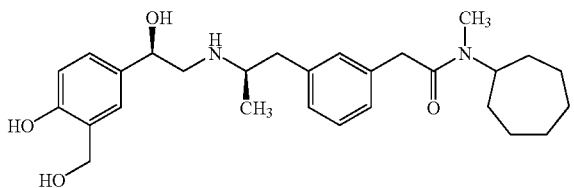

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-cycloheptyl-N-methylacetamide (Preparation 17) using the method for example 1 to give the title compound as a white foam.

$^1$H NMR (400 MHz, CD$_3$OD): δ=7.23-6.96 (6H, m), 6.72-6.64 (1H, dd), 4.62-4.60 (2H, d), 4.61-4.58 (1H, m), 4.58-4.51 (0.5H, m), 3.70-3.63 (0.5H, m), 3.75-3.67 (2H, d), 2.95-2.50 (5H, m), 2.82-2.78 (3H, d), 1.72-1.20 (12H, m), 1.02-1.00 (3H, 2d) ppm. LRMS (electrospray): m/z [M+Na]$^+$ 491.

EXAMPLE 18

N-cyclohexyl-N-ethyl-2-{3-[(2R)-2-({(2R)-2-hydroxy-2-[4-hydroxy-3-(hydroxymethyl)phenyl]ethyl}amino)propyl]phenyl}acetamide

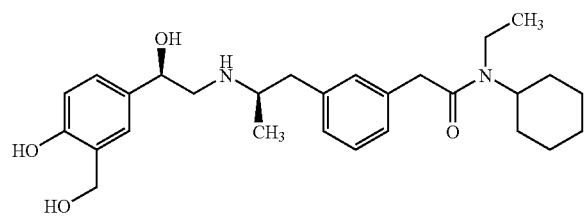

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-cyclohexyl-N-ethylacetamide (Preparation 18) using the method for example 1 to give the title compound as a white foam.

$^1$H NMR (400 MHz, CD$_3$OD): δ=7.25-6.98 (6H, m), 6.70-6.67 (1H, d), 4.61 (2H, s), 4.60-4.57 (1H, m), 3.72 (2H, s), 3.65-3.61 (1H, m), 3.30-3.24 (2H, q), 2.95-2.50 (5H, m), 1.84-1.08 (10H, m), 1.12-1.08 (3H, t), 1.04-1.02 (3H, d) ppm. LRMS (electrospray): m/z [M+Na]$^+$ 491.

EXAMPLE 19

N-(2-cyclohexylethyl)-2-{3-[(2R)-2-({(2R)-2-hydroxy-2-[4-hydroxy-3-(hydroxymethyl)phenyl]ethyl}amino)propyl]phenyl}acetamide

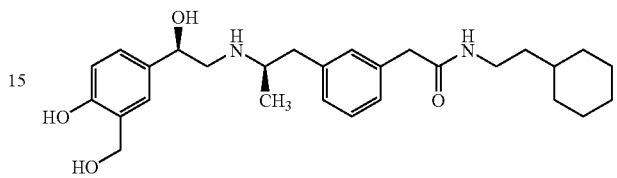

Prepared from 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(2-cyclohexylethyl)acetamide (Preparation 19) using the method for example 1 to give the title compound as a white foam. $^1$H NMR (400 MHz, CD$_3$OD): δ=7.22-6.98 (6H, m), 6.68-6.66 (1H, d), 4.61 (2H, s), 4.60-4.58 (1H, m), 3.42 (2H, s), 3.20-3.16 (2H, t), 2.96-2.56 (5H, m), 1.73-1.60 (5H, m), 1.40-1.35 (2H, q), 1.30-1.12 (4H, m), 1.07-1.05 (3H, d), 0.92-0.81 (2H, m) ppm. LRMS (electrospray): m/z [M+Na]$^+$ 491.

EXAMPLE 20

N-(4-chlorobenzyl)-2-{3-[2-({(2R)-2-hydroxy-2-[4-hydroxy-3-(hydroxymethyl)phenyl]ethyl}amino)-2-methylpropyl]phenyl}acetamide

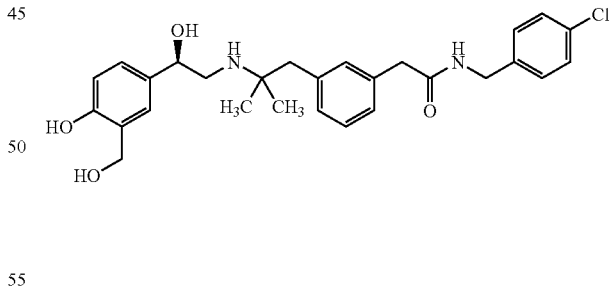

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam. $^1$H NMR (400 MHz, CD$_3$OD): δ=7.37-7.36 (1H, d), 7.32-7.17 (8H, m), 7.13-7.11 (1H, d), 6.82-6.80 (1H, d), 4.75-4.71 (1H, m), 4.70 (2H, s), 4.37 (2H, s), 3.58 (2H, s), 3.02-2.96 (1H, m), 2.93-2.89 (1H, m), 2.86-2.78 (2H, m), 1.16 (3H, s), 1.14 (3H, s) ppm. LRMS (electrospray): m/z [M+H]$^+$ 497, [M+Na]$^+$519, [M−H]$^−$ 495.

EXAMPLE 21

N-(2,6-dimethoxybenzyl)-2-{3-[2-({(2R)-2-hydroxy-2-[4-hydroxy-3-(hydroxymethyl)phenyl]ethyl}amino)-2-methylpropyl]phenyl}acetamide

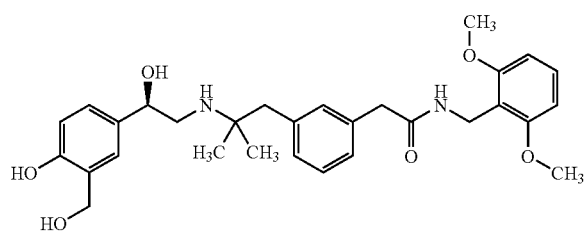

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam. $^1$H NMR (400 MHz, CD$_3$OD): δ=7.39-7.38 (1H, d), 7.32-7.13 (6H, m), 6.83-6.81 (1H, d), 6.66 (1H, s), 6.64 (1H, s), 4.80-4.77 (1H, m), 4.70 (2H, s), 4.46 (2H, s), 3.80 (6H, s), 3.52 (2H, s), 3.15-3.00 (2H, m), 2.88 (2H, m), 1.21 (3H, s), 1.20 (3H, s) ppm. LRMS (electrospray): m/z [M+H]$^+$ 523, [M+Na]$^+$ 545, [M−H]$^−$ 521.

EXAMPLE 22

N-benzyl-2-{3-[2-({(2R)-2-hydroxy-2-[4-hydroxy-3-(hydroxymethyl)phenyl]ethyl}amino)-2-methylpropyl]phenyl}acetamide

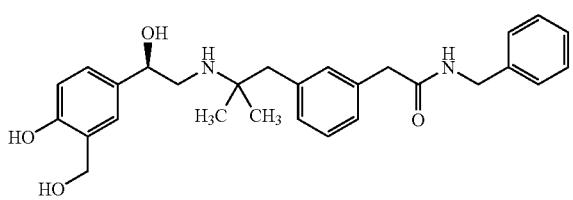

Prepared according to the procedure used for preparation 1 using {3-[2-({(2R)-2-hydroxy-2-[4-hydroxy-3-(hydroxymethyl )phenyl]ethyl}amino)-2-methylpropyl]phenyl}acetic acid (Preparation 50) and the appropriate amine to give the title compound as a white foam. $^1$H NMR (400 MHz, CD$_3$OD): δ=7.38-7.37 (1H, d), 7.33-7.17 (9H, m), 7.12-7.11 (1H, m), 6.82-6.80 (1H, d), 4.75-4.72 (1H, dd), 4.70 (2H, s), 4.40 (2H, s), 3.58 (2H, s), 3.02-2.96 (1H, m), 2.93-2.89 (1H, m), 2.86-2.78 (2H, m), 1.16 (3H, s), 1.15 (3H, s) ppm. LRMS (electrospray): m/z [M+H]$^+$ 463, [M+Na]$^+$ 485, [M−H]$^−$ 461.

EXAMPLE 23

4{(1R)-2-[(2-{3-[2-(3,4-dihydroisoquinolin-2(1H)-yl)-2-oxoethyl]phenyl}-1,1-dimethylethyl)amino]-1-hydroxyethyl}-2-(hydroxymethyl)phenol

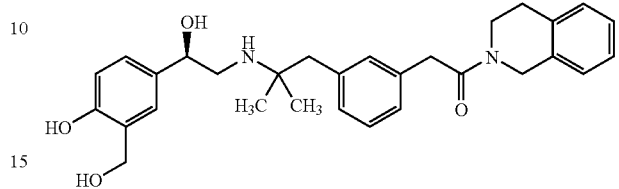

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam. $^1$H NMR (400 MHz, CD$_3$OD): δ=7.36-7.35 (1H, d), 7.29-7.24 (1H, m), 7.22-7.13 (5H, m), 7.12-7.09 (2H, m), 7.04-7.02 (1H, d), 6.80-6.78 (1H, m), 4.74 (1H, s), 4.71-4.66 (4H, m), 3.90-3.89 (2H, m), 3.86-3.82 (1H, m), 3.78-3.75 (1H, m), 2.94-2.86 (2H, m), 2.81-2.66 (4H, m), 1.08-1.01 (6H, m) ppm. LRMS (electrospray): m/z [M+H]$^+$ 489, [M+Na]$^+$ 511, [M−H]$^−$ 487.

EXAMPLE 24

N-[2-fluoro-5-(trifluoromethyl)benzyl]-2-{3-[2-({(2R)-2-hydroxy-2-[4-hydroxy-3-(hydroxymethyl)phenyl]ethyl}amino)-2-methylpropyl]phenyl}acetamide

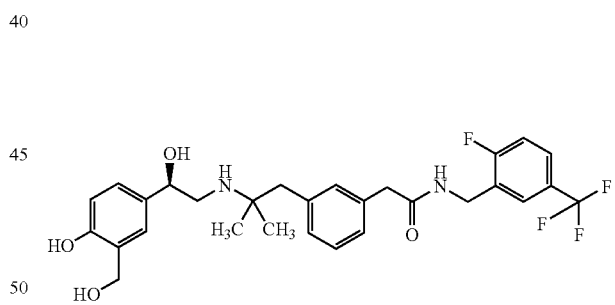

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam. $^1$H NMR (400 MHz, CD$_3$OD): δ=7.62-7.58 (1H, m), 7.56-7.54 (1H, m), 7.33-7.32 (1H, d), 7.28-7.12 (5H, m), 7.08-7.06 (1H, d), 6.78-6.76 (1H, d), 4.70-4.67 (1H, m), 4.65 (2H, s), 4.46 (2H, s), 3.55 (2H, s), 2.96-2.91 (1H, m), 2.86-2.81 (1H, m), 2.80-2.72 (2H, m), 1.10 (3H, s), 1.09 (3H, s) ppm. LRMS (electrospray): m/z [M+H]$^+$ 549, [M+Na]$^+$ 571, [M−H]$^−$ 547.

EXAMPLE 25

N-(2,6-dichlorobenzyl)-2-{3-[2-({(2R)-2-hydroxy-2-[4-hydroxy-3-(hydroxymethyl)phenyl]ethyl}amino)-2-methylpropyl]phenyl}acetamide

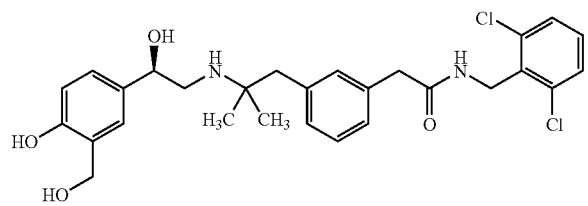

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam. $^1$H NMR (400 MHz, CD$_3$OD): δ=7.45-7.43 (2H, m), 7.39-7.38 (1H, d), 7.34-7.27 (2H, m), 7.23-7.19 (3H, m), 7.14-7.12 (1H, m), 6.83-6.81 (1H, d), 4.79-4.76 (1H, m), 4.71 (2H, s), 4.70 (2H, s), 3.55 (2H, s), 3.09-2.97 (2H, m), 2.88 (2H, s), 1.22 (3H, s), 1.21 (3H, s) ppm. LRMS (electrospray): m/z [M+H]$^+$ 531, [M+Na]$^+$ 553, [M−H]$^-$ 529.

EXAMPLE 26

2-{3-[2-({(2R)-2-hydroxy-2-[4-hydroxy-3-(hydroxymethyl)phenyl]ethyl}amino)-2-methyl propyl]phenyl}-N-[2-(methylthio)benzyl]acetamide

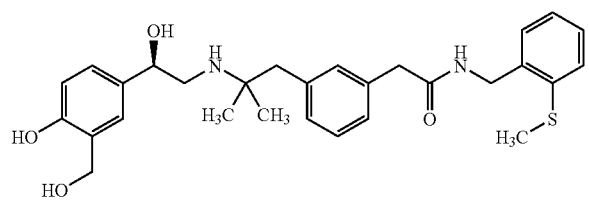

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam. $^1$H NMR (400 MHz, CD$_3$OD): δ=7.36-7.10 (10H, m), 6.81-6.79 (1H, d), 4.73-4.69 (1H, m), 4.69 (2H, s), 4.47 (2H, s), 3.59 (2H, s), 2.99-2.94 (1H, m), 2.89-2.84 (1H, m), 2.81-2.76 (2H, m), 2.48 (3H,s), 1.15 (3H, s), 1.13 (3H, s) ppm. LRMS (electrospray): m/z [M+H]$^+$ 509, [M+Na]$^+$ 531, [M−H]$^-$ 507.

EXAMPLE 27

N-(2,3-dimethylbenzyl)-2-{3-[2-({(2R)-2-hydroxy-2-[4-hydroxy-3-(hydroxymethyl)phenyl]ethyl}amino)-2-methylpropyl]phenyl}acetamide

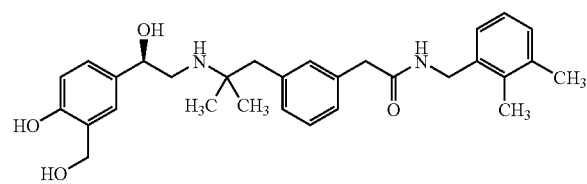

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam. $^1$H NMR (400 MHz, CD$_3$OD): δ=7.37-7.36 (1H, m), 7.30-7.16 (4H, m), 7.12-7.01 (4H, m), 6.82-6.80 (1H, d), 4.74-4.71 (1H, m), 4.69 (2H, s), 4.40 (2H, s), 3.56 (2H, s), 3.01-2.96 (1H, m), 2.92-2.88 (1H, m), 2.86-2.77 (2H, m), 2.29 (3H, s), 2.18 (3H, s), 1.16 (3H, s), 1.14 (3H, s) ppm. LRMS (electrospray) m/z [M+H]$^+$ 491, [M+Na]$^+$ 513, [M−H]$^-$ 489.

EXAMPLE 28

2-{3-[2-({(2R)-2-hydroxy-2-[4-hydroxy-3-(hydroxymethyl)phenyl]ethyl}amino)-2-methylpropyl]phenyl}-N-[3-(trifluoromethyl)benzyl]acetamide

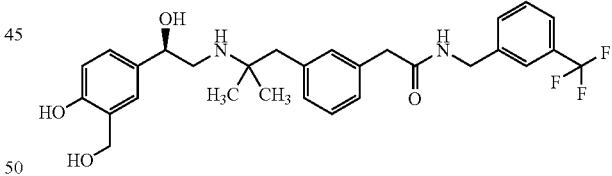

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam. $^1$H NMR (400 MHz, CD$_3$OD): δ=7.56-7.47 (4H, m), 7.36-7.35 (1H, m), 7.28-7.15 (4H, m), 7.11-7.09 (1H, d), 6.80-6.78 (1H, d), 4.73-4.69 (1H, m), 4.69 (2H, s), 4.47 (2H, s), 3.59 (2H, s), 2.99-2.94 (1H, m), 2.89-2.85 (1H, m), 2.84-2.75 (2H, m), 1.14 (3H, s), 1.13 (3H, s) ppm. LRMS (electrospray): m/z [M+H]$^+$ 531, [M+Na]$^+$ 553, [M−H]$^-$ 529.

EXAMPLE 29

N-[4-chloro-3-(trifluoromethyl)benzyl]-2-{3-[2-({(2R)-2-hydroxy-2-[4-hydroxy-3-(hydroxymethyl)phenyl]ethyl}amino)-2-methylpropyl]phenyl}acetamide

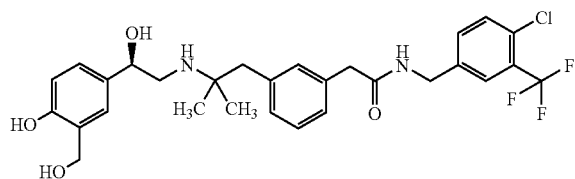

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam. $^{1}$H NMR (400 MHz, CD$_{3}$OD): δ=7.64-7.63 (1H, m), 7.54-7.52 (1H, m), 7.47-7.45 (1H, m), 7.34-7.33 (1H, m), 7.27-7.14 (4H, m), 7.09-7.08 (1H, d), 6.80-6.78 (1H, d), 4.71-4.67 (1H, m), 4.69 (2H, s), 4.43 (2H, s), 3.58 (2H, s), 2.96-2.91 (1H, m), 2.84-2.80 (1H, m), 2.81-2.72 (2H, m), 1.12 (3H, s), 1.09 (3H, s) ppm. LRMS (electrospray): m/z [M+H]$^{+}$ 565, [M+Na]$^{+}$ 587, [M−H]$^{−}$ 563.

EXAMPLE 30

N-[2-chloro-5-(trifluoromethyl)benzyl]-2-{3-[2-({(2R)-2-hydroxy-2-[4-hydroxy-3-(hydroxymethyl)phenyl]ethyl}amino)-2-methylpropyl]phenyl}acetamide

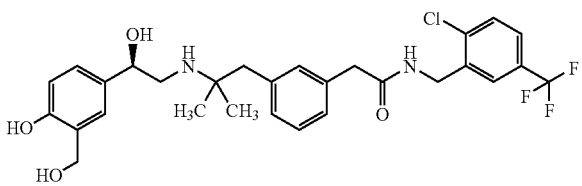

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam. $^{1}$H NMR (400 MHz, CD$_{3}$OD): δ=7.63-7.56 (3H, m), 7.36-7.35 (1H, d), 7.30-7.21 (3H, m), 7.18-7.16 (1H, dd), 7.12-7.11 (1H, d), 6.81-6.79 (1H, d), 4.73-4.69 (1H, m), 4.69 (2H, s), 4.54 (2H, s), 3.62 (2H, s), 3.03-2.91 (1H, m), 2.89-2.84 (1H, m), 2.86-2.75 (2H, m), 1.14 (3H, s), 1.12 (3H, s) ppm. LRMS (electrospray): m/z [M+H]$^{+}$ 565, [M+Na]$^{+}$ 587, [M−H]$^{−}$ 563.

EXAMPLE 31

N-[3,5-bis(trifluoromethyl)benzyl]-2-{3-[2-({(2R)-2-hydroxy-2-[4-hydroxy-3-(hydroxymethyl)phenyl]ethyl}amino)-2-methylpropyl]phenyl}acetamide

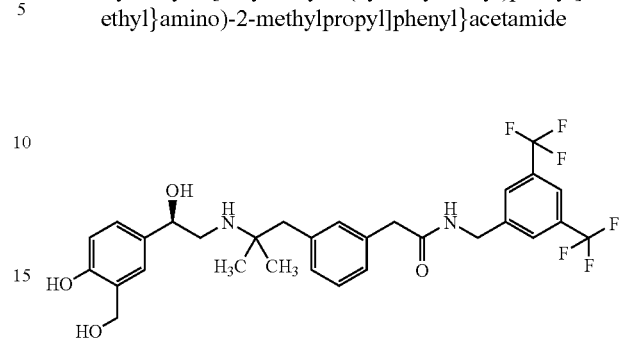

Prepared according to the procedure used for preparation 1 using {3-[2-({(2R)-2-hydroxy-2-[4-hydroxy-3-(hydroxymethyl )phenyl]ethyl}amino)-2-methylpropyl]phenyl}acetic acid (Preparation 50) and the appropriate amine to give the title compound as a white foam. $^{1}$H NMR (400 MHz, CD$_{3}$OD): δ=7.86-7.84 (3H, m), 7.35 (1H, s), 7.28-7.15 (4H, m), 7.11-7.09 (1H, d), 6.81-6.79 (1H, d), 4.71-4.68 (1H, m), 4.69 (2H, s), 4.54 (2H, s), 3.60 (2H, s), 2.96-2.91 (1H, m), 2.83-2.79 (1H, m), 2.80-2.71 (2H, m), 1.10 (3H, s), 1.08 (3H, s) ppm. LRMS (electrospray): m/z [M+H]$^{+}$599, [M+Na]$^{+}$ 621, [M−H]$^{−}$ 597.

EXAMPLE 32

N-[3-fluoro-5-(trifluoromethyl)benzyl]-2-{3-[2-({(2R)-2-hydroxy-2-[4-hydroxy-3-(hydroxymethyl)phenyl]ethyl}amino)-2-methylpropyl]phenyl}acetamide

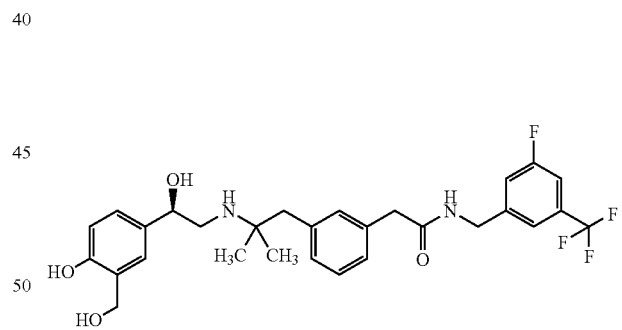

Prepared according to the procedure used for preparation 1 using {3-[2-({(2R)-2-hydroxy-2-[4-hydroxy-3-(hydroxymethyl)phenyl]ethyl}amino)-2-methylpropyl]phenyl}acetic acid (Preparation 50) and the appropriate amine to give the title compound as a white foam.

$^{1}$H NMR (400 MHz, CD$_{3}$OD): δ=7.40 (1H, s), 7.36-7.16 (7H, m), 7.13-7.11 (1H, d), 6.82-6.80 (1H, d), 4.74-4.69 (1H, m), 4.69 (2H, s), 4.47 (2H, s), 3.60 (2H, s), 3.01-2.94 (1H, m), 2.91-2.87 (1H, m), 2.85-2.77 (2H, m), 1.15 (3H, s), 1.13 (3H, s) ppm. LRMS (electrospray): m/z [M+H]$^{+}$549, [M+Na]$^{+}$ 571, [M−H]$^{−}$ 547.

EXAMPLE 33

N-[2-(4-chlorophenyl)ethyl]-3-{2-[(2R)-2-hydroxy-2-(4-hydroxy-3-hydroxymethyl-phenyl)ethylamino]-2-methylpropyl}benzamide

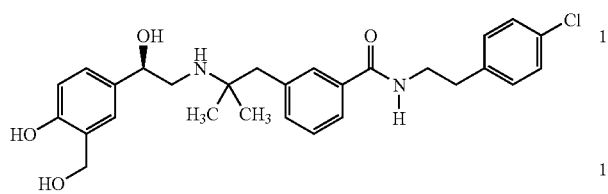

3-{2-[(2R)-2-(tert-butydimethylsilanyloxy)-2-(4-hydroxy-3-hydroxymethyl-phenyl)ethylamino]-2-methylpropyl}-N-[2-(4-chlorophenyl)ethyl]benzamide (Preparation 38) (470 mg, 0.77 mmol) and ammonium fluoride (280 mg, 7.70 mmol) in methanol (3 ml) and water (1.7 ml) were heated to 43° C. for 18 hours. The solvent was removed in vacuo and the product purified by flash column chromatography on silica gel eluting with dichloromethane:methanol:ammonia (95:5:0.5 by volume). The resulting compound was taken up in methanol and evaporated (×3) to yield a white foam (320 mg). A small sample was recrystallised (hexane:ethyl acetate) to give a white solid (mp 139-140° C.).

$^1$H NMR (400 MHz, CD$_3$OD) δ=7.64-7.60 (2H, m), 7.37-7.20 (7H, m), 7.11 (1H, dd), 6.74 (1H, d), 4.68-4.65 (3H, m), 3.57 (2H, m), 2.98-2.87 (4H, m), 2.77-2.70 (2H, m), 1.12 (3H, s), 1.05 (3H, s). LRMS (electrospray) m/z 497 [M+H]$^+$, 519 [M+Na]+Analysis for C$_{28}$H$_{33}$ClN$_2$O$_4$0.5H$_2$O 0.3 C$_4$H$_{10}$O Calc. (Found) C, 66.63 (66.39); H, 6.95 (7.06); N, 5.31 (5.30) %.

EXAMPLE 34

3-{2-[(2R)-2-hydroxy-2-(4-hydroxy-3-hydroxymethyl-phenyl)-ethylamino]-2-methylpropyl}-N-[2-(4-methylphenyl)ethyl]benzamide

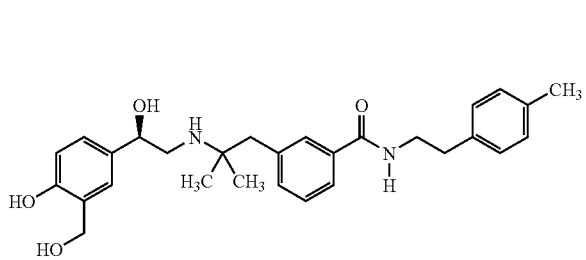

Prepared from 3-{2-[(2R)-2-(tert-butyldimethylsilanyloxy)-2-(4-hydroxy-3-hydroxymethyl-phenyl)ethylamino]-2-methylpropyl}-N-[2-(4-methylphenyl )ethyl]benzamide (Preparation 39) using the method for example 33 to give the title compound as a white foam.

$^1$H NMR (400 MHz, CD$_3$OD) δ=7.69-7.65 (2H, m), 7.37-7.30 (3H, m), 7.14-7.06 (5H, m), 6.75 (1H, d), 4.67-4.64 (3H, m), 3.59-3.54 (2H, m), 2.96-2.84 (4H, m), 2.77-2.69 (2H, m), 2.28 (3H, s), 1.11 (3H, s), 1.04 (3H, s). LRMS (electrospray) m/z 477 [M+H]$^+$, 499 [M+Na]+Analysis for C$_{29}$H$_{36}$N$_2$O$_4$.0.5H$_2$O 0.3 C$_4$H$_{10}$O Calc. (Found) C, 71.42 (71.62); H, 7.94 (7.88); N, 5.52 (5.57) %.

EXAMPLE 35

3-{2-[(2R)-2-hydroxy-2-(4-hydroxy-3-hydroxymethyl-phenyl)-ethylamino]-2-methyl-propyl}-N-[2-(4-trifluoromethylphenyl)ethyl]benzamide

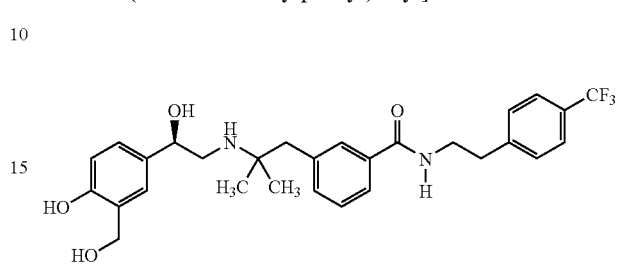

Prepared from 3-{2-[(2R)-2-(tert-butyldimethylsilanyloxy)-2-(4-hydroxy-3-hydroxymethyl-phenyl)ethylamino]-2-methyl-propyl}-N-[2-(4-trifluoromethylphenyl)ethyl]benzamide (Preparation 40) using the method for example 33 to give the title compound as a white foam. $^1$H NMR (400 MHz, CD$_3$OD) δ=7.68-7.62 (1H, m), 7.61 (1H, bs), 7.66 (2H, d), 7.42 (2H, d), 7.38-7.30 (3H, m), 7.12 (1H, dd), 6.75 (1H, dd), 4.68-4.65 (1H), 4.65 (2H, s), 3.61 (2H, m), 3.00 (2H, t), 2.92 (1H, dd), 2.86 (1H, d), 2.73 (1H, dd), 2.69 (1H, d), 1.11 (3H, s), 1.04 (3H, s). LRMS (electrospray) m/z 531 [M+H]$^+$ HRMS for C$_{29}$H$_{34}$F$_3$N$_2$O$_4$ 531.2447 [M+H]$^+$ found 531.2465.

EXAMPLE 36

N-[2-(3,4-dichlorophenyl)ethyl]-3-{2-[(2R)-2-hydroxy-2-(4-hydroxy-3-hydroxymethyl-phenyl)ethylamino]-2-methyl-propyl}-benzamide

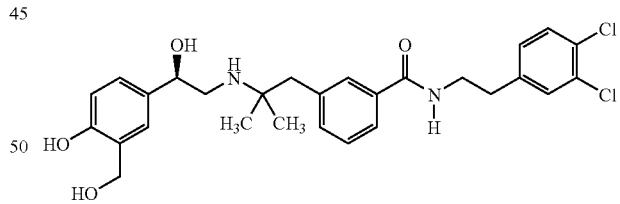

Prepared from 3-{2-[(2R)-2-(tert-butyldimethylsilanyloxy)-2-(4-hydroxy-3-hydroxymethyl-phenyl)ethylamino]-2-methyl-propyl}-N-[2-(3,4-dichlorophenyl)ethyl]benzamide (Preparation 41) using the method for example 33 to give the title compound as a white foam.

$^1$H NMR (400 MHz, CD$_3$OD) δ=7.62 (1H, d), 7.60 (1H, s), 7.42-7.40 (2H, m), 7.38-7.31 (3H, m), 7.18-7.11 (2H, m), 6.75 (1H, d), 4.68-4.66 (1H), 4.65 (2H, s), 3.56 (2H, m), 2.86-2.97 (4H, m), 2.69-2.77 (2H, m), 1.11 (3H, s), 1.04 (3H, s). LRMS (electrospray) m/z 531 [M+H]$^+$ HRMS for C$_{28}$H$_{33}$Cl$_2$N$_2$O$_4$ 531.1801 [M+H]$^+$ found 531.1812.

EXAMPLE 37

N-[2-(3,4-dimethylphenyl)ethyl]-3-{2-[(2R)-2-hydroxy-2-(4-hydroxy-3-hydroxymethyl-phenyl)-ethylamino]-2-methylpropyl}benzamide

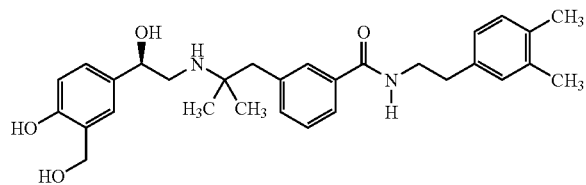

Prepared from 3-{2-[(2R)-2-(tert-butyldimethylsilanyloxy)-2-(4-hydroxy-3-hydroxymethyl-phenyl)ethylamino]-2-methyl-propyl}-N-[2-(3,4-dimethylphenyl)ethyl]benzamide (Preparation 42) using the method for example 33 to give the title compound as a white foam. $^1$H NMR (400 MHz, CD$_3$OD) δ=7.63 (1H, m), 7.61 (1H, bs), 7.38-7.31 (3H, m), 7.12 (1H, dd), 7.02-6.99 (2H, m), 6.92 (1H, dd), 6.75 (1H, d), 4.67-4.64 (1H, m), 4.65 (2H, s), 3.53 (2H, t), 2.92 (1H, dd), 2.86 (1H, d), 2.82 (2H, t), 2.72 (1H, dd), 2.69 (1H, d), 2.20 (6H, s), 1.11 (3H, s), 1.04 (3H, s). LRMS (electrospray) m/z 491 [M+H]$^+$ HRMS for C$_{30}$H$_{39}$N$_2$O$_4$ 491.2905 [M+H]$^+$ found 491.2892.

EXAMPLE 38

3-{2-[(2R)-2-hydroxy-2-(4-hydroxy-3-hydroxymethyl-phenyl)ethylamino]-2-methyl-propyl}-N-(2-naphthalen-2-yl-ethyl)benzamide

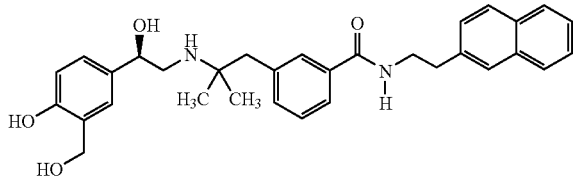

Prepared from 3-{2-[(2R)-2-(tert-butyldimethylsilanyloxy)-2-(4-hydroxy-3-hydroxymethyl-phenyl)ethylamino]-2-methyl-propyl}-N-(2-naphthalen-2-yl-ethyl)benzamide (Preparation 43) using the method for example 33 to give the title compound as a white foam.

$^1$H NMR (400 MHz, CD$_3$OD) δ 7.80-7.75 (3H, m), 7.68 (1H, bs), 7.62 (1H, m), 7.57 (1H, bs), 7.44-7.29 (6H, m), 7.12 (1H, dd), 6.75 (1H, d), 4.67-4.63 (1H, m), 4.66 (2H, s), 3.67 (2H, m), 3.06 (2H, t), 2.90 (1H, dd), 2.82 (1h, d), 2.71 (1H, dd), 2.66 (1H, d), 1.08 (3H, s), 1.01 (3H, s). LRMS (electrospray) m/z 513 [M+H]$^+$ HRMS for C$_{32}$H$_{37}$N$_2$O$_4$ 513.2748 [M+H]$^+$ found 513.2726.

EXAMPLE 39

N-(1,1-dimethyl-2-phenylethyl)-3-{2-[(2R)-2-hydroxy-2-(4-hydroxy-3-hydroxymethyl-phenyl)-ethylamino]-2-methylpropyl}benzamide

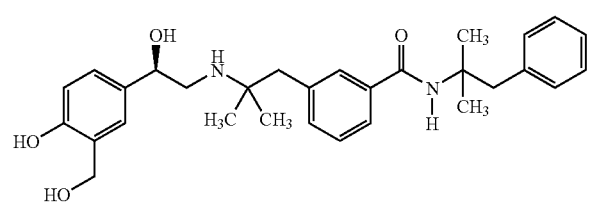

Prepared from 3-{2-[(2R)-2-(tert-butyldimethylsilanyloxy)-2-(4-hydroxy-3-hydroxymethyl-phenyl)ethylamino]-2-methyl-propyl}-N-(1,1-dimethyl-2-phenyl-ethyl )benzamide (Preparation 44) using the method for example 33 to give the title compound as a white foam.

$^1$H NMR (400 MHz, CD$_3$OD) δ=7.64 (1H, m), 7.60 (1H, bs), 7.35-7.27 (3H, m), 7.24-7.15 (5H, m), 7.06 (1H, dd), 6.72 (1H, d), 4.64 (2H, s), 4.64-4.61 (1H, m), 3.20 (1H, d), 3.12 (1H, d), 2.86 (1H, dd), 2.81 (1H, d), 2.73-2.69 (2H, m), 1.42 (3H, s), 1.39 (3H, s), 1.09 (3H, s), 1.05 (3H, s). LRMS (electrospray) m/z 491 [M+H]$^+$ HRMS for C$_{32}$H$_{37}$N$_2$O$_4$ 491.2905 [M+H]$^+$ found 491.2885.

EXAMPLE 40

3-{2-[(2R)-2-hydroxy-2-(4-hydroxy-3-hydroxymethyl phenyl)-ethylamino]-2-methylpropyl}-N-(2-methyl-2-phenylpropyl)benzamide

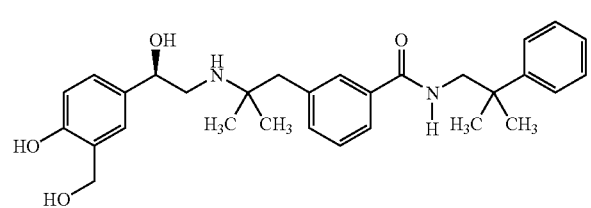

Prepared from 3-{2-[(2R)-2-(tert-butyldimethylsilanyloxy)-2-(4-hydroxy-3-hydroxymethyl-phenyl)ethylamino]-2-methylpropyl}-N-(2-methyl-2-phenylpropyl)-benzamide (Preparation 45) using the method for example 33 to give the title compound as a white foam.

$^1$H NMR (400 MHz, CD$_3$OD) δ 7.53 (1H, m), 7.60 (1H, bs), 7.43 (1H, dd), 7.34-7.28 (5H, m), 7.20-7.16 (1H, m), 7.10 (1H, dd), 6.74 (1H, d), 4.65 (2H, s), 4.65-4.61 (1H, dd), 3.57 (2H, s), 2.87 (1H, dd), 2.79 (1H, d), 2.75-2.69 (2H, m), 1.38 (6H, s), 1.07 (3H, s), 1.03 (3H, s). LRMS (electrospray) m/z 491 [M+H]$^+$ HRMS for C$_{30}$H$_{39}$N$_2$O$_4$ 491.2905 [M+H]$^+$ found 491.2897.

EXAMPLE 41

N-(4-chlorobenzyl)-3-{2-[((2R)-2-hydroxy-2-(4-hydroxy-3-hydroxymethyl-phenyl)ethylamino]-2-methylpropyl}benzamide

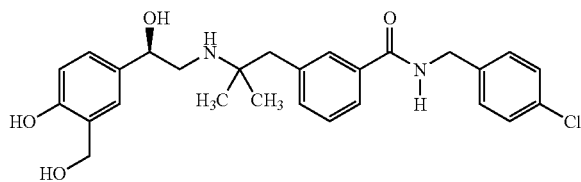

Prepared from 3-{(2R)-2-[2-(tert-butyldimethylsilanyloxy)-2-(4-hydroxy-3-hydroxymethyl-phenyl)ethylamino]-2-methylpropyl}-N-(4-chlorobenzyl)benzamide (Preparation 46) using the method for example 33 to give the title compound as a white foam.

$^1$H NMR (400 MHz, CD$_3$OD) δ=7.74-7.70 (3H, m), 7.40-7.29 (7H, m), 7.07 (1H, dd), 6.71 (1H, d), 4.67-4.63 (1H, dd), 4.63 (2H, s), 4.60 (2H, dd), 2.96-2.88 (2H, m), 2.76-2.70 (2H, m), 1.12 (3H, s), 1.04 (3H, s). LRMS (electrospray) m/z 481/483 [M+H]$^+$ HRMS for C$_{30}$H$_{32}$ClN$_2$O$_4$ 483.2045 [M+H]$^+$ found 483.2038.

EXAMPLE 42

N-(2,6-dimethoxybenzyl)-2-{3-[2-({(2R)-2-hydroxy-2-[4-hydroxy-3-(hydroxymethyl)phenyl]ethyl}amino)ethyl]phenyl}acetamide

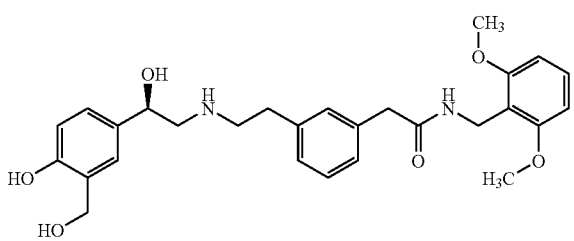

Prepared according to the procedure used for Preparation 1 using {3-[2-({(2R)-2-hydroxy-2-[4-hydroxy-3-(hydroxymethyl)phenyl]ethyl}amino)ethyl]phenyl}acetic acid (Preparation 51) and the appropriate amine to give the title compound as a white foam. $^1$H NMR (400 MHz, CD$_3$OD): δ=7.26-7.19 (3H, m), 7.11-7.07 (4H, m), 6.74-6.72 (1H, d), 6.61-6.59 (2H, d), 4.70-4.67 (1H, m), 4.63 (2H, s), 4.41 (2H, s), 3.75 (6H, s), 3.45 (2H, s), 2.91-2.75 (6H, m) ppm. LRMS (electrospray): m/z [M+H]$^+$ 495, [M+Na]$^+$ 517, [M−H]$^-$ 493. CHN analysis: found C, 66.15%; H, 6.89%; N, 5.53%. C$_{28}$H$_{34}$N$_2$O$_6$+0.75H$_2$O requires C, 66.19%; H, 7.04%; N, 5.51%.

EXAMPLE 43

N-(3,4-dichlorobenzyl)-2-{3-[2-({(2R)-2-hydroxy-2-[4-hydroxy-3-(hydroxymethyl)phenyl]ethyl}amino)ethyl]phenyl}acetamide

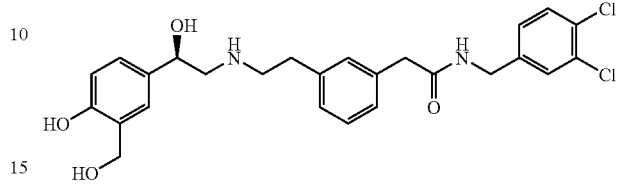

Prepared according to the procedure used for Preparation 1 using {3-[2-({(2R)-2-hydroxy-2-[4-hydroxy-3-(hydroxymethyl)phenyl]ethyl}amino)ethyl]phenyl}acetic acid (Preparation 51) and the appropriate amine to give the title compound as a white foam. $^1$H NMR (400 MHz, CD$_3$OD): δ=7.43-7.41 (1H, d), 7.36-7.35 (1H, d), 7.26-7.23 (2H, m), 7.15-7.06 (5H, m), 6.74-6.72 (1H, d), 4.70-4.66 (1H, m), 4.63 (2H, s), 4.32 (2H, s), 3.53 (2H, s), 2.94-2.75 (6H, m) ppm. LRMS (electrospray): m/z [M+H]$^+$ 503, [M+Na]$^+$ 525, [M−H]$^-$ 501. CHN analysis: found C, 59.26%; H, 5.52%; N, 5.20%. C$_{26}$H$_{28}$N$_2$O$_4$Cl$_2$+1.35H$_2$O requires C, 59.17%; H, 5.86%; N, 5.31%.

EXAMPLE 44

N-benzyl-2-{3-[2-({(2R)-2-hydroxy-2-[4-hydroxy-3-(hydroxymethyl)phenyl]ethyl}amino)ethyl]phenyl}acetamide

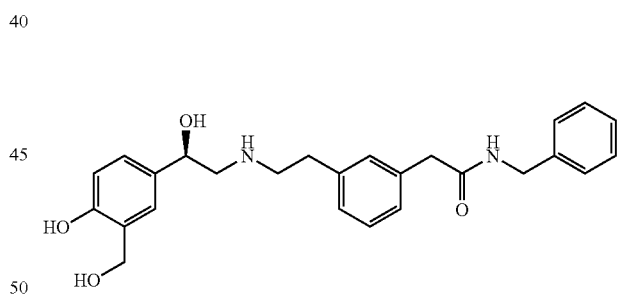

Prepared according to the procedure used for Preparation 1 using {3-[2-({(2R)-2-hydroxy-2-[4-hydroxy-3-(hydroxymethyl)phenyl]ethyl}amino)ethyl]phenyl}acetic acid (Preparation 51) and the appropriate amine to give the title compound as a white foam. $^1$H NMR (400 MHz, CD$_3$OD): δ=7.30-7.19 (7H, m), 7.15-7.14 (2H, m), 7.11-7.06 (2H, m), 6.74-6.72 (1H, d), 4.70-4.67 (1H, m), 4.63 (2H, s), 4.35 (2H, s), 3.52 (2H, s), 2.95-2.77 (6H, m) ppm. LRMS (electrospray): m/z [M+H]$^+$ 435, [M+Na]$^+$ 457, [M−H]$^-$ 433. CHN analysis: found C, 67.21%; H, 6.70%; N, 5.99%. C$_{26}$H$_{30}$N$_2$O$_4$+0.45CH$_2$Cl$_2$ requires C, 67.20%; H, 6.59%; N, 5.93%.

EXAMPLE 45

N-(2,3-dihydro-1H-inden-2-yl)-2-{3-[2-({(2R)-2-hydroxy-2-[4-hydroxy-3-(hydroxymethyl)phenyl]ethyl}amino)ethyl]phenyl}acetamide

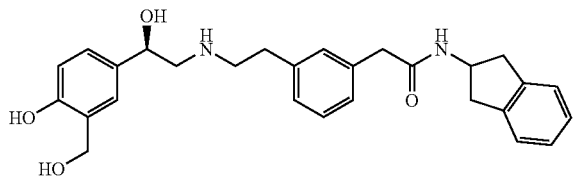

Prepared according to the procedure used for Preparation 1 using {3-[2-({(2R)-2-hydroxy-2-[4-hydroxy-3-(hydroxymethyl)phenyl]ethyl}amino)ethyl]phenyl}acetic acid (Preparation 51) and the appropriate amine to give the title compound as a white foam. $^1$H NMR (400 MHz, CD$_3$OD): δ=7.26 (1H, s), 7.24-7.17 (3H, m), 7.13-7.07 (6H, m), 6.74-6.72 (1H, d), 4.72-4.68 (1H, m), 4.63 (2H, s), 4.59-4.52 (1H, m), 3.45 (2H, s), 3.26-3.24 (1H, d), 3.22-3.20 (1H, d), 2.97-2.79 (8H, m) ppm. LRMS (electrospray): m/z [M+H]$^+$ 461, [M+Na]$^+$ 483, [M–H]$^-$ 459. CHN analysis: found C, 65.30%; H, 6.57%; N, 5.57%. C$_{28}$H$_{32}$N$_2$O$_4$+0.80CH$_2$Cl$_2$+0.10H$_2$O requires C, 65.23%; H, 6.42%; N, 5.28%.

EXAMPLE 46

2-{3-[2-({(2R)-2-hydroxy-2-[4-hydroxy-3-(hydroxymethyl)phenyl]ethyl}amino)ethyl]phenyl}-N-(2-phenylethyl)acetamide

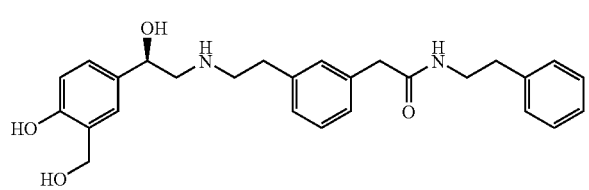

Prepared according to the procedure used for Preparation 1 using {3-[2-({(2R)-2-hydroxy-2-[4-hydroxy-3-(hydroxymethyl)phenyl]ethyl}amino)ethyl]phenyl}acetic acid (Preparation 51) and the appropriate amine to give the title compound as a white foam. $^1$H NMR (400 MHz, CD$_3$OD): δ=7.27-7.26 (1H, d), 7.24-7.06 (10H, m), 6.74-6.72 (1H, d), 4.72-4.69 (1H, m), 4.64 (2H, s), 3.44-3.39 (4H, m), 3.00-2.92 (2H, m), 2.89-2.82 (4H, m), 2.79-2.75 (2H, t) ppm. LRMS (electrospray): m/z [M+H]$^+$ 449, [M+Na]$^+$ 471, [M–H]$^-$ 447. CHN analysis: found C, 64.80%; H, 6.70%; N, 5.52%. C$_{27}$H$_{32}$N$_2$O$_4$+0.75CH$_2$Cl$_2$ requires C, 65.07%; H, 6.59%; N, 5.47%.

EXAMPLE 47

2-{3-[2-({(2R)-2-hydroxy-2-[4-hydroxy-3-(hydroxymethyl)phenyl]ethyl}amino)ethyl]phenyl}-N-(3-phenylpropyl)acetamide

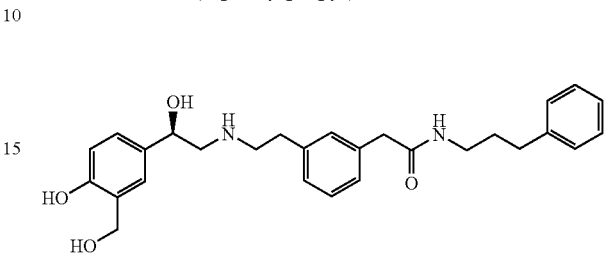

Prepared according to the procedure used for Preparation 1 using {3-[2-({(2R)-2-hydroxy-2-[4-hydroxy-3-(hydroxymethyl)phenyl]ethyl}amino)ethyl]phenyl}acetic acid (Preparation 51) and the appropriate amine to give the title compound as a white foam. $^1$H NMR (400 MHz, CD$_3$OD): δ=7.25-7.19 (4H, m), 7.15-7.05 (7H, m), 6.74-6.72 (1H, d), 4.69-4.64 (3H, m), 3.47 (2H, s), 3.21-3.17 (2H, t), 2.96-2.74 (6H, m), 2.60-2.56 (2H, t), 1.75-1.73 (2H, m) ppm. LRMS (electrospray) m/z [M+H]$^+$ 463, [M+Na]$^+$ 485, [M–H]$^-$ 461. CHN analysis: found C, 68.54%; H, 7.17%; N, 5.80%. C$_{28}$H$_{34}$N$_2$O$_4$+0.40CH$_2$Cl$_2$+0.10H$_2$O requires C, 68.45%; H, 7.08%; N, 5.62%.

EXAMPLE 48

N-benzyl-3-[(2R)-2-({(2R)-2-hydroxy-2-[4-hydroxy-3-(hydroxymethyl)phenyl]ethyl}amino)propyl]benzamide

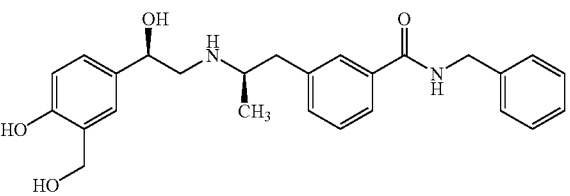

To a solution of 3-[(2R)-2-({(2R)-2-hydroxy-2-[4-hydroxy-3-(hydroxymethyl)phenyl]ethyl}amino)propyl]benzoic acid (Preparation 59) (116 mg, 0.22 mmol) in DMF (2 ml) was added triethylamine (62 μl, 0.45 mmol), benzylamine (29 μl, 0.27 mmol), HOBt (33 mg, 0.25 mmol) and WSCDl (47 mg, 0.25 mmol) and the resulting solution stirred at room temperature for 18 hours. The solvent was removed in vacuo and the residue partitioned between saturated aqueous sodium hydrogen carbonate solution (5 ml) and dichloromethane/methanol (95/5) (10 ml). The aqueous layer was separated and extracted with further dichloromethane/methanol (95/5) (4×10 ml). The combined organic layers were dried (sodium sulfate), filtered and evaporated in vacuo. The resulting oil was purified by flash column chromatography on silica gel eluting with dichloromethane:methanol:880 ammonia (90:10:1, by volume) to give the title compound as a white foam (70 mg). $^1$H NMR (400 MHz, CD$_3$OD): δ=7.70-7.68

(1H, d), 7.66 (1H, s), 7.38-7.29 (6H, m), 7.26-7.21 (1H, m), 7.21 (1H, s), 7.03-7.01 (1H, d), 6.69-6.67 (1H, d), 4.64-4.61 (1H, m), 4.61 (2H, s), 4.58 (2H, s), 3.05-2.98 (1H, m), 2.92-2.86 (1H, dd), 2.84-2.79 (1H, dd), 2.75-2.71 (1H, dd), 2.68-2.63 (1H, dd), 1.10-1.08 (3H, d) ppm. LRMS (electrospray): m/z [M+H]$^+$ 435, [M+Na]$^+$ 457, [M−H]$^−$ 433. CHN analysis: found C, 69.79; H, 6.96; N, 6.37; $C_{26}H_{30}N_2O_4$+0.7H$_2$O requires C, 69.84; H, 7.08; N, 6.26.

EXAMPLE 49

N-(3,4-dichlorobenzyl)-3-[(2R)-2-({(2R)-2-hydroxy-2-[4-hydroxy-3-(hydroxymethyl)phenyl]ethyl)amino)propyl]benzamide

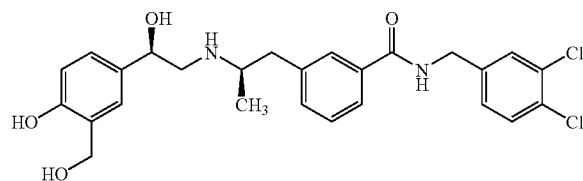

Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.69-7.67 (1H, d), 7.65 (1H, s), 7.51 (1H, s ), 7.48-7.46 (1H, d), 7.36-7.27 (3H, m), 7.21 (1H, s), 7.03-7.02 (1H, d), 6.69-6.66 (1H, d), 4.65-4.61 (1H, m), 4.61 (2H, s), 4.54 (2H, s), 3.02-2.97 (1H, m), 2.91-2.86 (1H, dd), 2.83-2.77 (1H, dd), 2.74-2.69 (1H, dd), 2.68-2.63 (1H, dd), 1.09-1.08 (3H, d) ppm. LRMS (electrospray): m/z [M+H]$^+$ 503, [M+Na]$^+$ 525, [M−H]$^−$ 501.

EXAMPLE 50

N-[2-fluoro-5-(trifluoromethyl)benzyl]-3-[(2R)-2-({(2R)-2-hydroxy-2-[4-hydroxy-3-(hydroxymethyl)phenyl]ethyl}amino)propyl]benzamide

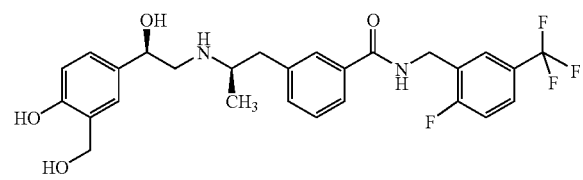

Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.74-7.60 (4H, m), 7.38-7.29 (3H, m), 7.22 (1H, s), 7.04-7.02 (1H, d), 6.69-6.67 (1H, d), 4.67 (2H, s), 4.67-4.61 (1H, m) 4.61 (2H, s), 3.04-2.99 (1H, m), 2.93-2.80 (2H, m), 2.76-2.71 (1H, m), 2.68-2.63 (1H, m), 1.09-1.08 (3H, d) ppm. LRMS (electrospray): m/z [M+H]$^+$ 521, [M+Na]$^+$ 543, [M−H]$^−$ 519. CHN analysis: found C, 60.88; H, 5.58; N, 5.58; $C_{27}H_{28}F_4N_2O_4$+0.7H$_2$O requires C, 60.83; H, 5.56; N, 5.25.

EXAMPLE 51

N-(2,6-dimethoxybenzyl)-3-[(2R)-2-({(2R)-2-hydroxy-2-[4-hydroxy-3-(hydroxymethyl)phenyl]ethyl}amino)propyl]benzamide

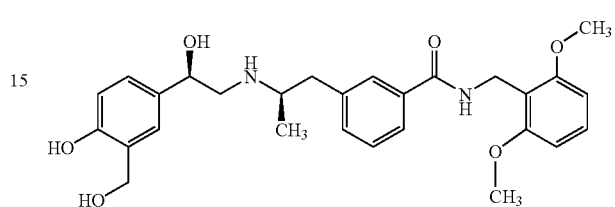

Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.58-7.55 (2H, m), 7.31-7.24 (3H, m), 7.19 (1H, s), 7.00-6.98 (1H, dd), 6.68-6.64 (3H, m), 4.63 (2H, s), 4.63-4.58 (1H, m) 4.60 (2H, s), 3.84 (6H, s), 3.00-2.94 (1H, m), 2.90-2.85 (1H, m), 2.78-2.61 (3H, m), 1.08-1.06 (3H, d) ppm. LRMS (electrospray): m/z [M+H]$^+$ 495, [M+Na]$^+$ 517, [M−H]$^−$ 493. CHN analysis: found C, 65.52; H, 6.89; N, 5.43. $C_{28}H_{34}N_2O_6$+1.0H$_2$O requires C, 65.61; H, 7.08; N, 5.46.

EXAMPLE 52

N-[2-(4-chlorophenyl)ethyl]-3-[(2R)-2-({(2R)-2-hydroxy-2-[4-hydroxy-3-(hydroxymethyl)phenyl]ethyl}amino)propyl]benzamide

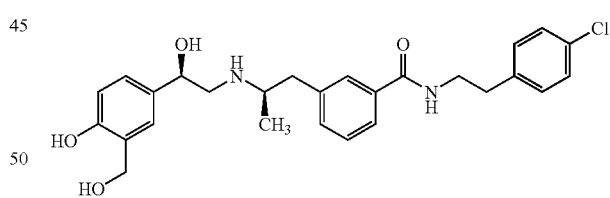

Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.60-7.58 (1H, d), 7.54 (1H, s), 7.35-7.23 (7H, m), 7.04-7.01 (1H, dd), 6.70-6.68 (1H, d), 4.64-4.61 (1H, m), 4.61 (2H, s), 3.60-3.57 (2H, t), 3.02-2.96 (1H, m), 2.92-2.87 (3H, m), 2.83-2.78 (1H, m), 2.75-2.71 (1H, dd), 2.66-2.61 (1H, dd), 1.09-1.08 (3H, d) ppm. LRMS (electrospray): m/z [M+H]$^+$ 483, [M+Na]$^+$ 505, [M−H]$^−$ 481. CHN analysis: found C, 65.90; H, 6.68; N, 5.55. $C_{27}H_{31}ClN_2O_4$+0.5H$_2$O requires C, 65.91; H, 6.56; N, 5.69.

EXAMPLE 53

N-(2,3-dihydro-1H-inden-2-yl)-3-[(2R)-2-({(2R)-2-hydroxy-2-[4-hydroxy-3-(hydroxymethyl)phenyl]ethyl}amino)propyl]benzamide

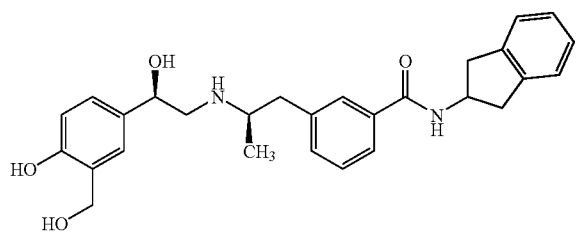

Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.66-7.63 (2H, m), 7.35-7.28 (2H, m), 7.22-7.21 (3H, m), 7.15-7.13 (2H, m), 7.03-7.02 (1H, dd), 6.70-6.68 (1H, d), 4.84-4.79 (1H, m), 4.64-4.60 (1H, m), 4.61 (2H, s), 3.37-3.30 (2H, dd), 3.03-2.97 (3H, m), 2.92-2.87 (1H, m), 2.84-2.78 (1H, m), 2.76-2.71 (1H, m), 2.68-2.63 (1H, dd), 1.09-1.08 (3H, d) ppm. LRMS (electrospray): m/z [M+H]$^+$ 461, [M+Na]$^+$ 483, [M−H]$^−$ 459. CHN analysis: found C, 70.42; H, 6.87; N, 5.91. C$_{28}$H$_{32}$N$_2$O$_4$+0.9H$_2$O requires C, 70.54; H, 7.15; N, 5.88.

EXAMPLE 54

3-[(2R)-2-({(2R)-2-hydroxy-2-[4-hydroxy-3-(hydroxymethyl)phenyl]ethyl}amino)propyl]-N-(2-phenylethyl)benzamide

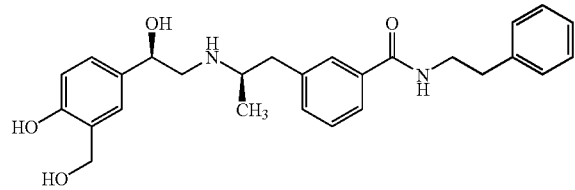

Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.60-7.58 (1H, d), 7.56 (1H, s), 7.35-7.17 (8H, m), 7.05-7.02 (1H, dd), 6.70-6.68 (1H, d), 4.64-4.60 (1H, m), 4.62 (2H, s), 3.61-3.57 (2H, t), 3.03-2.97 (1H, m), 2.93-2.87 (3H, m), 2.84-2.78 (1H, m), 2.77-2.71 (1H, m), 2.66-2.61 (1H, dd), 1.09-1.08 (3H, d) ppm. LRMS (electrospray): m/z [M+H]$^+$ 449, [M+Na]$^+$ 471, [M−H]$^−$ 447. CHN analysis: found C, 70.10; H, 7.16; N, 6.09. C$_{27}$H$_{32}$N$_2$O$_4$+0.75H$_2$O requires C, 70.18; H, 7.31; N, 6.06.

EXAMPLE 55

3-[(2R)-2-({(2R)-2-hydroxy-2-[4-hydroxy-3-(hydroxymethyl)phenyl]ethyl}amino)propyl]-N-[(1R)-1-phenylethyl]benzamide

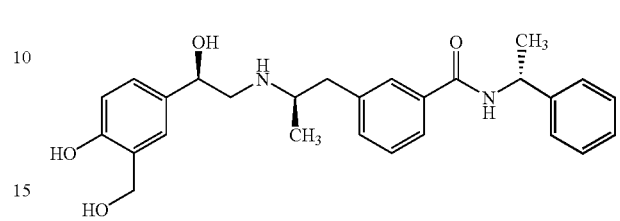

Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.67-7.64 (2H, m), 7.41-7.39 (2H, d), 7.34-7.28 (4H, m), 7.24-7.21 (2H, m), 7.02-7.00 (1H, dd), 6.68-6.66 (1H, d), 5.26-5.21 (1H, q), 4.63-4.60 (1H, m), 4.60 (2H, s), 3.03-2.99 (1H, m), 2.91-2.86 (1H, dd), 2.83-2.78 (1H, dd), 2.74-2.70 (1H, dd), 2.69-2.63 (1H, dd), 1.57-1.55 (3H, d), 1.09-1.08 (3H, d) ppm. LRMS (electrospray): m/z [M+H]$^+$ 449, [M+Na]$^+$ 471, [M−H]$^−$ 447. CHN analysis: found C, 68.96; H, 7.07; N, 5.91. C$_{27}$H$_{32}$N$_2$O$_4$+1.2H$_2$O requires C, 68.97; H, 7.37; N, 5.96.

EXAMPLE 56

3-[(2R)-2-({(2R)-2-hydroxy-2-[4-hydroxy-3-(hydroxymethyl)phenyl]ethyl}amino)propyl]-N-(3-phenylpropyl)benzamide

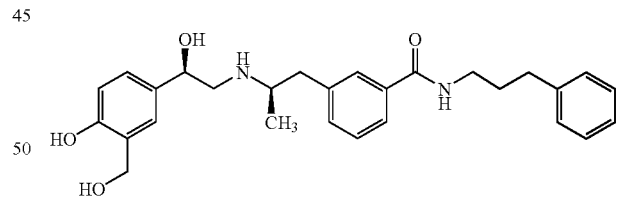

Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.63-7.61 (1H, d), 7.59 (1H, s), 7.35-7.21 (7H, m), 7.16-7.13 (1H, m), 7.03-7.01 (1H, dd), 6.69-6.67 (1H, d), 4.61 (3H, m), 3.42-3.39 (2H, t), 3.00-2.96 (1H, q), 2.91-2.86 (1H, dd), 2.81-2.76 (1H, dd), 2.74-2.61 (4H, m), 1.98-1.91 (2H, quin), 1.09-1.07 (3H, d) ppm. LRMS (electrospray): m/z [M+H]$^+$ 463, [M+Na]$^+$ 485, [M−H]$^−$ 461.

EXAMPLE 57

4-[(1R)-2-({(1R)-2-[3-(3,4-dihydroisoquinolin-2(1H)-ylcarbonyl)phenyl]-1-methylethyl}amino)-1-hydroxyethyl]-2-(hydroxymethyl)phenol

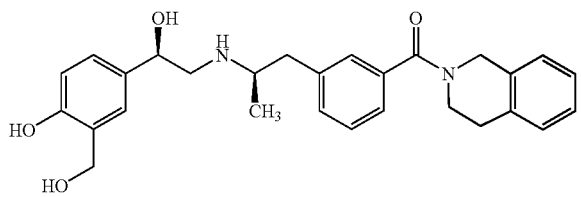

Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.68-7.66 (1H, d), 7.64 (1H, s), 7.36-7.28 (2H, m), 7.21 (1H, d), 7.14-7.12 (1H, d), 7.08-6.99 (3H, m), 6.68-6.68 (1H, d), 4.63-4.59 (1H, m), 4.61 (2H, s), 4.59 (2H, s), 3.04-2.99 (1H, q), 2.92-2.89 (1H, dd), 2.83-2.79 (1H, dd), 2.75-2.71 (1H, dd), 2.69-2.64 (1H, dd), 2.30 (3H, s), 2.28 (3H, s), 1.11-1.09 (3H, d) ppm. LRMS (electrospray): m/z [M+H]$^+$ 463, [M+Na]$^+$ 485, [M–H]$^-$ 461. CHN analysis: found C, 70.17; H, 7.33; N, 5.90. C$_{28}$H$_{34}$N$_2$O$_4$+0.90H$_2$O requires C, 70.24; H, 7.54; N, 5.85.

EXAMPLE 59

N-(5,6-diethyl-2,3-dihydro-1H-inden-2-yl)-3-[(2R)-2-({(2R)-2-hydroxy-2-[4-hydroxy-3-(hydroxymethyl)phenyl]ethyl}amino)propyl]benzamide

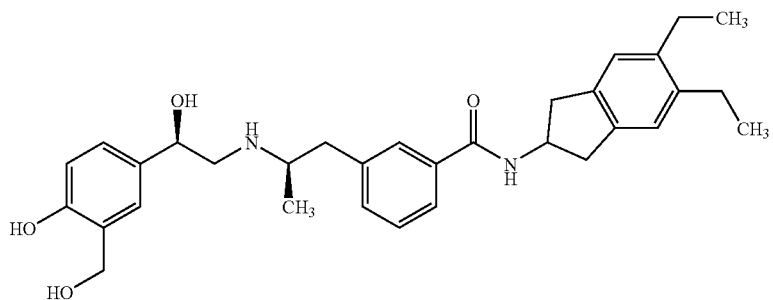

compound as a white foam. $^1$H NMR (400 MHz, CD$_3$OD): δ=7.39-7.36 (1H, m), 7.29-7.17 (6H, m), 7.12-7.01 (3H, m), 6.71-6.69 (1H, d), 4.62 (2H, s), 4.62-4.55 (2H, m), 3.96 (2H, s), 3.60-3.56 (1H, m), 3.11-2.64 (7H, m), 1.10-1.08 (3H, d) ppm. LRMS (electrospray): m/z [M+H]$^+$ 461, [M+Na]$^+$ 483, [M–H]$^-$ 459. CHN analysis: found C, 71.65; H, 7.12; N, 6.39; C$_{28}$H$_{32}$N$_2$O$_4$+0.41H$_2$O requires C, 71.87; H, 7.07; N, 5.99.

EXAMPLE 58

N-(2,3-dimethylbenzyl)-3-[(2R)-2-({(2R)-2-hydroxy-2-[4-hydroxy-3-(hydroxymethyl)phenyl]ethyl}amino)propyl]benzamide Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.65-7.63 (1H, d), 7.61 (1H, s), 7.34-7.26 (2H, m), 7.21 (1H, s), 7.03-7.01 (1H, m), 7.01 (2H, s), 6.69-6.67 (1H, d), 4.81-4.77 (1H, dd), 4.63-4.60 (1H, m), 4.61 (2H, s), 3.31-3.26 (2H, dd), 3.03-2.99 (1H, q), 2.97-2.92 (2H, dd), 2.92-2.87 (1H, dd), 2.83-2.78 (1H, dd), 2.75-2.71 (1H, dd), 2.68-2.61 (5H, m), 1.22-1.18 (6H, t), 1.10-1.09 (3H, d) ppm. LRMS (electrospray): m/z [M+H]$^+$ 517, [M+Na]$^+$ 539, [M–H]$^-$ 515. CHN analysis: found C, 72.58; H, 7.80; N, 5.34. C$_{32}$H$_{40}$N$_2$O$_4$+0.7H$_2$O requires C, 72.62; H, 7.88; N, 5.29.

EXAMPLE 60

N-(4-chlorobenzyl)-3-[(2R)-2-({(2R)-2-hydroxy-2-[4-hydroxy-3-(hydroxymethyl)phenyl]ethyl}amino)propyl]benzamide

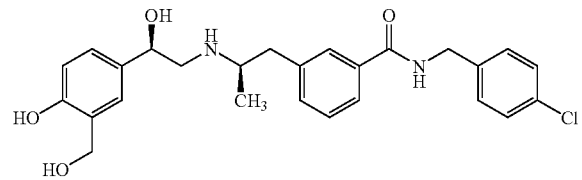

Prepared according to the procedure used for example 49 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title To a solution of 3-[(2R)-2-({(2R)-2-hydroxy-2-[4-hydroxy-3-(hydroxymethyl)phenyl]ethyl}amino)propyl]benzoic acid (Preparation 59) (120 mg, 0.27 mmol) in DMF (3 ml) was added triethylamine (111 μl, 0.79 mmol), 4-chlorobenzylamine (39 μl, 0.32 mmol), and HBTU (110 mg, 0.29 mmol) and the resulting solution stirred at room temperature for 18 hours. The solvent was removed in vacuo and the residue purified by flash column chromatography on silica gel eluting with dichloromethane:methanol:880 ammonia (93:7:0.7 changing to 90:10:1, by volume) to give the title compound as a white foam (97 mg). $^1$H NMR (400 MHz, CD$_3$OD): δ=7.70-7.68 (1H, d), 7.66 (1H, s), 7.38-7.30 (6H, m), 7.23 (1H, d), 7.05-7.03 (1H, dd), 6.70-6.68 (1H, d), 4.67-4.64 (1H, dd), 4.62 (2H, s), 4.55 (2H, s), 3.15-3.07 (1H, m), 3.00-2.86 (2H, m), 2.82-2.78 (1H, dd), 2.72-2.67 (1H, dd), 1.13-1.12 (3H, d) ppm. LRMS (electrospray): m/z [M+H]$^+$ 469, [M+Na]$^+$ 491, [M–H]$^-$ 467.

EXAMPLE 61

3-[(2R)-2-({(2R)-2-hydroxy-2-[4-hydroxy-3-(hydroxymethyl)phenyl]ethyl}amino)propyl]-N-phenylbenzamide

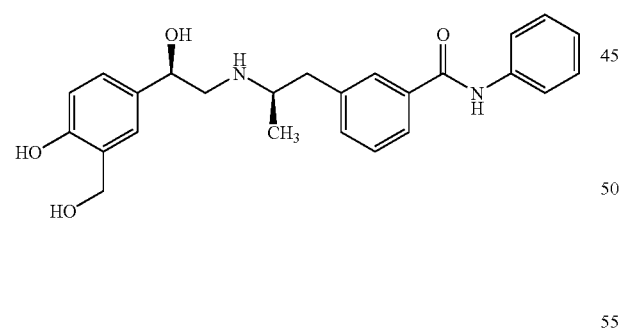

Prepared according to the procedure used for example 60 using 3-[(2R)-2-({(2R)-2-hydroxy-2-[4-hydroxy-3-(hydroxymethyl)phenyl]ethyl}amino)propyl]benzoic acid (Preparation 59) and the appropriate amine to give the title compound as a white foam. $^1$H NMR (400 MHz, CD$_3$OD): δ=7.77-7.74 (2H, m), 7.69-7.67 (2H, d), 7.41-7.33 (4H, m), 7.22 (1H, d), 7.16-7.12 (1H, t), 7.05-7.03 (1H, dd), 6.70-6.68 (1H, d), 4.66-4.61 (1H, m), 4.62 (2H, s), 3.09-3.04 (1H, m), 2.96-2.84 (2H, m), 2.79-2.69 (2H, m), 1.14-1.12 (3H, d) ppm. LRMS (electrospray): m/z [M+H]$^+$ 421, [M+Na]$^+$ 443[M–H]$^-$ 419. CHN analysis: found C, 67.98; H, 6.64; N, 6.48. , C$_{25}$H$_{28}$N$_2$O$_4$+0.06CH$_2$Cl$_2$+0.95H$_2$O requires C, 67.99; H, 6.83; N, 6.33.

EXAMPLE 62

N-[4-(aminosulfonyl)benzyl]-3-[(2R)-2-({(2R)-2-hydroxy-2-[4-hydroxy-3-(hydroxymethyl)phenyl]ethyl}amino)propyl]benzamide

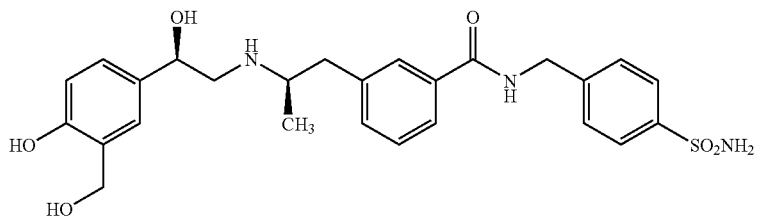

Prepared according to the procedure used for example 60 using 3-[(2R)-2-({(2R)-2-hydroxy-2-[4-hydroxy-3-(hydroxymethyl)phenyl]ethyl}amino)propyl]benzoic acid (Preparation 59) and the appropriate amine, substituting with dichloromethane:methanol:880 ammonia (85:15:2, by volume) as eluent to give the title compound as a white foam. $^1$H NMR (400 MHz, CD$_3$OD): δ=7.87-7.85 (2H, d), 7.71-7.69 (1H, d), 7.67 (1H, s), 7.53-7.50 (2H, d), 7.39-7.32 (2H, m), 7.23 (1H, d), 7.05-7.03 (1H, dd), 6.70-6.68 (1H, d), 4.67-4.65 (1H, m), 4.65 (2H, s), 4.62 (2H, s), 3.14-3.07 (1H, m), 2.97-2.92 (1H, dd), 2.91-2.86 (1H, dd), 2.82-2.78 (1H, dd), 2.72-2.67 (1H, dd), 1.13-1.12 (3H, d) ppm. LRMS (electrospray): m/z [M+H]$^+$ 514, [M+Na]$^+$ 536, [M–H]$^-$ 512. CHN analysis: found C, 56.26; H, 6.01; N, 7.45. C$_{26}$H$_{31}$N$_3$O$_6$S+2.1H$_2$O requires C, 56.63; H, 6.43; N, 7.62.

EXAMPLE 63

N-[2-(3-Fluorophenyl)ethyl]-3-[2-({(2R)-2-hydroxy-2-[4-hydroxy-3-(hydroxymethyl)phenyl]ethyl}amino)-2-methylpropyl]benzamide 3-[2-({(2R)-2-{[tert-Butyl(dimethyl)silyl]oxy}-2-[4-hydroxy-3-(hydroxylmethyl)phenyl]ethyl}amino)-2-methylpropyl]-N-[2-(3-fluorophenyl)ethyl]benzamide (preparation 157), (343 mg, 0.58 mmol) and ammonium fluoride (213 mg, 5.76 mmol) in methanol (12 mL) and water (2 mL) were stirred at room temperature for 42 hours. The solvent was removed in vacuo and the residue was purified by column chromatography on silica gel, eluting with dichloromethane:methanol:0.88 ammonia, 100:0:0 to 90:10:1. The appropriate fractions were concentrated in vacuo and the residue was azeotroped (×2) in ethanol to give a white solid. This solid was then re-crystallised with ethanol/water and dried under vacuum to afford the title compound as very pale yellow crystals in 52% yield, 144 mg. $^1$H NMR (400 MHz, CD$_3$OD) δ: 7.63 (2H, m) 7.38-7.23 (4H, m), 7.13 (1H, m), 7.05 (1H, m), 7.00 (1H, m), 6.91 (1H, m), 6.85 (1H, d), 4.65 (3H, m), 3.59 (2H, m), 2.96-2.84 (2H, m), 2.78-2.68 (2H, m), 1.10 (3H, s), 1.04 (3H, s) ppm. LRMS ESI m/z 481 [M+H]$^+$.

EXAMPLES 64 TO 78

The following compounds, of the general formula shown below, were prepared by a similar method to that described for example 63, using the appropriate starting material and ammonium fluoride. The reaction mixtures were warmed to 40° C. until thin layer chromatography analysis indicated that all of the starting materials had been consumed.

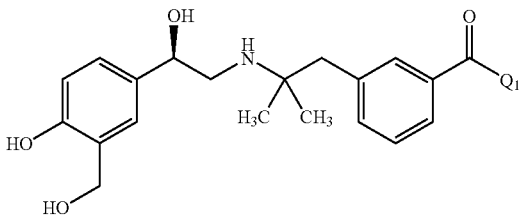

| No. | Q$_1$ | Data | Yield |
|---|---|---|---|
| 64 | N-CH$_2$CH$_2$-pyrrolidine | $^1$H NMR (400 MHz, CD$_3$OD) δ: 7.78-7.71 (2H, m) 7.40-7.31 (3H, m), 7.15 (1H, m), 6.76 (1H, m), 4.70-4.64 (3H, m), 3.62-3.50 (2H, m), 3.01-2.94 (2H, m), 2.76-2.63 (4H, m), 2.59-2.46 (4H, m), 1.78-1.65 (4H, m), 1.13 (3H, s), 1.01 (3H, s) ppm; LRMS APCI m/z 456 [M + H]$^+$ | |
| 65 | N-CH$_2$CH$_2$-(2,6-dichlorophenyl) | $^1$H NMR (400 MHz, CD$_3$OD) δ: 7.65 (2H, m) 7.37-7.29 (5H, m), 7.21-7.11 (2H, m), 6.77 (1H, m), 4.70-4.63 (3H, m), 3.66 (2H, m), 3.30 (2H, m), 2.96-2.69 (4H, m), 1.10 (3H, s), 1.05 (3H, s) ppm; LRMS APCI m/z 531 [M + H]$^+$ | 81% |
| 66 | N-CH$_2$-indanyl | $^1$H NMR (400 MHz, CD$_3$OD) δ: 7.64 (m, 2H), 7.40-7.30 (3H, m), 7.19-7.05 (5H, m), 6.75 (1H, m), 4.65 (3H, m), 3.42 (2H, m), 2.69-3.10 (9H, m), 1.14 (3H, s), 1.05 (3H, s) ppm LRMS APCI m/z 489 [M + H]$^+$ | 35% |
| 67 | N-CH$_2$CH$_2$-(4-(C(O)NH-butyl)phenyl) | $^1$H NMR (400 MHz, CD$_3$OD) δ: 7.74 (2H, m), 7.66-7.59 (2H, m), 7.37-7.25 (5H, m), 7.13 (1H, m), 6.75 (1H, d), 4.65 (3H, m), 3.62 (2H, m), 3.32 (2H, m), 3.00-2.68 (6H, m), 1.59 (2H, m), 1.39 (2H, m), 1.12 (3H, s), 1.04 (3H, s), 0.97 (3H, t) ppm LRMS APCI m/z 562 [M + H]$^+$ | 31% |
| 68 | N-CH$_2$CH$_2$-(2-(phenylthio)phenyl) | $^1$H NMR (400 MHz, CD$_3$OD) δ: 7.68-7.56 (2H, m), 7.40-7.07 (13H, brm), 6.74 (1H, m), 4.86-4.74 (3H, m), 3.70-3.58 (2H, m), 3.11 (2H, m), 2.68-2.95 (4H, m), 1.12 (3H, s), 1.06 (3H, s) ppm; LRMS APCI m/z 571 [M + H]$^+$ | 34% |

-continued

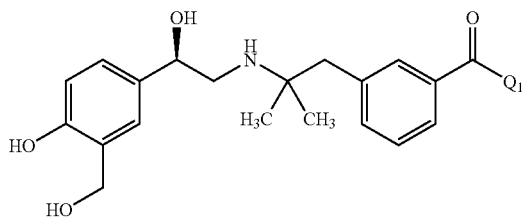

| No. | Q₁ | Data | Yield |
|---|---|---|---|
| 69 | N-CH₂CH₂-cyclohexyl | ¹H NMR (400 MHz, CD₃OD) δ: 7.66 (2H, m), 7.34 (3H, m), 7.13 (1H, m), 6.74 (1H, d), 4.67 (1H, d), 4.65 (2H, s), 3.42-3.34 (2H, m), 2.87-2.97 (2H, m), 2.70-2.77 (2H, m), 1.80-1.59 (5H, m), 1.47 (2H, q), 1.15-1.30 (4H, m), 1.12 (3H, s), 1.05 (3H, s), 1.00-0.90 (2H, m) ppm<br>LRMS ESI m/z 469 [M + H]⁺ | 69% |
| 70 | N-(CH₂)₃-Ph | ¹H NMR (400 MHz, CD₃OD) δ: 7.67 (2H, m), 7.39-7.32 (3H, m), 7.26-7.12 (6H, m), 6.75 (1H, d), 4.68-4.63 (3H, t), 3.43-3.38 (2H, m), 2.98-2.88 (2H, m), 2.76-2.64 (4H, m), 1.97-1.89 (2H, m), 1.12 (3H, s), 1.05 (3H, s) ppm;<br>LRMS APCI m/z 477 [M + H]⁺ | 89% |
| 71 | N-CH₂CH₂-Ph | ¹H NMR (400 MHz, CD₃OD) δ: 7.64 (2H, m), 7.38-7.13 (9H, m), 6.76 (1H, d), 4.65 (3H, m), 3.60 (2H, m), 2.97-2.86 (4H, m), 2.76-2.70 (2H, m), 1.11 (3H, s), 1.05 (3H, s) ppm;<br>LRMS APCI m/z 463 [M + H]⁺ | 72% |
| 72 | N-CH₂CH₂-(2,6-dichloro-3-methylphenyl) | ¹H NMR (400 MHz, CD₃OD) δ: 7.68-7.63 (2H, m), 7.39-7.31 (3H, m), 7.25 (2H, m), 7.26-7.19 (1H, m), 6.76 (1H, d), 4.69-4.64 (3H, m), 3.58-3.53 (2H, t), 3.23-3.18 (2H, m), 3.00-2.80 (2H, m), 2.71-2.69 (2H, t), 2.47 (3H, s), 1.12 (3H, s), 1.06 (3H, s) ppm;<br>LRMS ESI m/z 545 [M + H]⁺ | 16% |
| 73 | N-CH₂CH₂-(2-methoxy-5-chlorophenyl) | ¹H NMR (400 MHz, CD₃OD) δ: 7.61 (2H, m), 7.40-7.30 (3H, m), 7.20-7.10 (3H, m), 6.90 (1H, d), 6.77 (1H, d), 4.75-4.60 (3H, m), 3.80 (3H, s), 3.60-3.50 (2H, m), 3.00-2.80 (4H, m), 2.80-2.70 (2H, m), 1.95-1.15 (3H, m), 1.10 (3H, s) ppm | 48% |
| 74 | N-CH₂CH₂-(3-methoxyphenyl) | ¹H NMR (400 MHz, CD₃OD) δ: 7.75-7.65 (2H, m), 7.40-7.10 (6H, m), 6.80-6.70 (3H, m), 4.70-4.60 (3H, m), 3.67 (3H, s), 3.60-3.50 (2H, m), 3.00-2.70 (6H, brm), 1.15 (3H, s), 1.05 (3H, s) ppm; LRMS APCI 493 [M + H]⁺ | 10% |

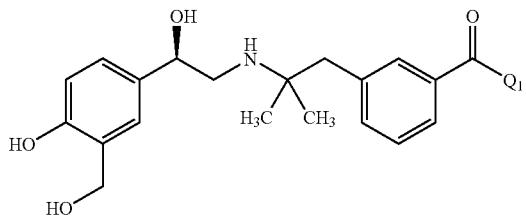
| No. | Q₁ | Data | Yield |
|---|---|---|---|
| 75 | 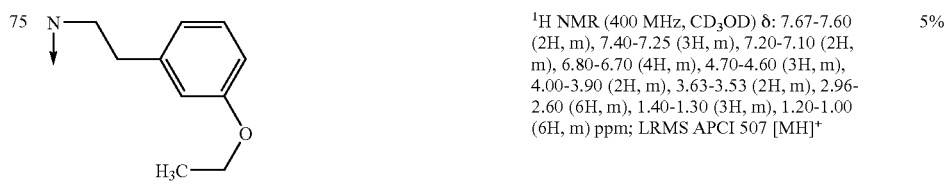 | ¹H NMR (400 MHz, CD₃OD) δ: 7.67-7.60 (2H, m), 7.40-7.25 (3H, m), 7.20-7.10 (2H, m), 6.80-6.70 (4H, m), 4.70-4.60 (3H, m), 4.00-3.90 (2H, m), 3.63-3.53 (2H, m), 2.96-2.60 (6H, m), 1.40-1.30 (3H, m), 1.20-1.00 (6H, m) ppm; LRMS APCI 507 [MH]⁺ | 5% |
| 76 | 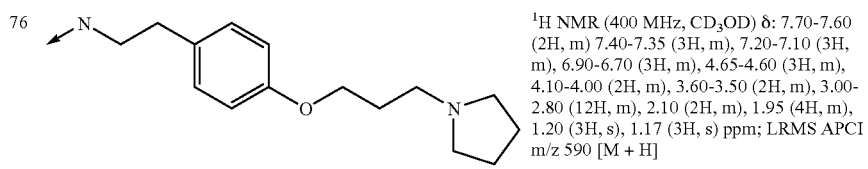 | ¹H NMR (400 MHz, CD₃OD) δ: 7.70-7.60 (2H, m) 7.40-7.35 (3H, m), 7.20-7.10 (3H, m), 6.90-6.70 (3H, m), 4.65-4.60 (3H, m), 4.10-4.00 (2H, m), 3.60-3.50 (2H, m), 3.00-2.80 (12H, m), 2.10 (2H, m), 1.95 (4H, m), 1.20 (3H, s), 1.17 (3H, s) ppm; LRMS APCI m/z 590 [M + H] | |
| 77 | 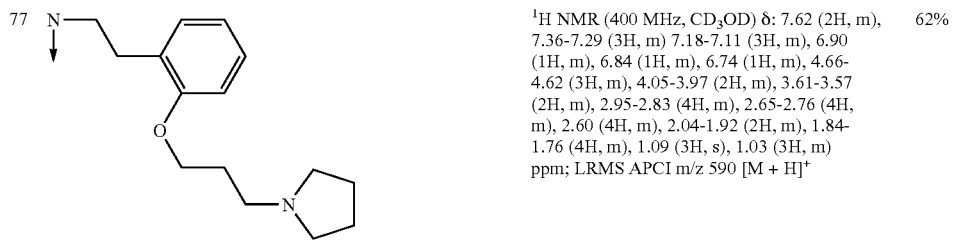 | ¹H NMR (400 MHz, CD₃OD) δ: 7.62 (2H, m), 7.36-7.29 (3H, m) 7.18-7.11 (3H, m), 6.90 (1H, m), 6.84 (1H, m), 6.74 (1H, m), 4.66-4.62 (3H, m), 4.05-3.97 (2H, m), 3.61-3.57 (2H, m), 2.95-2.83 (4H, m), 2.65-2.76 (4H, m), 2.60 (4H, m), 2.04-1.92 (2H, m), 1.84-1.76 (4H, m), 1.09 (3H, s), 1.03 (3H, m) ppm; LRMS APCI m/z 590 [M + H]⁺ | 62% |
| 78 | 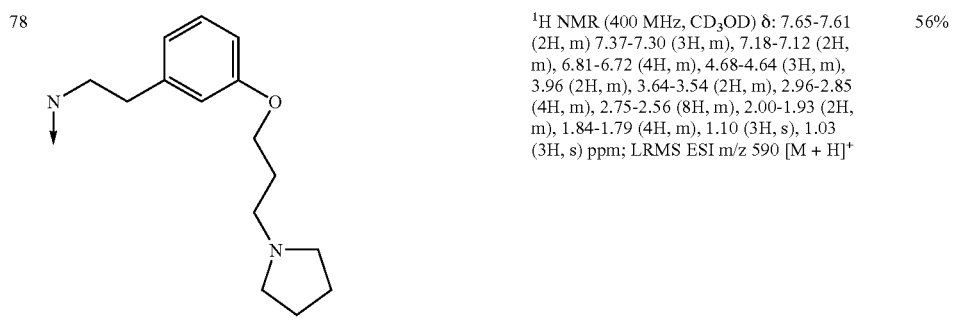 | ¹H NMR (400 MHz, CD₃OD) δ: 7.65-7.61 (2H, m) 7.37-7.30 (3H, m), 7.18-7.12 (2H, m), 6.81-6.72 (4H, m), 4.68-4.64 (3H, m), 3.96 (2H, m), 3.64-3.54 (2H, m), 2.96-2.85 (4H, m), 2.75-2.56 (8H, m), 2.00-1.93 (2H, m), 1.84-1.79 (4H, m), 1.10 (3H, s), 1.03 (3H, s) ppm; LRMS ESI m/z 590 [M + H]⁺ | 56% |

EXAMPLE 65

Compound was further purified by trituration with diethyl ether.

EXAMPLE 72

Purified by column chromatography using an ISCO® silica cartridge, eluting with dichloromethane:methanol:0.88 ammonia, 100:0 to 90:10:1.

EXAMPLE 75

Purified by column chromatography using a 4 g RediSep® silica cartridge, eluting with, dichloromethane:methanol: 0.88 ammonia, 100:0:0 to 90:10:1, followed by ethyl acetate: methanol:0.88 ammonia, 100:0:0 to 80:20:2.

EXAMPLE 78

Crude compound was further purified by trituration with diethyl ether.

EXAMPLE 79

N-[2-(4-Chlorophenyl)ethyl]-N-ethyl-3-[2-({(2R)-2-hydroxy-2-[4-hydroxy-3-(hydroxymethyl)phenyl]ethyl}amino)-2-methylpropyl]benzamide

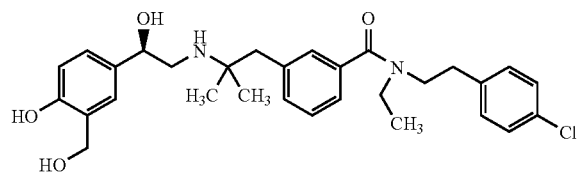

The title compound was prepared from 3-[2-({(2R)-2-{[tert-butyl(dimethyl)silyl]oxy}-2-[4-hydroxy-3-(hydroxymethyl)phenyl]ethyl}amino)-2-methylpropyl]-N-[2-(4-chlorophenyl)ethyl]-N-ethylbenzamide (preparation 110), using a similar method to example 33, as a colourless solid in 61% yield. $^1$H NMR (400 MHz, CD$_3$OD) 7.30-7.10 (8H, m), 6.87 (2H, m), 6.73 (1H, d), 4.63 (3H, m), 3.71 (1H, m), 3.61 (1H, m), 3.50 (1H, m), 3.16 (1H, m), 3.01-2.69 (6H, m), 1.29-1.26, 1.07-1.01 (9H, 2×m) ppm; LRMS APCI m/z 525 [M+H]$^+$.

EXAMPLE 80

23-[2-({(2R)-2-hydroxy-2-[4-hydroxy-3-(hydroxymethyl)phenyl]ethyl)amino)-2-methylpropyl]phenyl}-N-(3-pyrrolidin-1-ylpropyl)acetamide

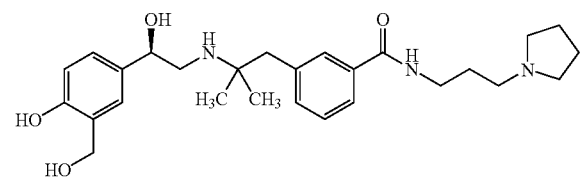

The title compound was prepared from 2-{3-[2-({(2R)-2-{[tert-butyl(dimethyl)silyl]oxy}-2-[4-hydroxy-3-(hydroxymethyl )phenyl]ethyl}amino)-2-methylpropyl]phenyl}-N-(3-pyrrolidin-1-ylpropyl)acetamide (preparation 109), using a similar method to that of example 33. The crude residue was further purified by column chromatography on Biotage® amino silica gel, eluting with dichloromethane: methanol, 80:20, to afford the title compound as a colourless gum in 54% yield. $^1$H NMR (400 MHz, CD$_3$OD) 7.70-7.64 (2H, m), 7.40-7.30 (3H, m), 7.13 (1H, m), 6.75 (m, 1H), 4.69-4.64 (3H, m), 3.42 (2H, m), 3.00-2.90 (2H, m), 2.77-2.64 (2H, m), 2.60-2.50 (6H, m), 1.88-1.75 (6H, m), 1.12 (3H, s), 1.03 (s, 3H) ppm; LRMS APCI m/z 470 [M+H]$^+$.

EXAMPLE 81

N-(Cycloheptylmethyl)-2-{3-[2-({(2R)-2-hydroxy-2-[4-hydroxy-3-(hydroxymethyl)phenyl]ethyl}amino)-2-methylpropyl]phenyl}acetamide

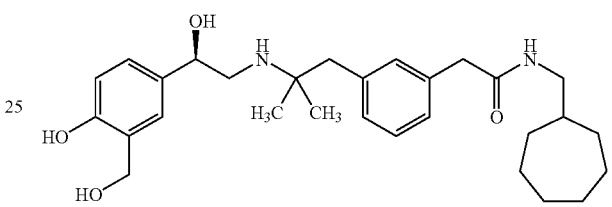

The title compound was prepared from 2-{3-[2-({(2R)-2-{[tert-butyl(dimethyl)silyl]oxy}-2-[4-hydroxy-3-(hydroxymethyl)phenyl]ethyl}amino)-2-methylpropyl]phenyl}-N-(cycloheptylmethyl)acetamide (preparation 151), using a similar method to that of example 33 as a white foam in 69% yield. $^1$H NMR (400 MHz, CD$_3$OD) δ: 7.65 (1H, m), 7.38 (1H, s), 7.18-7.07 (4H, m), 6.90 (1H, d), 4.93-4.78 (1H, m), 4.04 (2H, m), 3.51 (2H, d), 3.18-3.07 (2H, m), 3.02-2.93 (4H, m), 1.72-1.36 (10H, m), 1.28 (6H, m), 1.19-1.07 (3H, m) ppm; LRMS ESI m/z 483 [M+H]$^+$.

EXAMPLE 82

N-1-Adamantyl-2-{3-[2-({(2R)-2-hydroxy-2-[4-hydroxy-3-(hydroxymethyl)phenyl]ethyl}amino)-2-methylpropyl]phenyl}acetamide

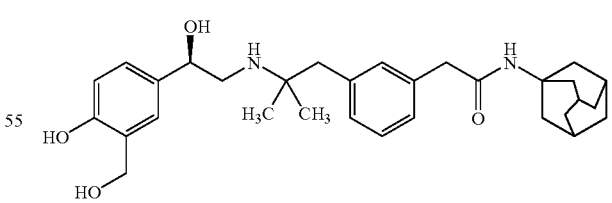

The title compound was prepared from N-1-adamantyl-2-{3-[2-({(2R)-2-{[tert-butyl(dimethyl)silyl]oxy}-2-[4-hydroxy-3-(hydroxymethyl)phenyl]ethyl}amino)-2-methylpropyl]phenyl}acetamide (preparation 152), using a method similar to that of example 33, as a white foam in 41% yield. $^1$H NMR (400 MHz, CD$_3$OD) δ: 7.19-7.12 (5H, m), 7.02 (1H, dd), 6.78 (1H, d), 4.65 (3H, m), 3.40 (2H, d), 2.97 (1H, m), 2.82 (1H, m), 2.78 (2H, dd), 2.03 (9H, m), 1.64 (6H, m), 1.05 (6H, dd) ppm; LRMS ESI m/z 507 [M+H]$^+$.

EXAMPLE 83

N-Benzyl-2-{3-[2-({(2R)-2-hydroxy-2-[4-hydroxy-3-(hydroxymethyl) phenyl]ethyl}amino)-2-methyl-propyl]phenyl}-N-methylacetamide

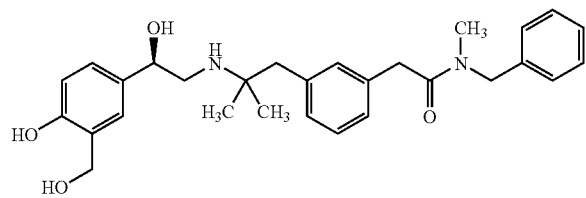

The title compound was prepared from N-benzyl-2-{3-[2-({(2R)-2-{[tert-butyl(dimethyl)silyl]oxy}-2-[4-hydroxy-3-(hydroxymethyl)phenyl]ethyl}amino)-2-methylpropyl]phenyl}-N-methylacetamide (preparation 156), using a similar method to example 33, as a colourless solid in 75% yield.

$^1$H NMR (400 MHz, CD$_3$OD) δ: 7.18 (11H, m), 6.75 (1H, m), 4.61 (5H, m), 3.80 (2H, m), 2.60-2.95 (7H, m), 1.01 (6H, m) ppm; LRMS APCI m/z 477 [M+H]$^+$.

EXAMPLE 84

N-[2-(4-Fluorophenyl)ethyl]-3-[2-({(2R)-2-hydroxy-2-[4-hydroxy-3-(hydroxymethyl)phenyl]ethyl}amino)-2-methylpropyl]benzamide

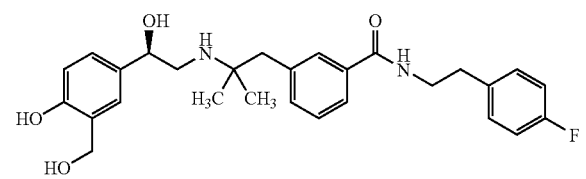

Solutions of 3-{2-[(2R)-2-(tert-butyldimethylsilanyloxy)-2-(4-hydroxy-3-hydroxy methylphenyl)ethylamino]-2-methylpropyl}benzoic acid (preparation 37) (90 mg, 0.19 mmol) in N,N-dimethylacetamide (1 mL) and O-(1H-benzotriazol-1-yl)-N,N,N',N'-tetramethyluronium hexafluorophosphate (61 mg, 0.16 mmol) in N,N-dimethylacetamide (0.5 mL) were added to a solution of 4-fluorophenethylamine (33 mg, 0.19 mmol) in N,N-dimethylacetamide (0.5 mL). The resulting mixture was stirred for 72 hours at room temperature. The solvent was removed in vacuo and the residue was partitioned between dichloromethane (4 mL) and saturated sodium hydrogen carbonate solution (1 mL). The mixture was then filtered through a phase separation tube and the organic solution was concentrated in vacuo. Ammonium fluoride (70 mg, 1.9 mmol) was added to a suspension of the residue in methanol (2 mL) and water (1 mL) and the mixture was stirred at room temperature for 72 hours. The reaction mixture was then concentrated in vacuo and the residue was purified by column chromatography on silica gel, eluting with dichloromethane:methanol:0.88 ammonia, 100:0:0 to 91:9:1, followed by trituration with diethyl ether, to afford the title compound in 50% yield, 45 mg. $^1$H NMR (400 MHz, CD$_3$OD) δ: 7.63 (2H, m), 7.40-7.30 (3H, m), 7.23 (2H, m), 7.14 (1H, m), 7.00 (2H, m), 6.75 (1H, d), 4.65 (3H, m), 3.58 (2H, m), 2.98-2.64 (6H, m), 1.11 (3H, s), 1.05 (3H, s) ppm; LRMS APCI m/z 481 [M+H]$^+$.

EXAMPLES 85 TO 91

The following compounds, of the general formula shown below, were prepared by a similar method to that described for example 84, using 3-{2-[(2R)-2-(tert-butyldimethylsilanyloxy)-2-(4-hydroxy-3-hydroxymethyl-phenyl)ethylamino]-2-methylpropyl}benzoic acid (preparation 37) and the appropriate amine starting material. The amines were either commercially available or prepared as described in preparations 69-108

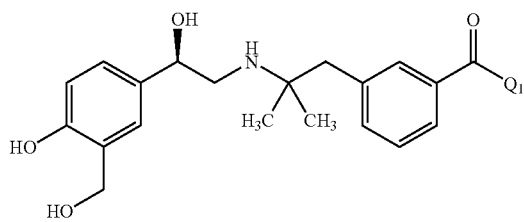

| No. | Q$^1$ | Data | Yield |
|---|---|---|---|
| 85 | ![phenoxyphenylethyl] | $^1$H NMR (400 MHz, CD$_3$OD) δ: 7.63 (2H, m), 7.39-7.27 (5H, m), 7.22 (2H, m), 7.13 (1H, m), 7.06 (1H, m), 6.98-6.85 (4H, m), 6.75 (1H, d), 4.65 (3H, m), 3.59 (2H, m), 2.96-2.66 (6H, m), 1.10 (3H, s), 1.03 (3H, s) ppm; LRMS APCI m/z 555 [M + H]$^+$ | 58% |

-continued

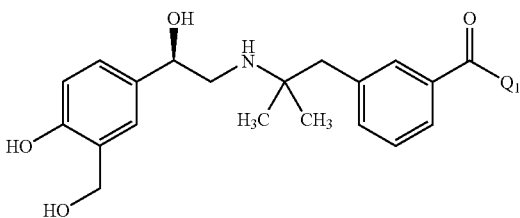

| No. | Q¹ | Data | Yield |
|---|---|---|---|
| 86 | H₃C—O—⟨phenyl⟩—CH₂CH₂—N↓ | ¹H NMR (400 MHz, CD₃OD) δ: 7.63 (2H, m), 7.39-7.27 (3H, m), 7.16-7.09 (3H, m), 6.84-6.72 (3H, m), 4.65 (3H, m), 3.99 (2H, q), 3.56 (2H, m), 2.96-2.80 (4H, m), 2.78-2.66 (2H, m), 1.35 (3H, t), 1.10 (3H, s), 1.05 (3H, s) ppm; LRMS APCI m/z 507 [M + H]⁺ | 45% |
| 87 | H₃C—CH₂—⟨phenyl⟩—CH₂CH₂—N↓ | ¹H NMR (400 MHz, CD₃OD) δ: 7.63 (2H, m), 7.39-7.27 (3H, m), 7.16-7.07 (5H, m), 6.76 (1H, d), 4.65 (3H, m), 3.58 (2H, m), 2.96-2.83 (4H, m), 2.78-2.66 (2H, m), 2.59 (2H, q), 1.19 (3H, t), 1.11 (3H, s), 1.05 (3H, s) ppm; LRMS APCI m/z 491 [M + H]⁺ | 45% |
| 88 | H₃C—⟨pyridyl⟩—CH₂CH₂—N↓ | ¹H NMR (400 MHz, CD₃OD) δ: 7.66-7.59 (3H, m), 7.39-7.29 (3H, m), 7.15-7.08 (3H, m), 6.75 (1H, d), 4.65 (3H, m), 3.70 (2H, t), 3.04 (2H, t), 2.99-2.83 (2H, m), 2.80-2.68 (2H, m), 2.49 (3H, s), 1.10 (3H, s), 1.03 (3H, s) ppm; LRMS APCI m/z 478 [M + H]⁺ | 22% |
| 89 | N↓—CH₂CH₂—⟨phenyl⟩—OCH₃ | ¹H NMR (400 MHz, CD₃OD) δ: 7.60 (2H, m), 7.42-7.10 (6H, m), 6.90-6.70 (3H, d), 4.65 (3H, m), 3.75 (3H, s), 3.50-3.60 (2H, m), 2.95-2.60 (6H, m), 1.15 (3H, s), 1.05 (3H, s) ppm; LRMS APCI m/z 493 [M + H]⁺ | 25% |
| 90 | N↙—⟨phenyl⟩—C(O)OCH₃ | ¹H NMR (400 MHz, CD₃OD) δ: 8.00-7.90 (2H, m), 7.80-7.70 (2H, m), 7.50-7.10 (6H, m), 6.80-6.70 (1H, m), 4.65 (3H, m), 3.90 (2H, s), 3.32 (3H, s), 2.80-3.00 (2H, m), 2.80-2.70 (2H, m), 1.17 (3H, s), 1.07 (3H, s) ppm; LRMS APCI m/z 507 [M + H]⁺ | 32% |
| 91 | N↙—⟨phenyl⟩—N(CH₃)₂ | ¹H NMR (400 MHz, CD₃OD) δ: 7.80-7.60 (2H, m), 7.40-7.10 (6H, m), 6.80-6.60 (3H, m), 5.00-4.80 (3H, m), 4.60-4.40 (2H, m), 2.80-3.00 (6H, m), 2.80-2.60 (4H, m), 1.15 (3H, s), 1.05 (3H, s) ppm; LRMS APCI m/z 492 [M + H]⁺ | 52% |

Upon addition of ammonium fluoride, examples: 89, 90 and 91 were warmed at 50° C. for 18 hours.

EXAMPLE 92

N-[2-(4-Ethoxy-3-methoxyphenyl)ethyl]-3-[2-({(2R)-2-hydroxy-2-[4-hydroxy-3-(hydroxymethyl)phenyl]ethyl}amino)-2-methylpropyl]benzamide

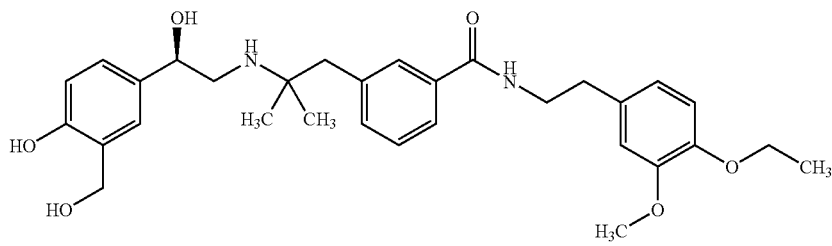

Solutions of 3-{2-[(2R)-2-(tert-butyldimethylsilanyloxy)-2-(4-hydroxy-3-hydroxy methylphenyl)ethylamino]-2-methylpropyl}benzoic acid (preparation 37) (90 mg, 0.19 mmol) in N,N-dimethylacetamide (1 mL) and 0-(1H-benzotriazol-1-yl)-N,N,N',N'-tetramethyluronium hexafluorophosphate (61 mg, 0.16 mmol) in N,N-dimethylacetamide (0.5 mL) were added to a solution of 4-ethoxy-3-methoxyphenethylamine (37 mg, 0.19 mmol) in N,N-dimethylacetamide (0.5 mL). The resulting mixture was stirred for 72 hours at room temperature. The solvent was removed in vacuo and the residue was partitioned between dichloromethane (4 mL) and saturated sodium hydrogen carbonate solution (1 mL). The mixture was then filtered through a phase separation tube and the organic solution was concentrated in vacuo. The residue was dissolved in dimethylsulfoxide (700 μL), triethylamine trihydrofluoride (30 μL, 0.19 mmol) was added and the mixture was stirred at room temperature for 72 hours. The reaction mixture was then purified directly by HPLC using a Phenomenex Luna C18 system, eluting with water/0.05% diethylamine:acetonitrile, 5:95 to 95:5, to afford the title compound in 30% yield (30.9 mg).

$^1$H NMR (400 MHz, CD$_3$OD) δ: 7.60-7.68 (2H, m), 7.39-7.29 (3H, m), 7.13 (1H, m), 6.85-6.81 (2H, m), 6.78-6.72 (2H, m), 4.67-4.62 (3H, m), 4.00 (2H, q), 3.75 (3H, s), 3.58 (2H, m), 2.98-2.64 (6H, m), 1.37 (3H, t), 1.10 (3H, s), 1.03 (3H, s) ppm; LCMS m/z 537.28 [M+H]$^+$.

EXAMPLES 93 TO 112

The following compounds, of the general formula shown below were prepared by a similar method to that described for example 92, using 3-{2-[(2R)-2-(tert-butyldimethylsilanyloxy)-2-(4-hydroxy-3-hydroxymethyl-phenyl)ethylamino]-2-methylpropyl}benzoic acid (preparation 37) and the appropriate amine as starting material. The amines were either commercially available or prepared as described in preparations 69-108.

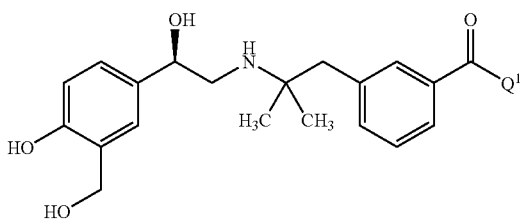

| No. | Q$^1$ | Data | Yield |
|---|---|---|---|
| 93 | 2-F, 4-CH(CF$_2$)F-phenyl ethylamino (structure with CF$_3$, F on benzene ring, ethylamine linker) | $^1$H NMR (400 MHz, CD$_3$OD) δ: 7.60 (3H, m), 7.35 (3H, m), 7.22 (2H, m), 7.13 (1H, m), 6.76 (1H, m), 4.64 (3H, m), 3.62 (2H, m) 2.92 (4H, m), 2.75 (2H, m), 1.10 (3H, s), 1.03 (3H, s) ppm; LRMS ESI m/z 549 [M + H]$^+$ | 11% |
| 94 | 3-F, 4-CH$_3$-phenyl ethylamino | $^1$H NMR (400 MHz, CD$_3$OD) δ: 7.62 (2H, m), 7.35 (3H, m), 7.10 (2H, m), 6.90 (2H, m), 6.75 (1H, m), 4.65 (3H, m), 3.58 (2H, m), 2.90 (3H, m) 2.70 (3H, m), 2.20 (3H, s) 1.10 (3H, s), 1.03 (3H, s) ppm; LRMS APCI m/z 495 [M + H]$^+$ | 36% |

-continued

| No. | Q¹ | Data | Yield |
|---|---|---|---|
| 95 | ![structure: 2,3-difluoro-4-methylphenethyl] | ¹H NMR (400 MHz, CD₃OD) δ: 7.62 (2H, m), 7.32 (3H, m), 7.13 (1H, m), 6.90 (2H, m), 6.75 (1H, m), 4.65 (3H, m), 3.60 (2H, m) 2.80 (6H, m), 2.22 (3H, s) 1.10 (3H, s), 1.05 (3H, s) ppm; LRMS APCI m/z 513 [M + H]⁺ | 63% |
| 96 | ![structure: 2,4,6-trimethylphenethyl] | ¹H NMR (400 MHz, CD₃OD) δ: 7.69 (2H, m), 7.37 (3H, m), 7.15 (1H, m), 6.78 (3H, m), 4.63 (3H, m), 3.42 (2H, m), 2.95 (4H, m), 2.74 (2H, m), 2.32 (6H, s), 2.20 (3H, 1.12 (3H, s), 1.05 (3H, s) ppm; LRMS APCI m/z 505 [M + H]⁺ | 80% |
| 97 | ![structure: 2,6-difluoro-3-methylphenethyl] | ¹H NMR (400 MHz, CD₃OD) δ: 7.60 (2H, m), 7.32 (3H, m), 7.10 (2H, m), 6.78 (2H, m), 4.63 (3H, m), 3.60 (2H, m), 2.66 (6H, m), 2.19 (3H, s) 1.10 (3H, s), 1.05 (3H, s) ppm; LRMS APCI m/z 513 [M + H]⁺ | 44% |
| 98 | ![structure: 6-chloro-2-fluoro-3-methylphenethyl] | ¹H NMR (400 MHz, CD₃OD) δ: 7.62 (2H, m), 7.35 (3H, m), 7.10 (3H, m), 6.76 (1H, m), 4.65 (3H, m), 3.62 (2H, m) 3.14 (2H, m), 2.81 (4H, m), 2.19 (3H, s) 1.10 (3H, s), 1.05 (3H, s) ppm; LRMS APCI m/z 529 [M + H]⁺ | 28% |
| 99 | ![structure: 2-chloro-6-fluoro-3-methylphenethyl] | ¹H NMR (400 MHz, CD₃OD) δ: 7.61 (2H, m), 7.32 (2H, m), 7.17 (2H, m), 6.93 (1H, m), 6.76 (1H, m), 4.65 (3H, m), 3.62 (2H, m) 3.17 (2H, m), 2.81 (4H, m), 2.32 (3H, s) 1.10 (3H, s), 1.05 (3H, s) ppm; LRMS APCI m/z 529 [M + H]⁺ | 64% |
| 100 | ![structure: 5-fluoro-2-methylphenethyl] | ¹H NMR (400 MHz, CD₃OD) δ: 7.67-7.61 (2H, m), 7.40-7.32 (3H, m), 7.17 (2H, m), 6.93 (1H, m), 6.82 (1H, m), 6.76 (1H, m), 4.65 (3H, m), 3.62 (2H, m) 3.17 (2H, m), 3.00-2.64 (4H, m), 2.32 (3H, s) 1.10 (3H, s), 1.05 (3H, s) ppm; LRMS APCI m/z 529 [M + H]⁺ | 46% |

-continued

[Structure: 4-hydroxy-3-(hydroxymethyl)phenyl group with (R)-CH(OH)-CH2-NH-C(CH3)2-CH2-(3-substituted phenyl)-C(=O)-Q¹]

| No. | Q¹ | Data | Yield |
|---|---|---|---|
| 101 | 3-fluoro-5-(trifluoromethyl)phenethylamino | ¹H NMR (400 MHz, CD₃OD) δ: 7.60 (4H, m), 7.34 (4H, m), 7.25 (1H, m), 7.13 (1H, m), 6.75 (1H, m), 4.65 (3H, m), 3.63 (2H, m), 3.04 (2H, m), 2.81 (4H, m), 1.10 (3H, s), 1.05 (3H, s) ppm; LRMS APCI m/z 549 [M + H]⁺ | 35% |
| 102 | 2-(trifluoromethyl)phenethylamino | ¹H NMR (400 MHz, CD₃OD) δ: 7.66 (3H, m), 7.50 (2H, m), 7.37 (4H, m), 7.13 (1H, m), 6.75 (1H, m), 4.65 (3H, m), 3.63 (2H, m), 3.11 (2H, m), 2.90 (2H, m), 2.75 (2H, m), 1.10 (3H, s), 1.05 (3H, s) ppm; LRMS APCI m/z 531 [M + H]⁺ | 50% |
| 103 | 2,4,5-trimethoxyphenethylamino | ¹H NMR (400 MHz, CD₃OD) δ: 7.66 (2H, m), 7.36 (3H, m), 7.15 (1H, m), 6.88 (2H, m), 6.76 (1H, m), 4.65 (3H, m), 3.83 (6H, m), 3.50 (2H, m), 2.25 (3H, s), 2.14 (6H, m), 1.10 (3H, s), 1.05 (3H, s) ppm; LRMS APCI m/z 505 [M + H]⁺ | 38% |
| 104 | 2-(pyridin-2-yl)ethylamino | ¹H NMR (400 MHz, CD₃OD) δ: 8.44 (m, 1H), 7.75 (m, 1H), 7.64-7.60 (2H, m), 7.38-7.23 (5H, m), 7.12 (1H, m), 6.76 (1H, m), 4.69-4.60 (3H, m), 3.73 (2H, m), 3.09 (2H, m), 2.98-2.65 (4H, m), 1.11 (3H, s), 1.04 (3H, s) ppm; LCMS m/z 464.29 [M + H]⁺ | 52% |
| 105 | 2-(1H-benzimidazol-2-yl)ethylamino | ¹H NMR (400 MHz, CD₃OD) δ: 7.67-7.61 (m, 2H), 7.50-7.43 (2H, m), 7.38-7.27 (3H, m), 7.20-7.10 (3H, m), 6.76 (1H, m), 4.69-4.64 (3H, m), 3.83 (2H, t), 3.20 (2H, t), 2.97-2.61 (4H, m), 1.08 (3H, s), 1.01 (3H, s) ppm; LCMS m/z 503.23 [M + H]⁺ | 19% |
| 106 | 2-[4-(morpholinosulfonyl)phenyl]ethylamino | ¹H NMR (400 MHz, CD₃OD) δ: 7.68-7.46 (6H, m), 7.28-7.38 (3H, m), 7.11 (1H, m), 6.76 (1H, m), 4.67-4.62 (3H, m), 3.60-3.70 (6H, m), 3.03 (2H, t), 2.98-2.66 (8H, m), 1.10 (3H, s), 1.04 (3H, s) ppm; LCMS m/z 612.23 [M + H]⁺ | 25% |

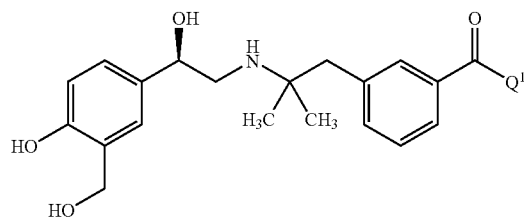

| No. | Q¹ | Data | Yield |
|---|---|---|---|
| 107 | Cl, OH (phenyl with ethyl-N) | LCMS m/z 513.17 [M + H]⁺ | 46% |
| 108 | F, CF₃ (phenyl with methyl-N) | $^1$H NMR (400 MHz, CD$_3$OD) δ: 7.81 (m, 2H), 7.60 (1H, m), 7.49 (3H, m), 7.36 (2H, m), 7.20 (1H, m), 6.80 (1H, m), 4.84 (1H, m), 4.76 (2H, s), 4.65 (2H, m), 3.20 (2H, m), 3.08 (2H, s), 1.34 (6H, m) ppm; LRMS APCI m/z 535 [M + H]⁺ | 33% |
| 109 | Cl (3-chlorophenyl with methyl-N) | $^1$H NMR (400 MHz, CD$_3$OD) δ: 7.83-7.78 (m, 2H), 7.50-7.20 (8H, m), 6.90-6.80 (1H, d), 4.65 (2H, s), 4.58-4.50 (3H, m), 3.22-3.05 (4H, m), 1.40-1.25 (6H, m) ppm; LCMS m/z 483.2045 [M + H]⁺ | 45% |
| 110 | Cl (2-chlorophenyl with methyl-N) | $^1$H NMR (400 MHz, CD$_3$OD) δ: 7.82-7.78 (2H, m), 7.45-7.20 (8H, m), 6.82-6.78 (1H, d), 4.90-4.80 (1H, s), 4.75-4.60 (4H, m), 3.25-3.05 (4H, m), 1.30-1.22 (6H, m) ppm; LCMS m/z 483.2045 [M + H]⁺ | 21% |
| 111 | 4,6-dimethylpyrimidin-2-yl ethyl-N | $^1$H NMR (400 MHz, CD$_3$OD) δ: 7.65-7.61 (2H, m), 7.38-7.27 (3H, m), 7.13 (1H, m), 7.09 (1H, s), 6.76 (1H, m), 4.68-4.62 (3H, m), 3.82 (2H, t), 3.13 (2H, t), 2.98-2.64 (4H, m), 1.11 (3H, s), 1.04 (3H, s) ppm; LRMS APCI m/z 493.29 [M + H]⁺ | 33% |
| 112 | 3-methylpyridin-2-yl ethyl-N | LRMS APCI m/z 478.28 [M + H]⁺ | 25% |

EXAMPLE 102

{2-[2-(trifluoromethyl)phenyl]ethyl}amine can be prepared as described in WO 093231.

EXAMPLE 106

4-[[4-(2-aminoethyl)phenyl]sulfonyl]-morpholine is commercially available from Scientific Exchange Product List (K-046583).

EXAMPLE 107 amine precursor (2-(2-aminoethyl)-6-chlorophenol) can be prepared as described in DE1959898.

EXAMPLE 108 crude compound was purified by HPLC using a Phenomenex Luna C18 system, eluting with water/acetonitrile/trifluoroacetic acid (5:95:0.1):acetonitrile, 95:5 to 5:95, to isolate the trifluoroacetic acid salt of the desired product.

EXAMPLE 109 AND 110 crude compound was purified by HPLC using a Phenomenex Luna C18 system, eluting with water/0.1% formic acid:acetonitrile/0.1% formic acid, 85:15 to 15:85.

EXAMPLE 113

N-[2-(2-Chlorophenyl)ethyl]-3-[2-({(2R)-2-hydroxy-2-[4-hydroxy-3-(hydroxymethyl)phenyl]ethyl}amino)-2-methylpropyl]benzamide

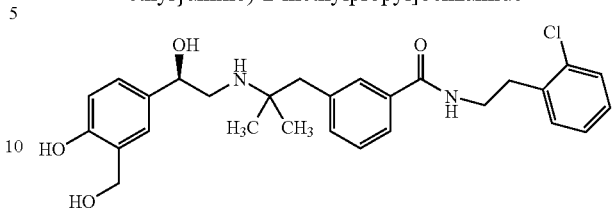

A mixture of 3-[2-({(2R)-2-{[tert-butyl(dimethyl)silyl]oxy}-2-[4-hydroxy-3-(hydroxymethyl)phenyl]ethyl}amino)-2-methylpropyl]-N-[2-(2-chlorophenyl)ethyl]benzamide (preparation 118), (147 mg, 0.24 mmol) and triethylamine trihydrofluoride (39 μL, 0.24 mmol) was stirred at room temperature for 3 days. The mixture was then concentrated in vacuo and the residue was purified by column chromatography on silica gel, eluting with dichloromethane:methanol:0.88 ammonia, 100:0:0 to 95:5:0.5. The appropriate fractions were evaporated under reduced pressure and the residue was azeotroped with methanolic ammonia to afford the title compound as a colourless solid in 77% yield, 75 mg.
$^1$H NMR (400 MHz, CD$_3$OD) δ: 7.61 (2H, m), 7.37-7.29 (5H, m), 7.23-7.16 (2H, m), 7.12 (1H, dd), 6.74 (1H, d), 4.66 (1H, m), 4.64 (2H, s), 3.63 (2H, m), 3.05 (2H, t), 2.96-2.84 (2H, t), 2.76-2.69 (2H, m), 1.10 (3H, s), 1.04 (3H, s) ppm; LRMS ESI m/z 497 [M+H]$^+$.

EXAMPLES 114 TO 128

The following compounds, of the general formula shown below were prepared by a similar method to that described for example 113, using the appropriate starting material and triethylamine trihydrofluoride. The reactions were monitored by tlc analysis and were stirred at room temperature for 18-72 hours.

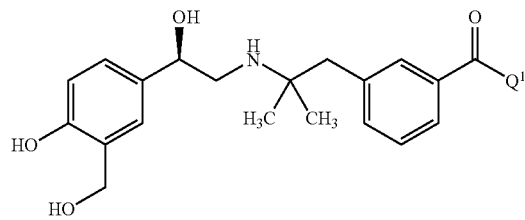

| No. | Q$^1$ | Data | Yield |
|---|---|---|---|
| 114 | ![adamantyl-ethyl-amino] | $^1$H NMR (400 MHz, CD$_3$OD) δ: 7.66 (2H, m), 7.38-7.31 (3H, m), 7.13 (1H, m), 6.75 (1H, d), 4.67 (1H, m), 4.65 (2H, d), 3.44-3.36 (2H, m), 2.99-2.88 (2H, m), 2.78-2.69 (2H, m), 1.94 (3H, s), 1.67-1.77 (6H, m), 1.58 (6H, m), 1.37 (2H, m), 1.12 (3H, s), 1.05 (3H, s) ppm; LRMS APCI m/z 521 [M + H]$^+$ | 67% |

-continued

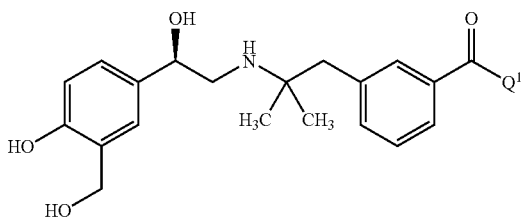

| No. | Q¹ | Data | Yield |
|---|---|---|---|
| 115 | (naphthalen-1-yl)ethyl-N | ¹H NMR (400 MHz, CD₃OD) δ: 8.21 (1H, m), 7.85 (1H, m), 7.74 (1H, m), 7.65 (2H, m), 7.47 (2H, m), 7.39-7.31 (5H, m), 7.14 (1H, dd), 6.75 (1H, m), 4.68 (1H, m), 4.64 (2H, d), 3.71 (2H, m), 3.39 (2H, m), 2.99-2.87 (2H, m), 2.79-2.70 (2H, m), 1.12 (3H, s), 1.05 (3H, s) ppm; LRMS APCI m/z 513 [M + H]⁺ | 50% |
| 116 | 2,6-dimethylphenethyl-N | ¹H NMR (400 MHz, CD₃OD) δ: 7.68-7.61 (2H, m), 7.36 (2H, m), 7.33 (1H, m), 7.14 (1H, dd), 6.96 (3H, m), 6.75 (1H, m), 4.67 (1H, m), 4.63 (2H, m), 3.47 (2H, m), 3.00-2.89 (4H, m), 2.77-2.71 (2H, m), 2.35 (6H, s), 1.13 (3H, s), 1.05 (3H, s) ppm; LRMS APCI m/z 491 [M + H]⁺ | 75% |
| 117 | 4-(methylthio)phenethyl-N | ¹H NMR (400 MHz, CD₃OD) δ: 7.63 (2H, m), 7.37-7.31 (3H, m), 7.20-7.12 (5H, m), 6.74 1H m), 4.67 (1H, m), 4.65 (2H, d), 3.55-3.59 (2H, m), 2.97-2.85 (4H, m), 2.70-2.77 (2H, m), 2.42 (3H, s), 1.11 (3H, s), 1.05 (3H, s) ppm LRMS APCI m/z 509 [M + H]⁺ | 30% |
| 118 | 2-fluoro-5-chlorophenethyl-N | ¹H NMR (400 MHz, CD₃OD) δ: 7.61 (2H, m), 7.36-7.28 (4H, m), 7.21 (1H, m), 7.11 (1H, m), 7.02 (1H, m), 6.74 (1H, d), 4.65 (2H, m), 3.60 (2H, m), 2.96-2.84 (4H, m), 2.77-2.69 (2H, m), 1.10 (3H, s), 1.04 (3H, s) ppm; LCMS m/z 515 [M]⁺ | 23% |
| 119 | 2-chloro-4-fluorophenethyl-N | ¹H NMR (400 MHz, CD₃OD) δ: 7.62 (2H, m), 7.30-7.37 (4H, m), 7.17 (1H, m), 7.11 (1H, dd), 6.96 (1H, m), 6.74 (1H, d), 4.67 (1H, m), 4.64 (2H, m), 3.61 (2H, m), 3.02 (2H, t), 2.96-2.85 (2H, m), 2.78-2.70 (2H, m), 1.11 (3H, s), 1.04 (3H, s) ppm; LRMS APCI m/z 515 [M + H]⁺ | 45% |
| 120 | 2,5-dimethyl-4-methoxyphenethyl-N | ¹H NMR (400 MHz, CD₃OD) δ: 7.65 (2H, m), 7.38-7.31 (3H, m), 7.12 (1H, dd), 6.88 (1H, s), 6.75 (1H, d), 6.66 (1H, s), 4.67 (1H, m), 4.65 (2H, m), 3.77 (3H, s), 3.49 (2H, m), 2.98-2.87 (2H, m), 2.84-2.70 (4H, m), 2.30 (3H, s), 2.08 (3H, s), 1.12 (3H, s), 1.05 (3H, s) ppm; LRMS ESI m/z 521 [M + H]⁺ | 52% |
| 121 | 2,3-dichlorophenethyl-N | ¹H NMR (400 MHz, CD₃OD) δ: 7.62 (2H, m), 7.38 (1H, dd), 7.32 (3H, m), 7.25 (1H, m), 7.19 (1H, m), 7.12 (1H, d), 6.74 (1H, d), 4.68 (1H, m), 4.65 (2H, m), 3.68 (2H, m), 3.10 (2H, m), 2.96 (2H, m), 2.73 (2H, m), 1.11 (3H, s), 1.05 (3H, s) ppm; LRMS APCI m/z 531 [M + H]⁺ | 67% |

-continued

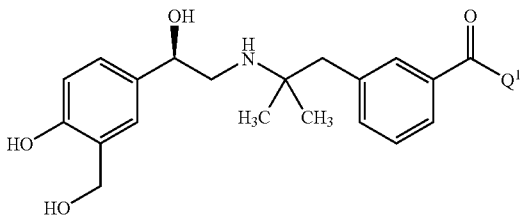

| No. | Q¹ | Data | Yield |
|---|---|---|---|
| 122 | (2,3-dimethyl-4-methoxyphenethyl) | ¹H NMR (400 MHz, CD₃OD) δ: 7.65 (1H, m) 7.63 (1H, m), 7.38-7.31 (3H, m), 7.13 (1H, dd), 6.95 (1H, s), 6.75 (1H, d), 6.67 (1H, d), 4.67 (1H, m), 4.65 (2H, m), 3.76 (3H, s), 3.49 (2H, m), 2.98-2.87 (4H, m), 2.79-2.70 (2H, m), 2.25 (3H, s), 2.12 (3H, s), 1.12 (3H, s), 1.05 (3H, s) ppm LRMS ESI m/z 521 [M + H]⁺ Microanalysis: C₃₁H₄₀N₂O₅. 0.1H₂O requires (%): C 71.27; H 7.76; N 5.36; found (%) C 70.87; H 7.36, N 5.36. | 83% |
| 123 | (biphenyl-4-ylethyl) | ¹H NMR (400 MHz, CD₃OD) δ: 7.63 (1H, m), 7.60 (1H, bs), 7.57-7.50 (4H, m), 7.41-7.26 (8H, m), 7.11 (1H, m), 6.73 (1H, dd), 4.66-4.62 (3H, m), 3.69 (2H, t), 2.96-2.83 (4H, m), 2.75-2.67 (2H, m), 1.09 (3H, s), 1.02 (3H, s) ppm LRMS ESI m/z 539 [M + Na]⁺ | 74% |
| 124 | (2,4-dimethylphenethyl) | ¹H NMR (400 MHz, CD₃OD) δ: 7.65 (2H, m) 7.63 (2H, m), 7.39-7.30 (1H, d), 7.12 (1H, dd), 7.01 (1H, d), 6.95 (1H, bs), 6.88 (1H, d), 6.74 (1H, d), 4.69-4.63 (3H, m), 3.60 (2H, m), 2.98-2.85 (4H, m), 2.78-2.68 (2H, m), 2.29 (3H, s), 2.24 (3H, s), 1.11 (3H, s), 1.04 (3H, s) ppm; LRMS ESI m/z 513 [M + Na]⁺ | 79% |
| 125 | (2,3-dimethylphenethyl) | ¹H NMR (400 MHz, CD₃OD) δ: 7.65 (2H, m), 7.39-7.31 (3H, m), 7.13 (1H, dd), 7.02-6.94 (3H, m), 6.75 (1H, d), 4.65 (3H, m), 3.64-3.60 (2H, m), 2.99-2.93 (3H, m), 2.88 (1H, m), 2.74 (1H, dd), 2.71 (1H, m), 2.26 (3H, s), 2.25 (3H, s), 1.12 (3H, s), 1.06 (3H, s) ppm LRMS APCI m/z 491 [M + H]⁺ | 58% |
| 126 | (3-trifluoromethylphenethyl) | ¹H NMR (400 MHz, CD₃OD) δ: 7.66-7.46 (6H, m), 7.33 (3H, m), 7.13 (1H, d), 6.75 (1H, d), 4.67 (3H, m), 3.66-3.60 (2H, m), 3.04-2.85 (4H, m), 2.89-2.76 (2H, m), 1.11 (3H, s), 1.04 (3H, s) ppm LRMS APCI m/z 531 [M + H]⁺ | 79% |
| 127 | (4-chloro-2-fluorophenethyl) | ¹H NMR (400 MHz, CDCl₃) δ: 7.60 (2H, m), 7.36-7.26 (4H, m), 7.16-7.09 (3H, m), 6.75 (1H, d), 4.66 (3H, m), 3.83-3.57 (2H, m), 2.98-2.69 (6H, m), 1.10 (3H, s), 1.04 (3H, s) ppm; LRMS APCI m/z 515 [M + H]⁺ | 85% |
| 128 | (2,5-dimethylbenzyl) | ¹H NMR (400 MHz, CD₃OD) δ: 7.72 (2H, m) 7.39-7.32 (2H, m), 7.26 (1H, d), 7.11 (1H, bs), 7.09-7.03 (2H, dd), 6.95 (1H, d), 6.68 (1H, d), 4.63 (3H, m), 4.49 (2H, dd), 2.94-2.86 (2H, m), 2.73 (2H, dd), 2.29 (3H, s), 2.24 (3H, s), 1.11 (3H, s), 1.04 (3H, s) ppm; LRMS ESI m/z 499 [M + Na]⁺ | 44% |

EXAMPLE 129

N-(3,4-Dichlorobenzyl)-3-{3-[2-({(2R)-2-hydroxy-2-[4-hydroxy-3-(hydroxymethyl)phenyl]ethyl}amino)-2-methylpropyl]phenyl}propanamide

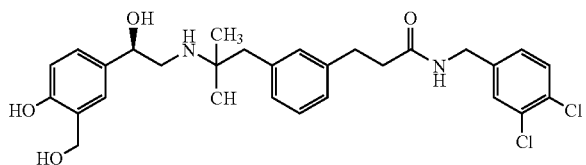

The title compound was prepared from 3-{3-[2-({(2R)-2-{[tert-butyl(dimethyl)silyl]oxy}-2-[4-hydroxy-3-(hydroxymethyl)phenyl]ethyl}amino)-2-methylpropyl]phenyl}-N-(3,4-dichlorobenzyl) propanamide (preparation 145), using a method similar to that of example 113, as a white foam in 71% yield. $^1$H NMR (400 MHz, CD$_3$OD) δ: 7.38 (1H, d), 7.35 (2H, d), 7.08 (6H, m), 6.78 (1H, d), 5.61 (3H, m), 4.23 (2H, s), 2.95 (3H, m), 2.68 (3H, m), 2.58 (2H, t), 1.01 (6H, s) ppm; LRMS ESI m/z 545 [M+H]$^+$.

EXAMPLE 130

N-[2-({(2R)-2-Hydroxy-2-[4-hydroxy-3-(hydroxymethyl)phenyl]ethyl}amino)-2-methylpropyl]-N-2-[4-(trifluoromethoxy)phenyl]ethyl)benzamide

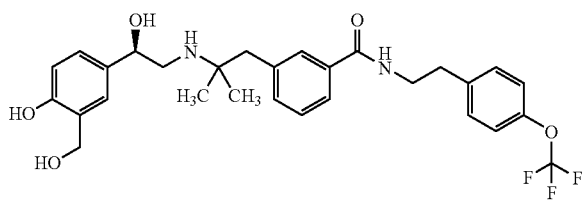

A mixture of 3-[2-({(2R)-2-hydroxy-2-[4-hydroxy-3-(hydroxymethyl)phenyl]ethyl}amino)-2-methylpropyl]benzoic acid (preparation 140) (100 mg, 0.28 mmol), 2-(4-trifluoromethoxyphenyl)ethylamine (US20020082454A1, p2), (46 mg, 0.28 mmol), 1-(3-dimethylaminopropyl)-3-ethylcarbodiimide hydrochloride (43 mg, 0.28 mmol), 1-hydroxybenzotriazloe hydrate (35 mg, 0.28 mmol) and triethylamine (600 L, 0.45 mmol) in N,N-dimethylformamide (5 mL) was stirred at room temperature for 20 hours. The reaction mixture was then concentrated in vacuo and the residue was dissolved in dichloromethane. The solution was then washed with saturated sodium carbonate solution and brine, dried over magnesium sulfate and concentrated in vacuo. Purification of the residue by column chromatography on silica gel, eluting with dichloromethane:methanol:0.88 ammonia, 100:0:0 to 95:5:1, afforded the title compound as a white powder in 51% yield, 79 mg. $^1$H NMR (400 MHz, CD$_3$OD) δ: 7.63 (2H, m), 7.38-7.30 (5H, m), 7.17 (2H, m), 7.12 (1H, dd), 6.75 (1H, d), 4.66 (3H, m), 3.57 (2H, d), 2.99-2.85 (4H, m), 2.79-2.69 (2H, m), 1.12 (3H, s), 1.06 (3H, s) ppm; LRMS APCI m/z 547 [M+H]$^+$.

EXAMPLES 131 TO 137

The following compounds, of the general formula shown below, were prepared by a similar method to that described for example 130, using the appropriate acid and amine starting materials. The amines were either commercially available or prepared as described in preparations 69-108.

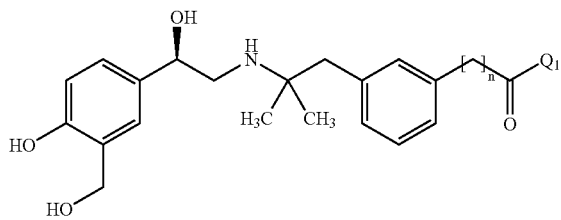

| No. | Q$^1$ | Data | Yield |
|---|---|---|---|
| n = 0: | | | |
| 131 | ![structure] | $^1$H NMR (400 MHz, CD$_3$OD) δ: 7.54 (1H, m), 7.50 (1H, m), 7.34-7.28 (3H, m), 7.25 (2H, m), 7.10 (1H, dd), 6.73 (3H, m), 4.62 (3H, m), 3.51 (2H, s), 2.92-2.87 (1H, m), 2.81 (1H, m), 2.76-2.70 (2H, m), 1.33 (6H, s), 1.08 (3H, s), 1.04 (3H, s) ppm; LRMS APCI m/z 507 [M + H]$^+$ | 6% |

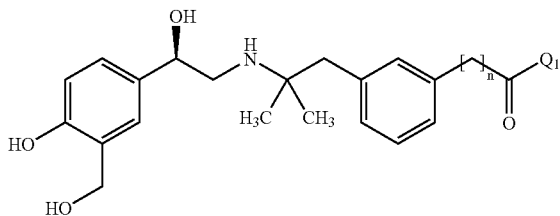

| No. | Q¹ | Data | Yield |
|---|---|---|---|
| 132 | (4-OH, 3-CH₃ phenyl, connected via N-CH₂CH₂) | $^1$H NMR (400 MHz, CD$_3$OD) δ: 7.88-7.80 (3H, m), 7.63 (2H, m), 7.12 (1H, dd), 6.92 (1H, m), 6.84 (1H, dd), 6.75 (1H, d), 6.63 (1H, d), 4.67 (1H, m), 4.65 (2H, m), 3.51 (2H, m), 2.99-2.86 (2H, m), 2.78-2.70 (4H, m), 2.13 (3H, s), 1.12 (3H, s), 1.05 (3H, s) ppm; LRMS APCI m/z 493 [M + H]$^+$ | 22% |
| 133 | (4-OH, 2,3-diCH₃ phenyl, connected via N-CH₂CH₂) | $^1$H NMR (400 MHz, CD$_3$OD) δ: 7.98 (2H, m), 7.43-7.36 (3H, m), 7.16 (1H, dd), 6.82-6.77 (2H, m), 6.52 (1H, d), 4.75 (1H, m), 4.66 (2H, m), 3.47 (2H, m), 3.07 (1H, m), 2.98 (2H, m), 2.92 (1H, m), 2.85 (2H, m), 2.24 (3H, s), 2.11 (3H, s), 1.23 (3H, s), 1.19 (3H, s) ppm; LRMS APCI m/z 507 [M + H]$^+$ | 6% |
| 134 | (4-OH, 2,5-diCH₃ phenyl, connected via N-CH₂CH₂) | $^1$H NMR (400 MHz, CD$_3$OD) δ: 7.66 (2H, m), 7.40-7.34 (3H, m), 7.14 (1H, dd), 6.83 (1H, s), 6.76 (1H, m), 6.50 (1H, d), 4.69 (1H, m), 4.66 (2H, s), 3.49 (2H, m), 3.04-2.98 (2H, m), 2.87 (1H, m), 2.82-2.77 (3H, m), 2.22 (3H, s), 2.08 (3H, s), 1.17 (3H, s), 1.12 (3H, s) ppm; LRMS APCI m/z 507 [M + H]$^+$ | 16% | n = 1:

| No. | Q¹ | Data | Yield |
|---|---|---|---|
| 135 | 3,4-dichlorobenzyl | $^1$H NMR (400 MHz, CD$_3$OD) δ: 7.41-7.05 (9H, m), 6.78 (1H, d), 4.65 (3H, m), 4.36 (2H, s), 3.55 (2H, s), 2.87 (2H, m), 2.81-2.69 (2H, m), 1.12 (3H, s), 1.05 (3H, s) ppm; LRMS ESI m/z 531 [M + H]$^+$ | 41% |
| 136 | 3,5-dichlorobenzyl | $^1$H NMR (400 MHz, CD$_3$OD) δ: 7.34-7.03 (9H, m), 6.79 (1H, d), 4.63 (3H, m), 4.37 (2H, s), 3.54 (2H, s), 2.90 (2H, m), 2.81-2.64 (2H, m), 1.12 (3H, s), 1.05 (3H, s) ppm; LRMS ESI m/z 531 [M + H]$^+$ | 24% |
| 137 | pyridin-2-ylmethyl | $^1$H NMR (400 MHz, CD$_3$OD) δ: 8.42 (1H, d), 7.77 (1H, t), 7.31-7.04 (8H, m), 6.76 (1H, d), 4.62 (3H, m), 4.44 (2H, s), 3.59 (2H, s), 2.92-2.65 (4H, m), 1.06 (3H, s), 1.04 (3H, s) ppm; LRMS ESI m/z 464 [M + H]$^+$ | 66% |

EXAMPLE 131 amine precursor (4-(2-amino-1,1-dimethylethyl)phenol) can be prepared as described in *Acta Chem. Scand.* 8, 1203, 1207; 1954.

EXAMPLES 138 TO 147

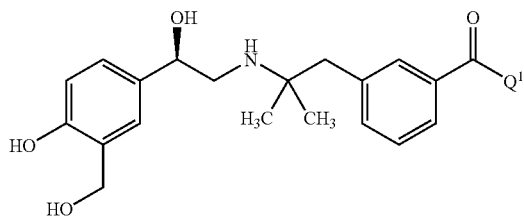

A mixture of 3-[2-({(2R)-2-hydroxy-2-[4-hydroxy-3-(hydroxymethyl)phenyl]ethyl}amino)-2-methylpropyl]benzoic acid (preparation 140), (0.2M in dimethylacetamide/3.75% triethylamine, 225 μL, 45 μmol), the appropriate amine (0.2M in dimethylacetamide/3.75% triethylamine, 150 μL, 30 μmol) and O-(1H-benzotriazol-1-yl)-N,N,N',N'-tetramethyluronium hexafluorophosphate (0.2M in dimethylacetamide, 225 μL, 45 μmol) was stirred at 60° C. for 3 days. The reaction mixture was then concentrated in vacuo, re-dissolved in dimethylsulfoxide (300 μL) and stirred for 30 minutes at room temperature. The mixture was diluted with further dimethylsulfoxide (50 μL) and water 100 μL), stirred for one minute at room temperature and then purified by HPLC using a Phenomenex Luna C18 system, eluting with water/acetonitrile/diethylamine (5:95:0.05):acetonitrile, 95:5 to 5:95, to afford the desired compound.

| No. | Q¹ | Data |
|---|---|---|
| 138 | ![ethyl-N-propyl-phenyl] | LRMS ESI m/z 504.30 [M]⁺ |
| 139 | ![N-propyl-4-hydroxyphenyl] | LRMS ESI m/z 492.26 [M]⁺ |
| 140 | ![N-ethyl-3-methylphenyl] | LRMS ESI m/z 476.26 [M]⁺ |
| 141 | ![N-ethyl-6-methoxypyridin-3-yl] | LRMS ESI m/z 493.26 [M]⁺ |
| 142 | ![N-propyl-3-methoxyphenyl] | LRMS ESI m/z 506.28 [M]⁺ |
| 143 | ![N-propyl-4-chlorophenyl] | LRMS ESI m/z 510.23 [M − H]⁻ |
| 144 | ![N-ethoxy-4-(pyrazol-1-yl)phenyl] | LRMS ESI m/z 544.27 [M]⁺ |

| No. | Q¹ | Data |
|---|---|---|
| 145 | 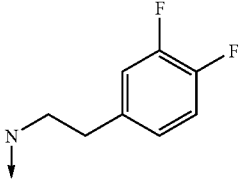 | LRMS ESI m/z 498.23 [M]⁺ |
| 146 | 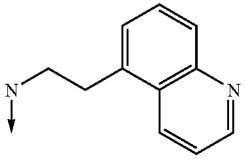 | LRMS ESI m/z 513.26 [M]⁺ |
| 147 | 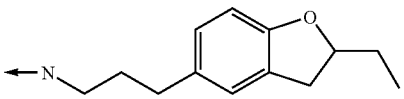 | LRMS ESI m/z 546.31 [M]⁺ |

EXAMPLE 138

N-ethyl-3-phenylpropylamine can be prepared as described in *J. Med. Chem.* 34, 248; 1991.

EXAMPLE 141

6-methoxy-3-pyridineethanamine can be prepared as described in *Drug Design and Discovery*, 10, 35; 1993.

EXAMPLE 143

2-[4-(Pyrazol-1-yl)phenoxy]ethylamine can be prepared as described in WO2002032897, p55.

EXAMPLE 146

5-Quinolineethanamine can be prepared as described in *J. Med. Chem.*, 28, 1803-10; 1985.

Preparation 1: 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl)-N-cycloheptylacetamide

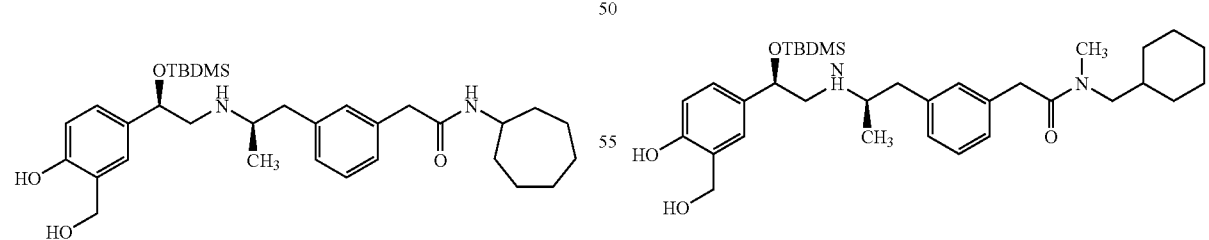

A solution of (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetic acid (Preparation 20) (250 mg, 0.45 mmol), 1-(3-dimethylaminopropyl)-3-ethylcarbodiimide hydrochloride (94 mg, 0.49 mmol), hydroxybenzotriazole monohydrate (66 mg, 0.49 mmol) in N,N-dimethylformamide (4 ml) was treated with triethylamine (0.12 ml, 0.89 mmol) and cycloheptylamine (56 mg, 0.49 mmol) and the resulting suspension left to stir at room temperature under a nitrogen atmosphere for 18 hours. The solvent was removed in vacuo and the residue partitioned between ethyl acetate (10 ml) and saturated aqueous sodium bicarbonate (10 ml). The organic phase was separated, and the aqueous phase extracted with further ethyl acetate (2×10 ml). The combined organic extracts were washed with water (5 ml), brine (5 ml), dried (sodium sulfate) and the solvent removed in vacuo. The residue was purified by flash column chromatography on silica gel eluting with dichloromethane:methanol:880 ammonia (95:5:0.5 by volume) to give the title compound as a pale yellow oil (150 mg). ¹H NMR (400 MHz, CD₃OD): δ=7.20-6.98 (6H, m), 6.68 (1H, d), 4.60 (3H, m), 3.80 (1H, m), 3.40 (2H, s), 2.85 (2H, m), 2.63 (2H, m), 2.58 (1H, m), 1.80 (2H, m), 1.75-1.40 (10H, m), 1.03 (3H, d), 0.83 (9H, s), 0.00 (3H, s), −0.20 (3H, s) ppm. LRMS (electrospray): m/z [M+H]⁺ 569.

Preparation 2: 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(cyclohexylmethyl)-N-methylacetamide Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetic acid (Preparation 20) and the appropriate amine to give the title compound as a colourless oil.

¹H NMR (400 MHz, CD₃OD): δ=7.20-6.95 (6H, m), 6.63 (1H, d), 4.60 (3H, m), 3.68 (2H, s), 3.20 (2H, m), 2.85 (5H, m), 2.63 (2H, m), 2.57 (1H, m), 1.60 (5H, m), 1.20 (4H, m), 1.03 (3H, d), 0.81 (11H, m), 0.00 (3H, s), −0.21 (3H, s) ppm. LRMS (electrospray): m/z [M+H]+ 583.

Preparation 3: 2-{3-[(2R)-2-({(2R)-2{[tert-butyl (dimethyl)silyl]oxy}-2-[4-hydroxy-3-(hydroxymethyl)phenyl]ethyl}amino)propyl]phenyl}-N-[(1S)-1-cyclohexylethyl]acetamide

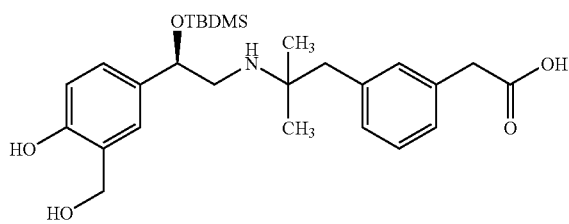

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino-propyl}-phenyl)-acetic acid (Preparation 20) and the appropriate amine to give the title compound as a colourless oil.

1H NMR (400 MHz, CD3OD): δ=7.20 (3H, m), 7.03 (1H, s), 6.98 (2H, dd), 6.68 (1H, d), 4.60 (3H, m), 3.68 (1H, m), 3.42 (1H, d), 3.38 (1H, d), 2.85 (2H, m), 2.63 (2H, m), 2.58 (1H, dd), 1.65 (4H, m), 1.40-0.83 (13H, m), ppm. LRMS (electrospray): m/z [M+H]+ 583, [M+Na]+ 605, [M−H]− 582.

Preparation 4: 2-{3-[(2R)-2-({(2R)-2-{[tert-butyl (dimethyl)silyl]oxy}-2-[4-hydroxy-3-(hydroxymethyl)phenyl]ethyl}amino)propyl]phenyl}-N-isopropylacetamide

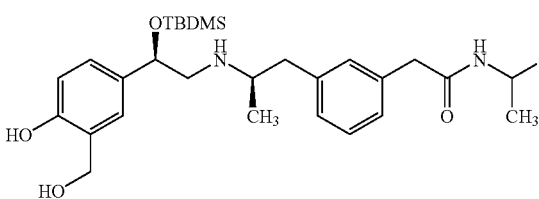

Prepared according to the procedure used for preparation 1 using (3-{(2R)-2-[(2R)-2-{[tert-butyl(dimethyl)silyl]oxy}-2-(4-hydroxy-3-hydroxymethyl-phenyl )-ethylamino]-propyl}-phenyl)-acetic acid (Preparation 20) and the appropriate amine to give the title compound as a colourless oil.

1H NMR (400 MHz, CD3OD): δ=7.19-7.15 (2H, m), 7.11-7.10 (1H, d), 7.04 (1H, s), 6.99-6.96 (2H, t), 6.69-6.67 (1H, d), 4.71-4.67 (1H, dd), 4.65-4.58 (2H, m), 3.96-3.90 (1H, m), 3.39 (2H, s), 2.93-2.84 (2H, m), 2.70-2.62 (2H, m), 2.56-2.52 (1H, m), 1.12-1.11 (6H, d), 1.05-1.03 (3H, d), 0.83 (9H, s), −0.01 (3H, s), −0.20 (3H, s) ppm. LRMS (electrospray): m/z [M+H]+ 515, [M−H]− 513.

Preparation 5: 2-{3-[(2R)-2-({(2R)-2-{[tert-butyl (dimethyl)silyl]oxy}-2-[4-hydroxy-3-(hydroxymethyl)phenyl]ethyl}amino)propyl]phenyl}-N-cyclopentylacetamide

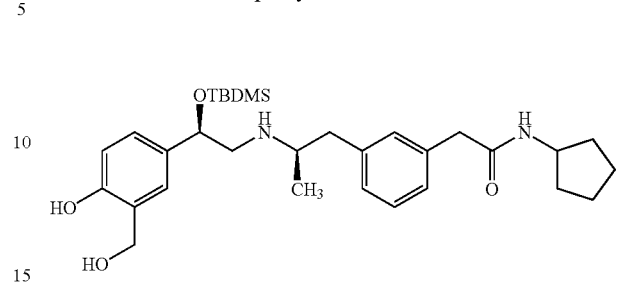

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetic acid (Preparation 20) and the appropriate amine to give the title compound as a colourless oil.

1H NMR (400 MHz, CD3OD): δ=7.19 (1H, d), 7.17-7.15 (1H, d), 7.11-7.09 (1H, d), 7.04 (1H, s), 6.99-6.95 (2H, t), 6.69-6.67 (1H, d), 4.71-4.67 (1H, dd), 4.65-4.58 (2H, m), 4.10-4.04 (1H, m), 3.40 (2H, s), 2.92-2.84 (2H, m), 2.69-2.62 (2H, m), 2.56-2.51 (1H, m), 1.94-1.86 (2H, m), 1.73-1.65 (2H, m), 1.62-1.53 (2H, m), 1.47-1.39 (2H, m), 1.05-1.03 (3H, d), 0.83 (9H, s), −0.01 (3H, s), −0.20 (3H, s) ppm. LRMS (electrospray): m/z [M+H]+ 541, [M−H]− 539.

Preparation 6: 2-{3-[(2R)-2-({(2R)-2-{[tert-butyl (dimethyl)silyl]oxy}-2-[4-hydroxy-3-(hydroxymethyl)phenyl]ethyl}amino)propyl]phenyl}-N-(cyclobutylmethyl)acetamide

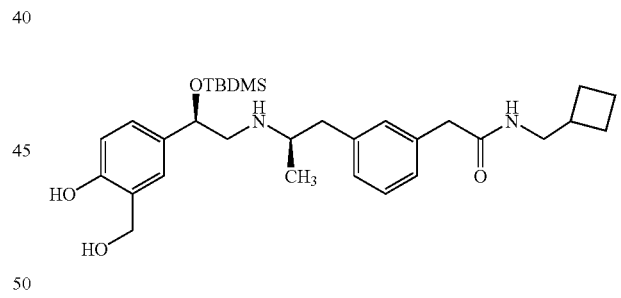

Prepared according to the procedure used for preparation 1 using (3-{(2R)-2-[(2R)-2-{[tert-butyl(dimethyl)silyl]oxy}-2-(4-hydroxy-3-hydroxymethyl-phenyl )-ethylamino]-propyl}-phenyl)-acetic acid (Preparation 20) and the appropriate amine to give the title compound as a colourless oil.

1H NMR (400 MHz, CD3OD): δ=7.19-7.15 (2H, m), 7.12-7.10 (1H, m), 7.04 (1H, s), 7.00-6.96 (2H, m), 6.69-6.67 (1H, d), 4.71-4.67 (1H, dd), 4.65-4.58 (2H, m), 3.43 (2H, s), 3.19-3.17 (2H, d), 2.93-2.85 (2H, m), 2.70-2.62 (2H, m), 2.56-2.51 (tH, m), 2.48-2.43 (1H, m), 2.04-1.96 (2H, m), 1.90-1.78 (2H, m), 1.72-1.65 (2H, m), 1.05-1.03 (3H, d), 0.83 (9H, s), 0.00 (3H, s), -0.20 (3H, s) ppm. LRMS (electrospray): m/z [M+H]+ 541, [M−H]− 539.

Preparation 7: 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(cyclopentyl methyl)acetamide

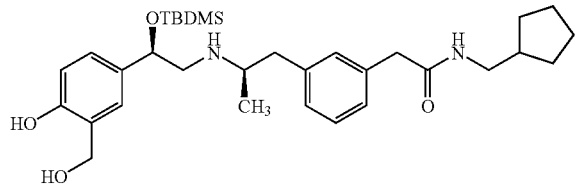

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetic acid (Preparation 20) and the appropriate amine to give the title compound as a colourless oil.

$^1$H NMR (400 MHz, CD$_3$OD): δ=7.18 (1H, s), 7.16-7.14 (1H, d), 7.11-7.09 (1H, d), 7.04 (1H, s), 6.99-6.95 (2H, m), 6.68-6.66 (1H, d), 4.70-4.67 (1H, dd), 4.65-4.57 (2H, m), 3.43 (2H, s), 3.10-3.08 (2H, d), 2.93-2.85 (2H, m), 2.70-2.63 (2H, m), 2.56-2.51 (1H, m), 2.08-2.00 (1H, m), 1.74-1.67 (2H, m), 1.64-1.50 (4H, m), 1.22-1.14 (2H, m), 1.06-1.04 (3H, d), 0.84 (9H, s), 0.01 (3H, s), −0.18 (3H, s) ppm. LRMS (electrospray): m/z [M+H]$^+$ 555, [M−H]$^−$ 554.

Preparation 8: 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-cyclohexylacetamide

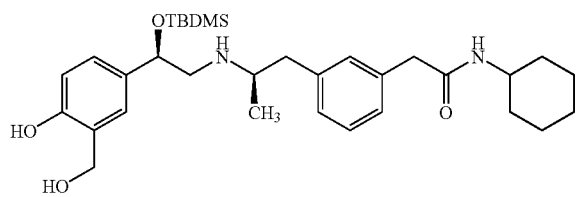

Prepared according to the procedure used for preparation 1 using (3-{(2R)-2-[(2R)-2-{[tert-butyl(dimethyl)silyl]oxy}-2-(4-hydroxy-3-hydroxymethyl-phenyl )-ethylamino]-propyl}-phenyl)-acetic acid (Preparation 20) and the appropriate amine to give the title compound as a colourless oil.

$^1$H NMR (400 MHz, CD$_3$OD): δ=7.19 (1H, d), 7.17-7.15 (1H, d), 7.11-7.09 (1H, d), 7.04 (1H, s), 6.99-6.95 (2H, t), 6.69-6.67 (1H, d), 4.70-4.67 (1H, dd), 4.65-4.58 (2H, m), 3.65-3.57 (1H, m), 3.40 (2H, s), 2.92-2.84 (2H, m), 2.69-2.61 (2H, m), 2.56-2.51 (1H, m), 1.86-1.80 (2H, m), 1.75-1.70 (2H, m), 1.64-1.59 (1H, m), 1.39-1.28 (2H, m), 1.24-1.15 (3H, m), 1.05-1.03 (3H, d), 0.83 (9H, s), −0.01 (3H, s), −0.20 (3H, s) ppm. LRMS (electrospray): m/z [M+H]$^+$ 555, [M−H]$^−$ 554.

Preparation 9: 2-{3-[(2R)-2-({(2R)-2{[tert-butyl(dimethyl)silyl]oxy}-2-[4-hydroxy-3-(hydroxymethyl)phenyl]ethyl}amino)propyl]phenyl}-N-cyclobutylacetamide

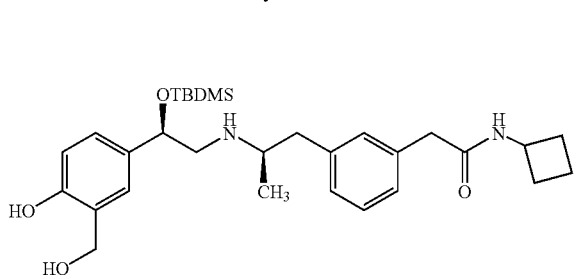

Prepared according to the procedure used for preparation 1 using (3-{(2R)-2-[(2R)-2-{[tert-butyl(dimethyl)silyl]oxy}-2-(4-hydroxy-3-hydroxymethyl-phenyl )-ethylamino]-propyl}-phenyl)-acetic acid (Preparation 20) and the appropriate amine to give the title compound as a colourless oil.

$^1$H NMR (400 MHz, CD$_3$OD): δ=7.19 (1H, d), 7.17-7.15 (1H, d), 7.11-7.09 (1H, d), 7.03 (1H, s), 6.99-6.95 (2H, m), 6.68-6.66 (1H, d), 4.70-4.65 (1H, dd), 4.62-4.61 (2H, d), 4.29-4.21 (1H, m), 3.39 (2H, s), 2.92-2.84 (2H, m), 2.68-2.61 (2H, m), 2.57-2.52 (1H, m), 2.29-2.21 (2H, m), 1.98-1.87 (2H, m), 1.74-1.66 (2H, m), 1.05-1.03 (3H, d), 0.82 (9H, s), −0.01 (3H, s), −0.20 (3H, s) ppm. LRMS (electrospray): m/z [M+H]$^+$ 527, [M−H]$^−$ 525.

Preparation 10: 2-{3-[(2R)-2-({(2R)-2{[tert-butyl(dimethyl)silyl]oxy}-2-[4-hydroxy-3-(hydroxymethyl)phenyl]ethyl}amino)propyl]phenyl}-N-(cyclohexylmethyl)acetamide

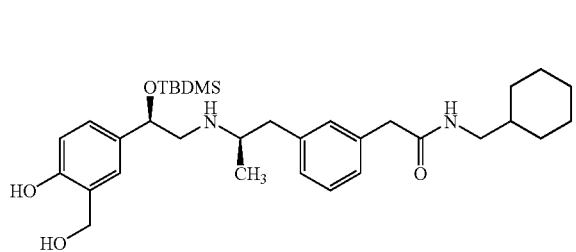

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetic acid (Preparation 20) and the appropriate amine to give the title compound as a white foam.

$^1$H NMR (400 MHz, CD$_3$OD): δ=7.18-7.14 (2H, m), 7.11-7.09 (1H, m), 7.03 (1H, s), 6.98-6.95 (2H, m), 6.68-6.66 (1H, d), 4.70-4.67 (1H, dd), 4.62-4.61 (2H, d), 3.43 (2H, s), 3.00-2.99 (2H, d), 2.91-2.84 (2H, m), 2.70-2.62 (2H, m), 2.55-2.50 (1H, m), 1.69-1.67 (5H, m), 1.49-1.43 (1H, m), 1.27-1.14 (3H, m), 1.05-1.03 (2H, m), 0.84 (9H, s), 0.01 (3H, s), −0.18 (3H, s) ppm. LRMS (electrospray): m/z [M+H]$^+$ 569, [M+Na]$^+$ 591, [M−H]$^−$ 567.

Preparation 11: 2-{3-[(2R)-2-({(2R)-2{[tert-butyl(dimethyl)silyl]oxy}-2-[4-hydroxy-3-(hydroxymethyl)phenyl]ethyl}amino)propyl]phenyl}-N-(cyclopropylmethyl)acetamide

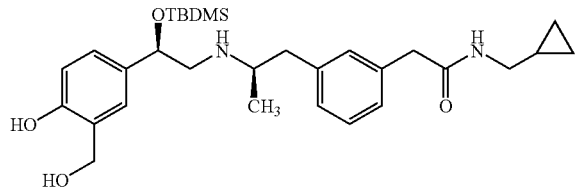

Prepared according to the procedure used for preparation 1 using (3-{(2R)-2-[(2R)-2-{[tert-butyl(dimethyl)silyl]oxy}-2-(4-hydroxy-3-hydroxymethyl-phenyl )-ethylamino]-propyl}-phenyl)-acetic acid (Preparation 20) and the appropriate amine to give the title compound as a white foam.

$^1$H NMR (400 MHz, CD$_3$OD): δ=7.15-7.07 (3H, m), 7.01 (1H, s), 6.95-6.92 (2H, m), 6.65-6.63 (1H, d), 4.66-4.63 (1H, m), 4.58-4.57 (2H, d), 3.40 (2H, s), 3.00-2.98 (2H, d), 2.89-2.80 (2H, m), 2.65-2.57 (2H, m), 2.53-2.48 (1H, dd), 1.01-1.00 (3H, d), 0.93-0.87 (1H, m), 0.79 (9H, s), 0.44-0.40 (2H, q), 0.15-0.12 (2H, q), −0.04 (3H, s), −0.24 (3H, s) ppm. LRMS (electrospray): m/z [M+H]$^+$ 527, [M+Na]$^+$ 549, [M−H]$^-$ 525.

Preparation 12: 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(cycloheptylmethyl)acetamide

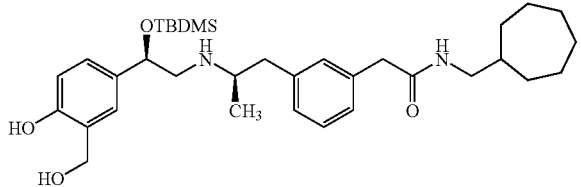

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl )-acetic acid (Preparation 20) and the appropriate amine to give the title compound as a white foam. $^1$H NMR (400 MHz, CD$_3$OD): δ 7.24-6.95 (6H, m), 6.70-6.67 (1H, d), 4.72-4.68 (1H, m), 4.67-4.58 (2H, m), 3.24 (2H, s), 3.02-2.99 (2H, d), 2.92-2.50 (5H, m), 1.72-1.08 (13H, m), 1.06-1.04 (3H, d), 0.92 (9H, s), 0.00 (3H, s), −0.19 (3H, s) ppm. LRMS (electrospray): m/z [M+H]$^+$ 583, [M+Na]$^+$ 605.

Preparation 13: N-1-adamantyl-2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}acetamide

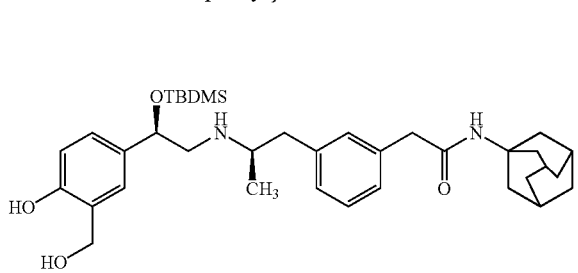

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetic acid (Preparation 20) and the appropriate amine to give the title compound as a white foam. $^1$H NMR (400 MHz, CD$_3$OD): δ 7.20-6.93 (6H, m), 6.68-6.65 (1H, d), 4.74-4.68 (1H, m), 4.65-4.58 (2H, m), 3.40 (s, 2H), 2.96-2.85 (m, 2H), 2.72-2.54 (3H, m), 2.04 (3H, s), 2.01 (6H, s), 1.70 (6H, s), 1.07-1.05 (3H, d), 0.85 (9H, s), 0.02 (3H, s), −0.19 (3H, s) ppm. LRMS (electrospray): m/z [M−H]$^-$ 605.

Alternative Method:

The title compound was prepared from N-1-adamantyl-2-{3-[(2R)-2-({(2R)-2-[4-(benzyloxy)-3-(hydroxymethyl)phenyl]-2-hydroxyethyl}amino)propyl]phenyl}acetamide (preparation 164) using a similar method to that of preparation 25, as a colourless foam in 91% yield.

Preparation 14: N-(1-adamantylmethyl)-2-{3-[(2R)-2-({(2R)-2{[tert-butyl(dimethyl)silyl]oxy}-2-[4-hydroxy-3-(hydroxymethyl)phenyl]ethyl}amino)propyl]phenyl}acetamide

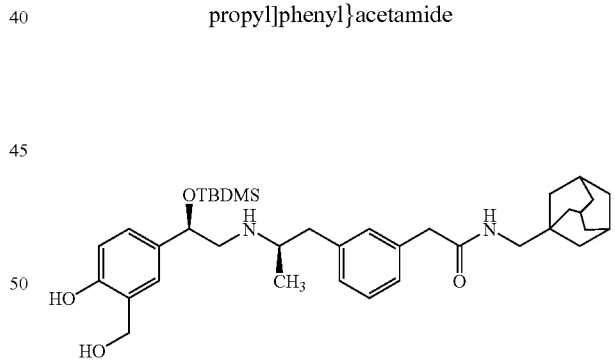

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl )-acetic acid (Preparation 20) and the appropriate amine to give the title compound as a white foam. $^1$H NMR (400 MHz, CD$_3$OD): δ 7.22-6.96 (6H, m), 6.71-6.68 (1H, d), 4.75-4.67 (1H, m), 4.66-4.58 (2H, m), 3.26 (2H, s), 2.88-2.50 (5H, m), 2.84 (2H, s), 1.90 (3H, s), 1.74-1.58 (6H, m), 1.44 (6H, s), 1.08-1.06 (3H, d), 0.84 (9H, s), 0.01 (3H, s), −0.19 (3H, s) ppm. LRMS (electrospray): m/z [M−H]$^-$ 619.

Preparation 15: N-2-adamantyl-2-{3-[(2R)-2-({(2R)-2{[tert-butyl(dimethyl)silyl]oxy}-2-[4-hydroxy-3-(hydroxymethyl)phenyl]ethyl}amino)propyl]phenyl}acetamide

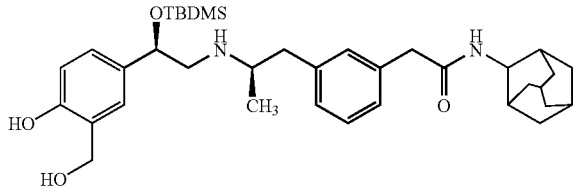

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetic acid (Preparation 20) and the appropriate amine to give the title compound as a white foam. $^1$H NMR (400 MHz, CD$_3$OD): δ 7.22-6.96 (6H, m), 6.70-6.68 (1H, d), 4.72-4.68 (1H, m), 4.67-4.58 (2H, m), 3.95 (1H, s), 3.52 (2H, s), 2.94-2.50 (5H, m), 1.96-1.78 (12H, m), 1.62-1.56 (2H, d), 1.05-1.03 (3H, d), 0.83 (9H, s), 0.00 (3H, s), −0.19 (3H, s) ppm. LRMS (electrospray): m/z [M−H]$^−$ 605.

Preparation 16: 2{-3-[(2R)-2-({(2R)-2{[tert-butyl(dimethyl)silyl]oxy}-2-[4-hydroxy-3-(hydroxymethyl)phenyl]ethyl}amino)propyl]phenyl}-N-(2-cyclohexylethyl)-N-methylacetamide

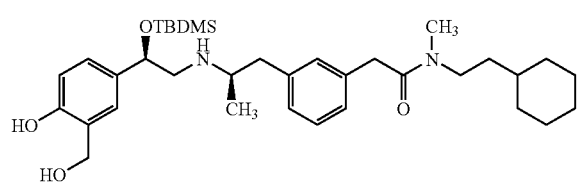

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetic acid (Preparation 20) and the appropriate amine to give the title compound as a white foam.
$^1$H NMR (400 MHz, CD$_3$OD): δ=7.22-6.98 (6H, m), 6.70-6.68 (1H, d), 4.75-4.71 (1H, m), 4.70-4.58 (2H, m), 3.70-3.64 (2H, m), 3.45-3.37 (2H, m), 2.98-2.52 (8H, m), 1.80-0.80 (25H, m), 0.04 (3H, s), −0.19 (3H, s) ppm. LRMS (electrospray): m/z [M+H]$^+$ 619.

Preparation 17: 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-cycloheptyl-N-methylacetamide

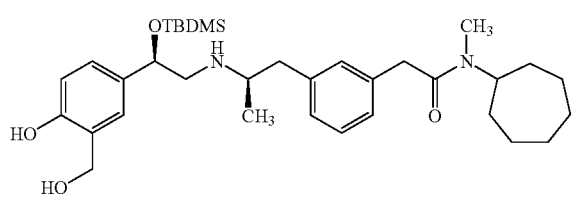

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetic acid (Preparation 20) and the appropriate amine to give the title compound as a white foam.
$^1$H NMR (400 MHz, CD$_3$OD): δ=7.22-6.96 (6H, m), 6.72-6.64 (1H, dd), 4.72-4.65 (1H, m), 4.62-4.60 (2H, m), 4.58-4.51 (0.5H, m), 3.90-3.83 (0.5H, m), 3.77 (1H, s), 3.66 (1H, s), 2.96-2.50 (5H, m), 2.82-2.78 (3H, d), 1.76-1.20 (12H, m), 1.06-1.04 (3H, dd), 0.82-0.80 (9H, 2s), 0.01-0.00 (3H, 2s), −0.18--0.19 (3H, 2s) ppm. LRMS (electrospray): m/z [M+H]$^+$ 583, [M+Na]$^+$ 605.

Preparation 18: 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-cyclohexyl-N-ethylacetamide

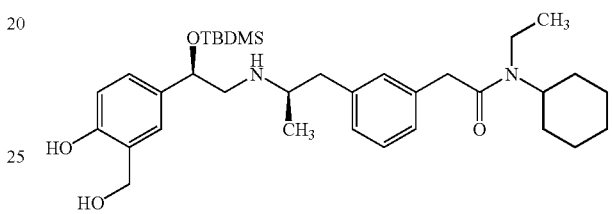

Prepared according to the procedure used for preparation 1 using (3-{(2R)-2-[(2R)-2-{[tert-butyl(dimethyl)silyl]oxy}-2-(4-hydroxy-3-hydroxymethyl-phenyl )-ethylamino]-propyl}-phenyl)-acetic acid (Preparation 20) and the appropriate amine to give the title compound as a white foam.
$^1$H NMR (400 MHz, CD$_3$OD): δ=7.25-6.94 (6H, m), 6.70-6.66 (1H, d), 4.72-4.68 (1H, m), 4.64-4.58 (2H, m), 3.73 (2H, s), 3.70-3.60 (1H, m), 3.73 (2H, s), 3.70-3.60 (1H, m), 3.30-3.24 (2H, q), 2.95-2.48 (5H, m), 1.85-1.10 (10H, m), 1.12-1.08 (3H, t), 1.04-1.02 (3H, d), 0.92 (9H, s), 0.01 (3H, s), −0.20 (3H, s) ppm. LRMS (electrospray): m/z [M+H]$^+$ 605.

Preparation 19: 2-{3-[(2R)-2-({(2R)-2-{[tert-butyl(dimethyl)silyl]oxy}-2-[4-hydroxy-3-(hydroxymethyl)phenyl]ethyl}amino)propyl]phenyl}-N-(2-cyclohexylethyl)acetamide

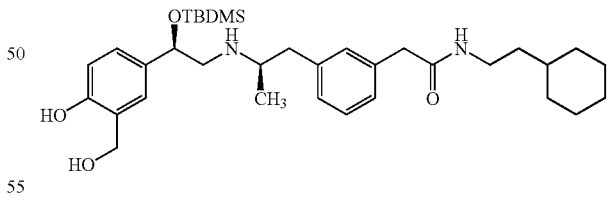

Prepared according to the procedure used for preparation 1 using (3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetic acid (Preparation 20) and the appropriate amine to give the title compound as a white foam.
$^1$H NMR (400 MHz, CD$_3$OD): δ=7.22-6.96 (6H, m), 6.68-6.66 (1H, d), 4.70-4.65 (1H, m), 4.64-4.58 (2H, m), 3.42 (2H, s), 3.21-3.17 (2H, t), 2.93-2.50 (5H, m), 1.74-1.60 (5H, m), 1.39-1.34 (2H, q), 1.30-1.12 (4H, m), 1.04-1.02 (3H, d), 0.96-0.91 (2H, m), 0.90 (9H, s), 0.00 (3H, s), −0.19 (3H, s) ppm. LRMS (electrospray): m/z [M+Na]$^+$ 605.

Preparation 20: (3-{(2R)-2-[(2R)-2-{[tert-Butyl(dimethyl)silyl]oxy}-2-(4-hydroxy-3-hydroxymethyl-phenyl)-ethylamino]-propyl}-phenyl)-acetic acid

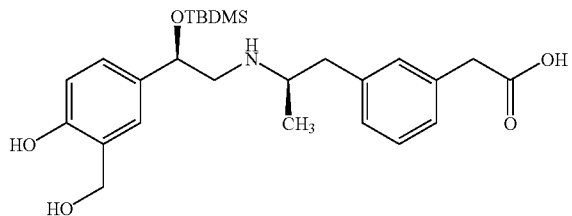

A solution of methyl(3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetate (Preparation 21) (7.04 g, 14.43 mmol) in tetrahydrofuran (40 ml) was treated with lithium hydroxide (28.9 ml of a 1M aqueous solution, 28.9 mmol) and the reaction left to stir at room temperature for 16 hours. Hydrochloric acid (28.9 ml of a 1M aqueous solution, 28.9 mmol) was added and then the tetrahydrofuran was removed in vacuo. The remaining aqueous layer was decanted and the residue washed with further water (10 ml). The residue was redisolved in methanol (30 ml) and the solvent removed in vacuo to give the title compound as a colorless foam (5.95 g) which was used without further purification. $^1$H NMR (400 MHz, CD$_3$OD): δ=7.32 (1H, s), 7.25-7.18 (2H, m), 7.13 (1H, s), 7.12-7.10 (1H, d), 7.02-7.01 (1H, d), 6.79-6.77 (1H, d), 4.98-4.95 (1H, m), 4.65-4.64 (2H, d), 3.48 (2H, s), 3.48-3.43 (1H, m), 3.28-3.23 (1H, dd), 3.13-3.09 (1H, dd), 2.98-2.93 (1H, dd), 2.77-2.72 (1H, dd), 1.23-1.21 (3H, d), 0.86 (9H, s), 0.06 (3H, s), −0.13 (3H, s) ppm. LRMS (electrospray): m/z [M+H]$^+$ 474, [M+Na]$^+$ 496, [M−H]$^−$ 472. CHN analysis: found C, 64.15%; H, 8.25%; N, 2.84%. C$_{26}$H$_{39}$NO$_5$Si+0.7H$_2$O requires C 64.22%, H 8.37%, N 2.88%.

Preparation 21: methyl(3-{(2R)-2-[(2R)-2-{[tert-butyl(dimethyl)silyl]oxy}-2-(4-hydroxy-3-hydroxymethyl-phenyl)-ethylamino]-propyl}-phenyl)-acetate

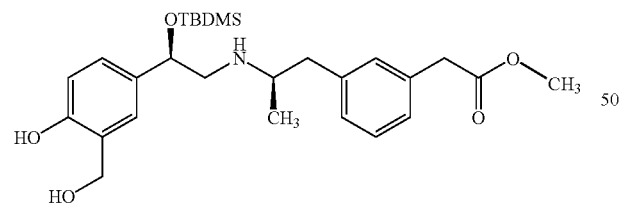

A suspension of methyl(3-{(2R)-2-[(2R)-2-{[tert-butyl(dimethyl)silyl]oxy}-2-(4-[benzyloxy]-3-hydroxymethyl-phenyl)-ethylamino]-propyl}-phenyl)-acetate (Preparation 22) (5.27 g, 9.12 mmol) and 10% palladium on carbon (1.00 g) in ethanol (50 ml) was stirred under an atmosphere of hydrogen (60 psi) at room temperature for 16 hours. The catalyst was filtered off through arbocel and the filtrate concentrated in vacuo. The residue was purified by flash column chromatography on silica gel eluting with dichloromethane: methanol:880 ammonia (96:4:0.4 changing to 95:5:0.5, by volume) to give the title compound as a pale yellow oil (1.99 g) which was used without further purification. $^1$H NMR (400 MHz, CD$_3$OD): δ=7.21-7.17 (2H, m), 7.11-7.09 (1H, d), 7.03-6.98 (3H, m), 6.69-6.67 (1H, d), 4.71-4.68 (1H, t), 4.62-4.61 (2H, d), 3.67 (3H, s), 3.59 (2H, s), 2.96-2.86 (2H, m), 2.69-2.55 (3H, m), 1.07-1.05 (3H, d), 0.82 (9H, s), −0.01 (3H, s), −0.20 (3H, s) ppm. LRMS (electrospray): m/z [M+H]$^+$ 488, [M+Na]$^+$ 510, [M−H]$^−$ 486.

Preparation 22: methyl(3-{(2R)-2-[(2R)-2-{[tert-butyl(dimethyl)silyl]oxy}-2-(4-[benzyloxy]-3-hydroxymethyl-phenyl)-ethylamino]-propyl}-phenyl)-acetate

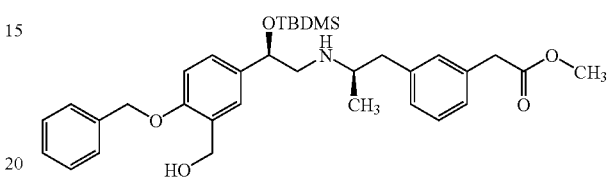

A solution of [2-(benzyloxy)-5-((1R)-2-bromo-1-{[tert-butyl(dimethyl)silyl]oxy}ethyl)phenyl]methanol (Preparation 23) (12.5 g, 27.7 mmol) and methyl {3-[(2R)-2-aminopropyl]phenyl}acetate (Preparation 25) (11.5 g, 55.4 mmol) in dichloromethane (130 ml) was heated to 90° C., allowing the dichloromethane to evaporate. The resulting melt was left at 90° C. for a further 16 hours. The reaction mixture was cooled to room temperature and purified by flash column chromatography on silica gel eluting with dichloromethane: methanol:880 ammonia (98:2:0.2 changing to 97:3:0.3, by volume) to give the title compound (12.1 g) as a white oil. $^1$H NMR (400 MHz, CD$_3$OD): δ=7.47-7.45 (2H, m), 7.39-7.29 (4H, m), 7.19-7.15 (1H, t), 7.13-7.07 (2H, m), 7.03 (1H, s), 7.01-6.99 (1H, d), 6.93-6.91 (1H, d), 5.12 (2H, s), 4.76-4.73 (1H, t), 4.67-4.66 (2H, d), 3.66 (3H, s), 3.58 (2H, s), 2.95-2.80 (2H, m), 2.68-2.55 (3H, m), 1.06-1.05 (3H, d), 0.83 (9H, s), 0.00 (3H, s), −0.19 (3H, s) ppm. LRMS (electrospray): m/z [M+H]$^+$ 578, [M+Na]$^+$ 600.

Preparation 23: [2-(benzyloxy)-5-((1R)-2-bromo-{[tert-butyl(dimethyl)silyl]oxy}ethyl)phenyl]methanol

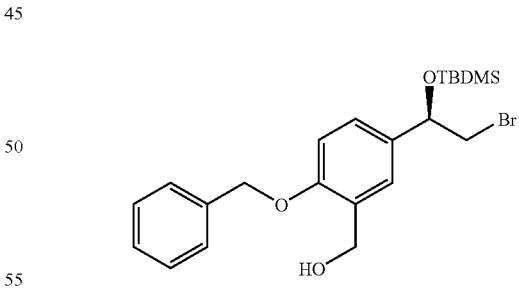

Borane dimethylsulfide complex (42.4 ml of 10M solution in tetrahydrofuran, 424 mmol) was added dropwise to a solution of methyl 2-(benzyloxy)-5-((1R)-2-bromo-1-{[tert-butyl(dimethyl)silyl]oxy}ethyl)benzoate (Preparation 24), (91.0 g, 189 mmol) in tetrahydrofuran (1600 ml). The resulting mixture was then heated to reflux for 2 hours and then cooled to 0° C. before quenching with methanol (270 ml). The mixture was left to stir at room temperature for 16 hours and then the solvent removed in vacuo. The residue was partitioned between dichloromethane (500 ml) and water (500 ml). The aqueous phase was separated and extracted with dichloromethane (500 ml) and the combined organic extracts washed with saturated aqueous sodium chloride (500 ml), dried (magnesium sulfate) and the solvent removed in vacuo. The residue was purified by flash column chromatography on silica gel eluting with cyclohexane:ethyl acetate (100:0 changing to 80:20, by volume) to give the title compound (68.7 g) as a colourless oil. $^1$H NMR (400 MHz, CDCl$_3$): δ=7.42-7.36 (5H, m), 7.29-7.25 (3H, m), 6.94 (1H, d), 5.12 (2H, s), 4.84-4.81 (1H, m), 4.74 (2H, s), 3.48-3.40 (2H, m), 0.90 (9H, s), 0.11 (3H, s), −0.07 (3H, s) ppm. LRMS (electrospray): m/z [M+Na]$^+$ 473/475.

Preparation 24: methyl 2-(benzyloxy)-5-((1R)-2-bromo-1{[tert-butyl (dimethyl)silyl]oxy}ethyl)benzoate

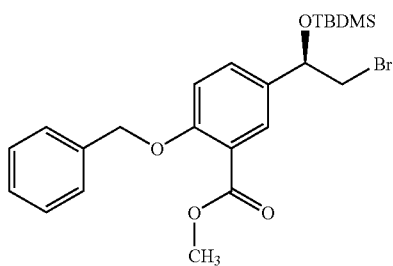

A solution of methyl 2-(benzyloxy)-5-[(1R)-2-bromo-1-hydroxyethyl]benzoate (71.05 g, 195 mmol), imidazole (18.52 g, 272 mmol), tert-butyldimethylsilyl chloride (32.23 g, 214 mmol) and 4-(N,N-dimethylamino)pyridine (0.44 g, 3.6 mmol) in N,N-dimethylformamide (270 ml) was left to stir at room temperature under a nitrogen atmosphere for a period of 24 hours. The solvent was removed in vacuo and the residue partitioned between ethyl acetate (500 ml) and water (500 ml). The organic phase was separated and washed with 2N hydrochloric acid (2-fold 500 ml), saturated aqueous sodium bicarbonate (2-fold 500 ml) saturated sodium chloride (500 ml), dried (magnesium sulfate) and the solvent removed in vacuo to give the title compound as a colourless oil (91.0 g). $^1$H NMR (400 MHz, CDCl$_3$): δ=7.81 (1H, bs), 7.51-7.30 (6H, m), 7.01 (1H, d), 5.19 (2H, s), 4.85-4.82 (1H, m), 3.91 (3H, s), 3.48-3.39 (2H, m), 0.90 (9H, s), 0.11 (3H, s), -0.08 (3H, s) ppm. LRMS (electrospray): m/z [M+Na]$^+$ 501/503.

Preparation 25: methyl{3-[(2R)-2-aminopropyl]phenyl}acetate

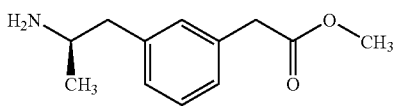

A solution of methyl[3-((2R)-2-{[(1R)-1-phenyl-ethyl]-amino}-propyl)-phenyl]-acetate hydrochloride (Preparation 26) (7.69 g, 22 mmol) and ammonium formate (6.94 g, 110 mmol) was heated to 75° C. in the presence of 20% palladium hydroxide-on-charcoal (Pd(OH)$_2$/C, 2.00 g). After 90 minutes the reaction mixture was cooled to room temperature, filtered through arbocel and the filtrate concentrated in vacuo. The residue was partitioned between dichloromethane (100 ml) and 880 ammonia (100 ml) and the organic phase separated. The aqueous phase was extracted dichloromethane (100 ml) and the combined organic extracts dried (magnesium sulfate) and reduced in vacuo to give the title compound as a colourless oil (4.78 g). $^1$H NMR (400 MHz, CD$_3$OD): δ 7.27-7.23 (1H, t), 7.13-7.09 (3H, m), 3.67 (3H, s), 3.63 (2H, s), 3.12-3.05 (1H, m), 2.67-2.57 (2H, m), 1.06 (3H, d) ppm. LRMS (electrospray): m/z [M+H]$^+$ 208, [M+Na]$^+$ 230.

Preparation 26: methyl[3-((2R)-2-{[(1R)-1-phenyl-ethyl]-amino}-propyl)-phenyl]-acetate hydrochloride

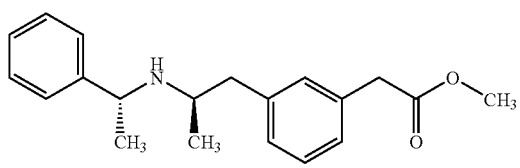

A solution of methyl [3-(2-oxopropyl)phenyl]acetate (Preparation 27) (8.5 g, 41.2 mmol), (R)-α-methyl benzylamine (4.8 ml, 37.2 mmol), sodium triacetoxyborohydride (11.6 g, 56 mmol) and acetic acid (2.2 ml, 38 mmol) in dichloromethane (400 ml) was stirred at room temperature for 48 hours. The reaction mixture was quenched by addition of saturated aqueous sodium bicarbonate (200 ml) and allowed to stir until effervescence ceased. The organic phase was separated and the aqueous phase extracted with dichloromethane (100 ml). The combined organic extracts were dried (magnesium sulfate) and reduced in vacuo. Purification by flash column chromatography eluting with dichloromethane:methanol: ammonia (99:1:0.1 to 95:5:0.5 by volume) gave a 4:1 mixture of diastereomers (R,R major) as a pale yellow oil (8.71 g). Treatment with hydrogen chloride (40 ml of a 1M solution in methanol, 40 mmol) followed by three successive crystallisations (diisopropylether/methanol) gave the title compound as a white crystalline solid (5.68 g). $^1$H NMR (400 MHz, CD$_3$OD): δ=7.52-7.48 (5H, m), 7.28-7.25 (1H, m), 7.18-7.16 (1H, m), 7.02-6.99 (2H, m), 4.59 (1H, q), 3.62 (2H, s), 3.30 (3H, s), 3.30-3.25 (1H, m), 3.26-3.15 (1H, m), 2.66-2.60 (1H, m), 1.68 (3H, d), 1.18, (3H, d) ppm. LRMS (electrospray): m/z [M+H]$^+$ 312, [M+Na]$^+$ 334.

Preparation 27: methyl[3-(2-oxopropyl)phenyl]acetate

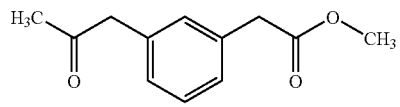

Tributyltin methoxide (28.3 ml, 98 mmol), preparation 28 (15.0 g, 65 mmol), isopropenyl acetate (10.8 ml, 98 mmol), palladium(II)acetate (750 mg, 3.30 mmol) and tri-ortho-tolylphosphine (2.0 g, 6.5 mmol) were stirred together in toluene (75 ml) at 100° C. under nitrogen for 5 hours. After cooling the reaction was diluted with ethyl acetate (150 ml) and 4M aqueous potassium fluoride solution (90 ml) and stirred for 15 minutes. The mixture was filtered through arbocel and the organic phase separated and reduced in vacuo. The residue was purified by flash column chromatography silica gel eluting with a solvent gradient of diethyl ether:

pentane (0:100 to 25:75, by volume) changing to dichloromethane to give the title compound as a pale yellow oil (12.6 g).
$^1$H NMR (400 MHz, CDCl$_3$): δ=7.30 (1H, t), 7.19 (1H, d), 7.13-7.10 (2H, m), 3.69 (5H, s), 3.61 (2H, s), 2.15 (3H, s) ppm. LRMS (electrospray): m/z [M+NH$_4$]$^+$ 224, [M+Na]$^+$ 229.

Preparation 28: Methyl(3-bromophenyl)acetate

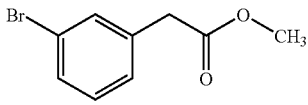

Acetyl chloride (0.7 ml, 9.3 mmol) was slowly added to a solution of (3-bromo-phenyl)-acetic acid (20.0 g, 93 mmol) in methanol (500 ml) at 0° C. under nitrogen and the reaction was allowed to warm gradually to room temperature over a period of 5 hours. The solvent was removed in vacuo and the residual oil was redissolved in dichloromethane, dried (sodium sulfate) and concentrated in vacuo to give the title compound as a colourless oil (20.6 g). $^1$H NMR (400 MHz, CDCl$_3$): δ=7.37-7.45 (2H, m), 7.24-7.17 (2H, m), 3.70 (3H, s), 3.59 (2H, s) ppm. LRMS (electrospray): m/z [M+Na]$^+$ 253.

Preparation 29:
1-(3-bromophenyl)-2-methylpropan-2-ol)

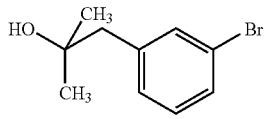

Methylmagnesium bromide (3M solution in diethylether, 51.6 ml, 155 mmol) was slowly added to a solution of 1-(3-bromo-phenyl)propan-2-one (15.0 g, 70 mmol) in dry diethylether (200 ml) at 0° C. The resulting mixture was left for 3 hours, then cooled to 0° C. and slowly quenched with saturated aqueous ammonium chloride solution. The organic phase was washed with brine, dried (sodium sulfate). The yellow oil was then purified by column chromatography on silica gel eluting with dichloromethane:pentane:methanol (90:5:5 by volume to afford a pale yellow oil (13.26 g). $^1$H NMR (400 MHz, CDCl$_3$) δ=7.40 (2H, m), 7.15 (2H, m), 2.74 (2H, s), 1.42 (1H, bs), 1.22 (6H, s).

Preparation 30: N-[2-(3-bromophenyl)-1,1-dimethylethyl]-2-chloroacetamide

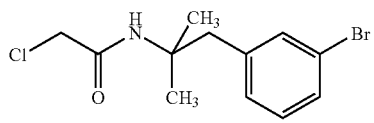

Chloroacetonitrile (6.63 ml, 105 mmol) was added to a stirred solution of 1-(3-bromophenyl)-2-methylpropan-2-ol) (Preparation 29) (12.0 g, 52.0 mmol) in acetic acid (25 ml) at room temperature. The resulting solution was cooled to 0° C. and concentrated sulfuric acid (25 ml) was added keeping the temperature<10° C. The resulting solution was left to stir for 1 hour and then poured onto ice and basified by the addition of solid potassium carbonate. The product was extracted with ethyl acetate (2×500 ml), the organics combined and washed with water (50 ml), dried (sodium sulfate) and the solvent removed in vacuo to afford the title compound as an orange solid (16.08 g). $^1$H NMR (400 MHz, CDCl$_3$) δ 7.39-7.32 (1H, d), 7.26 (1H, s), 7.1-7.13 (1H, t), 7.08-7.03 (1H, d), 6.17 (1H, bs), 3.94 (2H, s), 3.02 (2H, s), 1.37 (6H, s). CHN for C$_{12}$H$_{15}$BrClNO calc. (found): C, 47.32 (47.26); H, 4.96 (4.87); N, 4.60 (4.65). LRMS (electrospray) m/z 306 [M+H]$^+$ Preparation 31:
2-(3-bromophenyl)-1,1-dimethylethylamine

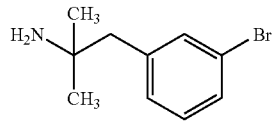

A solution of N-[2-(3-bromophenyl)-1,1-dimethylethyl]-2-chloroacetamide (Preparation 30) (32.0 g, 105 mmol), thiourea (9.60 g, 126 mmol) and acetic acid (50 ml) in ethanol (250 ml) was heated to reflux overnight. The reaction mixture was cooled to room temperature and filtered, the filtrate was concentrated in vacuo and basified using aqueous sodium hydroxide solution (1M, 450 ml). The product was extracted with dichloromethane (2×500 ml) and the combined organics washed with brine (50 ml), dried (sodium sulfate) and the solvent removed in vacuo to afford the title compound as a black oil (23 g). $^1$H NMR (400 MHz, CDCl$_3$) δ=7.36-7.32 (2H, m), 7.16-7.08 (2H, m), 2.62 (2H, s), 1.84 (2H, bs), 1.12 (6H, s). LRMS (electrospray) m/z 228 [M+H]$^+$ Preparation 32:
[2-(3-bromophenyl)-1,1-dimethylethyl]carbamic acid tert-butyl ester

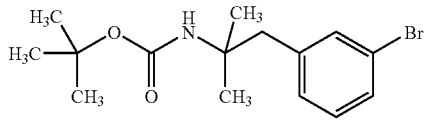

2-(3-bromophenyl)-1,1-dimethylethylamine (Preparation 31) (5.0 g, 22 mmol) was treated with di-tert-butyl dicarbonate (5.26 g, 24 mmol) in dichloromethane (50 ml) and stirred for 20 hours. The reaction mixture was washed with water (50 ml) and the combined organics dried (sodium sulfate) and the solvent removed in vacuo. The crude material was purified using a cation exchange column (methanol followed by 2M ammonia in methanol), followed by purification by flash column chromatography on silica gel eluting with dichloromethane to afford the title compound as a brown oil (7.23 g). $^1$H NMR (400 MHz, CDCl$_3$) δ=7.35 (1H, d), 7.30 (1H, s), 7.15-7.11 (1H, t), 7.05 (1H, d), 4.24 (1H, bs), 2.97 (2H, s), 1.50 (9H, s), 1.27 (6H, s). LRMS (electrospray) m/z 350 [M+NH$_4$]$^+$

Preparation 33: 3-(2-tert-butoxycarbonylamino-2-methylpropyl)benzoic acid methyl ester

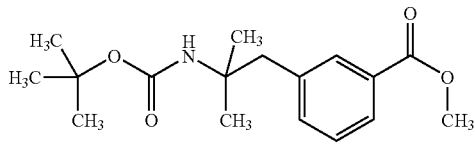

A solution of [2-(3-bromophenyl)-1,1-dimethylethyl]carbamic acid tert-butyl ester (Preparation 32) (7.0 g, 21 mmol), [1,1'-bis(diphenylphosphino)ferrocene]dichloropalladium (II) (1.74 g, 2.1 mmol) and triethylamine (5.94 ml, 43 mmol) in methanol (250 ml) was heated to 100° C. under 100 psi carbon monoxide for 12 hours. The reaction mixture was filtered through arbocel and the filtrate concentrated in vacuo and purified by flash column chromatography on silica gel eluting with dichloromethane:pentane (50:50 by volume) to afford the title compound as a yellow solid (3.76 g). $^1$H NMR (400 MHz, CDCl$_3$) δ=7.92-7.90 (1H, m), 7.82 (1H, s), 7.35-7.34 (2H, m), 4.24 (1H, bs), 3.90 (3H, s), 3.05 (2H, s), 1.48 (9H, s), 1.26 (6H, s). LRMS (electrospray) m/z 208 [M+H–BOC]$^+$

Preparation 34: 3-(2-amino-2-methylpropyl)benzoic acid methyl ester

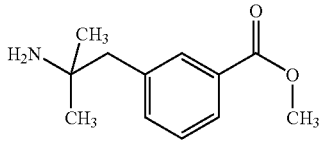

A solution of 3-(2-tert-butoxycarbonylamino-2-methylpropyl)benzoic acid methyl ester (Preparation 33) (1.6 g, 5.2 mmol) in dichloromethane (160 ml) at 0° C. was treated with trifluoroacetic acid (13.6 ml) and left to warm to room temperature over 2 hours. The solvent was removed in vacuo and the product purified by cation exchange chromatography (methanol followed by 2M ammonia in methanol) to yield the title compound as an amber oil (1.06 g).

$^1$H NMR (400 MHz, CDCl$_3$) δ=7.90-7.88 (1H, m), 7.84 (1H, s), 7.36-7.35 (2H, m), 3.90 (3H, s), 2.71 (2H, s), 1.67 (2H, bs), 1.12 (6H, s). LRMS (electrospray) m/z 208 [M+H]$^+$

Preparation 35: 3-(2-[(2R)-2-(4-benzyloxy-3-hydroxymethyl-phenyl)-2-(tert-butyldimethylsilanyloxy)ethylamino]-2-methylpropyl}benzoic acid methyl ester

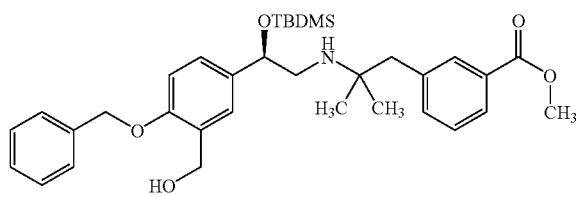

3-(2-amino-2-methylpropyl)benzoic acid methyl ester (Preparation 34) (1.36 g, 6.60 mmol), [2-(benzyloxy)-5-((1R)-2-bromo-1-{[tert-butyl(dimethyl)silyl]oxy}ethyl)phenyl]methanol (Preparation 23) (2.96 g, 6.60 mmol), sodium iodide (980 mg, 6.60 mmol) and diisopropylethylamine (3.44 ml, 19.7 mmol) in acetonitrile (10 ml) were heated to reflux for 48 hours under a nitrogen atmosphere. The solvent was then removed in vacuo and saturated aqueous sodium hydrogen carbonate solution (20 ml) added and the product extracted with ethyl acetate (3×30 ml). The combined organics were washed with brine (3×20 ml), dried (sodium sulfate) and the solvent removed in vacuo. The residue was purified by flash column chromatography on silica gel eluting with dichloromethane:methanol:ammonia (95:5:0.5 by volume) to furnish the title compound, the purified product was dissolved in diethylether and evaporated (×3) to yield a white foam (1.70 g).

$^1$H NMR (400 MHz, CDCl$_3$) δ=7.89-7.84 (2H, m), 7.44-7.21 (9H, m), 6.88 (1H, d), 5.10 (2H, s), 4.73-4.69 (3H, m), 3.91 (3H, s), 2.83-2.62 (4H, m), 2.86 (1H, t), 1.05 (3H, s), 1.02 (3H, s), 0.79 (9H, s), −0.04 (3H, s), −0.19 (3H, s). LRMS (electrospray) m/z 578 [M+H]$^+$, 600 [M+Na]$^+$

Preparation 36: 3-{2-[(2R)-2-(tert-butyldimethylsilanyloxy)-2-(4-hydroxy-3-hydroxymethyl-phenyl)ethylamino]-2-methylpropyl}benzoic acid methyl ester

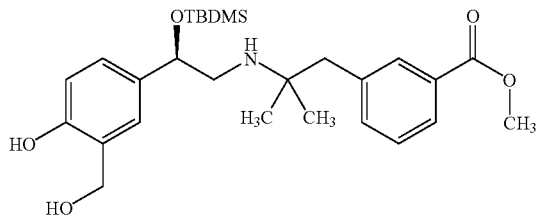

3-{2-[(2R)-2-(4-benzyloxy-3-hydroxymethyl-phenyl)-2-(tert-butyldimethyl-silanyloxy)ethylamino]-2-methylpropyl}benzoic acid methyl ester (Preparation 35) (2.12 g, 3.70 mmol) and palladium-on-carbon (10%, 300 mg) in methanol (50 ml) were hydrogenated at room temperature and 60 psi for 18 hours. The reaction mixture was filtered through arbocel and the filtrate concentrated in vacuo, the residue was purified by flash column chromatography on silica gel eluting with dichloromethane:methanol:ammonia (95:5:0.5 by volume) to furnish the title compound, this material was taken up in diethylether and evaporated (×3) to yield a white foam (1.50 g).

$^1$H NMR (400 MHz, CDCl$_3$) δ=7.89-7.86 (1H, m), 7.82 (1H, bs), 7.33-7.31 (2H, m), 7.13 (1H, dd), 6.96 (1H, d), 6.79 (1H, d), 4.81 (2H, dd), 4.66 (1H, dd), 3.91 (3H, s), 2.81-2.76 (1H, m), 2.67 (2H, dd), 2.58 (1H, dd), 1.06 (3H, s), 1.03 (3H, s), 0.79 (9H, s), -0.03 (3H, s), -0.19 (3H, s). LRMS (electrospray) m/z 488 [M+H]$^+$, 510 [M+Na]$^+$

Preparation 37: 3-{2-[(2R)-2-(tert-butyldimethylsilanyloxy)-2-(4-hydroxy-3-hydroxymethyl-phenyl)ethylamino]-2-methylpropyl}benzoic acid

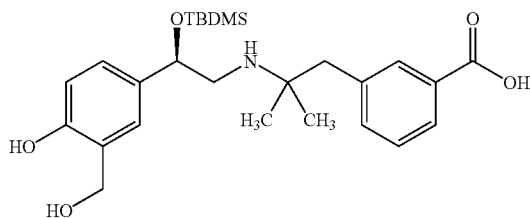

3-{2-[(2R)-2-(tert-butyldimethylsilanyloxy)-2-(4-hydroxy-3-hydroxymethyl-phenyl)ethylamino]-2-methylpropyl}benzoic acid methyl ester (Preparation 36) (1.50 g, 3.08 mmol), aqueous sodium hydroxide solution (5M, 3.07 ml, 15.0 mmol), water (2 ml) and dioxane (20 ml) were stirred at room temperature for 18 hours. The solvent was removed in vacuo and the residue dissolved in water (30 ml) and acidified with aqueous hydrochloric acid (1N, 15.38 ml). The resulting white precipitate was filtered off and dried in vacuo for 72 hours to furnish the title compound as a white solid (1.28 g). $^1$H NMR (400 MHz, CD$_3$OD) δ=7.88 (1H, d), 7.81 (1H, bs), 7.38-7.28 (3H, m), 7.10 (1H, dd), 6.77 (1H, d), 4.92 (1H, m, partially under solvent peak), 4.61 (2H, dd), 3.23-3.12 (2H, m), 2.95 (2H, dd), 1.08 (6H, s), 0.81 (9H, s), −0.04 (3H, s), −0.15 (3H, s). LRMS (electrospray) m/z 474 [M+H]$^+$

Preparation 38: 3-{2-[(2R)-2-(tert-butyldimethylsilanyloxy)-2-(4-hydroxy-3-hydroxymethyl-phenyl)ethylamino]-2-methylpropyl}-N-[2-(4-chlorophenyl)ethyl]benzamide

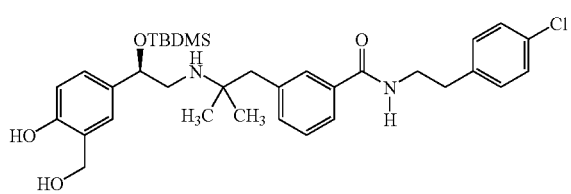

2-(4-Chlorophenyl)ethylamine (164 mg, 1.06 mmol) was added to a mixture of 1-(3-dimethylaminopropyl)-3-ethylcarbodiimide hydrochloride (203 mg, 1.06 mmol), 3-{2-[(2R)-2-(tert-butyldimethylsilanyloxy)-2-(4-hydroxy-3-hydroxymethyl-phenyl)ethylamino]-2-methylpropyl}benzoic acid (Preparation 37) (500 mg, 1.06 mmol), 1-hydroxybenzotriazole hydrate (160 mg, 1.06 mmol) and triethylamine (440 □l, 3.20 mmol) in dichloromethane (30 ml). The resulting solution was stirred for 48 hours under nitrogen. The solvent was removed in vacuo and the residue taken up in ethyl acetate (30 ml), washed with water (20 ml), sodium hydrogen carbonate (0.5 M, 2×20 ml), brine (2×20 ml), dried (sodium sulfate) and the solvent removed in vacuo. The residue was purified by flash column chromatography on silica gel eluting with dichloromethane:methanol:ammonia (95:5:0.5 by volume) to furnish the title compound, the resulting material was taken up in methanol and evaporated, then taken up in diethylether and evaporated to yield a white foam (480 mg). $^1$H NMR (400 MHz, CD$_3$OD) δ=7.64-7.60 (2H, m), 7.36-7.19 (7H, m), 7.05 (1H, dd), 6.72 (1H, d), 4.71-4.67 (1H, m), 4.60 (2H, dd), 3.57 (2H, t), 2.93-2.61 (6H, m), 1.09 (3H, s), 1.06 (3H, s), 0.78 (9H, s), −0.04 (3H, s), −0.22 (3H, s). LRMS (electrospray) m/z 611 [M+H]$^+$, 633 [M+Na]$^+$

Preparation 39: 3-{2-[(2R)-2-(tert-butyldimethylsilanyloxy)-2-(4-hydroxy-3-hydroxymethyl-phenyl)ethylamino]-2-methylpropyl}-N-[2-(4-methylphenyl)ethyl]benzamide

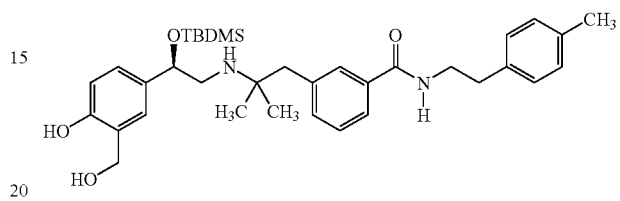

Prepared according to the procedure used for preparation 38 using 3-{2-[(2R)-2-(tert-butyldimethylsilanyloxy)-2-(4-hydroxy-3-hydroxymethyl-phenyl)ethylamino]-2-methylpropyl}benzoic acid (Preparation 37) and the appropriate amine to give the title compound as a white foam. $^1$H NMR (400 MHz, CD$_3$OD) δ=7.65-7.61 (2H, m), 7.36-7.30 (2H, m), 7.27 (1H, d), 7.14-7.06 (5H, m), 6.72 (1H, d), 4.71-4.68 (1H, m), 4.60 (2H, dd), 3.54 (2H, t), 2.90-2.83 (3H, m), 2.70 (2H, dd), 2.61 (1H, dd), 2.28 (3H, s), 1.09 (3H, s), 1.05 (3H, s), 0.78 (9H, s), -0.04 (3H, s), -0.22 (1H, s). LRMS (electrospray) m/z 591 [M+H]$^+$, 613 [M+Na]$^+$

Preparation 40: 3-{2-[(2R)-2-(tert-butyldimethylsilanyloxy)-2-(4-hydroxy-3-hydroxymethyl-phenyl)ethylamino]-2-methyl-propyl}-N-[2-(4-trifluoromethylphenyl)ethyl]benzamide

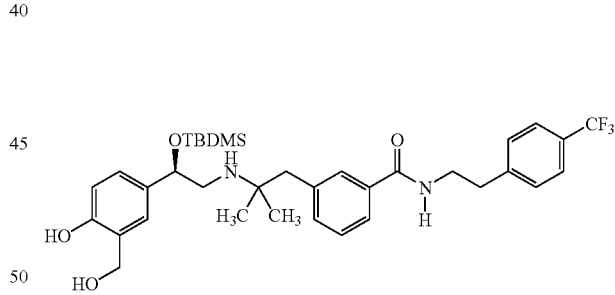

Prepared according to the procedure used for preparation 38 using 3-{2-[(2R)-2-(tert-butyldimethylsilanyloxy)-2-(4-hydroxy-3-hydroxymethyl-phenyl)ethylamino]-2-methylpropyl}benzoic acid (Preparation 37) and the appropriate amine to give the title compound as a white foam. $^1$H NMR (400 MHz, CDCl$_3$) δ=7.66 (2H, d), 7.45 (1H, m), 7.38 (1H, s), 7.33 (2H, d), 7.29-7.22 (2H, m), 7.07 (1H, dd), 6.88 (1H, dd), 6.75 (1H, dd), 6.15 (1H, t), 4.75 (1H, dd), 4.57 (1H, t), 3.73-3.68 (2H, m), 2.99 (2H, t), 2.76 (1H, dd), 2.65 (2H, s), 2.58 (1H, dd), 1.03 (3H, s), 1.00 (3H, s), 0.79 (9H, s), −0.05 (3H, s), −0.20 (3H, s). LRMS (electrospray) m/z 646 [M+H]$^+$

Preparation 41: 3-{2-[(2R)-2-(tert-butyldimethylsilanyloxy)-2-(4-hydroxy-3-hydroxymethyl-phenyl)ethylamino]-2-methyl-propyl}-N-[2-(3,4-dichlorophenyl)ethyl]benzamide

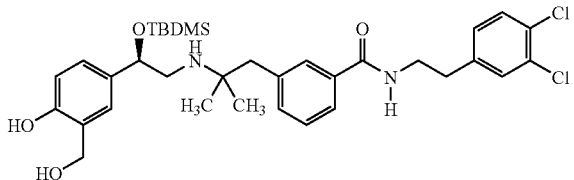

Prepared according to the procedure used for preparation 38 using 3-{2-[(2R)-2-(tert-butyldimethylsilanyloxy)-2-(4-hydroxy-3-hydroxymethyl-phenyl)ethylamino]-2-methylpropyl}benzoic acid (Preparation 37) and the appropriate amine to give the title compound as a white foam. $^1$H NMR (400 MHz, CDCl$_3$) δ=7.45 (1H, d), 7.40-7.36 (2H, m), 7.33 (1H, d), 7.30-7.22 (2H, m), 7.05 (2H, m), 6.88 (1H, dd), 6.75 (1H, d), 6.17 (1H, t), 4.75 (1H, dd), 4.69 (1H, t), 3.63 (2H, m), 2.89 (1H, t), 2.76 (1H, dd), 2.66 (2H, s), 2.59 (1H, dd), 1.04 (3H, s), 1.00 (3H, s), 0.79 (9H, s), −0.05 (3H, s), −0.20 (3H, s). LRMS (electrospray) m/z 646 [M+H]$^+$

Preparation 42: 3-{2-[(2R)-2-(tert-butyldimethylsilanyloxy)-2-(4-hydroxy-3-hydroxymethyl-phenyl)ethylamino]-2-methyl-propyl}-N-[2-(3,4-dimethylphenyl)ethyl]benzamide

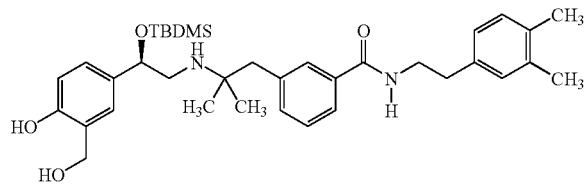

Prepared according to the procedure used for preparation 38 using 3-{2-[(2R)-2-(tert-butyldimethylsilanyloxy)-2-(4-hydroxy-3-hydroxymethyl-phenyl)ethylamino]-2-methylpropyl}benzoic acid (Preparation 37) and the appropriate amine to give the title compound as a white foam. $^1$H NMR (400 MHz, CDCl$_3$) δ=7.43 (1H, d), 7.37 (1H, s), 7.20-7.27 (2H, m), 7.06-7.09 (2H, m), 7.01 (1H, s), 6.94 (1H, d), 6.88 (1H, dd), 6.74 (1H, dd), 6.13 (1H, t), 4.75 (1H, dd), 4.59 (1H, t), 3.64 (1H, dd), 2.85 (1H, t), 2.77 (1H, dd), 2.65 (2H, s), 2.59 (1H, dd), 2.24 (3H, s), 2.23 (3H, s), 1.03 (3H, s), 1.00 (3H, s), 0.79 (9H, s), −0.05 (3H, s), −0.20 (3H, s).
LRMS (APCI) m/z 606 [M+H]$^+$

Preparation 43: 3-{2-[(2R)-2-(tert-butyldimethylsilanyloxy)-2-(4-hydroxy-3-hydroxymethyl-phenyl)ethylamino]-2-methyl-propyl}-N-(2-naphthalen-2-yl-ethyl)benzamide

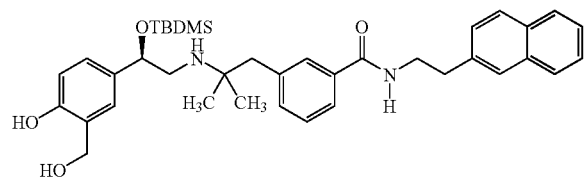

Prepared according to the procedure used for preparation 38 using 3-{2-[(2R)-2-(tert-butyldimethylsilanyloxy)-2-(4-hydroxy-3-hydroxymethyl-phenyl)ethylamino]-2-methylpropyl}benzoic acid (Preparation 37) and the appropriate amine to give the title compound as a white foam. $^1$H NMR (400 MHz, CDCl$_3$) δ 7.77 (3H, m), 7.67 (1H, s), 7.48-7.35 (5H, m), 7.23-7.19 (2H, m), 7.06 (1H, dd), 7.37 (1H, dd), 6.74 (1H, d), 6.17 (1H, t), 4.74 (2H, dd), 4.67 (1H, t), 3.76 (2H, dd), 3.09 (2H, t), 2.75 (1H, dd), 2.62 (2H, s), 2.57 (1H, dd), 1.00 (3H, s), 0.97 (3H, s), 0.78 (9H, s), −0.05 (3H, s), −0.21 (3H, s). LRMS (electrospray) m/z 628 [M+H]$^+$

Preparation 44: 3-{2-[(2R)-2-(tert-butyldimethylsilanyloxy)-2-(4-hydroxy-3-hydroxymethyl-phenyl)ethylamino]-2-methyl-propyl}-N-(1,1-dimethyl-2-phenyl-ethyl)benzamide

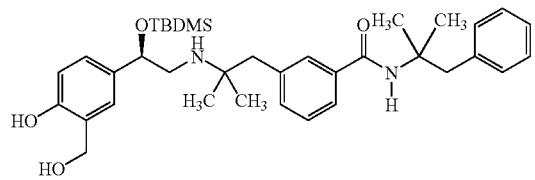

Prepared according to the procedure used for preparation 38 using 3-{2-[(2R)-2-(tert-butyldimethylsilanyloxy)-2-(4-hydroxy-3-hydroxymethyl-phenyl)ethylamino]-2-methylpropyl}benzoic acid (Preparation 37) and the appropriate amine to give the title compound as a white foam. $^1$H NMR (400 MHz, CDCl$_3$) δ=7.43 (1H, m), 7.36 (1H, s), 7.31-7.13 (7H, m), 7.08 (1H, dd), 6.84 (1H, dd), 6.75 (1H, d), 5.70 (1H, s), 4.73 (2H, dd), 4.68 (1H, t), 3.10 (2H, dd), 2.77 (1H, dd), 2.65 (2H, s), 2.68 (1H, dd), 1.45 (3H, s), 1.44 (3H, s), 1.06, (3H, s), 1.01 (3H, s), 0.79 (9H, s), -0.04 (3H, s), -0.21 (3H, s). LRMS (electrospray) m/z 605 [M+H]$^+$

Preparation 45: 3-{2-[(2R)-2-(tert-butyldimethylsilanyloxy)-2-(4-hydroxy-3-hydroxymethyl-phenyl)ethylamino]-2-methylpropyl}-N-(2-methyl-2-phenylpropyl)-benzamide

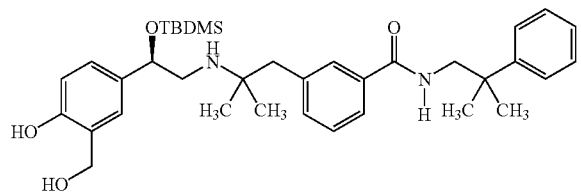

Prepared according to the procedure used for preparation 38 using 3-{2-[(2R)-2-(tert-butyldimethylsilanyloxy)-2-(4-hydroxy-3-hydroxymethyl-phenyl)ethylamino]-2-methylpropyl}benzoic acid (Preparation 37) and the appropriate amine to give the title compound as a white foam. $^1$H NMR (400 MHz, CDCl$_3$) δ=7.42-7.34 (4H, m), 7.29-7.15 (5H, m), 7.05 (1H, dd), 6.87 (1H, dd), 6.74 (1H, d), 5.73 (1H, t), 4.74 (2H, dd), 4.64 (1H, dd), 3.62 (2H, dd), 2.75 (1H, dd), 2.61 (2H, dd), 2.66 (1H, dd), 1.40 (6H, s), 1.00 (3H, s), 0.97 (3H, s), 0.79 (9H, s), −0.05 (3H, s), −0.20 (3H, s). LRMS (electrospray) m/z 605 [M+H]$^+$

Preparation 46: 3-{(2R)-2-[2-(tert-butyldimethylsilanyloxy)-2-(4-hydroxy-3-hydroxymethyl-phenyl)ethylamino]-2-methylpropyl}-N-(4-chlorobenzyl)benzamide

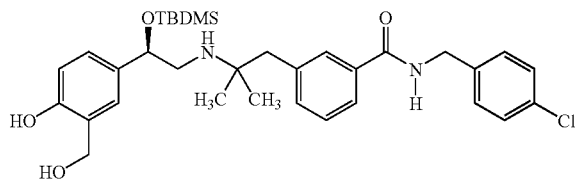

Prepared according to the procedure used for preparation 38 using 3-{2-[(2R)-2-(tert-butyldimethylsilanyloxy)-2-(4-hydroxy-3-hydroxymethyl-phenyl)ethylamino]-2-methylpropyl}benzoic acid (Preparation 37) and the appropriate amine to give the title compound as a white foam. $^1$H NMR (400 MHz, CDCl$_3$) δ 7.55=(1H, m), 7.49 (1H, m), 7.33-7.24 (4H, m), 7.06 (1H, dd), 6.88 (1H, dd), 6.74 (1H, d), 6.49 (1H, t), 4.73 (1H, dd), 4.57 (2H, dd), 2.75 (1H, dd), 2.66 (2H, s), 2.66 (1H, dd), 1.04 (3H, s), 1.00 (3H, s), 0.78 (9H, s), -0.06 (3H, s), -0.21 (3H, s). LRMS (electrospray) m/z 597/599 [M+H]$^+$

Preparation 47: [3-(2-amino-2-methyl-propyl)-phenyl]-acetic acid ethyl ester

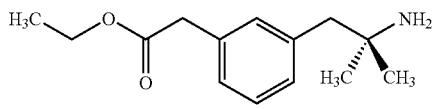

A solution of {3-[2-(2-chloro-acetylamino)-2-methyl-propyl]-phenyl}-acetic acid (Preparation 48) (5.1 g, 18 mmol), thiourea (1.6 g, 21 mmol) and acetic acid (18 ml) in ethanol (80 ml) was heated to reflux under a nitrogen atmosphere for 16 hours. The reaction mixture was cooled and filtered. The filtrate was reduced in vacuo, the residue dissolved in ethanol (150 ml), saturated with hydrogen chloride gas and the resulting solution heated to reflux for 16 hours. The solvent was reduced in vacuo and the residue partitioned between ethyl acetate (200 ml) and 5% aqueous sodium carbonate (200 ml). The organic extract was washed with saturated sodium chloride (100 ml), dried (sodium sulfate) and reduced in vacuo. The residue was purified by strong cation exchange resin, eluting with methanol and then 2N ammonia in methanol to elute the product. The eluent was concentrated in vacuo giving the title compound as a yellow oil (2.68 g, 63%).

$^1$H NMR (400 MHz, CDCl$_3$): δ=7.29-7.04 (4H, m), 4.08 (2H, q), 3.64 (2H, s), 2.57 (2H, s), 1.18 (3H, t), 0.99 (6H, s) ppm. LRMS (electrospray): m/z [M+H]$^+$ 236, [M+NH$_4$]$^+$ 258.

Preparation 48: {3-[2-(2-chloro-acetylamino)-2-methyl-propyl]-phenyl}-acetic acid

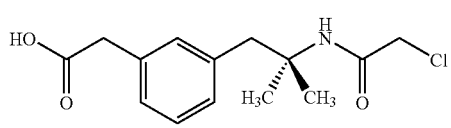

Concentrated sulphuric acid (21 ml) was added dropwise to a solution of [3-(2-hydroxy-2-methylpropyl)-phenyl]-acetic acid (Preparation 49) (10.6 g, 51.0 mmol) and chloroacetonitrile (4.8 ml, 76.0 mmol) in glacial acetic acid (16 ml) at 0° C. The reaction was allowed to warm to room temperature and after 2 hours was poured onto iced water (500 ml). The aqueous was extracted with ethyl acetate (2×250 ml) and the combined organics washed with brine (50 ml), dried (sodium sulfate), and the solvent removed in vacuo to furnish the title compound as a golden oil (14.0 g). $^1$H NMR (400 MHz, CDCl$_3$): δ=7.31-7.06 (4H, m), 6.19 (1H, bs), 3.95 (2H, s), 3.62 (2H, s), 3.02 (2H, s), 1.36 (6H, s) ppm. LRMS (electrospray): m/z [M−H]$^-$ 282/284.

Preparation 49: [3-(2-hydroxy-2-methyl-propyl)-phenyl]-acetic acid

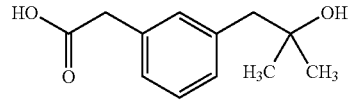

Methyl magnesium chloride (51 ml of a 3M solution in tetrahydrofuran, 153 mmol) was added dropwise to a stirred solution of the ester (11.6 g, 51 mmol) (International Journal of Peptide and Protein Research, 1987, 29(3), 331) in tetrahydrofuran (300 ml) at 0° C. under nitrogen. The reaction was allowed to warm to room temperature overnight with the formation of a thick white precipitate and then water (50 ml) and 2N hydrochloric acid (80 ml) were cautiously added. The aqueous was extracted with ethyl acetate (2×300 ml) and the combined organics washed with brine (50 ml), dried (sodium sulfate), and the solvent removed in vacuo to furnish the title compound as a golden oil (11.2 g). $^1$H NMR (400 MHz, CDCl$_3$): δ=7.30-7.12 (4H, m), 3.63 (2H, s), 2.75 (2H, s), 1.22 (6H, s) ppm. LRMS (electrospray): m/z [M+H]$^+$ 209.

Preparation 50: {3-[2-({(2R)-2-hydroxy-2-[4-hydroxy-3-(hydroxymethyl)phenyl]ethyl}amino)-2-methylpropyl]phenyl}acetic acid

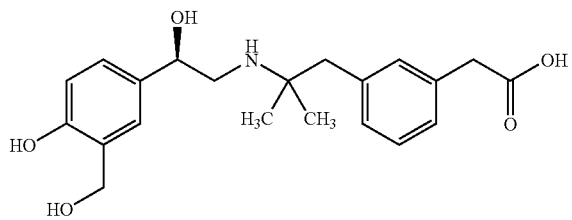

Prepared according to the procedure used for preparation 20 using ethyl {3-[2-({(2R)-2-hydroxy-2-[4-hydroxy-3-(hydroxymethyl)phenyl]ethyl}amino)-2-methylpropyl]phenyl}acetate (Preparation 68) to give the title compound as a cream solid. $^1$H NMR (400 MHz, CD$_3$OD): δ=7.43-7.42 (1H, d), 7.37-7.22 (4H, m), 7.15-7.13 (1H, m), 6.85-6.83 (1H, d), 4.90-4.86 (1H, m), 4.71 (2H, s), 3.56-3.55 (2H, m), 3.25-3.13 (2H, m), 3.05-2.98 (2H, m), 1.40 (3H, s), 1.38 (3H, s) ppm. LRMS (electrospray): m/z [M+H]$^+$ 374, [M−H]$^-$ 372.

Preparation 51: {3-[2-({(2R)-2-hydroxy-2-[4-hydroxy-3-(hydroxymethyl)phenyl]ethyl}amino)ethyl]phenyl}acetic acid

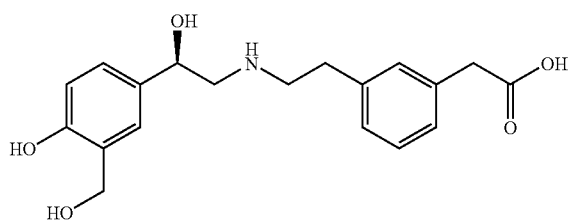

Prepared according to the procedure used for preparation 20 using ethyl {3-[2-({(2R)-2-hydroxy-2-[4-hydroxy-3-(hydroxymethyl)phenyl]ethyl}amino)ethyl]phenyl}acetate (Preparation 52) to give the title compound as a white solid. $^1$H NMR (400 MHz, CD$_3$OD): δ 7.26 (1H, d), 7.20-7.16 (1H, t), 7.09-6.97 (5H, m), 6.74-6.72 (1H, d), 4.68-4.65 (1H, m), 4.44 (2H, s), 3.42 (2H, s), 2.95-2.71 (6H, m) ppm. LRMS (electrospray): m/z [M−H]$^-$ 344.

Preparation 52: ethyl {3-[2-({(2R)-2-hydroxy-2-[4-hydroxy-3-(hydroxymethyl)phenyl]ethyl}amino)ethyl]phenyl}acetate

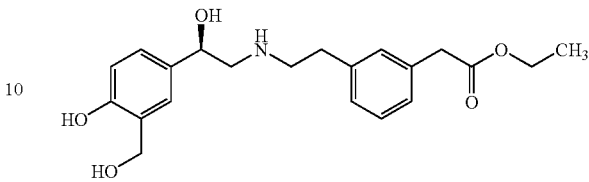

Prepared according to the procedure used for preparation 21 using ethyl {3-[2-({(2R)-2-[4-(benzyloxy)-3-(hydroxymethyl)phenyl]-2-hydroxyethyl}amino)ethyl]phenyl}acetate (Preparation 53) to give the title compound as an orange oil. $^1$H NMR (400 MHz, CD$_3$OD): δ 7.25-7.20 (2H, m), 7.11-7.05 (4H, m), 6.73-6.71 (1H, d), 4.68-4.63 (3H, m), 4.15-4.09 (2H, m), 3.59 (2H, s), 2.89-2.71 (6H, m), 1.24-1.21 (3H, t) ppm. LRMS (electrospray): m/z [M+H]$^+$ 374, [M−H]$^-$ 372.

Preparation 53: ethyl {3-[2-({(2R)-2-[4-(benzyloxy)-3-(hydroxymethyl)phenyl]-2-hydroxyethyl}amino)ethyl]phenyl}acetate

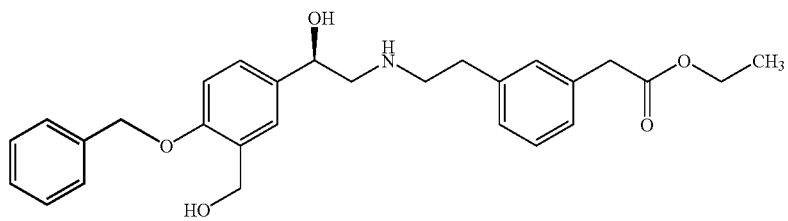

A solution of ethyl(3-{2-[((2R)-2-[4-(benzyloxy)-3-(hydroxymethyl)phenyl]-2-{[tert-butyl(dimethyl)silyl]oxy}ethyl)amino]ethyl}phenyl)acetate (Preparation 54) (2.39 g, 4.14 mmol) in methanol (15 ml) and water (10 ml) was treated with ammonium fluoride (1.53 g, 41.4 mmol) and the reaction heated to 40° C. for 16 hours. The methanol was removed in vacuo and the aqueous residue extracted with dichloromethane (3×50 ml). The combined organics were dried (sodium sulfate) and the sovent removed in vacuo and the residue purified by flash column chromatography on silica gel eluting with dichloromethane:methanol:880 ammonia (97:3:0.3 changing to 95:5:0.5, by volume) to give the title compound as an orange gum (1.90 g).

$^1$H NMR (400 MHz, CD$_3$OD): δ=7.45-7.34 (5H, m), 7.31-7.27 (1H, m), 7.24-716 (2H, m), 7.11-7.09 (3H, m), 2.96-2.94 (1H, d), 5.12 (2H, s), 4.72-4.68 (3h, M), 4.15-4.09 (2H, m), 3.59 (2H, s), 2.91-2.74 (6H, m), 1.24-1.20 (3H, t) ppm. LRMS (electrospray): m/z [M+H]$^+$ 464, [M−H]$^-$ 462.

Preparation 54: ethyl(3-{2-[((2R)-2-[4-(benzyloxy)-3-(hydroxymethyl)phenyl]-2-{[tert-butyl(dimethyl)silyl]oxy}ethyl)amino]ethyl}phenyl)acetate

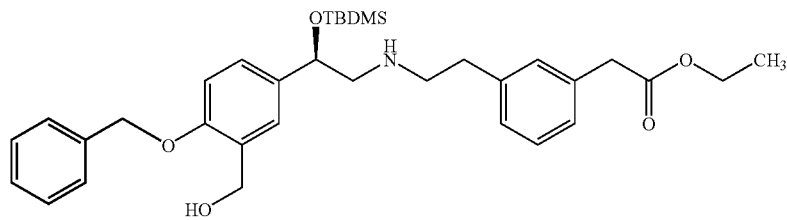

Prepared according to the procedure used for preparation 22 using [2-(benzyloxy)-5-((1R)-2-bromo-1-{[tert-butyl(dimethyl)silyl]oxy}ethyl)phenyl]methanol (Preparation 23) and ethyl[3-(2-aminoethyl)phenyl]acetate (Preparation 58) to give the title compound as a yellow oil.

$^1$H NMR (400 MHz, CD$_3$OD): δ=7.44-7.43 (2H, d), 7.37-7.33 (3H, m), 7.30-7.27 (1H, t), 7.24-7.20 (1H, t), 7.15-7.08 (4H, m), 6.94-6.92 (1H, d), 5.10 (2H, s), 4.77-4.74 (1H, m), 4.67-4.66 (2H, d), 4.14-4.09 (2H, m), 3.58 (2H, s), 2.90-2.75 (5H, m), 2.66-2.62 (1H, m), 1.24-1.21 (3H, t), 0.78 (9H, s), −0.05 (3H, s), −0.22 (3H, s) ppm. LRMS (electrospray): m/z [M+H]$^+$ 578, [M−H]$^−$ 576.

Preparation 55: ethyl[3-(2-hydroxyethyl)phenyl]acetate

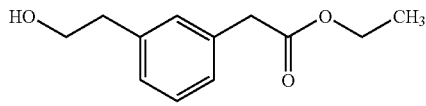

Carbonyl diimidazole (5.11 g, 31.5 mmol) was added in one portion to a stirred solution of the ester (International Journal of Peptide and Protein Research, 1987, 29(3), 331) (7.00 g, 31.5 mmol) in tetrahydrofuran (100 ml) at room temperature under nitrogen. The reaction was stirred for 2 hours and water (26 ml) was added and the reaction cooled to 0° C. Sodium borohydride (6.00 g, 0.15 mmol) was then added portionwise and the reaction allowed to warm to room temperature with continued stirring over 2 hours. Ethyl acetate (300 ml) was added followed by dropwise addition of 2N aqueous hydrochloric acid (20 ml). The organic layer was separated and the aqueous extracted with ethyl acetate (2×75 ml), the combined organics were dried (sodium sulfate) and the solvent removed in vacuo to furnish a white solid which was purified by flash column chromatography on silica gel eluting with ethyl acetate:penatane (50:50, by volume) to give the title compound as a colourless oil (4.60 g). $^1$H NMR (400 MHz, CDCl$_3$): δ=7.28-7.24 (1H, m), 7.15-7.11 (3H, m), 4.17-4.08 (2H, m), 3.84-3.81 (2H, t), 3.59 (2H, s), 2.86-2.82 (2H, t), 1.29-1.23 (3H, t) ppm. LRMS (electrospray): m/z [M+Na]$^+$ 231, [M−H]$^−$ 207.

Preparation 56: ethyl(3-{2-[(methylsulfonyl)oxy]ethyl}phenyl)acetate

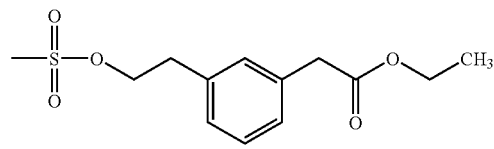

Methane sulfonyl chloride (2.78 g, 24.3 mmol) was added dropwise to a solution of ethyl[3-(2-hydroxyethyl)phenyl]acetate (Preparation 55) (4.60 g, 22.1 mmol) and triethylamine (3.40 ml, 24.3 mmol) in dichloromethane (250 ml) at 0° C. under nitrogen. The reaction was allowed to warm to room temperature over 1 hour and washed with saturated aqueous sodium hydrogen carbonate (75 ml). The aqueous was washed with dichloromethane (2×100 ml) and the combined organics washed with water (25 ml), dried (sodium sulfate) and the solvent removed in vacuo to furnish the title compound as a colourless oil (6.2 g). $^1$H NMR (400 MHz, CDCl$_3$): δ=7.29-7.25 (1H, t), 7.17-7.12 (3H, t), 4.41-4.38 (2H, t), 4.16-4.10 (2H, m), 3.58 (2H, s), 3.04-3.00 (2H, t), 2.81 (3H, s), 1.26-1.22 (3H, t) ppm. LRMS (electrospray): m/z [M+H]$^+$ 578, [M−H]$^−$ 576.

Preparation 57: ethyl[3-(2-azidoethyl)phenyl]acetate

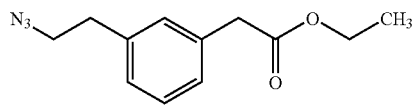

Sodium azide (2.82 g, 43.3 mmol) was added in one portion to a stirred solution of ethyl(3-{2-[(methylsulfonyl)oxy]ethyl}phenyl)acetate (Preparation 56) (6.20 g, 21.7 mmol) in N,N-dimethylformamide (400 ml) at room temperature. The reaction was heated at 60° C. for 1 hour and then allowed to cool to room temperature and the solvent removed in vacuo. Ethyl acetate (200 ml) and water (75 ml) was added and the organics separated, the aqueous was washed with ethyl acetate (2×100 ml) and the combined organics evaporated in vacuo to yield an oil that was purified by flash column chromatography on silica gel eluting with ethyl acetate:penatane (5:95, by volume) to give the title compound as a colourless oil (4.65 g). $^1$H NMR (400 MHz, CDCl$_3$): δ=7.27-7.23 (1H, t), 7.17-7.12 (3H, m), 4.15-4.06 (2H, m), 3.60 (2H, s), 3.51-

3.47 (2H, t), 2.87-2.84 (2H, t), 1.24-1.20 (3H, t) ppm. LRMS (electrospray): M/Z [M+NA]+256, [M–H]− 232.

Preparation 58: ethyl[3-(2-aminoethyl)phenyl]acetate

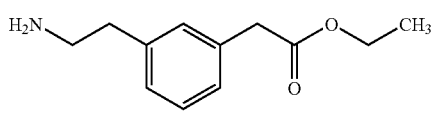

Triphenylphosphine (3.88 g, 23.3 mmol) was added in one portion to a stirred solution of ethyl[3-(2-azidoethyl)phenyl]acetate (Preparation 57) (3.88 g, 16.6 mmol) in tetrahydrofuran (100 ml) at room temperature under nitrogen. The reaction was stirred for 18 hours and water (5 ml) added and the reaction heated at 50° C. for 4 hours, the reaction was cooled to room temperature and the solvent removed in vacuo. The residue was dissolved in saturated aqueous sodium hydrogen carbonate (40 ml) and the aqueous extracted with dichloromethane (3×50 ml). The combined organics were dried (sodium sulfate), the solvent removed in vacuo and the residue purified by flash column chromatography on silica gel eluting with dichlromethane:methanol (95:5, by volume) to give the title compound as a colourless oil (3.11 g). $^1$H NMR (400 MHz, CDCl$_3$): δ 7.26-7.22 (1H, t), 7.13-7.08 (3H, t), 4.16-4.11 (2H, m), 3.58 (2H, s), 2.96-2.93 (2H, t), 2.74-2.71 (2H, t), 1.25-1.22 (3H, t) ppm. LRMS (electrospray): M/Z [M+H]+ 208, [M+NA]+ 230, [M–H]− 206.

Preparation 59: 3-[(2R)-2-({(2R)-2-hydroxy-2-[4-hydroxy-3-(hydroxymethyl)phenyl]ethyl}amino) propyl]benzoic acid

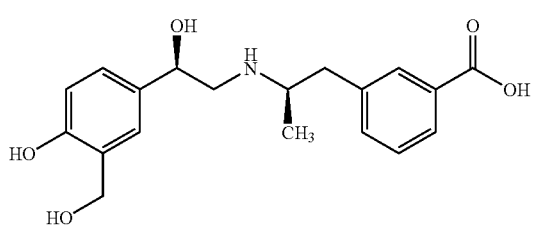

To a solution of methyl 3-[(2R)-2-({(2R)-2-hydroxy-2-[4-hydroxy-3-(hydroxymethyl)phenyl]ethyl}amino)propyl]benzoate (Preparation 60) (5.12 g, 14.24 mmol) in tetrahydrofuran (35 ml), was added aqueous lithium hydroxide solution (1M, 29 ml, 29 mmol) and the solution left to stir at room temperature for 18 hours. Aqueous hydrochloric acid (1M, 29 ml, 29 mmol) was added and the tetrahydrofuran/water removed in vacuo to give the title compound as an off-white solid (5.87 g) that was used without further purification. $^1$H NMR (400 MHz, CD$_3$OD): δ=7.86-7.84 (1H, d), 7.82 (1H, s), 7.37-7.30 (3H, m), 7.17-7.15 (1H, dd), 6.79-6.77 (1H, d), 4.89-4.85 (1H, m), 4.65 (2H, s), 3.60-3.50 (1H, m), 3.21-3.15 (3H, m), 2.84-2.78 (1H, dd), 1.25-1.23 (3H, d) ppm. LRMS (electrospray): m/z [M+H]+ 346, [M+Na]+ 368, [M–H]− 344. CHN analysis: found C, 50.29; H, 6.07; N, 3.07. C$_{19}$H$_{23}$NO$_5$+2.0LiCl+1.3H$_2$O requires C, 50.31; H, 5.69; N, 3.09.

Preparation 60: methyl 3-[(2R)-2-({(2R)-2-hydroxy-2-[4-hydroxy-3-(hydroxymethyl)phenyl] ethyl}amino)propyl]benzoate

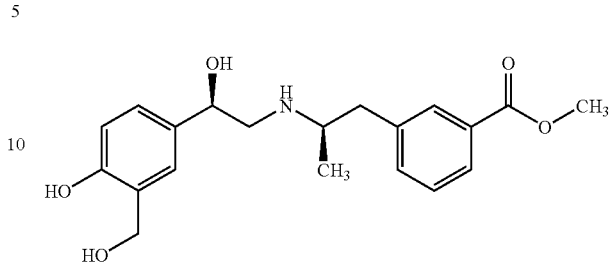

A suspension of methyl 3-[(2R)-2-({(2R)-2-[4-(benzyloxy)-3-(hydroxymethyl)phenyl]-2-hydroxyethyl}amino) propyl]benzoate (Preparation 61) (6.83 g, 15.2 mmol) and 10% palladium on carbon (683 mg) in ethanol (100 ml) was stirred under an atmosphere of hydrogen (60 psi) at room temperature for 18 hours. The catalyst was filtered off through arbocel and the filtrate concentrated in vacuo. The residue was purified by flash column chromatography on silica gel eluting with dichloromethane:methanol:880 ammonia (95:5:0.5 changing to 90:10:1, by volume) to give the title compound as a pale yellow gum (5.12 g). $^1$H NMR (400 MHz, CD$_3$OD): δ=7.85-7.83 (1H, m), 7.79 (1H, s), 7.36-7.35 (2H, m), 7.20 (1H, s), 7.02-6.99 (1H, dd), 6.68-6.65 (1H, d), 4.61-4.58 (1H, m), 4.60 (2H, s), 3.90 (3H, s), 2.97-2.87 (2H, m), 2.80-2.62 (3H, m), 1.08-1.07 (3H, d) ppm. LRMS (electrospray): m/z [M+H]+ 360, [M+Na]+ 382, [M–H]− 358.

Preparation 61: methyl 3-[(2R)-2-({(2R)-2-[4-(benzyloxy)-3-(hydroxymethyl)phenyl]-2-hydroxyethyl}amino)propyl]benzoate

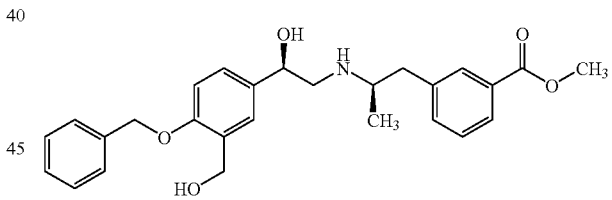

A solution of methyl 3-{(2R)-2-[((2R)-2-[4-(benzyloxy)-3-(hydroxymethyl)phenyl]-2-{[tert-butyl(dimethyl)silyl]oxy}ethyl)amino]propyl}benzoate (Preparation 62) (10 g, 17.74 mmol) and ammonium fluoride (6.57 g, 177 mmol) in methanol (180 ml) and water (60 ml) was heated at 40° C. for 18 hrs. The methanol was removed in vacuo and the remaining aqueous layer extracted with dichloromethane (2×100 ml). The combined organic layers were dried (sodium sulfate), filtered and evaporated in vacuo. The resulting oil was purified by flash column chromatography on silica gel eluting with dichloromethane:methanol:880 ammonia (95:5:0.5, by volume) to give the title compound (6.83 g) as a pale yellow gum. $^1$H NMR (400 MHz, CD$_3$OD): δ=7.83-7.82 (1H, d), 7.78 (1H, s), 7.47-7.45 (2H, m), 7.39-7.28 (6H, m), 7.11-7.10 (1H, d), 6.89-6.87 (1H, d), 5.11 (2H, s), 4.65 (2H, s), 4.65-4.62 (1H, m), 3.88 (3H, s), 2.98-2.89 (2H, m), 2.79-2.64 (3H, m), 1.09-1.08 (3H, d) ppm. LRMS (electrospray): m/z [M+H]+ 450, [M+Na]+ 472, [M–H]− 448.

Preparation 62: methyl 3-{(2R)-2-[((2R)-2-[4-(benzyloxy)-3-(hydroxymethyl)phenyl]-2-{[tert-butyl(dimethyl)silyl]oxy}ethyl)amino]propyl}benzoate

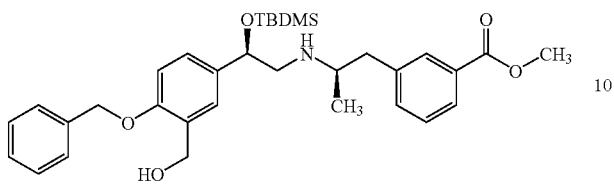

A solution of [2-(benzyloxy)-5-((1R)-2-bromo-1-{[tert-butyl(dimethyl)silyl]oxy}ethyl) phenyl]methanol (Preparation 23) (9.23 g, 20.5 mmol) and methyl {3-[(2R)-2-aminopropyl]phenyl}acetate (Preparation 63) (8.48 g, 40.9 mmol) in dichloromethane (70 ml) was heated to 90° C., allowing the dichloromethane to evaporate. The resulting melt was left at 90° C. for a further 18 hours. The reaction mixture was cooled to room temperature and purified by flash column chromatography on silica gel eluting with dichloromethane:methanol:880 ammonia (98:2:0.2 changing to 97.5:2.5:0.25, by volume) to give the title compound (10 g) as an orange oil. $^1$H NMR (400 MHz, CD$_3$OD): δ=7.84-7.82 (1H, m), 7.79 (1H, s), 7.47-7.43 (2H, m), 7.39-7.30 (6H, m), 7.08-7.06 (1H, d), 6.89-6.86 (1H, d), 5.10 (2H, s), 4.74-4.71 (1H, t), 4.65-4.64 (2H, d), 3.88 (3H, s), 2.97-2.87 (2H, m), 2.69-2.68 (2H, d), 2.65-2.61 (1H, dd), 1.08-1.07 (3H, d), 0.80 (9H, s), −0.03 (3H, s), −0.21 (3H, s) ppm. LRMS (electrospray): m/z [M+H]$^+$ 564, [M+Na]$^+$ 586.

Preparation 63: methyl {3-[(2R)-2-aminopropyl]phenyl}acetate

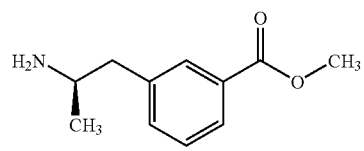

A solution of methyl[3-((2R)-2-{[(1R)-1-phenyl-ethyl]-amino}-propyl)-phenyl]-acetate (Preparation 64) (13.65 g, 40.9 mmol) and ammonium formate (12.9 g, 204 mmol) in ethanol (200 ml) was heated at reflux in the presence of 20% of palladium hydroxide on charcoal (Pd(OH)$_2$/C, 1.36 g). After 3 hours the reaction mixture was cooled to room temperature, filtered through arbocel and the filtrate concentrated in vacuo. The residue was partitioned between dichloromethane (200 ml) and 880 ammonia (100 ml) and the organic phase separated. The aqueous phase was extracted with further dichlorormethane (3×100 ml) and the combined organic extracts washed with brine (100 ml), dried (sodium sulfate) and reduced in vacuo to give the title compound (8.48 g) as a pale yellow oil. $^1$H NMR (400 MHz, CDCl$_3$): δ=7.90-7.87 (2H, m), 7.38-7.34 (2H, m), 3.90 (3H, s), 3.26-3.17 (1H, m), 2.78-2.73 (1H, dd), 2.64-2.59 (1H, dd), 1.14-1.12 (3H, d) ppm. LRMS (electrospray): m/z [M+H]$^+$ 194.

Preparation 64: methyl[3-((2R)-2-{[(1R)-1-phenyl-ethyl]-amino}-propyl)-phenyl]-acetate hyrdrochloride

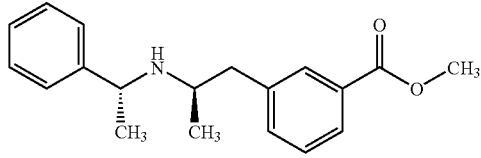

A solution of methyl[3-(2-oxopropyl)phenyl]acetate (Preparation 65) (45.3 g, 236 mmol), (R)-α-methyl benzylamine (27.6 ml, 214 mmol), sodium triacetoxyborohydride (68.1 g, 321 mmol) and acetic acid (14.7 ml, 257 mmol) in dichloromethane (1500 ml) was stirred at room temperature for 18 hours. The reaction mixture was quenched by addition of saturated aqueous sodium bicarbonate (600 ml) and allowed to stir until effervescence ceased. The organic phase was separated and the aqueous phase extracted with further dichloromethane (2×100 ml). The combined organic extracts were washed with brine (100 ml), dried (sodium sulfate), filtered through celite and reduced in vacuo. The oil was dissolved in methanol (200 ml), treated with 1M hydrogen chloride in methanol (300 ml) and reduced in vacuo to give a 4:1 mixture of diastereomers (R,R major) as an off-white, hydrochloride salt. Two successive crystallisations (diisopropylether/methanol) gave the title compound (27.3 g) as a colourless crystalline solid.
$^1$H NMR (400 MHz, CD$_3$OD): δ=7.92-7.90 (1H, d), 7.75 (1H, s), 7.55-7.49 (5H, m), 7.45-7.42 (1H, dd), 7.35-7.33 (1H, d), 4.68-4.63 (1H, q), 3.90 (3H, s), 3.43-3.38 (1H, dd), 3.25-3.19 (1H, m), 2.71-2.65 (1H, dd), 1.71-1.69 (3H, d), 1.17-1.16, (3H, d) ppm.

Preparation 65: methyl[3-(2-oxopropyl)phenyl]acetate

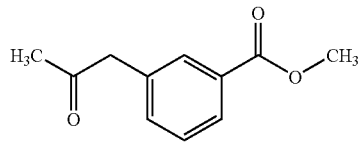

Tributyltin methoxide (80.3 ml, 279 mmol), methyl 3-bromobenzoate (53.5 g, 249 mmol), isopropenyl acetate (39.4 ml, 358 mmol), palladium(II)acetate (2.6 g, 11.6 mmol) and tri-o-tolylphosphine (7.1 g, 23.2 mmol) were stirred together in toluene (350 ml) at 100° C. under nitrogen for 18 hours. After cooling, the reaction was treated with 4M aqueous potassium fluoride solution (560 ml) and stirred for 2 hours. The resulting mixture was diluted with further toluene (200 ml) and filtered through celite, washing the filter pad with ethyl acetate. The organic phase was separated, dried (sodium sulfate) and reduced in vacuo. The residue was purified by flash column chromatography on silica gel eluting with ethylacetate:pentane (10:90, changing to 20:80, by volume) to give the title compound (45.3 g) as an orange oil.
$^1$H NMR (400 MHz, CDCl$_3$): δ=7.95-7.93 (1H, d), 7.87 (1H, s), 7.43-7.37 (2H, m), 3.91 (3H, s), 3.75 (2H, s), 2.18 (3H, s) ppm. LRMS (electrospray): m/z [M+Na]$^+$ 215, [M−H]$^−$ 191.

Preparation 66: ethyl(3-{2-[((2R)-2-[4-(benzyloxy)-3-(hydroxymethyl)phenyl]-2-{[tert-butyl(dimethyl)silyl]oxy}ethyl)amino]-2-methylpropyl}phenyl)acetate

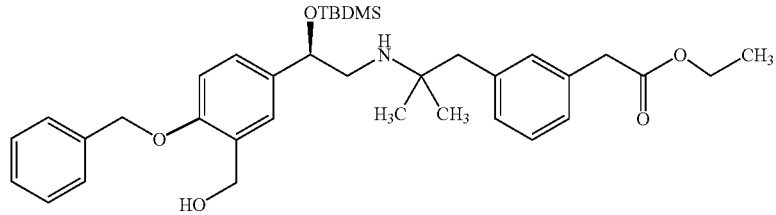

Prepared according to the procedure used for preparation 22 using [2-(benzyloxy)-5-((1R)-2-bromo-1-{[tert-butyl(dimethyl)silyl]oxy}ethyl)phenyl]methanol (Preparation 23) and [3-(2-amino-2-methyl-propyl)-phenyl]-acetic acid ethyl ester (Preparation 47) to give the title compound as a yellow oil. $^1$H NMR (400 MHz, CD$_3$OD): δ=7.48-7.05 (11H, m), 7.04-6.96 (1H, d), 5.10 (2H, s), 4.80-4.74 (1H, m), 4.78-4.63 (2H, q), 4.16-4.05 (2H, q), 3.60 (2H, s), 2.89-2.63 (2H, m), 2.70-2.62 (2H, m), 1.24-1.20 (3H, t), 1.07-1.04 (6H, d), 0.81 (9H, s), 0.00 (3H, s), -0.18 (3H, s) ppm. LRMS (electrospray): m/z [M+H]$^+$ 606, [M−H]$^−$ 604.

Preparation 67: ethyl {3-[2-({(2R)-2-[4-(benzyloxy)-3-(hydroxymethyl)phenyl]-2-hydroxyethyl}amino)-2-methylpropyl]phenyl}acetate

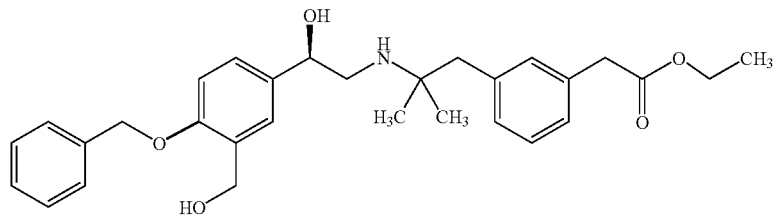

Prepared according to the procedure used for preparation 53 using ethyl(3-{2-[((2R)-2-[4-(benzyloxy)-3-(hydroxymethyl)phenyl]-2-{[tert-butyl(dimethyl)silyl]oxy}ethyl)amino]-2-methylpropyl}phenyl)acetate (Preparation 66) to give the title compound as an oil.
$^1$H NMR (400 MHz, CD$_3$OD): δ=7.47-7.03 (11H, m), 6.98-6.95 (1H, d), 5.14 (2H, s), 4.68 (2H, s), 4.68-4.66 (1H, m), 4.15-4.10 (2H, q), 3.60 (2H, s), 2.90-2.64 (4H, m), 1.26-1.22 (3H, t), 1.08-1.05 (6H, d) ppm. LRMS (electrospray): m/z [M+H]$^+$ 492, [M−H]$^−$ 490.

Preparation 68: ethyl {3-[2-({(2R)-2-hydroxy-2-[4-hydroxy-3-(hydroxymethyl)phenyl]ethyl}amino)-2-methylpropyl]phenyl}acetate

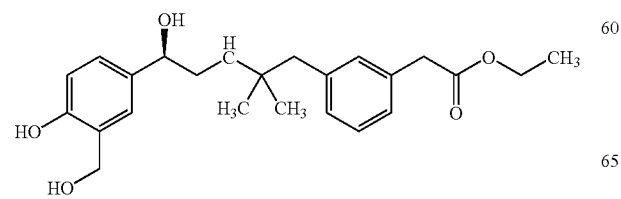

Prepared according to the procedure used for preparation 21 using ethyl {3-[2-({(2R)-2-[4-(benzyloxy)-3-(hydroxymethyl)phenyl]-2-hydroxyethyl}amino)-2-methylpropyl]phenyl}acetate (Preparation 67) to give the title compound as a colourless oil.

$^1$H NMR (400 MHz, CD$_3$OD): δ=7.30-7.02 (6H, m), 6.77-6.75 (1H, d), 4.62 (2H, s), 4.62-4.60 (1H, m), 4.17-4.09 (2H, q), 3.65-3.50 (2H, m), 2.90-2.63 (4H, m), 1.14-1.10 (3H, t), 1.08-1.05 (6H, d) ppm. LRMS (electrospray): m/z [M+H]$^+$ 402, [M−H]$^−$ 400.

Preparation 69:
2-(3-Fluoro-4-trifluoromethyl-phenyl)-ethylamine

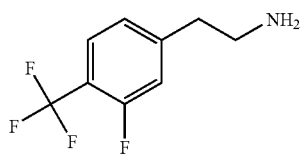

Chlorotrimethylsilane (2 mL, 16 mmol) was added dropwise to lithium borohydride (2M in tetrahydrofuran, 4 mL, 8 mmol). A solution of 3-fluoro-4-(trifluoromethyl)phenylacetonitrile (312 mg, 4 mmol) in tetrahydrofuran (2 mL) was then added at 0° C. and the mixture was allowed to stir for 24 hours, whilst warming to room temperature. The mixture was then diluted with methanol (20 mL) and concentrated in vacuo. The residue was taken up in 20% potassium hydroxide solution (20 mL), extracted with dichloromethane (3×20 mL) and the combined organic solution was dried over magnesium sulfate and concentrated in vacuo. The residue was purified by column chromatography using an Isolute® SCX-2 cartridge, eluting with methanol followed by 1M ammonia in methanol, to give an oily residue. The oil was triturated with diethyl ether to afford the title compound in 59% yield, 485 mg. H NMR (400 MHz, CDCl$_3$) δ: 7.53 (1H, m), 7.08 (2H, m), 3.02 (2H, t) 2.82 (2H, t) ppm; LRMS APCI m/z 208 [M+H]$^+$ Preparation 70:
2-(5-Chloro-2-methoxy-phenyl)-ethylamine

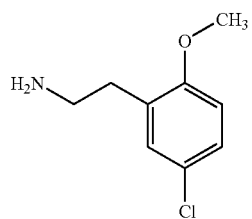

The title compound was prepared from (5-chloro-2-methoxy-phenyl)acetonitrile (WO2004039377, p40), using a similar method to that of preparation 69, in 52% yield.

$^1$H NMR (400 MHz, CDCl$_3$) δ: 7.11-7.00 (2H, m), 6.75-6.65 (1H, m) 3.72 (3H, s), 2.90-2.80 (2H, m), 2.70-2.60 (2H, m) ppm Preparations 71 to 79

The following compounds, of the general formula shown below were prepared by a similar method to that described for preparation 69 using the appropriate phenylacetonitrile starting material. Unless otherwise stated R$^3$ to R$^7$ are hydrogen.

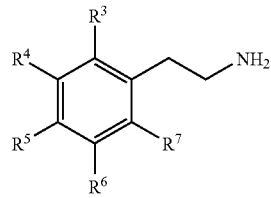

| No. | Data | Yield |
|---|---|---|
| 71 | R$^3$ = H; R$^4$ = F; R$^5$ = CH$_3$<br>$^1$H NMR (400 MHz, CDCl$_3$) δ: 7.12 (1H, m), 6.90 (2H, m), 2.95 (2H, t) 2.70 (2H, t) 2.25 (3H, s) ppm;<br>LRMS APCI m/z 154 [M + H]$^+$ | 95% |
| 72 | R$^3$ = F; R$^4$ = F; R$^5$ = CH$_3$<br>$^1$H NMR (400 MHz, CDCl$_3$) δ: 6.83 (2H, m), 2.94 (2H, t) 2.78 (2H, t) 2.25 (3H, s) ppm;<br>LRMS APCI m/z 172 [M + H]$^+$ | 61% |
| 73 | R$^3$ = CH$_3$; R$^5$ = CH$_3$; R$^7$ = CH$_3$CH$_3$<br>$^1$H NMR (400 MHz, CDCl$_3$) δ: 6.84 (2H, m), 2.88-2.69 (4H, m) 2.30 (6H, s) 2.24 (3H, s) ppm; | 80% |
| 74 | R$^3$ = F; R$^4$ = CH$_3$; R$^7$ = F<br>$^1$H NMR (400 MHz, CDCl$_3$) δ: 6.97 (1H, m), 6.75 (1H, m), 2.92 (2H, t) 2.82 (2H, t) 2.24 (3H, s) ppm;<br>LRMS APCI m/z 172 [M + H]$^+$ | 66% |
| 75 | R$^3$ = F; R$^4$ = CH$_3$; R$^7$ = Cl<br>$^1$H NMR (400 MHz, CDCl$_3$) δ: 7.05 (1H, m), 6.97 (1H, m), 2.96 (4H, m) 2.23 (3H, s) ppm;<br>LRMS APCI m/z 228 [M + CH$_3$CN]$^+$ | 58% |
| 76 | R$^3$ = Cl; R$^4$ = CH$_3$; R$^7$ = F<br>$^1$H NMR (400 MHz, CDCl$_3$) δ: 7.14-6.99 (1H, m), 6.97-6.73 (1H, m), 3.07-2.83 (4H, m) 2.35 (3H, s) ppm;<br>LRMS APCI m/z 228 [M + CH$_3$CN]$^+$ | 63% |
| 77 | R$^3$ = H; R$^4$ = F; R$^7$ = CH$_3$<br>$^1$H NMR (400 MHz, CDCl$_3$) δ: 7.07 (1H, m), 6.83 (2H, m), 2.97 (2H, t), 2.78 (2H, m) 2.27 (3H, s) ppm;<br>LRMS APCI m/z 154 [M + H]$^+$ | 62% |
| 78 | R$^4$ = F; R$^5$ = H; R$^6$ = CF$_3$<br>$^1$H NMR (400 MHz, CDCl$_3$) δ: 7.44-7.26 (1H, m), 7.09-6.86 (2H, m), 2.98-2.84 (2H, t) 2.72-2.84 (2H, t) ppm;<br>LRMS APCI m/z 208 [M + H]$^+$ | 53% |
| 79 | R$^3$ = CH$_3$; R$^4$ = CH$_3$; R$^7$ = CH$_3$<br>$^1$H NMR (400 MHz, CDCl$_3$) δ: 6.98 (2H, m), 2.95 (2H, m), 2.77 (2H, m), 2.25 (3H, s), 2.19 (6H, s) ppm;<br>LRMS APCI m/z 164 [M + H]$^+$ | 62% |

Preparation 79: compound was purified by use of sulfonic acid functionalised lanterns.

Preparation 80:
2-(4-Chloro-phenyl)-N-ethyl-acetamide

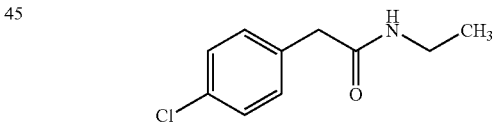

A mixture of 4-chlorophenyl acetic acid (1 g, 5.88 mmol), ethylamine (2M in tetrahydrofuran, 5.88 mL, 11.76 mmol), 1-hydroxybenzotriazole hydrate (90 mg, 5.88 mmol), 1-(3-dimethylaminopropyl)-3-ethylcarbodiimide hydrochloride (1.13 g, 5.88 mmol), and triethylamine 1.78 g, 17.64 mmol) in dichloromethane (30 mL) was stirred at room temperature for 18 hours. The mixture was then diluted with 1M sodium hydroxide solution (30 mL) and the aqueous layer was extracted with dichloromethane (30 mL). The combined organic solution was washed with 1M hydrochloric acid and brine, dried over magnesium sulfate and concentrated in vacuo. The residue was purified by column chromatography on silica gel, eluting with dichloromethane:methanol, 100:0 to 90:10, to afford the title compound as a colourless solid in 37% yield, 443 mg. $^1$H NMR (400 MHz, CDCl$_3$) δ: 7.31-7.28

(2H, m), 7.27-7.24 (2H, m), 3.45 (2H, s), 3.18 (2H, m), 1.08 (3H, t) ppm; LRMS APCI m/z 198 [M+H]+

Preparation 81:
[2-(4-Chloro-phenyl)-ethyl]-ethyl-amine hydrochloride

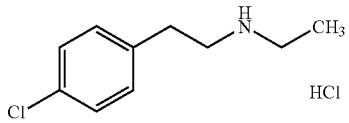

A mixture of 2-(4-chloro-phenyl)-N-ethyl-acetamide (preparation 80), (437 mg, 2.22 mmol) and borane tetrahydrofuran complex (1M, 8.88 mL, 8.88 mmol) in tetrahydrofuran was heated under reflux for 18 hours. The cooled reaction mixture was then diluted with methanol (5 mL) and 12M hydrochloric acid (2 mL) and the re-heated to reflux for a further hour. The mixture was cooled to room temperature and concentrated in vacuo. Trituration of the residue with ethyl acetate afforded the title compound as a colourless solid in 99% yield, 403 mg.

$^1$H NMR (400 MHz, CDCl$_3$) δ: 7.35 (2H, m), 7.27 (2H, m), 3.22 (2H, m), 3.05 (2H, q), 2.97 (2H, m), 1.29 (3H, t) ppm; LRMS APCI m/z 184 [M+H]+

Preparation 82:
2-(4-Methylsulfanyl-phenyl)-ethylamine

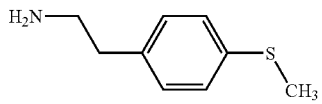

A solution of 4-(methylthio)phenylacetonitrile (828 mg, 5.08 mmol) in tetrahydrofuran (10 mL) was added dropwise to lithium aluminium hydride (1M in tetrahydrofuran, 5.6 mL, 5.6 mmol) and the mixture was stirred for 1 hour at 0° C. Further lithium aluminium hydride (1M in tetrahydrofuran, 5.6 mL, 5.6 mmol) was added and the mixture was stirred at room temperature for 18 hours then heated under reflux for 1 hour. The reaction mixture was cooled to 0° C., 1M sodium hydroxide solution (3 mL) was added dropwise, and stirring continued for a further hour. The mixture was then filtered through Celite®, washing through with ethyl acetate, and the filtrate was washed with 1M sodium hydroxide solution. The organic solution was then loaded onto an Isolute® SCX cartridge, washed with methanol and eluted with 1M ammonia in methanol. The relevant fractions were concentrated in vacuo and the residue was purified by column chromatography on silica gel, eluting with dichloromethane:methanol:0.88 ammonia, 100:0:0 to 95:5:0.5, to afford the title compound as a yellow oil in 18% yield, 154 mg. $^1$H NMR (400 MHz, CDCl$_3$) δ: 7.20 (2H, m), 7.14 (2H, m), 2.84 (2H, m), 2.71 (2H, m), 2.43 (3H, s) ppm; LRMS APCI m/z 168 [M+H]+

Preparation 83:
(4-Hydroxy-3-methyl-phenyl)-acetonitrile

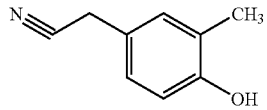

Boron tribromide (1M in dichloromethane, 6.2 mL, 6.2 mmol) was added to a solution of 4-methoxy-3-methylphenylacetonitrile (0.2 g, 1.24 mmol) in dichloromethane (10 mL), cooled to −78° C. The reaction mixture was stirred at this temperature for 1 hour and then at room temperature for 2 hours. The mixture was then re-cooled to −78° C., diluted with sodium hydrogen carbonate solution and allowed to warm to room temperature. The organic layer was separated, washed with brine, dried over sodium sulfate and concentrated in vacuo to afford the title compound as a white solid in 87% yield, 0.16 g. $^1$H NMR (400 MHz, CDCl$_3$) δ:7.07 (1H, s), 7.00 (1H, d), 6.76 (1H, d), 3.65 (2H, s), 2.25 (3H, s) ppm; LRMS APCI m/z 146 [M−H]−.

Preparation 84:
(4-Hydroxy-2,5-dimethyl-phenyl)-acetonitrile.

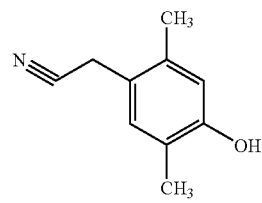

The title compound was prepared from (4-methoxy-2,5-dimethylphenyl)acetonitrile using a similar method to that of preparation 83, as a colourless solid in 60% yield.

$^1$H NMR (400 MHz, CDCl$_3$) δ: 6.98 (1H, s), 6.60 (1H, s), 3.66 (2H, s), 2.25 (3H, s), 2.13 (3H, s) ppm; LRMS APCI m/z 160 [M−H]−

Preparation 85:
(4-Hydroxy-2,3-dimethyl-phenyl)-acetonitrile

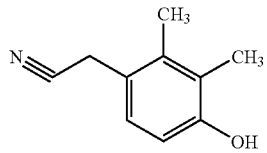

The title compound was prepared from (4-methoxy-2,3-dimethyl-phenyl)-acetonitrile using a similar method to that of preparation 83, as a colourless solid in 94% yield.

$^1$H NMR (400 MHz, CDCl$_3$) δ: 7.03 (1H, d), 6.64 (1H, d), 3.62 (2H, s), 2.24 (3H, s), 2.20 (3H, s) ppm; LRMS APCI m/z 160 [M−H]$^−$

Preparation 86:
2-(4-Methoxy-2,5-dimethyl-phenyl)-ethylamine

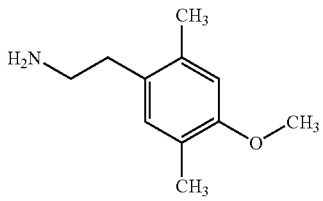

A mixture of (4-methoxy-2,5-dimethyl-phenyl)-acetonitrile (200 mg, 1.14 mmol) and Raney® nickel (50 mg) in 2M methanolic ammonia (10 mL) was stirred under 60 psi of hydrogen gas at room temperature for 18 hours. Tlc analysis showed that not all of the starting material had been consumed and so further Raney® nickel (50 mg) in 2M methanolic ammonia (10 mL) was added. The reaction mixture was stirred under 60 psi of hydrogen gas for an additional 18 hours at room temperature and was then filtered through Arbocel®. The filtrate was concentrated in vacuo and the residue was purified by column chromatography on silica gel, eluting with dichloromethane:methanol:0.88 ammonia, 100:0:0 to 90:10:1 to afford the title product as a pale brown solid in 38% yield, 98 mg. $^1$H NMR (400 MHz, CDCl$_3$) δ: 6.87 (1H, s), 6.68 (1H, s), 3.77 (3H, s), 2.80 (2H, m), 2.69 (2H, m), 2.28 (3H, s), 2.10 (3H, s) ppm; LRMS APCI m/z 180 [M+H]$^+$

Preparation 87:
2-(4-Methoxy-2,3-dimethyl-phenyl)-ethylamine

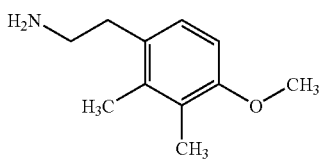

The title compound was prepared from (4-methoxy-2,3-dimethyl-phenyl)-acetonitrile, using a similar method to that of preparation 86, as a clear oil in 93% yield.

$^1$H NMR (400 MHz, CDCl$_3$) δ: 6.96 (1H, d), 6.66 (1H, d), 3.80 (3H, s), 2.96-2.84 (2H, m), 2.81-2.73 (2H, m), 2.22 (3H, s), 2.17 (3H, s), 1.63 (2H, s) ppm; LRMS APCI m/z 180 [M+H]$^+$

Preparation 88: 4-(2-Amino-ethyl)-2-methyl-phenol

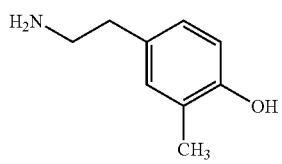

The title compound was prepared from (4-hydroxy-3-methylphenyl)acetonitrile (preparation 83), using a similar method to that of preparation 86, as a clear oil in 85% yield.

$^1$H NMR (400 MHz, CDCl$_3$) δ: 6.90 (1H, s), 6.82 (1H, d), 6.65 (1H, d), 2.83-2.79 (2H, m), 2.61 (2H, m), 2.15 (3H, s) ppm; LRMS APCI m/z 152 [M+H]$^+$

Preparation 89:
4-(2-Amino-ethyl)-2,5-dimethyl-phenol

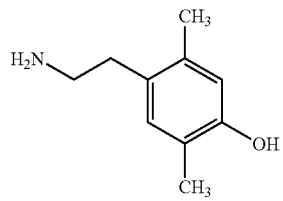

The title compound was prepared from (4-hydroxy-2,5-dimethyl-phenyl)-acetonitrile (preparation 84), using a similar method to that of preparation 86, as a solid in 73% yield.

$^1$H NMR (400 MHz, CDCl$_3$) δ: 6.81 (1H, s), 6.54 (1H, s), 2.79-2.64 (4H, m), 2.19 (3H, s), 2.11 (3H, s) ppm; LRMS APCI m/z 166 [M+H]$^+$

Preparation 90:
4-(2-Amino-ethyl)-2,3-dimethyl-phenol

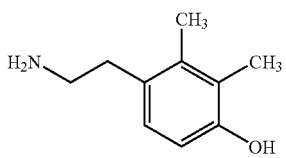

The title compound was prepared from (4-hydroxy-2,3-dimethyl-phenyl)-acetonitrile (preparation 85) using a similar method to that of preparation 86, as a colourless solid in 95% yield.

$^1$H NMR (400 MHz, CDCl$_3$) δ: 6.78 (1H, d), 6.55 (1H, d), 2.75-2.68 (4H, m), 2.19 (3H, s), 2.12 (3H, s) ppm; LRMS APCI m/z 166 [M+H]$^+$ Preparation 91: 2-(2,3-Dimethyl-phenyl)-ethylamine

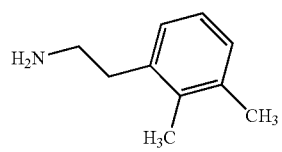

A mixture of 2,3-dimethylphenylacetonitrile (*J. Org Chem*, 51(26), 5157-60; 1986), (190 mg, 1.31 mmol) and Raney® nickel (100 mg) in 2M methanolic ammonia (5 mL) was stirred under 50 psi of hydrogen gas for 4 days. The mixture was then filtered through Arbocel® and concentrated in vacuo to afford the title compound as a solid in 66% yield, 130 mg. $^1$H NMR (400 MHz, CDCl$_3$) δ: 7.02-6.94 (3H, m), 2.26-2.13 (10H, m) ppm; LRMS ESI m/z 150 [M+H]$^+$ Preparation 92: 2-(2,3-Dichloro-phenyl)-ethylamine

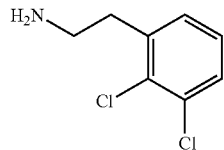

A solution of 2,3-dichlorophenylacetonitrile (0.5 g, 2.7 mmol) in diethyl ether (5 mL) was added to an ice-cold solution of lithium aluminium hydride (1M in diethyl ether, 2.7 mL, 2.7 mmol) and aluminium trichloride (359 mg, 2.7 mmol). The mixture was stirred at room temperature 2.5 hours and was then quenched with 1M sodium hydroxide solution (5 mL). The mixture was stirred for a further 30 minutes and filtered through Celite®. The layers of the filtrate were separated and the organic solution was concentrated in vacuo. Purification of the residue by column chromatography on silica gel, eluting with dichloromethane:methanol:0.88 ammonia, 100:0:0 to 95:5:0.5 afforded the title compound as a clear oil in 26% yield, 135 mg. $^1$H NMR (400 MHz, CDCl$_3$) δ 7.38 (1H, dd), 7.27-7.19 (2H, m), 2.95 (2H, m), 2.87 (2H, m) ppm; LRMS APCI m/z 190 [M+H]$^+$ Preparation 93:
2-(5-Chloro-2-fluoro-phenyl)-ethylamine

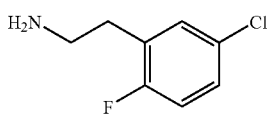

Sodium borohydride (1.73 g, 45.51 mmol) was added portionwise to a solution of 5-chloro-2-fluorophenylacetonitrile (1.04 g, 6.15 mmol) and cobalt (II) chloride hexahydrate (2.18 g, 9.22 mmol) in methanol (30 mL) and the mixture was stirred at room temperature for 3 hours. The suspension was then filtered though Celite®, concentrated in vacuo and the residue was partitioned between 1M hydrochloric acid (40 mL) and dichloromethane (40 mL). The aqueous phase was separated, basified to pH 11 with 1M ammonia solution and extracted with dichloromethane (2×40 mL). The combined organic solution was washed with brine (30 mL), dried over magnesium sulfate and concentrated in vacuo. The residue was purified by column chromatography on silica gel, eluting with dichloromethane:methanol:0.88 ammonia, 100:0:0 to 98:2:0.2, to afford the title compound as a yellow oil in 33% yield, 350 mg. $^1$H NMR (400 MHz, CDCl$_3$) δ: 7.28 (1H, m), 7.22 (1H, m), 7.05 (1H, m), 2.85 (2H, m), 2.77 (2H, m) ppm; LRMS APCI m/z 174 [M+H]$^+$ Preparation 94:
2-(2-Chloro-4-fluoro-phenyl)-ethylamine

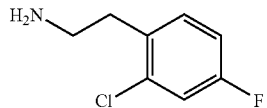

The title compound was prepared from 2-chloro-4-fluorophenylacetonitrile, using a similar method to that of preparation 93, as a light brown oil in 46% yield. $^1$H NMR (400 MHz, CDCl$_3$) δ: 7.30 (1H, dd), 7.17 (1H, dd), 6.99 (1H, m), 2.86 (4H, m) ppm; LRMS APCI m/z 174 [M+H]$^+$ Prepartion 95:
2-(4-Chloro-2-fluoro-phenyl)-ethylamine

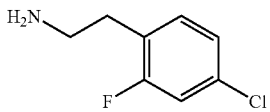

The title compound was prepared from 4-chloro-2-fluorophenylacetonitrile, using a similar method to that of preparation 93. The crude compound was purified using an Isco SCX® cartridge, eluting with methanol followed by 1M methanolic ammonia. The appropriate fractions were concentrated in vacuo and the residue was further purified by column chromatography on silica gel, eluting with dichloromethane:methanol:0.88 ammonia, 95:5:0.3 to afford the title compound as a pale yellow oil in 29% yield. $^1$H NMR (400 MHz, CDCl$_3$) δ: 7.30 (1H, dd), 7.17 (1H, dd), 6.99 (1H, dt), 2.86 (4H, m) ppm; LRMS APCI m/z 174 [M+H]$^+$ Preparation 96:
(2,3-Dihydro-benzofuran-2-yl)-methanol

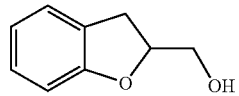

A solution of meta-chloroperbenzoic acid (96.4 g, 335 mmol) in dichloromethane (500 mL) was added to an ice-cold solution of 2-allylphenol (30 g, 224 mmol) in dichloromethane (1 L) and the mixture was stirred at 0° C. for 30 minutes and at room temperature for 18 hours. The reaction mixture was then re-cooled to 0° C., quenched with 2M sodium hydroxide solution (700 mL) and stirred for 30 minutes. The organic layer was then separated, dried over magnesium sulfate and concentrated in vacuo to give a yellow oil. The oil was purified by HPLC using a Chiralpak AD 250*4.6 mm column and hexane:isopropanol (90:10) as the eluant, to afford the title compound.

$^1$H NMR (400 MHz, CDCl$_3$) δ: 7.20-7.10 (2H, m), 6.85 (1H, m), 6.78 (1H, m), 4.90 (1H, m), 3.86 (1H, m), 3.70 (1H, m), 3.30-3.20 (1H, m) 3.10 (1H, m) ppm

Preparation 97: 2,3-Dihydro-1-benzofuran-2-ylmethyl4-methylbenzenesulfonate

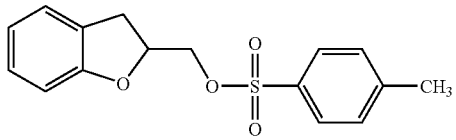

p-Toluenesulphonyl chloride (26.7 g, 140 mmol) was added to a solution of (2,3-dihydro-benzofuran-2-yl)-methanol (preparation 96) (21 g, 140 mmol) in pyridine (400 mL) and the mixture was stirred at room temperature for 4 days. The reaction mixture was then concentrated in vacuo and the residue was azeotroped with toluene, diluted with ethyl acetate (500 mL) and washed with 2M hydrochloric acid (2×300 mL). The organic solution was dried over magnesium sulfate and concentrated in vacuo to give a brown oil. Trituration of the oil in cyclohexane then afforded the title compound as a white solid in 79% yield, 33.5 g. LRMS APCI m/z 305 [M+H]$^+$

Preparation 98: 2-Ethyl-2,3-dihydro-benzofuran

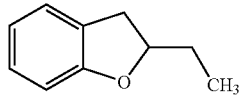

Methyl lithium (1.6M in diethyl ether, 313 mL, 500 mmol) was added to a solution of copper (I) iodide (47.6 g, 250 mmol) in diethyl ether (750 mL) at −70° C. The solution was then allowed to warm to −10° C. and was stirred for 30 minutes. The mixture was then added to a solution of 2,3-dihydro-1-benzofuran-2-ylmethyl4-methylbenzenesulfonate (preparation 97) (15.2 g, 50 mmol) in diethyl ether (500 mL) and the reaction mixture was stirred at −40° C. for 1 hour and at room temperature for 2 hours. The mixture was then cooled to −70° C. and quenched with 10% ammonium chloride solution (750 mL) and 2M hydrochloric acid (50 mL), diluted with 0.88 ammonia (100 mL) and then stirred for 18 hours. The reaction mixture was extracted with diethyl ether (3×500 mL) and the organic solution was dried over magnesium sulfate and concentrated in vacuo to afford the title compound as a brown oil in 98% yield, 7.25 g.

Preparation 99: (+) and (−) 5-Bromo-2-ethyl-2,3-dihydro-benzofuran

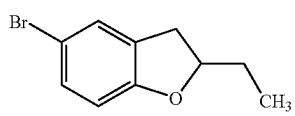

N-Bromosuccinimide (8.66 g, 48.6 mmol) was added to a solution of 2-ethyl-2,3-dihydrobenzofuran (preparation 98) in dichloromethane (70 mL) and the mixture was stirred at room temperature for 18 hours. The mixture was then diluted with dichloromethane (200 mL) and washed with water (200 mL) and sodium meta-bisulphite (200 mL). The organic solution was dried over magnesium sulfate and concentrated in vacuo to give a yellow oil that was purified by HPLC using a Chiralcel OJ 250*20 mm column and hexane:isopropanol (95:5) as the eluant to afford the first enantiomer of the title compound. Further elution provided the second isomer of the title compound, 2.95 g. $^1$H NMR (400 MHz, CDCl$_3$) δ: 7.24 (1H, m), 7.18 (1H, m), 6.62 (1H, d), 4.75 (1H, m), 3.30-3.20 (1H, m), 2.92-2.80 (1H, m), 1.77-1.88 (1H, m), 1.75-1.65 (1H, m) 1.00 (3H, m) ppm.

Preparation 100: di-tert-Butyl[3-(2-ethyl-2,3-dihydro-1-benzofuran-5-yl)propyl]imidodicarbonate

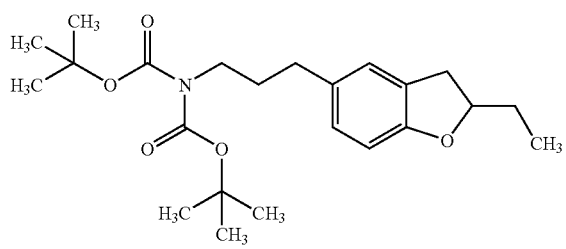

N,N-Bis-Boc-N-allylamine (2.99 g, 11.6 mmol) was azeotroped with toluene (2×50 mL) then dissolved in tetrahydrofuran (12 mL). The solution was cooled to 0° C., 9-borabicyclo[3.3.1]nonane dimer (0.5M in tetrahydrofuran, 46.5 mL, 23.2 mmol) was added and the mixture was stirred at 0° C. for 3 hours. A mixture of 5-bromo-2-ethyl-2,3-dihydro-benzofuran (preparation 98, enantiomer 2), (2.9 g, 12.8 mmol), tripotassium phosphate (7.7 mL, 23.2 mmol) and [1,1'-bis(diphenylphosphino)ferrocene]palladium(II) chloride (4.74 mg, 0.58 mmol) in N,N-dimethylformamide (12 mL) was added and the reaction mixture was stirred at room temperature for 18 hours. The reaction was then quenched with 2M sodium hydroxide solution (30 mL) and water (10 mL) and stirred for 1 hour at room temperature. The mixture was then extracted with diethyl ether, dried over magnesium sulfate and concentrated in vacuo. The residue was suspended in ethyl acetate:petroleum ether, 25:75, filtered and the filtrate was concentrated in vacuo. The residue was purified by column chromatography on silica gel, eluting with ethyl acetate:petroleum ether, 7:93, to afford the title compound as a clear oil in 46% yield, 2.15 g.

LRMS ESI m/z 428 [M+Na]$^+$

Preparation 101: 3-(2-Ethyl-2,3-dihydro-benzofuran-5-yl)-propylamine hydrochloride

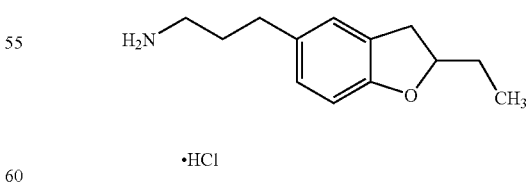

A solution of di-tert-butyl[3-(2-ethyl-2,3-dihydro-1-benzofuran-5-l)propyl]imidodicarbonate (preparation 100), (2.19 g, 5.4 mmol) in hydrochloric acid (4M in dioxane, 20 mL) was stirred at room temperature for 18 hours. The reaction mixture was then concentrated in vacuo to afford the title compound in quantitative yield.

¹H NMR (400 MHz, CDCl₃) δ: 7.00-6.85 (2H, m), 6.60 (1H, d), 4.75 (1H, m), 3.20 (1H, m), 2.97 (2H, m), 2.80 (1H, m), 2.60 (2H, m), 2.10-1.95 (2H, m), 1.90-1.60 (2H, m) 1.00 (3H, m) ppm Preparation 102: tert-Butyl(2-{4-[(butylamino)carbonyl]phenyl}ethyl)carbamate

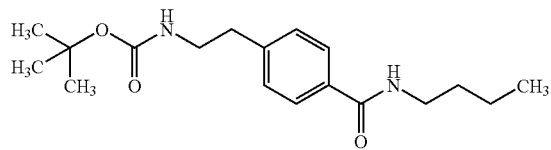

A mixture of 4-{2-[(tert-butoxycarbonyl)amino] ethyl}benzoic acid (22.2 g, 83.6 mmol) (EP0836839, p60) carbonyldiimidazole (21.36 g, 131.7 mmol), and N,N-diisopropylethylamine (20 mL, 115.1 mmol) in dichloromethane (600 mL) was stirred at room temperature for 2 hours. "Butylamine (10 mL, 101.18 mmol) was then added and the mixture was stirred for a further 18 hours at room temperature. The reaction mixture was concentrated in vacuo and the residue was dissolved in ethyl acetate and washed with 10% citric acid (2×50 mL), saturated sodium hydrogen carbonate solution (200 mL), water (200 mL) and brine (200 mL). The organic solution was dried over sodium sulfate and concentrated in vacuo to give a cream powder. The powder was purified by column chromatography on silica gel, eluting with dichloromethane:methanol, 99:1, to afford the title compound (17.5 g, 65%). LRMS Cl m/z 383.3 [M+NH₄]⁺, m.p.=118° C.

Preparation 103:
4-(2-Aminoethyl)-N-butylbenzamide hydrochloride

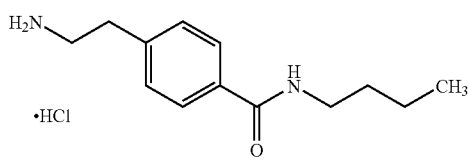

The title compound was prepared from tert-butyl(2-{4-[(butylamino)carbonyl]phenyl}ethyl)carbamate (preparation 102), using a similar method to preparation 101, as white powder in 84% yield. ¹H NMR (400 MHz, DMSO-d₆) δ: 8.38 (1H, m), 8.04 (3H, m), 7.78 (2H, d), 7.34 (2H, d), 3.24 (2H, m), 3.06 (2H, m), 2.82 (2H, m), 1.46 (2H, m), 1.28 (2H, m), 0.86 (3H, t) ppm. LRMS Cl m/z 221.2 [M+H]⁺

Preparation 104: [4-(3-Pyrrolidin-1-yl-propoxy)-phenyl]-acetonitrile

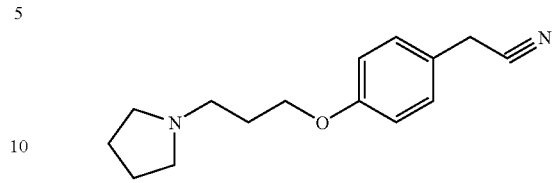

A mixture of 1-(3-chloropropyl)pyrrolidine (*J. Am. Chem. Soc.*, 77, 2270; 1955) (133 g, 0.9 mol), 4-hydroxybenzonitrile (100 g, 0.75 mol) and caesium carbonate (256 g, 0.78 mol) in acetonitrile (1 L) was stirred at 45° C. for 18 hours. The reaction mixture was then concentrated in vacuo and the residue was partitioned between ethyl acetate (800 mL) and water (800 mL). The aqueous layer was separated and extracted with ethyl acetate (800 mL) and the combined organic solution was washed with water (500 mL) and extracted with 2M hydrochloric acid (2×600 mL). The acidic solution was basified to pH8-9 with 40% potassium hydroxide solution and extracted with ethyl acetate (800 mL). The aqueous solution was then further basified to pH10-11 using 40% potassium hydroxide solution and extracted with ethyl acetate (800 mL). The combined organic solution was dried over sodium sulfate, filtered through a pad of silica and concentrated in vacuo to afford the title compound as a red oil in 79% yield, 150 g. ¹H NMR (400 MHz, CDCl₃) δ: 7.24 (2H, d), 6.85 (2H, d), 4.09-3.89 (2H, m), 3.75 (2H, s), 2.71-2.36 (6H, m), 2.14-1.93 (2H, m), 1.89-1.65 (4H, m) ppm; LRMS APCI m/z 245 [M+H]⁺

Preparation 105: 2-[4-(3-Pyrrolidin-1-yl-propoxy)-phenyl]-ethylamine

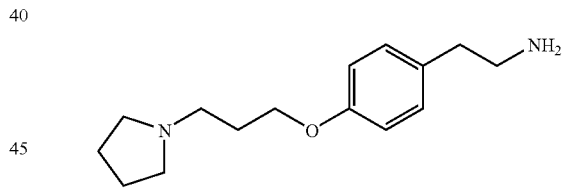

A mixture of [4-(3-pyrrolidin-1-yl-propoxy)-phenyl]-acetonitrile (preparation 104), (1 g, 4.1 mmol) and Raney® nickel (100 mg) in 2M methanolic ammonia (35 mL) was stirred under 60 psi of hydrogen gas at 50° C. for 6 hours. Tlc analysis showed that not all of the starting material had been consumed and so further Raney® nickel (200 mg) was added to the reaction mixture and heating continued for 5 hours. Tlc analysis again showed that starting material was still present and so additional Raney® nickel (200 mg) was added and the mixture was stirred at 50° C. for 3 hours. The reaction mixture was then filtered through Arbocel® and was concentrated in vacuo to give a yellow oil. The oil was purified by column chromatography using a 4 g RediSep® silica cartridge, eluting with dichloromethane:methanol:0.88 ammonia, 85:15:1.5 to 80:20:2, to afford the title compound in 16% yield, 160 mg.

¹H NMR (400 MHz, CDCl₃) δ: 7.10 (2H, d), 6.81 (2H, d), 4.10-4.00 (2H, m), 3.05-2.65 (10H, m), 2.25-2.14 (2H, m), 2.05-1.95 (4H, m) ppm; LRMS APCI m/z 249 [M+H]⁺

Preparation 106: [2-(3-Pyrrolidin-1-yl-propoxy)-phenyl]-acetonitrile

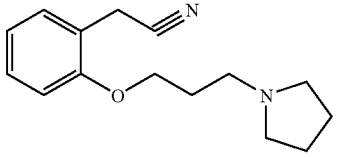

The title compound was prepared from 2-hydroxy-benzeneacetonitrile (*J. Org. Chem.*; 66, 3435; 2001) and 1-(3-chloropropyl)pyrrolidine, using a method similar to that of preparation 104, as a pale brown gum in 58% yield. $^1$H NMR (400 MHz, CD$_3$OD) δ: 7.33-7.25 (2H, m), 7.02-6.90 (2H, m), 4.12-4.09 (2H, m), 3.75 (2H, s), 2.76-2.72 (2H, m), 2.62-2.57 (4H, m), 2.09-2.02 (2H, m), 1.87-1.78 (4H, m); LRMS APCI m/z 245 [M+H]$^+$

Preparation 107: 2-[2-(3-Pyrrolidin-1-yl-propoxy)-phenyl]-ethylamine

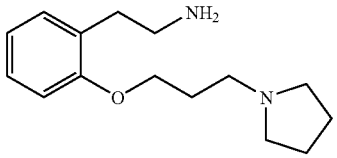

The title compound was prepared from the product of preparation 106, using a method similar to that of preparation 69, in 48% yield. $^1$H NMR (400 MHz, CD$_3$OD) δ: 7.19-7.16 (2H, m), 6.92 (1H, m), 6.86 (1H, m), 4.06-4.02 (2H, m), 2.87-2.83 (2H, m), 2.80-2.75 (2H, m), 2.71-2.67 (2H, m), 2.62-2.55 (4H, m), 2.07-2.00 (2H, m), 1.86-1.81 (4H, m); LRMS APCI m/z 249 [M+H]$^+$

Preparation 108: {2-[3-(3-Pyrrolidin-1-ylpropoxy)phenyl]ethyl}amine

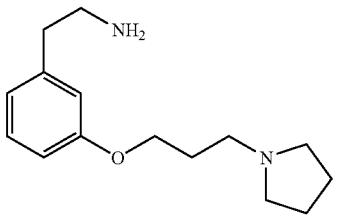

The title compound was prepared from [3-(3-pyrrolidin-1-ylpropoxy)phenyl]acetonitrile (170 mg, 0.70 mmol), using a method similar to that of preparation 69. The crude compound was then further purified by column chromatography using a 4 g RediSep® silica cartridge, eluting with dichloromethane:methanol:0.88 ammonia, 100:0:0 to 80:20:2, to afford the desired product in 30% yield. $^1$H NMR (400 MHz, CD$_3$OD) δ: 7.23-7.19 (1H, m), 6.81-6.78 (3H, m), 4.04-3.98 (2H, m), 2.99-2.95 (2H, m), 2.81-2.77 (2H, m), 2.74-2.70 (2H, m), 2.66-2.62 (4H, m), 2.05-1.98 (2H, m), 1.87-1.82 (4H, m); LRMS APCI m/z 249 [M+H]$^+$

Preparation 109: 3-{2-[(2R)-(tert-Butyl-dimethyl-silanyloxy)-2-(4-hydroxy-3-hydroxymethyl-phenyl)-ethylamino]-2-methyl-propyl}-N-(3-pyrrolidin-1-yl-propyl)-benzamide

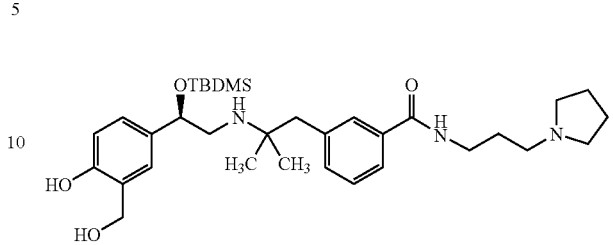

1-(3-Aminopropyl)pyrrolidine (38 μL, 0.30 mmol) was added to a mixture of 1-(3-dimethylaminopropyl)-3-ethylcarbodiimide hydrochloride (79 mg, 0.41 mmol), 3-{2-[(2R)-2-(tert-butyldimethylsilanyloxy)-2-(4-hydroxy-3-hydroxymethyl-phenyl)ethylamino]-2-methylpropyl}benzoic acid (preparation 37) (130 mg, 0.28 mmol), 1-hydroxybenzotriazole hydrate (40 mg, 0.29 mmol) and N,N-diisopropylethylamine (210 □L, 1.49 mmol) in N,N-dimethylformamide (4 mL). The resulting solution was stirred for 9 days at room temperature, after which time, tlc analysis showed that starting material still remained. Further 1-(3-dimethylaminopropyl)-3-ethylcarbodiimide hydrochloride (79 mg, 0.41 mmol), 1-hydroxybenzotriazole hydrate (40 mg, 0.29 mmol) and N,N-diisopropylethylamine (210 □l, 1.49 mmol) were then added and stirring continued for 2 days at room temperature. The solvent was removed in vacuo and the residue was partitioned between ethyl acetate (25 mL) and saturated sodium hydrogen carbonate solution (20 mL). The organic solution was separated, dried (sodium sulfate) and concentrated in vacuo to give an orange oil. The oil was purified by flash column chromatography on silica gel eluting with dichloromethane:methanol:0.88 ammonia, 100:0:0 to 75:25:2 to afford the title compound as a glass in 43% yield, 70 mg $^1$H NMR (400 MHz, CD$_3$OD) δ: 7.48 (2H, m) 7.40-7.31 (2H, m), 7.27 (1H, m), 7.07 (1H, dd), 6.74 (1H, d), 4.69 (1H, m), 4.64 (2H, m), 3.43 (2H, m), 2.90-2.50 (10H, m), 1.90-1.70 (6H, m), 1.11 (3H, s), 1.07 (3H, s), 0.79 (9H, s), −0.02 (3H, s), −0.21 (3H, s) ppm; LRMS APCI m/z 584 [M+H]$^+$

Preparation 110: 3-[2-({(2R)-2-{[tert-Butyl(dimethyl)silyl]oxy}-2-[4-hydroxy-3-(hydroxymethyl)phenyl]ethyl}amino)-2-methyl propyl]-N-[2-(4-chlorophenyl)ethyl]-N-ethylbenzamide

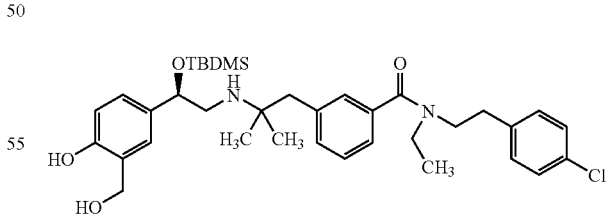

The title compound was prepared from 3-{2-[(2R)-2-(tert-butyldimethylsilanyloxy)-2-(4-hydroxy-3-hydroxy methyl-phenyl)ethylamino]-2-methylpropyl}benzoic acid (preparation 37) and [2-(4-chloro-phenyl)-ethyl]-ethyl-amine hydrochloride (preparation 81), using a similar method to that of preparation 109, as a white solid in 43% yield. $^1$H NMR (400 MHz, CD$_3$OD) 7.90-6.90 (10H, m), 6.72 (1H, d), 4.69 (1H, m), 4.63 (2H, m), 3.70 (1H, m), 3.61 (1H, m), 3.49 (1H, m), 3.10 (1H, m), 3.03-2.58 (6H, m), 1.29-1.26, 1.07-1.01 (9H, 2×m), 0.82 (9H, s), 0.01 (3H, s), -0.18 (3H, s) ppm; LRMS APCI m/z 639 [M+H]+

Preparation 111: 3-[2-({(2R)-2-{[tert-Butyl(dimethyl)silyl]oxy}-2-[4-hydroxy-3-(hydroxyl methyl)phenyl]ethyl}amino)-2-methylpropyl]-N-(2-pyrrolidin-1-ylethyl)benzamide

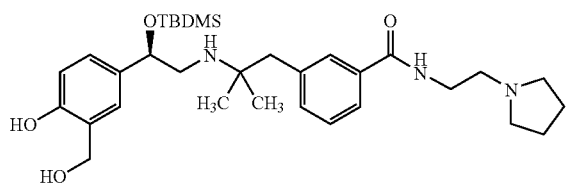

1-(2-Aminoethyl)pyrrolidine (83 μL, 0.63 mmol) was added to a mixture of 1-(3-dimethylaminopropyl)-3-ethylcarbodiimide hydrochloride (122 mg, 0.63 mmol), 3-{2-[(2R)-2-(tert-butyldimethylsilanyloxy)-2-(4-hydroxy-3-hydroxy methyl-phenyl)ethylamino]-2-methylpropyl}benzoic acid (preparation 37) (200 mg, 0.42 mmol), 1-hydroxybenzotriazole hydrate (63 mg, 0.47 mmol) and N,N-diisopropylethylamine (88 □L, 0.63 mmol) in N,N-dimethylformamide (5 mL). The resulting solution was stirred for 18 hours at room temperature. The solvent was removed in vacuo and the residue was partitioned between ethyl acetate (50 mL) and saturated sodium hydrogen carbonate solution (10 mL). The aqueous layer was separated and re-extracted with dichloromethane (30 mL), and the combined organic solution was dried (sodium sulfate) and concentrated in vacuo to give a yellow oil. The oil was purified by flash column chromatography on silica gel eluting with dichloromethane:methanol: 0.88 ammonia, 100:0:0 to 75:25:2 to afford the title compound as a pale yellow solid. ¹H NMR (400 MHz, CD₃OD) δ: 7.69 (2H, m) 7.40-7.31 (2H, m), 7.26 (1H, m), 7.14-7.03 (1H, dd), 6.85 (1H, d), 4.69 (1H, m), 4.62 (2H, m), 3.58 (2H, m), 2.89-2.59 (10H, m), 1.82-1.79 (4H, m), 1.12 (3H, s), 1.07 (3H, s), 0.79 (9H, s), -0.01 (3H, s), -0.21 (3H, s) ppm; LRMS APCI m/z 570 [M+H]+

Preparations 112 to 138

The following compounds, of the general formula shown below, were prepared by a similar method to that described for preparation 38, using 3-{2-[(2R)-2-(tert-butyldimethylsilanyloxy)-2-(4-hydroxy-3-hydroxymethyl-phenyl)ethylamino]-2-methylpropyl}benzoic acid (preparation 37) and the appropriate amine starting material. The reactions were monitored by tlc analysis and were stirred at room temperature for 18-72 hours.

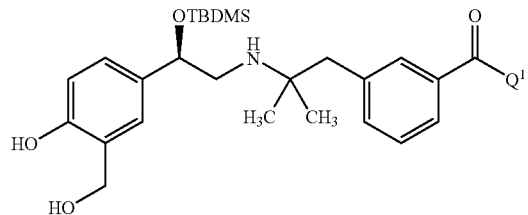

| No. | Q₁ | Data | Yield |
|---|---|---|---|
| 112 | 2,6-dichlorobenzyl-N | ¹H NMR (400 MHz, CD₃OD) δ: 7.64 (2H, m) 7.37-7.28 (5H, m), 7.20 (1H, m), 7.08 (1H, m), 6.75 (1H, d), 4.72 (1H, m), 4.65 (2H, m), 3.68 (2H, m), 3.30 (2H, m), 2.95-2.60 (4H, m), 1.12 (3H, s), 1.08 (3H, s), 0.80 (9H, s), -0.02 (3H, s), -0.19 (3H, s) ppm; LRMS APCI m/z 645 [M + H]+ | 44% |
| 113 | indanyl-N | ¹H NMR (400 MHz, CD₃OD) δ: 7.65 (2H, m), 7.40-7.05 (8H, m), 6.75 (1H, m), 4.78-4.63 (3H, m), 3.46 (2H, m), 3.15-2.70 (9H, m), 1.15 (3H, s), 1.11 (3H, s), 0.79 (9H, s), -0.01 (3H, s), -0.20 (3H, s) ppm; LRMS APCI m/z 603 [M + H]+ | 16% |
| 114 | 4-(N-butylcarbamoyl)benzyl-N | ¹H NMR (400 MHz, CD₃OD) δ: 7.75 (2H, m), 7.65 (2H, m), 7.40-7.25 (5H, m), 7.09 (1H, m), 6.73 (1H, m), 4.75-4.62 (3H, m), 3.62 (2H, m), 3.37 (2H, m), 3.02-2.62 (6H, m), 1.59 (2H, m), 1.41 (2H, m), 1.14-1.07 (6H, m), 0.97 (3H, t), 0.79 (9H, s), -0.01 to -0.21 (6H, m) ppm; LRMS APCI m/z 676 [M + H]+ | 22% |

-continued

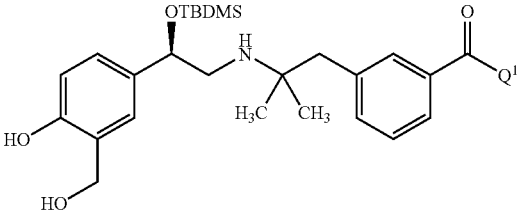

| No. | Q₁ | Data | Yield |
|---|---|---|---|
| 115 | 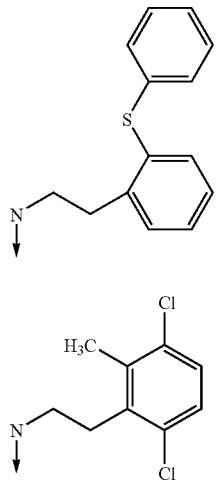 | ¹H NMR (400 MHz, CD₃OD) δ: 7.63 (2H, m), 7.25 (12H, m), 7.05 (1H, m), 6.73 (1H, m), 4.68 (3H, m), 3.62 (2H, m), 3.13 (2H, m), 2.80 (4H, brm), 1.08 (6H, m), 0.80 (9H, s), −0.05 (3H, s). −0.21 (3H, s) ppm LRMS ESI m/z 685 [M + H]⁺ | 34% |
| 116 | 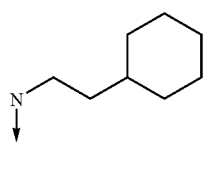 | ¹H NMR (400 MHz, CD₃OD) δ: 7.63 (2H, m), 7.40-7.20 (5H, m), 7.10 (1H, m), 6.75 (1H, m), 4.62 (3H, m), 3.59 (2H, m), 3.22 (2H, m), 2.92-2.64 (4H, brm), 2.51 (3H, s), 1.10 (6H, m), 0.80 (9H, s), −0.02 (3H, s), −0.21 (3H, s) ppm; LRMS ESI m/z 659 [M + H]⁺ | 30% |
| 117 | 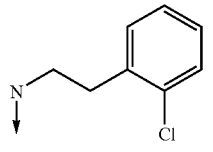 | ¹H NMR (400 MHz, CD₃OD) δ: 7.66 (2H, m), 7.34 (2H, m), 7.26 (1H, d), 7.07 (1H, m), 6.72 (1H, m), 4.69 (1H, m), 4.63 (2H, d), 3.39 (2H, t), 2.75 (3H, brm), 2.63 (1H, m), 1.81 (2H, m), 1.75-1.63 (3H, m), 1.52 (2H, m), 1.36 (1H, m), 1.28 (1H, m), 1.17-1.24 (2H, m), 1.11 (3H, s), 1.08 (3H, s), 1.03-0.92 (2H, m), 0.77 (9H, s), −0.05 (3H, s) −0.27 (3H, s) ppm LRMS ESI m/z 583 [M + H]⁺ | 34% |
| 118 | 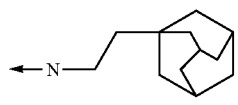 | ¹H NMR (400 MHz, CD₃OD) δ: 7.65 (2H, m), 7.38-7.31 (4H, m), 7.27 (1H, d), 7.20 (2H, m), 7.06 (1H, dd), 6.72 (1H, d), 4.69 (1H, m), 4.63 (2H, d), 3.62 (2H, m), 3.07 (2H, t), 2.89-2.82 (2H, t), 2.79-2.71 (1H, m), 2.65 (1H, m), 1.10 (3H, s), 1.07 (3H, s), 0.78 (9H, s), −0.04 (3H, s) −0.21 (3H, s) ppm; LRMS ESI m/z 611 [M + H]⁺ | 38% |
| 119 | 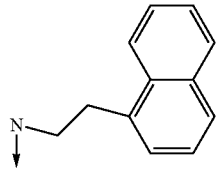 | ¹H NMR (400 MHz, CD₃OD) δ: 7.66 (2H, m), 7.37-7.30 (2H, m), 7.26 (1H, m), 7.09-7.00 (1H, m), 6.72 (1H, d), 4.69 (1H, m), 4.63 (2H, d), 3.43-3.38 (2H, m), 2.83-2.89 (2H, m), 2.80-2.71 (1H, m), 2.61-2.65 (1H, m), 1.96 (3H, s), 1.68 (6H, m), 1.61 (6H, d), 1.42 (2H, m), 1.10 (3H, s), 1.07 (3H, s) 0.78 (9H, s), −0.04 (3H, s) −0.22 (3H, s) ppm; LRMS ESI m/z 635 [M + H]⁺ | 37% |
| 120 | | ¹H NMR (400 MHz, CD₃OD) δ: 8.26 (1H, m), 7.86 (1H, m), 7.74 (1H, m), 7.64 (2H, m), 7.53 (1H, m), 7.46 (1H, m), 7.41-7.31 (4H, m), 7.27 (1H, m), 7.06 (1H, dd), 6.73 (1H, m), 4.70 (1H, m), 4.63 (2H, d), 3.72 (2H, m), 3.40 (2H, t), 2.90-2.70 (3H, m), 2.64 (1H, m), 1.09 (3H, s), 1.07 (3H, s), 0.78 (9H, s), −0.03 (3H, s), −0.21 (3H, s) ppm; LRMS ESI m/z 627 [M + H]⁺ | 24% |

-continued

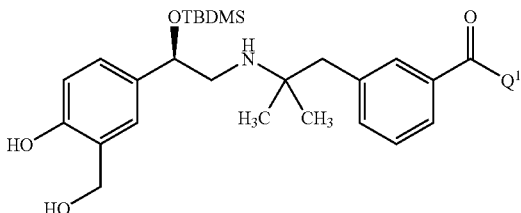

| No. | Q₁ | Data | Yield |
|---|---|---|---|
| 121 | (2,6-dimethylphenethyl) | ¹H NMR (400 MHz, CD₃OD) δ: 7.67 (2H, m), 7.39-7.32 (2H, m), 7.27 (1H, m), 7.07 (1H, dd), 6.98 (3H, m), 6.72 (1H, m), 4.70 (1H, m), 4.63 (2H, d), 3.46 (2H, t), 2.99 (2H, m), 2.87 (2H, m), 2.73 (1H, m), 2.66 (1H, m), 2.39 (6H, s), 1.11 (3H, s), 1.09 (3H, s), 0.79 (9H, s), −0.03 (3H, s), −0.21 (3H, s) ppm; LRMS ESI m/z 605 [M + H]⁺ | 40% |
| 122 | (4-methylthiophenethyl) | ¹H NMR (400 MHz, CD₃OD) δ: 7.63 (2H, m), 7.35 (2H, m), 7.27 (1H, m), 7.17 (4H, m), 7.06 (1H, dd) 6.72 (1H, m), 4.70 (1H, m), 4.63 (2H, d), 3.56 (2H, t), 2.87 (3H, m), 2.71 (2H, m), 2.64 (1H, m), 2.43 (3H, s), 1.09 (3H, s), 1.07 (3H, s), 0.78 (9H, s), −0.04 (3H, s), −0.22 (3H, s) ppm; LRMS ESI m/z 623 [M + H]⁺ | 46% |
| 123 | (2-fluoro-5-chlorophenethyl) | ¹H NMR (400 MHz, CD₃OD) δ: 7.62 (2H, m), 7.34-7.27 (3H, m), 7.22 (2H, m), 7.03-7.09 (2H, m), 6.72 (1H, d), 4.69 (1H, m), 4.63 (2H, m), 3.59 (2H, m), 2.96 (2H, m), 2.71 (2H, m), 2.63 (2H, m), 1.09 (3H, s), 1.06 (3H, s), 0.78 (9H, s,) −0.04 (3H, s), −0.21 (3H, s) ppm: LRMS APCI m/z 629 [M + H]⁺ | 61% |
| 124 | (2-chloro-4-fluorophenethyl) | ¹H NMR (400 MHz, CD₃OD) δ: 7.62 (2H, m), 7.34 (3H, m), 7.27 (1H, d), 7.18 (1H, m), 7.06 (1H, dd), 6.97 (1H, m), 6.72 (1H, d), 4.69 (1H, m), 4.63 (2H, m), 3.62 (2H, m), 3.04 (2H, t), 2.89-2.70 (3H, m), 2.61 (1H, m), 1.09 (3H, s), 1.07 (3H, s), 0.78 (9H, s), −0.04 (3H, s), −0.21 (3H, s) ppm; LRMS APCI m/z 629 [M + H]⁺ | 60% |
| 125 | (2,5-dimethyl-4-methoxyphenethyl) | ¹H NMR (400 MHz, CD₃OD) δ: 7.54-7.75 (2H, m), 7.42-7.24 (3H, m), 7.17-7.04 (1H, m), 6.98-6.83 (1H, dd), 6.79-6.64 (2H, m), 4.70 (1H, m), 4.63 (2H, d), 3.77 (3H, s), 3.51 (2H, t), 2.89-2.82 (4H, m), 2.79-2.71 (1H, m), 2.64 (1H, m), 2.33 (3H, s), 2.09 (3H, s), 1.07 (6H, s), 0.78 (9H, s), −0.03 (3H, s), −0.21 (3H, s) ppm; LRMS ESI m/z 635 [M + H]⁺ | 19% |
| 126 | (2,3-dichlorophenethyl) | ¹H NMR (400 MHz, CD₃OD) δ: 7.62 (2H, m) 7.44-7.14 (6H, m), 7.08 (1H, d), 6.73 (1H, d), 4.71 (1H, m), 4.60 (2H, m), 3.68 (2H, m), 3.14 (2H, m), 2.93-2.58 (4H, m), 1.10 (3H, s), 1.07 (3H, s), 0.78 (9H, s), −0.04 (3H, s), −0.21 (3H, s) ppm; LRMS APCI m/z 645 [M + H]⁺ | 67% |
| 127 | (2,3-dimethyl-4-methoxyphenethyl) | ¹H NMR (400 MHz, CD₃OD) δ: 7.65 (2H, m) 7.37-7.31 (2H, m), 7.27 (1H, d), 7.06 (1H, dd), 6.97 (1H, d), 6.73 (1H, d), 6.68 (1H, d), 4.73-4.68 (1H, m), 4.60 (2H, m), 3.76 (3H, s), 3.49 (2H, m), 2.93-2.60 (6H, m), 2.28 (3H, s), 2.13 (3H, s), 1.10 (3H, s), 1.07 (3H, s), 0.78 (9H, s), −0.04 (3H, s), −0.21 (3H, s) ppm LRMS APCI m/z 635 [M + H]⁺ | 39% |

-continued

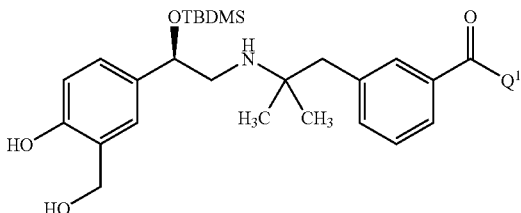

| No. | Q1 | Data | Yield |
|---|---|---|---|
| 128 | N-CH2CH2-(4-biphenyl) | ¹H NMR (400 MHz, CD3OD) δ: 7.67-7.62 (2H, m), 7.59-7.52 (4H, dd), 7.42-7.36 (2H, dd), 7.35-7.26 (6H, m), 7.05 (1H, dd), 6.71 (1H, dd), 4.67 (1H, dd), 4.60 (2H, dd), 3.61 (2H, t), 2.95 (2H, t), 2.83 (1H, dd), 2.70 (1H, dd), 2.60-2.65 (1H, m), 1.08 (3H, s), 1.06 (3H, s), 0.77 (9H, s), −0.05 (3H, s), −0.23 (3H, s) ppm; LRMS APCI m/z 653 [M + H]⁺ | 43% |
| 129 | N-CH2CH2-(2,4-dimethylphenyl) | ¹H NMR (400 MHz, CD3OD) δ: 7.65 (2H, m) 7.37-7.31 (2H, m), 7.27 (1H, d), 7.06 (1H, dd), 7.03 (1H, d), 6.96 (1H, bs), 6.90 (1H, d), 6.72 (1H, d), 4.72-4.68 (1H, m), 4.60 (2H, m), 3.51 (2H, m), 2.91-2.84 (3H, m), 2.71 (2H, dd), 2.64 (1H, m), 2.33 (3H, s), 2.24 (3H, s), 1.10 (3H, s), 1.07 (3H, s), 0.78 (9H, s), −0.04 (3H, s), −0.22 (3H, s) ppm; LRMS APCI m/z 605 [M + H]⁺ | 46% |
| 130 | N-CH2CH2-(2,3-dimethylphenyl) | ¹H NMR (400 MHz, CD3OD) δ: 7.87-7.80 (2H, m), 7.38-7.30 (2H, m), 7.27 (1H, d), 7.06 (1H, dd), 7.02-6.94 (3H, m), 6.72 (1H, d), 4.68 (1H, m), 4.60 (2H, m), 3.51 (2H, m), 2.94 (2H, m), 2.84 (1H, m), 2.71 (2H, dd), 2.61 (1H, m), 2.29 (3H, s), 2.27 (3H, s), 1.10 (3H, s), 1.07 (3H, s), 0.78 (9H, s), −0.04 (3H, s), −0.21 (3H, s) ppm; LRMS APCI m/z 605 [M + H]⁺ | 35% |
| 131 | N-CH2CH2CH2-Ph | ¹H NMR (400 MHz, CDCl3) δ: 7.44-7.38 (2H, m), 7.33-7.20 (7H, m), 7.06 (1H, d), 6.88 (1H, s), 6.75 (1H, d), 6.13-6.09 (1H, m), 4.82-4.60 (2H, m), 4.58 (1H, t), 3.51-3.44 (2H, m), 2.84-2.55 (6H, m), 2.00-1.90 (2H, m), 1.04 (3H, s), 1.00 (3H, s), 0.79 (9H, s), −0.05 (3H, s), −0.21 (3H, s) ppm; LRMS APCI m/z 592 [M + H]⁺ | 45% |
| 132 | N-CH2CH2-Ph | ¹H NMR (400 MHz, CDCl3) δ: 7.44 (1H, d), 7.38 (1H, m), 7.32-7.22 (7H, m), 7.08 (1H, d), 6.88 (1H, s), 6.75 (1H, d), 6.14 (1H, m), 4.83-4.75 (2H, m), 4.59 (1H, t), 3.72-3.68 (2H, q), 2.92 (2H, t), 2.82-2.75 (1H, m), 2.65-2.56 (3H, m), 1.03 (3H, s), 1.00 (3H, s), 0.79 (9H, s), −0.05 (3H, s), −0.20 (3H, s) ppm; LRMS APCI m/z 592 [M + H]⁺ | 45% |
| 133 | N-CH2CH2-(3-CF3-phenyl) | ¹H NMR (400 MHz, CDCl3) δ: 7.51-7.39 (6H, m), 7.27-7.23 (2H, m), 7.10 (1H, d), 6.89 (1H, s), 6.77-6.65 (1H, d), 6.16 (1H, m), 4.84-4.76 (2H, m), 4.62-4.58 (1H, t), 3.72-3.68 (2H, m), 2.99 (2H, t), 2.83-2.76 (1H, m), 2.66-2.58 (3H, m), 1.03 (3H, s), 1.00 (3H, s), 0.79 (9H, s), −0.04 (3H, s), −0.20 (3H, s) ppm; LRMS APCI m/z 645 [M + H]⁺ | 53% |
| 134 | N-CH2CH2-(4-Cl-2-F-phenyl) | ¹H NMR (400 MHz, CDCl3) δ: 7.45 (1H, d), 7.39 (1H, m), 7.29-7.23 (2H, m), 7.20-7.06 (4H, m), 6.90 (1H, s), 6.76 (1H, d), 6.19 (1H, m), 4.83-4.76 (2H, m), 4.59 (1H, t), 3.69-3.63 (2H, m), 2.99 (2H, m), 2.84-2.76 (1H, m), 2.66-2.60 (3H, m), 1.04 (3H, s), 1.01 (3H, s), 0.80 (9H, s), −0.04 (3H, s), −0.19 (3H, s) ppm; LRMS APCI m/z 629 [M + H]⁺ | 46% |

-continued

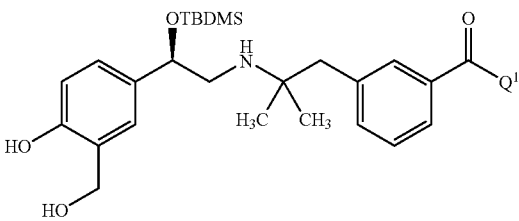

| No. | Q₁ | Data | Yield |
|---|---|---|---|
| 135 | 2,5-dimethylbenzyl | ¹H NMR (400 MHz, CD₃OD) δ: 7.73 (2H, m) 7.40-7.33 (2H, m), 7.26 (1H, d), 7.11 (1H, bs), 7.07-7.04 (2H, dd), 6.96 (1H, d), 6.71 (1H, d), 4.66 (2H, dd), 4.63 (2H, dd), 4.54 (2H, s), 2.83 (1H, t), 2.72 (2H, dd), 2.61 (1H, dd), 2.32 (3H, s), 2.26 (3H, s), 1.11 (3H, s), 1.08 (3H, s), 0.78 (9H, s), −0.06 (3H, s), −0.23 (3H, s) ppm; LRMS APCI m/z 591 [M + H]⁺ | 44% |
| 136 | 4-(3-pyrrolidin-1-ylpropoxy)phenethyl | ¹H NMR (400 MHz, CD₃OD) δ: 7.69-7.58 (2H, m) 7.39-7.03 (5H, m), 6.90-6.68 (4H, m), 4.75-4.57 (3H, m), 3.62-3.49 (2H, m), 3.18-3.07 (2H, m), 2.91-2.53 (10H, m), 2.05-1.90 (4H, m), 1.87-1.73 (2H, m), 1.11-1.06 (6H, m), 0.78 (9H, s), −0.05 (3H, s), −0.22 (3H, s) ppm; LRMS APCI m/z 691 [M + H]⁺ | 2% |
| 137 | 2-(3-pyrrolidin-1-ylpropoxy)phenethyl | ¹H NMR (400 MHz, CD₃OD) δ: 7.65-7.61 (2H, m), 7.34-7.30 (2H, m), 7.26 (2H, m), 7.17-7.15 (2H, m) 7.06 (1H, m), 6.93 (1H, m), 6.85 (1H, m), 6.73 (1H, m), 4.71-4.63 (3H, m), 4.06-4.02 (2H, m), 3.61-3.57 (2H, m), 2.96-2.58 (15H, m), 2.07-2.02 (2H, m), 1.84-1.79 (4H, m), 1.09-1.06 (6H, m), 0.79 (9H, s), −0.03 (3H, s), −0.21 (3H, s) ppm; LRMS APCI m/z 705 [M + H]⁺ | 78% |
| 138 | 3-(3-pyrrolidin-1-ylpropoxy)phenethyl | ¹H NMR (400 MHz, CD₃OD) δ: 7.63 (2H, m) 7.34-7.21 (3H, m), 7.17 (1H, m), 7.07 (1H, m), 6.79-6.65 (4H, m), 4.67-4.57 (3H, m), 3.95-3.92 (2H, m), 3.57-3.53 (2H, m), 2.86-2.53 (12H, m), 1.98-1.85 (2H, m), 1.82-1.70 (4H, m), 1.04-1.01 (6H, m), 0.78 (9H, s), −0.02 (3H, s), -0.20 (3H, s) ppm | 56% |

Preparation 115: 2-(2-phenylsulfanyl-phenyl)-ethylamine can be prepared as described in Collection of Czechoslovak Chemical Communications, 54(7), 1995-2008; 1989.

Preparation 116: appropriate fractions were concentrated in vacuo and the residue was further purified by column chromatography on amino silica gel, eluting with ethyl acetate:pentane, 100:0 to 80:20, followed by dichloromethane:methanol, 100:0 to 80:20.

Preparation 139: Methyl 3-[2-({(2R)-2-hydroxy-2-[4-hydroxy-3-(hydroxymethyl)phenyl]ethyl}amino)-2-methylpropyl]benzoate

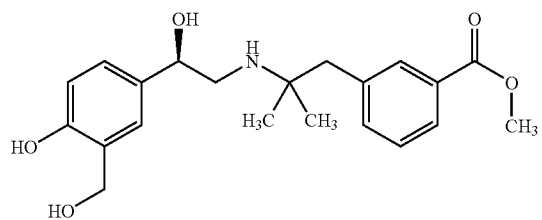

A mixture of 3-(2-[(2R)-2-(tert-butyldimethylsilanyloxy)-2-(4-hydroxy-3-hydroxymethyl-phenyl)ethylamino]-2-methylpropyl}benzoic acid methyl ester (preparation 36), (4.0 g, 8.21 mmol) and ammonium fluoride (3.04 g, 82.0 mmol) in methanol (20 mL) and water (5 mL) was heated at 40° C. for 18 hours. The reaction mixture was then concentrated in vacuo and the residue was purified by column chromatography on silica gel, eluting with dichloromethane: methanol: 0.88 ammonia, 100:0:0 to 90:10:0.1, to afford the title compound as a white foam in 81% yield, 2.42 g.

$^1$H NMR (400 MHz, CD$_3$OD) δ: 7.87 (2H, m), 7.40 (2H, m), 7.29 (1H, m), 7.09 (1H, dd), 6.72 (1H, d), 4.69-4.61 (3H, m), 3.90 (3H, s), 2.90-2.73 (4H, m), 1.08 (3H, s), 1.06 (3H, s) ppm; LRMS ESI m/z 374 [M+H]$^+$ Preparation 140: 3-[2-({(2R)-2-Hydroxy-2-[4-hydroxy-3-(hydroxymethyl)phenyl]ethyl}amino)-2-methylpropyl]benzoic acid

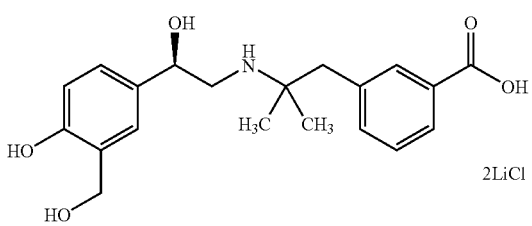

A mixture of 3-{2-[2-hydroxy-2-(4-hydroxy-3-hydroxymethyl-phenyl)-ethylamino]-2-methylpropyl}-benzoic acid methyl ester (preparation 139) (2.35 g, 6.32 mmol) and lithium hydroxide (303 mg, 12.64 mmol) in tetrahydrofuran (20 mL) and water (20 mL) was stirred at room temperature for 3 days. The reaction mixture was then concentrated in vacuo and the residue was diluted with water and acidified with 1M hydrochloric acid (12 mL). The mixture was stirred for 2 hours at room temperature and was then concentrated in vacuo. The crude residue was used in subsequent reactions without further purification. $^1$H NMR (400 MHz, CD$_3$OD) δ: 7.87 (1H, m), 7.84 (1H, bs), 7.39-7.31 (3H, m), 7.19 (1H, dd), 6.79 (1H, d), 4.86 (1H, m), 4.66 (2H, s), 3.22-3.11 (2H, m), 3.02 (2H, m), 1.32 (6H, s) ppm; LRMS ESI m/z 360 [M+H]$^+$ Preparation 141: 3-[3-(2-tert-Butoxycarbonylamino-2-methyl-propyl)-phenyl]-acrylic acid benzyl ester

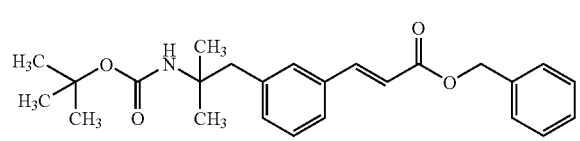

A mixture of [2-(3-bromophenyl)-1,1-dimethylethyl]carbamic acid tert-butyl ester (preparation 32), (2 g, 6.09 mmol), benzyl acrylate (2 g, 12.19), palladium (II) acetate (204 mg, 0.91 mmol), tri-p-tolyl phosphite (556 mg, 1.83 mmol) and triethylamine (2.12 mL, 15.22 mmol) in acetonitrile (100 mL) was heated under reflux for 48 hours. The reaction mixture was then concentrated in vacuo and the residue was purified by column chromatography on silica gel, eluting with ethyl acetate:pentane to afford the title compound as a pale yellow oil in 90% yield, 2.23 g.

$^1$H NMR (400 MHz, CD$_3$OD) δ: 7.75 (1H, d), 7.35 (7H, m), 7.20 (1H, d), 6.58 (1H, d), 6.00 (1H, brs), 5.20 (2H, s), 3.00 (2H, s), 1.43 (9H, s), 1.22 (6H, s) ppm; LRMS ESI m/z 310 [M+H]$^+$ Preparation 142: 3-[3-(2-Amino-2-methyl-propyl)-phenyl]-acrylic acid benzyl ester

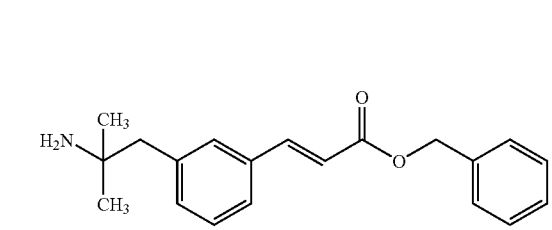

A mixture of 3-[3-(2-tert-butoxycarbonylamino-2-methyl-propyl)-phenyl]-acrylic acid benzyl ester (preparation 141), (2.23 g, 5.45 mmol), and trifluoroacetic acid (5 mL) in dichloromethane (10 mL) was stirred for 1 hour at room temperature. The mixture was then concentrated in vacuo and the residue was diluted with sodium hydrogen carbonate solution (10 mL) and extracted with ethyl acetate (3×20 mL). The combined organic solution was dried over magnesium sulfate and concentrated in vacuo to afford the title compound as a yellow oil in quantitative yield.

$^1$H NMR (400 MHz, CD$_3$OD) δ: 7.78 (1H, d), 7.60 (1H, d), 7.48 (1H, s), 7.38 (7H, m), 6.60 (1H, brs), 5.23 (2H, s), 2.91 (2H, s), 1.30 (6H, s) ppm; LRMS ESI m/z 408 [M−H]$^−$

Preparation 143: Benzyl-3-(3-{2-[((2R)-2-[4-(benzyloxy)-3-(hydroxymethyl)phenyl]-2-{[tert-butyl(dimethyl)silyl]oxy}ethyl)amino]-2-methyl propyl}phenyl)acrylate

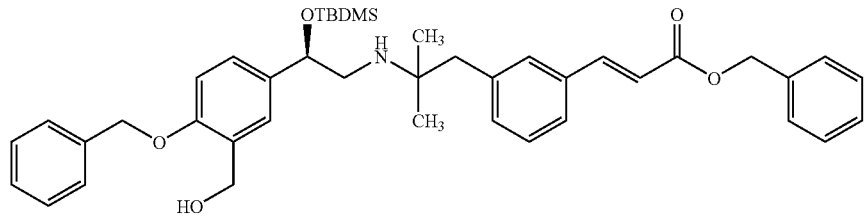

A mixture of [2-(benzyloxy)-5-((1R)-2-bromo-1-{[tert-butyl(dimethyl)silyl]oxy}ethyl) phenyl]methanol (Preparation 23) (800 mg, 1.77 mmol) and 3-[3-(2-amino-2-methyl-propyl)phenyl]-acrylic acid benzyl ester (preparation 142), (1.10 g, 3.55 mmol) was stirred at 90° C. for 18 hours. The reaction mixture was then cooled to room temperature, diluted with diethyl ether (40 mL) and stirred for 4 hours. The resulting precipitate was filtered off, washing though with diethyl ether, and the filtrate was concentrated in vacuo to give a brown oil. Purification of the oil by column chromatography on silica gel, eluting with dichloromethane:methanol:0.88 ammonia afforded the title compound in 25% yield, (4-benzyloxy-3-hydroxymethyl-phenyl)-2-(tert-butyl-dimethyl-silanyloxy)ethylamino]-2-methyl-propyl}-phenyl)-acrylic acid benzyl ester (preparation 143), (300 mg, 0.44 mmol) in ethanol (10 mL) and the mixture was heated under reflux for 30 minutes. The reaction mixture was then cooled, filtered through Arbocel® and concentrated in vacuo to afford the title compound in 90% yield, 200 mg. $^1$H NMR (400 MHz, CD$_3$OD) δ: 7.30 (1H, s), 7.20 (1H, m), 7.18 (1H, d), 7.09 (2H, m), 7.00 (1H, d), 6.78 (1H, d), 4.88 (1H, m), 4.63 (2H, m), 3.11 (2H, m), 2.83 (4H, m), 2.48 (2H, m), 1.23 (6H, s), 0.81 (9H, s), −0.03 (3H, s), −0.18 (3H, s) ppm; LRMS ESI m/z 502 [M+H]$^+$

Preparation 145: 3-{3-[2-({(2R)-2-{[tert-Butyl(dimethyl)silyl]oxy}-2-[4-hydroxy-3-(hydroxymethyl)phenyl]ethyl}amino)-2-methylpropyl]phenyl}-N-(3,4-dichlorobenzyl) propanamide

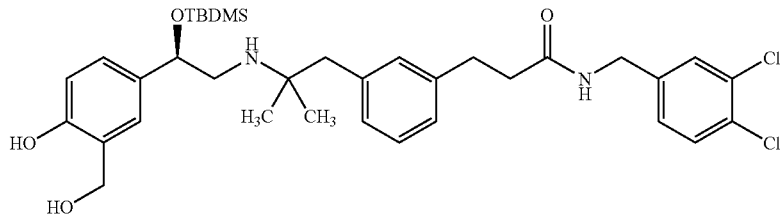

300 mg. $^1$H NMR (400 MHz, CD$_3$OD) δ: 7.78 (1H, d), 7.38 (16H, m), 6.95 (1H, m), 6.58 (1H, d), 5.25 (2H, s), 5.04 (2H, s), 4.78 (1H, m), 4.64 (2H, m), 2.80 (2H, m), 2.68 (2H, m), 1.14 (3H, s), 1.10 (3H, s), 0.78 (9H, s), −0.03 (3H, s), −0.21 (3H, s) ppm; LRMS ESI m/z 680 [M+H]$^+$

Preparation 144: 3-{3-[2-({(2R)-2-{[tert-Butyl(dimethyl)silyl]oxy}-2-[4-hydroxy-3-(hydroxymethyl)phenyl]ethyl}amino)-2-methylpropyl]phenyl}propanoic acid

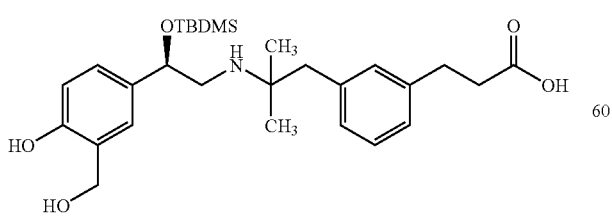

Ammonium formate (139 mg, 2.20 mmol) and palladium (II) hydroxide (50 mg) was added to a solution of 3-(3-{2-[2-

The title compound was prepared from 3-{3-[2-({(2R)-2-{[tert-butyl(dimethyl)silyl]oxy}-2-[4-hydroxy-3-(hydroxymethyl)phenyl]ethyl}amino)-2-methylpropyl]phenyl}propanoic acid (preparation 144) and 3,4-dichlorobenzylamine, using a method similar to that of preparation 38, as a clear oil in 64% yield. $^1$H NMR (400 MHz, CD$_3$OD) δ: 7.40 (3H, m), 7.18 (1H, m), 7.08 (5H, m), 6.78 (1H, d), 4.61 (3H, m), 4.23 (2H, s), 2.90 (3H, m), 2.60 (5H, m), 1.08 (3H, s), 1.04 (3H, s), 0.81 (9H, s), 0.00 (3H, s), -0.18 (3H, s) ppm; LRMS ESI m/z 659 [M+H]$^+$

Preparation 146: [3-(2-Amino-2-methyl-propyl)-phenyl]-acetic acid methyl ester

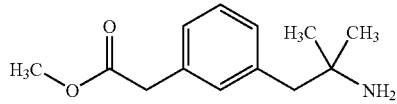

Acetyl chloride (154.5 g, 1.97 mol) was added to a solution of {3-[2-(2-chloro-acetylamino)-2-methyl-propyl]-phenyl}- acetic acid (preparation 48), (20 g, 0.66 mol) in methanol (350 mL) and the mixture was heated under reflux for 18 hours. The reaction mixture was then concentrated in vacuo to afford the title compound as a brown oil in 87% yield, 154.5 g. ¹H NMR (300 MHz, CDCl₃) δ: 7.22 (1H, m), 7.18-7.05 (3H, m), 3.71 (3H, s), 3.58 (2H, s), 2.62 (2H, s), 1.12 (6H, s) ppm; GCMS m/z 206 [M−H]⁻.

Preparation 147: Methyl(3-{2-[((2R)-2-[4-(benzyloxy)-3-(hydroxymethyl)phenyl]-2-{[tert-butyl(dimethyl)silyl]oxy}ethyl)amino]-2-methylpropyl}phenyl)acetate

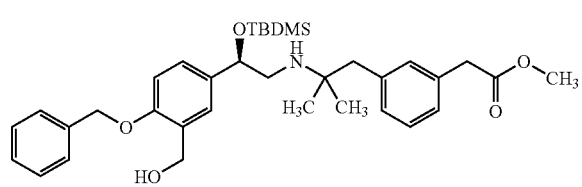

A mixture of [2-(benzyloxy)-5-((1R)-2-bromo-1-{[tert-butyl(dimethyl)silyl]oxy}ethyl) phenyl]methanol (preparation 23), (3.4 g, 7.5 mmol), [3-(2-amino-2-methylpropyl) phenyl]acetic acid (preparation 146), (1.7 g, 7.5 mmol) and N,N-diisopropylethylamine (1.4 mL, 8 mmol) in dimethylsulfoxide (7.5 mL) was stirred at 90° C. for 28 hours. The reaction mixture was then cooled, diluted with ethyl acetate and washed with water. The organic solution was then dried over magnesium sulfate, concentrated in vacuo and the residue was purified by column chromatography on silica gel, eluting with ethyl acetate:pentane, 66:33, to afford the title compound as a colourless oil in 50% yield, 2.2 g. ¹H NMR (400 MHz, CDCl₃) δ: 7.44-7.31 (6H, m), 7.30-7.19 (3H, m), 7.13-7.05 (2H, m), 6.80 (1H, d), 4.75-4.66 (3H, m), 3.68 (3H, s), 3.59 (2H, s), 2.90-2.72 (4H, m), 1.22-1.09 (6H, m), 0.70 (9H, s), −0.06 (3H, s), −0.28 (3H, s) ppm.

Preparation 148: (3-{2-[((2R)-2-[4-(Benzyloxy)-3-(hydroxymethyl)phenyl]-2-{(tert-butyl(dimethyl)silyl]oxy}ethyl)amino]-2-methylpropyl}phenyl)acetic acid

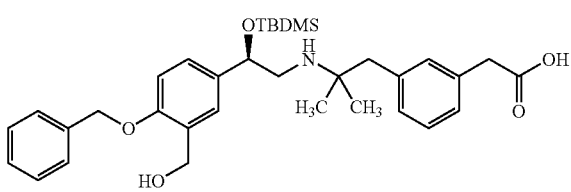

Lithium hydroxide solution (1M in water, 16.2 mL, 16.2 mmol) was added to a solution of methyl (3-{2-[((2R)-2-[4-(benzyloxy)-3-(hydroxymethyl)phenyl]-2-{[tert-butyl(dimethyl)silyl]oxy}ethyl)amino]-2-methylpropyl}phenyl)acetate (preparation 147), (4.80 g, 8.1 mmol) in tetrahydrofuran (49 mL) and methanol (17 mL) and the mixture was stirred at room temperature for 18 hours. The reaction mixture was then concentrated in vacuo and the residue was diluted with water and acidified to pH 7 with 1M hydrochloric acid. The resulting precipitate was filtered off and washed with water to afford the title compound as a pale yellow solid in 94% yield, 4.37 g ¹H NMR (400 MHz, DMSO-d₆) δ: 7.45-7.38 (6H, m), 7.31 (2H, m), 7.13 (1H, m) 7.02 (3H, m), 5.04 (3H, m), 4.52 (2H, d), 3.52 (2H, d), 2.43 (2H, d), 3.37 (2H, d), 1.24 (6H, m), 0.78 (9H, s), 0.02 (3H, s), -0.92 (3H, s) ppm; LRMS ESI m/z 659 [M+H]⁺

Preparation 149: 2-(3-{2-[((2R)-2-[4-(Benzyloxy)-3-(hydroxymethyl)phenyl]-2{[tert-butyl(dimethyl)silyl]oxy}ethyl)amino]-2-methyl propyl}phenyl)-N-(cycloheptylmethyl)acetamide

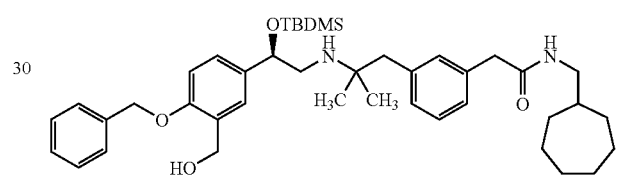

The title compound was prepared from (3-{2-[((2R)-2-[4-(benzyloxy)-3-(hydroxymethyl)phenyl]-2-{[tert-butyl(dimethyl)silyl]oxy}ethyl)amino]-2-methyl propyl}phenyl)acetic acid (preparation 148) and cycloheptane methylamine, using a similar method to that of preparation 38, as a white solid in 97% yield. ¹H NMR (400 MHz, CD₃OD) δ: 7.72 (1H, dd), 7.44 (1H, d), 7.42 (2H, m), 7.38-7.21 (5H, m), 7.19 (1H, d), 7.07 (1H, d), 7.02 (1H, m), 5.08 (2H, d), 5.03 (1H, m), 4.71 (2H, d), 3.51 (2H, d), 3.03-2.96 (4H, m), 1.77-1.34 (13H, m), 1.28 (6H, m), 1.07 (2H, m), 0.93 (9H, s), 0.07 (3H, s), −0.92 (3H, s) ppm; LRMS ESI m/z 688 [M+H]⁺

Preparation 150: N-1-Adamantyl-2-(3-{2-[((2R)-2-[4-(benzyloxy)-3-(hydroxymethyl)phenyl]-2-{[tert-butyl(dimethyl)silyl]oxy}ethyl)amino]-2-methylpropyl}phenyl)acetamide

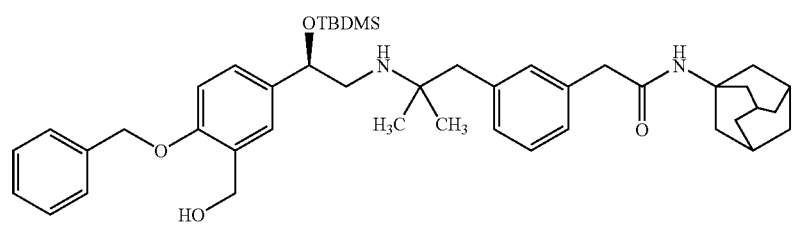

The title compound was prepared from (3-{2-[((2R)-2-[4-(benzyloxy)-3-(hydroxymethyl)phenyl]-2-{[tert-butyl(dimethyl)silyl]oxy}ethyl)amino]-2-methyl propyl}phenyl)acetic acid (preparation 148) and 1-adamantylamine, using a similar method to that of preparation 38, as a yellow oil in 71% yield. ¹H NMR (400 MHz, DMSO-d₆) δ: 7.52 (3H, m), 7.52-7.24 (4H, m), 7.18-7.08 (2H, m), 7.07-6.98 (2H, m), 6.94 (1H, m), 5.09 (2H, d), 5.01 (1H, t), 4.66-4.61 (1H, m), 4.54 (2H, d), 3.25 (2H, d), 3.15 (1H, d), 2.59-2.43 (2H, m), 1.98-1.92 (3H, m), 1.87 (6H, m), 1.57 (6H, m), 0.96 (6H, dd), 0.79 (9H, d), -0.98 (3H, s), -0.93 (3H, s) ppm; LRMS ESI m/z 712 [M+H]⁺

Preparation 151: 2-{3-[2-({(2R)-2-{[tert-Butyl(dimethyl)silyl]oxy}-2-[4-hydroxy-3-(hydroxymethyl)phenyl]ethyl}amino)-2-methylpropyl]phenyl}-N-(cycloheptylmethyl)acetamide

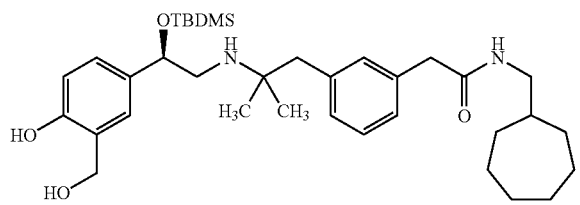

The title compound was prepared from 2-(3-{2-[((2R)-2-[4-(benzyloxy)-3-(hydroxymethyl)phenyl]-2-{[tert-butyl(dimethyl)silyl]oxy}ethyl)amino]-2-methyl propyl}phenyl)-N-(cycloheptylmethyl)acetamide (preparation 149), using a similar method to that of preparation 144, as a yellow oil in 96% yield. ¹H NMR (400 MHz, CD₃OD) δ: 7.67 (1H, m), 7.18-7.04 (5H, m), 6.79 (1H, d), 4.92-4.84 (1H, m), 4.67 (2H, m), 3.51 (2H, d), 3.21-3.03 (2H, m), 3.02 (2H, m), 2.96 (2H, m), 1.86-1.38 (11H, m), 1.24 (6H, m), 1.21-1.11 (2H, m), 0.82 (9H, s), 0.06 (3H, s), -0.93 (3H, s) ppm; LRMS ESI m/z 597 [M+H]⁺

Preparation 152: N-1-Adamantyl-2-{3-[2-({(2R)-2-{[tert-butyl(dimethyl)silyl]oxy}-2-[4-hydroxy-3-(hydroxymethyl)phenyl]ethyl}amino)-2-methylpropyl]phenyl}acetamide

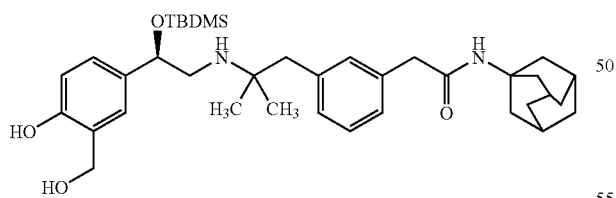

The title compound was prepared from N-1-adamantyl-2-(3-{2-[((2R)-2-[4-(benzyloxy)-3-(hydroxymethyl)phenyl]-2-{[tert-butyl(dimethyl)silyl]oxy}ethyl)amino]-2-methylpropyl}phenyl)acetamide (preparation 150), using a similar method to that of preparation 144, as a white solid in 73% yield. ¹H NMR (400 MHz, DMSO-d₆) δ: 7.42 (1H, m), 7.12 (1H, d), 7.09-7.05 (1H, m), 7.03-6.95 (4H, m), 6.64 (1H, d), 4.95 (1H, brs), 4.60 (1H, m), 4.42 (2H, d), 3.24 (2H, d), 2.75 (1H, d), 2.57 (2H, d), 1.97 (3H, m), 1.93 (6H, m), 1.57 (6H, m), 0.92 (6H, dd), 0.78 (9H, d), -0.03 (3H, s), -0.18 (3H, s) ppm; LRMS ESI m/z 621 [M+H]⁺

Preparation 153: Methyl {3-[2-({(2R)-2-{[tert-butyl(dimethyl)silyl]oxy}-2-[4-hydroxy-3-(hydroxymethyl)phenyl]ethyl}amino)-2-methylpropyl]phenyl}acetate

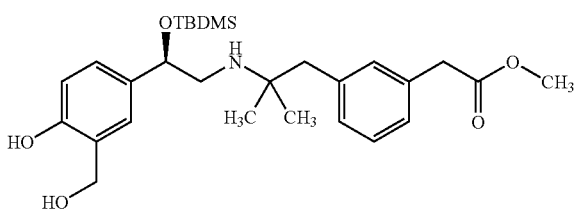

The title compound was prepared from methyl(3-{2-[((2R)-2-[4-(benzyloxy)-3-(hydroxymethyl)phenyl]-2-{[tert-butyl(dimethyl)silyl]oxy}ethyl)amino]-2-methylpropyl}phenyl)acetate (preparation 147), using a similar method to preparation 21 as a brown oil in 80% yield. ¹H NMR (400 MHz, CDCl₃) δ: 7.30-7.20 (2H, m), 7.19-7.00 (4H, m), 6.80 (1H, d), 4.75-4.66 (3H, m), 5.10 (2H, s), 3.68 (3H, s), 3.59 (2H, s), 2.85-2.62 (4H, m), 1.10-1.01 (6H, m), 0.80 (9H, s), -0.02 (3H, s), -0.20 (3H, s) ppm.

Preparation 154: {3-[2-({(2R)-2{[tert-Butyl(dimethyl)silyl]oxy}-2-[4-hydroxy-3-(hydroxymethyl)phenyl]ethyl}amino)-2-methylpropyl]phenyl}acetic acid

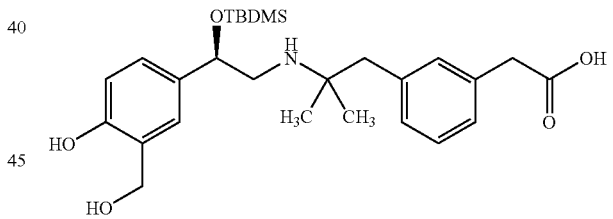

A mixture of methyl {3-[2-({(2R)-2-{[tert-butyl(dimethyl)silyl]oxy}-2-[4-hydroxy-3-(hydroxymethyl)phenyl]ethyl}amino)-2-methylpropyl]phenyl}acetate (preparation 153), (5 g, 10 mmol) and lithium hydroxide (1M in water, 30 mL, 30 mmol) in tetrahydrofuran (50 mL) was stirred for 48 hours at room temperature. The reaction mixture was then acidified with 1M hydrochloric acid (30 mL), concentrated in vacuo, and the residue was triturated with water and azeotroped (×3) with methanol to afford the title compound as a white solid in 84% yield, 4.1 g.

¹H NMR (400 MHz, CD₃OD) δ: 7.39-7.31 (2H, m), 7.28 (1H, m), 7.20-7.10 (3H, m), 6.81 (1H, d), 4.92-4.83 (1H, m), 4.65 (2H, m), 3.61 (2H, s), 3.34-3.24 (2H, m), 3.00 (2H, m), 1.33 (6H, s), 0.82 (9H, s), 0.06 (3H, s), -0.12 (3H, s) ppm

Preparation 155: 2-{3-[2-({(2R)-2-{[tert-Butyl(dimethyl)silyl]oxy}-2-[4-hydroxy-3-(hydroxymethyl)phenyl]ethyl}amino)-2-methyl propyl]phenyl}-N-(3-pyrrolidin-1-ylpropyl)acetamide

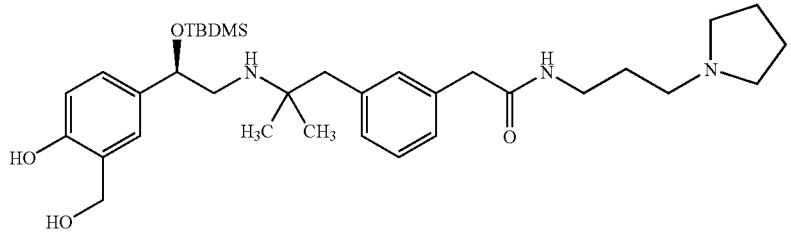

The title compound was prepared from {3-[2-({(2R)-2-{[tert-butyl(dimethyl)silyl]oxy}-2-[4-hydroxy-3-(hydroxymethyl)phenyl]ethyl}amino)-2-methylpropyl]phenyl}acetic acid (preparation 154) and 1-pyrrolidinepropanamine, using a similar method to that of preparation 38, in 16% yield.

$^1$H NMR (400 MHz, CDCl$_3$) δ: 7.20 (1H, m), 7.08-6.96 (3H, m), 6.85 (1H, m), 6.70 (1H, m), 6.58 (1H, m), 4.75 (2H, s), 4.64 (1H, m), 3.42 (2H, m), 3.24 (2H, m), 2.80 (1H, m), 2.62 (3H, m), 2.43 (6H, m), 1.68 (4H, m), 1.60 (2H, m), 1.00 (6H, s), 0.81 (9H, s), −0.05 (3H, s), −0.19 (3H, s) ppm

Preparation 156: N-Benzyl-2-{3-[2-({(2R)-2{[tert-butyl(dimethyl)silyl]oxy}-2-[4-hydroxy-3-(hydroxymethyl)phenyl]ethyl}amino)-2-methylpropyl]phenyl}-N-methylacetamide

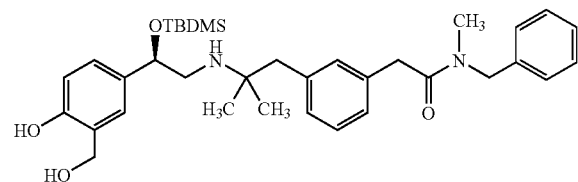

The title compound was prepared from {3-[2-({(2R)-2-{[tert-butyl(dimethyl)silyl]oxy}-2-[4-hydroxy-3-(hydroxymethyl)phenyl]ethyl}amino)-2-methylpropyl]phenyl}acetic acid (preparation 154) and N-benzylmethylamine, using a similar method to that of preparation 38 in 55% yield. $^1$H NMR (400 MHz, CD$_3$OD) δ: 7.55-7.01 (11H, m), 6.73 (1H, m), 4.63 (5H, m), 2.85 (2H, m), 2.80 (2H, m), 2.72 (1H, m), 2.68 (3H, m), 1.87 (1H, m), 1.03 (6H, s), 0.80 (9H, s), -0.00 (3H, s), −0.19 (3H, s) ppm

Preparation 157: 3-[2-({(2R)-2-{([tert-Butyl(dimethyl)silyl]oxy}-2-[4-hydroxy-3-(hydroxyl methyl)phenyl]ethyl}amino)-2-methylpropyl]-N-[2-(3-fluorophenyl)ethyl]benzamide

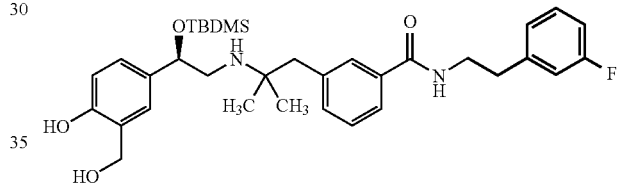

A mixture of 3-{2-[(2R)-2-(tert-butyldimethylsilanyloxy)-2-(4-hydroxy-3-hydroxy methylphenyl)ethylamino]-2-methylpropyl}benzoic acid (preparation 37) (473 mg, 1 mmol) and O-(1H-benzotriazol-1-yl)-N,N,N',N'-tetramethyluronium hexafluorophosphate (379 mg, 1 mmol) was added to a solution of 3-fluorophenethylamine (139 mg, 1 mmol) in N,N-dimethylacetamide (6 mL) and the mixture was stirred for 18 hours at room temperature. The solvent was removed in vacuo and the residue was re-dissolved in dichloromethane (100 mL) and washed with saturated sodium hydrogen carbonate solution (3×20 mL) and brine (10 mL). The organic solution was then dried over sodium sulfate, concentrated in vacuo and the residue was purified by column chromatography on silica gel, eluting with dichloromethane:methanol:0.88 ammonia, 100:0:0 to 90:10:1. The appropriate fractions were then concentrated in vacuo and the residue was re-dissolved in ethyl acetate, washed with saturated sodium hydrogen carbonate solution, dried over sodium sulfate and concentrated in vacuo to afford the title compound in 52% yield, 343 mg.

$^1$H NMR (400 MHz, CD$_3$OD) δ: 7.65-7.62 (2H, m), 7.38-7.23 (4H, m), 7.09-6.99 (3H, m), 6.92 (1H, d), 6.74 (1H, d), 4.70 (1H, m), 4.65 (2H, m), 3.61 (2H, m), 2.96-2.60 (6H, m), 1.10 (3H, s), 1.07 (3H, s), 0.79 (9H, s), −0.03 (3H, s), −0.21 (3H, s) ppm; LRMS ESI m/z 595 [M+H]$^+$

Preparation 158: 3-[2-({(2R)-2-{[tert-Butyl(dimethyl)silyl]oxy}-2-[4-hydroxy-3-(hydroxymethyl)phenyl]ethyl}amino)-2-methylpropyl]-N-[2-(5-chloro-2-methoxyphenyl)ethyl]benzamide

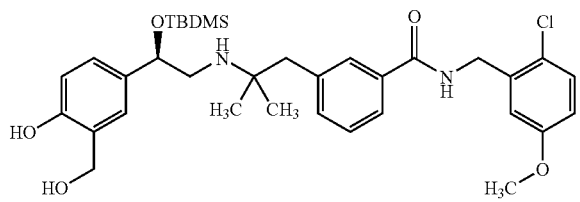

A mixture of 3-{2-[(2R)-2-(tert-butyldimethylsilanyloxy)-2-(4-hydroxy-3-hydroxy methylphenyl)ethylamino]-2-methylpropyl}benzoic acid (preparation 37) (400 mg, 0.85 mmol), O-(1H-benzotriazol-1-yl)-N,N,N',N'-tetramethyluronium hexafluorophosphate (320 mg, 0.85 mmol), triethylamine (225 μL, 1.6 mmol) and 2-(5-chloro-2-methoxy-phenyl)-ethylamine (preparation 70), (64 mg, 0.85 mmol) in N,N-dimethylacetamide (8 mL) was stirred for 18 hours at room temperature. The solvent was removed in vacuo and the residue was partitioned between dichloromethane (4 mL) and saturated sodium hydrogen carbonate solution (1 mL). The organic solution was then dried over magnesium sulfate, concentrated in vacuo and the residue was purified using an ISCO Companion® silica cartridge, eluting with dichloromethane:methanol:0.88 ammonia, 90:10:1 to 80:20:2, to afford the title compound in 22% yield.

$^{1}$H NMR (400 MHz, CD$_3$OD) δ: 7.70-7.60 (2H, m), 7.50-7.38 (3H, m), 7.20-7.10 (3H, m), 6.95 (1H, d), 6.85 (1H, d), 4.95 (1H, s), 4.75-4.60 (2H, m), 3.81 (3H, s), 3.57 (2H, m), 3.10-2.90 (6H, m), 1.25 (6H, s), 0.82 (9H, s), −0.03 (3H, s), −0.16 (3H, s) ppm

Preparation 159: 3-[2-({(2R)-2{[tert-Butyl(dimethyl)silyl]oxy}-2-[4-hydroxy-3-(hydroxymethyl)phenyl]ethyl}amino)-2-methylpropyl]-N-[2-(3-ethoxyphenyl)ethyl]benzamide

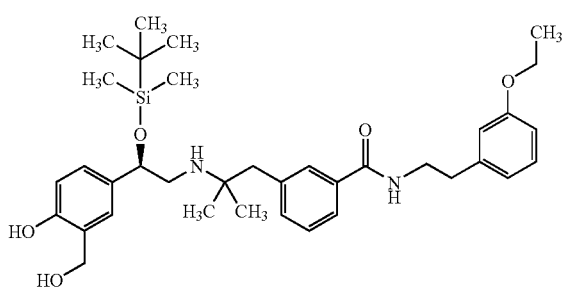

The title compound was prepared from 3-{2-[(2R)-2-(tert-butyldimethyl silanyloxy)-2-(4-hydroxy-3-hydroxymethylphenyl)ethylamino]-2-methylpropyl}benzoic acid (preparation 37) and 3-ethoxyphenethylamine, using a similar method to that of preparation 158, in 67% yield.

LRMS APCI m/z 621 [M+H]$^{+}$

Preparation 160: 3-[2-({(2R)-2-{[tert-Butyl(dimethyl)silyl]oxy}-2-[4-hydroxy-3-(hydroxymethyl)phenyl]ethyl}amino)-2-methylpropyl]-N-[2-(3-methoxyphenyl)ethyl]benzamide

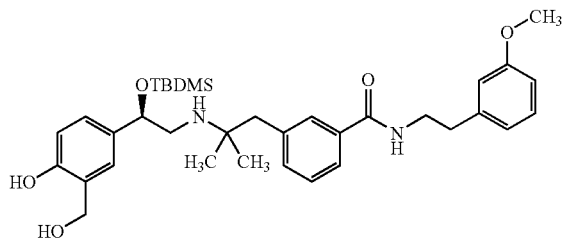

The title compound was prepared from 3-{2-[(2R)-2-(tert-butyldimethylsilanyloxy)-2-(4-hydroxy-3-hydroxy methylphenyl)ethylamino]-2-methylpropyl}benzoic acid (preparation 37) and 3-methoxyphenethylamine, using a similar method to that of preparation 158, in 98% yield.

LRMS ESI m/z 607 [M+H]$^{+}$

Preparation 161: [3-((2R)-2-{[(1R)-1-Phenylethyl]amino}propyl)phenyl]acetic acid

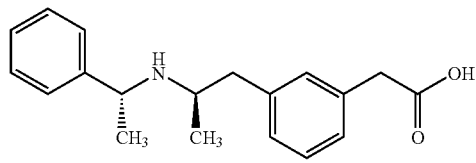

Lithium hydroxide solution (1M in water, 90 mL, 90 mmol) was added to a solution of methyl[3-((2R)-2-{[(1R)-1-phenyl-ethyl]-amino}-propyl)-phenyl]-acetate hydrochloride (preparation 26), (13.5 g, 43.5 mmol) in methanol (200 mL) and the mixture was stirred at room temperature for 18 hours. 1M Hydrochloric acid (90 mL) was then added to the reaction mixture and the methanol removed in vacuo. The resulting precipitate was filtered off and washed with water (20 mL) and a mixture of ethanol/diethyl ether, 20:80, to afford the title compound as a solid in 91% yield, 11.8 g $^{1}$H NMR (400 MHz, CD$_3$OD) δ: 7.52-7.45 (5H, m), 7.22-7.18 (2H, m), 7.19 (1H, s), 6.92 (1H, d), 4.56-4.48 (1H, q), 3.46 (2H, s), 3.26-3.13 (2H, m), 2.66-2.62 (1H, m), 1.62 (3H, d), 1.16 (3H, d) ppm; LRMS ESI m/z 298 [M+H]$^{+}$

Preparation 162: N-1-Adamantyl-2-[3-((2R)-2{[(1R)-1-phenylethyl]amino}propyl)phenyl]acetamide

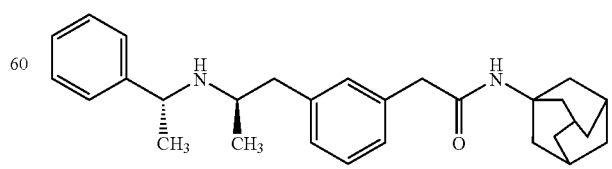

1-Adamantylamine (5.44 g, 36 mmol) and triethylamine (15 mL, 108 mmol) were added to a solution of [3-((2R)-2-{

[(1R)-1-phenylethyl]amino}propyl)phenyl]acetic acid (preparation 161), (10.7 g, 36 mmol) in dichloromethane (200 mL). 2-Chloro-1,3-dimethylimidazolidinum hexafluorophosphate (10 g, 36 mmol) was then added and the mixture was stirred at room temperature for 2 hours. The reaction mixture was washed with water and the organic solution was dried over magnesium sulfate and concentrated in vacuo. Purification of the residue by column chromatography on silica gel, eluting with dichloromethane:methanol:0.88 ammonia, 95:5:0.5, afforded the product as a foam in quantitative yield, 17.6 g. $^1$H NMR (400 MHz, CD$_3$OD) δ: 7.38-7.30 (4H, m), 7.27-7.22 (1H, m), 7.17 (1H, t), 7.09 (1H, d), 6.98 (1H, s), 6.89 (1H, d), 3.98 (1H, q), 3.36 (2H, s), 3.00-2.95 (1H, dd), 2.74-2.65 (1H, m), 2.42-2.37 (1H, dd), 2.04 (3H, m), 1.98 (6H, m), 1.75-1.65 (6H, m), 1.35 (d, 3H), 0.89 (d, 3H) ppm; LRMS ESI m/z 431 [M+H]$^+$ Preparation 163: N-1-Adamantyl-2-{3-[(2R)-2-aminopropyl]phenyl}acetamide

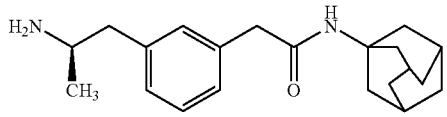

The title compound was prepared from N-1-adamantyl-2-[3-((2R)-2-{[(1R)-1-phenylethyl]amino}propyl)phenyl]acetamide (preparation 162), using a similar method to that of preparation 25, as a solid in 92% yield.

$^1$H NMR (400 MHz, CD$_3$OD) δ: 7.28-7.05 (4H, m), 3.40 (2H, s), 3.16-3.10 (1H, q), 2.70-2.58 (2H, m), 2.03 (3H, m), 2.00 (6H, m), 1.72-1.66 (6H, m), 1.09 (d, 3H) ppm; LRMS ESI m/z 327 [M+H]$^+$ Preparation 164: N-1-Adamantyl-2-{3-[(2R)-2-({ (2R)-2-[4-(benzyloxy)-3-(hydroxymethyl)phenyl]-2-hydroxyethyl}amino)propyl]phenyl}acetamide

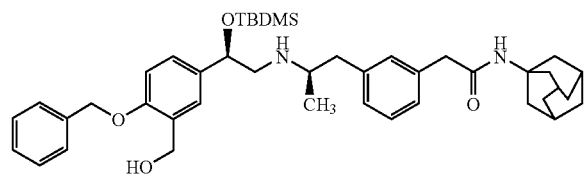

A mixture of [2-(benzyloxy)-5-((1R)-2-bromo-1-{[tert-butyl(dimethyl)silyl]oxy}ethyl) phenyl]methanol (preparation 23), (900 mg, 2 mmol) and N-1-adamantyl-2-{3-[(2R)-2-aminopropyl]pheny}acetamide (preparation 163), (1.3 g, 4 mmol) were heated at 90° C. for 24 hours. The reaction mixture was then cooled to room temperature and the crude product was purified by column chromatography on silica gel, eluting with dichloromethane:methanol:0.88 ammonia, 95:5:0.5, to afford the title compound as a pale foam in 83% yield, 1.16 g. $^1$H NMR (400 MHz, CD$_3$OD) δ: 7.48-7.28 (6H, m), 7.17-6.72 (6H, m), 5.14 (2H, s), 4.78-4.74 (1H, m), 4.73-4.64 (m, 2H), 3.36 (2H, s), 2.95-2.84 (2H, m), 2.70-2.63 (2H, m), 2.59-2.50 (1H, m), 2.03 (3H, m), 2.00 (6H, m), 1.70-1.64 (6H, m), 1.05 (3H, d), 0.84 (9H, s), 0.00 (3H, s), −0.18 (3H, s) ppm.

Abbreviations

TBDMS=tert-butyl(dimethyl)silyl

In Vitro Activity of the Compounds of Formula (1)

The ability of the compounds of the formula (1) to act as potent β2 agonists therefore mediating smooth muscle relaxation may be determined by the measure of the effect of beta-2 adrenergic receptor stimulation on electrical field stimulated-contraction of guinea pig trachea strips.

Guinea-Pig Trachea

Male, Dunkin-Hartley guinea pigs (475-525 g) are killed by CO$_2$ asphyxiation and exsanguination from the femoral artery and the trachea is isolated. Four preparations are obtained from each animal, starting the dissection immediately below the larynx and taking 2.5 cm length of trachea. The piece of trachea is opened by cutting the cartilage opposite the trachealis muscle, then transverse sections, 3-4 cartilage rings wide, are cut. The resulting strip preparations are suspended in 5 ml organ baths using cotton threads tied through the upper and lower cartilage bands. The strips are equilibrated, un-tensioned, for 20 minutes in a modified Krebs Ringer buffer (Sigma K0507) containing 3 μM Indomethacin (Sigma 17378), 10 μM Guanethidine (Sigma G8520) and 10 μM Atenolol (Sigma A7655), heated at 37° C. and gassed with 95% O$_2$/5% CO$_2$, before applying an initial tension of 1 g. The preparations are allowed to equilibrate for a further 30-45 minutes, during which time they are re-tensioned (to 1 g) twice at 15-minute intervals. Changes in tension are recorded and monitored via standard isometric transducers coupled to a data-collection system (custom-designed at Pfizer). Following the tensioning equilibration, the tissues are subjected to electrical field stimulation (EFS) using the following parameters: 10 s trains every 2 minutes, 0.1 ms pulse width, 10 Hz and just-maximal voltage (25 Volts) continuously throughout the length of the experiment. EFS of post-ganglionic cholinergic nerves in the trachea results in monophasic contractions of the smooth muscle and twitch height is recorded. The organ baths are constantly perfused with the above-described Krebs Ringer buffer by means of a peristaltic pump system (pump flow rate 7.5 ml/minute) throughout the experiment, with the exception of when a beta-2 agonist according to the present invention is added, the pump is then stopped for the time of the cumulative dosing to the bath and started again after maximal response is reached for the wash-out period.

Experimental Protocol for Assessment of Potency and Efficacy

Following equilibration to EFS, the peristaltic pump is stopped and the preparations 'primed' with a single dose of 300 nM isoprenaline (Sigma 15627) to establish a maximal response in terms of inhibition of the contractile EFS response. The isoprenaline is then washed out over a period of 40 minutes. Following the priming and wash-out recovery, a standard curve to isoprenaline is carried out on all tissues (Isoprenaline Curve 1) by means of cumulative, bolus addition to the bath using half log increments in concentration. The concentration range used is $1^{e-9}$ to $1^e/3^{e-6}$ M. At the end of the isoprenaline curve the preparations are washed again for 40 minutes before commencing a second curve, either to isoprenaline (as internal control) or a beta-2 agonist according to the present invention. Beta-2 agonist responses are expressed as percentage inhibition of the EFS response. Data for beta-2 agonist are normalised by expressing inhibition as a percentage of the maximal inhibition induced by isoprenaline in Curve 1. The EC$_{50}$ value for beta-2 agonist according to the present invention refers to the concentration of compound required to produce half maximal effect. Data for beta-2 agonists according to the present invention are then expressed as relative potency to isoprenaline defined by the ratio ($EC_{50}$ beta-2 agonist)/(EC50 Isoprenaline).

Confirmation of Beta-2 Mediated Functional Activity

Beta-2 agonist activity of test compounds is confirmed using the protocol above, however, prior to constructing the curve to beta-2 agonist according to the present invention, the preparations are pre-incubated (for a minimum of 45 minutes) with 300 nM ICI 118551 (a selective $\beta_2$ antagonist) which results in the case of a beta-2 mediated effect in a rightward-shift of the test compound dose response curve.

According to another alternative, the agonist potency for the β2 receptor of the compounds of the formula (1) may also be determined by the measure of the concentration of compound according to the present invention required to produce half maximal effect ($EC_{50}$) for the β2 receptor.

Compound Preparation 10 mM/100% DMSO (dimethylsulfoxide) stock of compound is diluted to required top dose in 4% DMSO. This top dose is used to construct a 10-point semi-log dilution curve, all in 4% DMSO. Isoprenaline (Sigma, I-5627) was used as a standard in every experiment and for control wells on each plate. Data was expressed as % Isoprenaline response.

Cell Culture

CHO (Chinese Hamster Ovary) cells recombinantly expressing the human β2 adrenergic receptor (from Kobilka et al., PNAS 84: 46-50, 1987 and Bouvier et al., Mol Pharmacol 33: 133-139 1988 CHOhβ2) were grown in Dulbeccos MEM/NUT MIX F12 (Gibco, 21331-020) supplemented with 10% foetal bovine serum (Sigma, F4135, Lot 90K8404 Exp 09/04), 2 mM glutamine (Sigma, G7513), 500 µg/ml geneticin (Sigma, G7034) and 10 µg/ml puromycin (Sigma, P8833). Cells were seeded to give about 90% confluency for testing.

Assay Method

25 µl/well each dose of compound was transferred into a cAMP-Flashplate® (NEN, SMP004B), with 1% DMSO as basal controls and 100 nM Isoprenaline as max controls. This was diluted 1:2 by the addition of 25 µl/well PBS. Cells were trypsinised (0.25% Sigma, T4049), washed with PBS (Gibco, 14040-174) and resuspended in stimulation buffer (NEN, SMP004B) to give $1 \times 10^6$ cells/ml CHOhB2. Compounds were incubated with 50 µl/well cells for 1 hour. Cells were then lysed by the addition of 100 µl/well detection buffer (NEN, SMP004B) containing 0.18 µCi/ml $^{125}$I-cAMP (NEN, NEX-130) and plates were incubated at room temperature for a further 2 hours. The amount of $^{125}$I-cAMP bound to the Flashplate® was quantified using a Topcount NXT (Packard), normal counting efficiency for 1 minute. Dose-response data was expressed as % Isoprenaline activity and fitted using a four parameter sigmoid fit.

It has thus been found that the compounds of formula (1) according to the present invention that have been tested show a β2 cAMP $EC_{50}$ below 10 nM.

The following table illustrate the activity of the compounds of the invention:

| Example | $EC_{50}$ (nM) |
|---------|----------------|
| 1       | 0.143          |
| 14      | 0.0640         |
| 16      | 0.874          |
| 23      | 0.0800         |
| 24      | 0.150          |
| 46      | 0.838          |
| 62      | 0.444          |
| 63      | 0.0750         |
| 66      | 1.16           |
| 88      | 0.434          |
| 102     | 0.100          |
| 114     | 0.134          |

The invention claimed is:

1. A compound of formula (1),

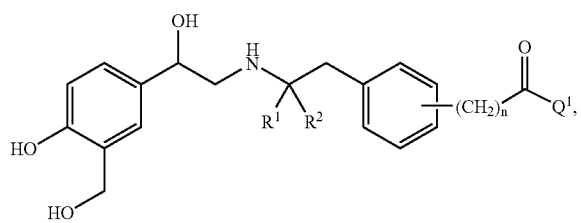

(1)

or a pharmaceutically acceptable salt thereof wherein
the $(CH_2)_n$—C(=O)$Q^1$ group is in the meta or para position;
$R^1$ and $R^2$ are independently H or $C_1$-$C_4$ alkyl;
n is 0, 1 or 2;
$Q^1$ is

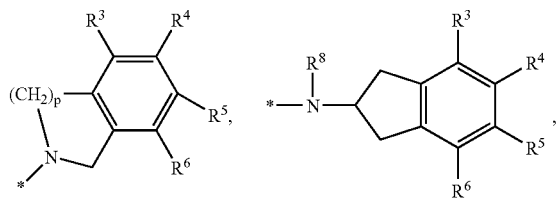

or *—N($R^8$)-$Q^2$-A;
$Q^2$ is a single bond or $C_1$-$C_4$ alkylene;
$R^8$ is H;
p is 1 or 2;
A is $C_3$-$C_{10}$ cycloalkyl, 2 or 3 carbon atoms of said cycloalkyl being optionally bridged by $C_1$-$C_4$ alkylene, said alkylene bridge being optionally branched; or

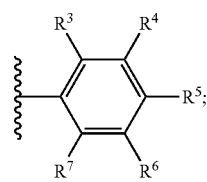

$R^3$, $R^4$, $R^5$, $R^6$ and $R^7$ are independently H, $C_1$-$C_4$ alkyl, $OR^9$, $SR^9$, $SOR^9$, $SO_2R^9$, halo, CN, $CF_3$, $OCF_3$, phenyl, phenoxy, phenylthio, morpholinylsulfonyl, pyrrolidinyl-n-propoxy, $COOR^9$, $SO_2NR^9R^{10}$, $CONR^9R^{10}$, $NR^9R^{10}$ or $NHCOR^{10}$;
$R^9$ and $R^{10}$ are independently H or $C_1$-$C_4$ alkyl; and \* represents the attachment point to the carbonyl group; provided that
1) when n is 1 or 2, then:
Q$^1$ is \*—N(R$^8$)-Q$^2$-A where A is
C$_3$-C$_{10}$ cycloalkyl, 2 carbon atoms of said cycloalkyl being optionally bridged by C$_1$-C$_4$ alkylene, said alkylene bridge being optionally branched;
a group of the formula

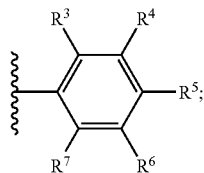

wherein one of R$^3$ to R$^7$ is CN, SOR$^9$, SO$_2$R$^9$, phenyl, O-phenyl, S-phenyl, SO$_2$-morpholinyl or O—(CH$_2$)$_3$-pyrrolidinyl; and
2) when one of R$^1$ or R$^2$ is H, the other is not CH$_3$.

2. A compound of claim 1 or a pharmaceutically acceptable salt thereof wherein Q$^1$ is \*—N(R$^8$)-Q$^2$-A; A is

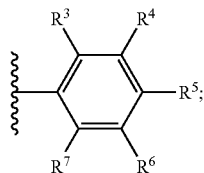

R$^3$, R$^4$ R$^5$, R$^6$ and R$^7$ are independently H, C$_1$-C$_4$ alkyl, OR$^9$, SR$^9$, Cl, F, CF$_3$, OCF$_3$, COOH, SO$_2$NR$^9$R$^{10}$ and at least 2 of R$^3$, R$^4$, R$^5$, R$^6$ and R$^7$ are H.

3. A compound of claim 2 or a pharmaceutically acceptable salt thereof wherein R$^3$, R$^4$ R$^5$, R$^6$ and R$^7$ are independently H, CH$_3$, OH, OCH$_3$, SCH$_3$, OCH$_2$CH$_3$, Cl, F, CF$_3$, OCF$_3$, COOH, SO$_2$NH$_2$, and at least 2 of R$^3$, R$^4$, R$^5$, R$^6$ and R$^7$ are H.

4. A compound of claim 3 or a pharmaceutically acceptable salt thereof wherein R$^3$, R$^4$ R$^5$, R$^6$ and R$^7$ are the same or different and are selected from H, CH$_3$, OH, OCH$_3$, SCH$_3$, OCH$_2$CH$_3$, Cl, F, CF$_3$, OCF$_3$, COOH, SO$_2$NH$_2$, and at least 3 of R$^3$ to R$^7$ are H.

5. A compound of claim 1 or a pharmaceutically acceptable salt thereof wherein Q$^1$ is \*—N(R$^8$)-Q$^2$-A where A is cyclopropyl, cyclobutyl, cyclopentyl, cyclohexyl, cycloheptyl or adamantyl.

6. A compound of claim 1 or a pharmaceutically acceptable salt thereof wherein Q$^1$ is

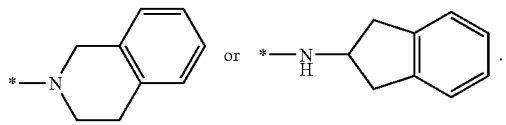

7. The (R,R)-stereoisomer of a compound of claim 1 or a pharmaceutically acceptable salt thereof.

8. A compound of claim 1 or a pharmaceutically acceptable salt thereof wherein the (CH$_2$)$_n$—C(=O)Q$^1$ group is in the meta position.

9. A pharmaceutical composition comprising an effective amount of a compound of claim 1 or a pharmaceutically acceptable salt thereof and a pharmaceutically acceptable exipient or additive.

10. A method of treating a disease, disorder or condition in a mammal, said method comprising administering to said mammal a therapeutically effective amount of a compound of claim 1, or a pharmaceutically acceptable salt thereof, wherein said disease, disorder or condition is asthma, chronic obstructive pulmonary disease, bronchitis, chronic or acute bronchoconstriction, adult respiratory distress syndrome, acute lung injury or bronchiectasis.

11. A method of claim 10 wherein said asthma is selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis; said bronchitis is selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis; and said bronchiectasis is selected from the group consisting of cylindric bronchiectasis, sacculated bronchiectasis, fusiform bronchiectasis, capillary bronchiectasis, cystic bronchiectasis, dry bronchiectasis and follicular bronchiectasis.

\* \* \* \* \*